US012544359B2

(12) United States Patent
Wilkinson et al.

(10) Patent No.: US 12,544,359 B2
(45) Date of Patent: Feb. 10, 2026

(54) 1-AMINOSULFONYL-2-CARBOXYPYRROLE DERIVATIVES AS METALLO-BETA-LACTAMASE INHIBITORS

(71) Applicant: INFEX Therapeutics Limited, Macclesfield (GB)

(72) Inventors: Andrew Wilkinson, Macclesfield (GB); Ian Cooper, Macclesfield (GB); David Orr, Macclesfield (GB); Jonathan Finlayson, Macclesfield (GB); Adam Bunt, Macclesfield (GB); Pia Appelqvist, Huddinge (SE); Hans Wallberg, Huddinge (SE); Fredrik Wångsell, Mölndal (SE); James Kirkham, Cheshire (GB)

(73) Assignee: INFEX Therapeutics Limited, Macclesfield (GB)

( * ) Notice: Subject to any disclaimer, the term of this patent is extended or adjusted under 35 U.S.C. 154(b) by 834 days.

(21) Appl. No.: 17/778,261

(22) PCT Filed: Nov. 19, 2020

(86) PCT No.: PCT/GB2020/052961
§ 371 (c)(1),
(2) Date: May 19, 2022

(87) PCT Pub. No.: WO2021/099793
PCT Pub. Date: May 27, 2021

(65) Prior Publication Data

US 2023/0018460 A1 Jan. 19, 2023

(30) Foreign Application Priority Data

Nov. 20, 2019 (GB) .................................. 1916915.0

(51) Int. Cl.

| | |
|---|---|
| ***A61K 31/40*** | (2006.01) |
| ***A61K 31/4025*** | (2006.01) |
| ***A61K 31/403*** | (2006.01) |
| ***A61K 31/407*** | (2006.01) |
| ***A61K 31/4162*** | (2006.01) |
| ***A61K 31/4178*** | (2006.01) |
| ***A61K 31/427*** | (2006.01) |
| ***A61K 31/431*** | (2006.01) |
| ***A61K 31/438*** | (2006.01) |
| ***A61K 31/4439*** | (2006.01) |
| ***A61K 31/454*** | (2006.01) |
| ***A61K 31/496*** | (2006.01) |
| ***A61K 31/5377*** | (2006.01) |
| ***A61K 31/541*** | (2006.01) |
| ***A61P 31/04*** | (2006.01) |
| ***C07D 207/48*** | (2006.01) |
| ***C07D 401/04*** | (2006.01) |

(Continued)

(52) U.S. Cl.
CPC .......... *A61K 31/40* (2013.01); *A61K 31/4025* (2013.01); *A61K 31/403* (2013.01); *A61K 31/407* (2013.01); *A61K 31/4162* (2013.01); *A61K 31/4178* (2013.01); *A61K 31/427* (2013.01); *A61K 31/431* (2013.01); *A61K 31/438* (2013.01); *A61K 31/4439* (2013.01); *A61K 31/454* (2013.01); *A61K 31/496* (2013.01); *A61K 31/5377* (2013.01); *A61K 31/541* (2013.01); *A61P 31/04* (2018.01); *C07D 207/48* (2013.01); *C07D 401/04* (2013.01); *C07D 401/06* (2013.01); *C07D 401/12* (2013.01); *C07D 401/14* (2013.01); *C07D 403/04* (2013.01); *C07D 403/12* (2013.01); *C07D 471/08* (2013.01); *C07D 487/10* (2013.01)

(58) Field of Classification Search
CPC ...................................................... A61K 31/40
See application file for complete search history.

(56) References Cited

FOREIGN PATENT DOCUMENTS

WO WO-03/070682 A1 8/2003
WO WO-2014/198849 A1 12/2014
(Continued)

OTHER PUBLICATIONS

International Preliminary Report and Written Opinion for International Application No. PCT/GB2020/052961 dated May 17, 2022.
(Continued)

*Primary Examiner* — John S Kenyon
*Assistant Examiner* — Sara Elizabeth Bell
(74) *Attorney, Agent, or Firm* — Foley Hoag LLP; Dana M. Gordon; Shejla S. Pollozi

(57) ABSTRACT

This invention relates to compounds of formula (I) and methods of treatment using the compounds. The compounds of the invention can be used in combination with antibacterial agents to treat bacterial infections. More specifically, the compounds of formula (I) can be used in combination with a class of antibacterial agents known as carbapenems. The novel compounds of the present invention are enzyme inhibitors and more particularly are metallo-β-lactamase inhibitors.

(I)

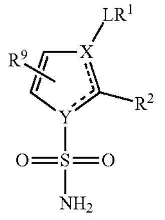

18 Claims, No Drawings

(51) Int. Cl.

| | |
|---|---|
| ***C07D 401/06*** | (2006.01) |
| ***C07D 401/12*** | (2006.01) |
| ***C07D 401/14*** | (2006.01) |
| ***C07D 403/04*** | (2006.01) |
| ***C07D 403/12*** | (2006.01) |
| ***C07D 471/08*** | (2006.01) |
| ***C07D 487/10*** | (2006.01) |

(56) References Cited

FOREIGN PATENT DOCUMENTS

| | | | |
|---|---|---|---|
| WO | WO-2015/112441 | A1 | 7/2015 |
| WO | WO-2017/093727 | A1 | 6/2017 |
| WO | WO-2019/220125 | A1 | 11/2019 |
| WO | WO-2019/221122 | A1 | 11/2019 |
| WO | WO-2021/099793 | A1 | 5/2021 |

OTHER PUBLICATIONS

International Search Report and Written Opinion for International Application No. PCT/GB2020/052961 dated Oct. 20, 2021.

United Kingdom Search Report for United Kingdom Application No. GB1916915.0 dated May 6, 2020.

Chen et al. "Facile Synthesis of Derivatives of 1, 1, 3-Trioxo-2H, 4H-pyrrolo [1, 2-b][1, 2, 4, 6] thiatriazine: A New Heterocyclic System." Heteroatom Chemistry 24(6) (2013): 495-501.

Nasief et al., "Modulating hydrogen-bond basicity within the context of protein-ligand binding: A case study with thrombin inhibitors that reveals a dominating role for desolvation." European Journal of Medicinal Chemistry 125 (2017): 975-991.

1-AMINOSULFONYL-2-CARBOXYPYRROLE DERIVATIVES AS METALLO-BETA-LACTAMASE INHIBITORS

RELATED APPLICATIONS

This application is the national stage under 35 U.S.C. § 371 of Patent Cooperation Treaty Application No.: PCT/GB2020/052961, filed Nov. 19, 2020; which claims the benefit of GB Patent Application No. 1916915.0, filed on Nov. 20, 2019.

INTRODUCTION

This invention relates to compounds that can be used to treat bacterial infections in combination with other antibacterial agents, and more specifically in combination with a class of antibacterial agents known as carbapenems. The novel compounds of the present invention are enzyme inhibitors and more particularly are metallo-β-lactamase inhibitors.

Each year, throughout Europe, over 4 million people contract a healthcare associated bacterial infection, resulting in ~37,000 deaths (Public Health England). The increasing prevalence of multi-drug resistant bacteria has worsened patient outcomes, prolonged hospital stays and necessitated use of 'last resort' and potentially toxic antimicrobials, such as colistin and polymyxin B. It has been estimated that by 2050, without intervention, antibiotic-resistant bacteria will cause the death of over 10 million people each year, and this will equate to an economic burden of 100 trillion US dollars.

In the clinic, antibiotic-resistant Gram-negative pathogens cause diverse infections, including pneumonia, blood stream infections, surgical site infections, skin and soft tissue infections, and urinary tract infections. There are limited effective treatment options for these organisms and empirical antibiotic therapy often fails in patients infected with Gram-negative organisms of the ESKAPE pathogen group (*Enterococcus faecium, Staphylococcus aureus, Klebsiella pneumoniae, Acinetobacter baumannii, Pseudomonas aeruginosa*, and *Enterobacter* species).

In February 2017, the World Health Organisation (WHO) issued a prioritised list of bacterial pathogens to assist member states in focusing research and development to the areas of greatest need. Of these bacteria, the WHO classed the following Gram-negative organisms as a critical priority: carbapenem resistant *A. baumannii*; carbapenem resistant *P. aeruginosa*; carbapenem resistant and ESBL-producing Enterobacteriaceae (including *K. pneumoniae* and *E. coli*). Consequently, carbapenem-resistant Gram-negative bacteria have been defined as a critical unmet medical need. The mode of action of β-lactams, such as carbapenems, involves covalently binding to the active site of transpeptidases that link peptidoglycan chains of the bacterial cell wall. This results in inhibition of cell wall synthesis and ultimately cell death. The advantage of carbapenems is a broader spectrum of activity compared with most other β-lactams and until recently their use had not been significantly impacted by resistance development.

The use of carbapenems as a last line of defence against multi-drug resistant Gram-negatives has been compromised by the emergence of carbapenemases from the metallo-β-lactamase (MBL) class. These enzymes bind to carbapenems and cleave the β-lactam ring, resulting in antibiotic deactivation. The Ambler classification system divides known β-lactamase enzymes into four classes according to amino acid sequence. Classes A, C and D β-lactamases cleave β-lactams through transient binding of a serine group within the enzyme's active site to the carbonyl of the β-lactam ring. This results in formation of an acyl-enzyme and cleavage of the β-lactam ring. Subsequently, an activated water molecule deacylates the acyl-enzyme intermediate, hydrolysing the bond between serine and carbonyl, releasing the deactivated β-lactam. MBLs are mechanistically and structurally discrete from class A, C and D serine-β-lactamases. In this case, cleavage of β-lactams occurs in a single step, without formation of a covalent intermediate. MBLs coordinate water molecules and zinc ions to His, Cys and Asp residues in their active site, where water molecules facilitate nucleophilic attack and bond cleavage within the β-lactam ring. The subclasses of MBLs are structurally divergent, with B1 and B3 enzymes containing two zinc ions in the active site and displaying a broad substrate profile. Group B2 enzymes rely upon a single zinc ion and hydrolyse only carbapenems. Clinically, MBLs of the B1 class, including NDM, VIM and IMP, are most prevalent and are frequently identified within mobile genetic elements.

Pre-existing serine-β-lactamase inhibitors (effective against Ambler Class A, C and some Class D β-lactamases) have successfully restored activity of numerous β-lactams. Inhibitors bind to the active site of the enzyme transiently or permanently with high affinity, effectively outcompeting binding of β-lactams. Marketed β-lactam/β-lactamase inhibitor combinations include amoxicillin and clavulanic acid (Co-amoxiclav) and ceftazidime and avibactam (Avycaz). Currently, there are no metallo-β-lactamase inhibitors (MBLIs) in clinical development or clinically available, indicating commercial potential for a broad spectrum MBLI that restores the activity of carbapenems.

The first carbapenem used clinically was imipenem, for the treatment of complex microbial infections. A disadvantage of imipenem is its hydrolysis in the mammalian kidney by dehydropeptidase I (DHPI) necessitating co-formulation with the dehydropeptidase inhibitor cilastatin. Subsequent carbapenem iterations, including meropenem, are insusceptible to DHPI hydrolysis due to the presence of a methyl group at the 1-β position of the carbapenem moiety. Meropenem is less potent than imipenem against Gram-positive pathogens but has enhanced potency against Gram-negative organisms and is employed widely in the clinic. To combat resistance to carbapenems, we have discovered a series of compounds that inhibit metallo-β-lactamase enzymes. The compounds significantly improve the efficacy of meropenem against drug resistant bacteria when co-administered with meropenem. The invention relates specifically to these compounds and to combinations of these compounds with a carbapenem such as meropenem. The invention also relates to methods of using said compounds and to pharmaceutical formulations comprising said compounds.

It is contemplated that other approved carbapenems might also benefit from co-formulation with the compounds of the invention. Other currently approved carbapenems include: ertapenem, doripenem, panipenem, biapenem and tebipenem.

BACKGROUND

Until comparatively recently, bacterial infections were one of the most common causes of death, disfigurement and disablement. During the $19^{th}$ century a series of antibiotic drug classes were developed, meaning that the successful treatment of bacterial infections has become routine. However, microbial resistance to antibiotics is becoming a significant problem and many consider that this will become one of the most significant challenges to human health. Indeed, in some bacterial pathogens, multidrug resistance has already become common.

The greatest unmet medical need is the dearth of effective treatments for multidrug resistant Gram-negative bacteria. Therefore discovery of novel antibiotics that are active against WHO listed pathogens of critical concern, or drugs that circumvent existing bacterial resistance mechanisms is essential.

WO2015/112441 discloses a series of novel metallo-β-lactamase inhibitors and their uses which are intended for reducing bacterial β-lactam antibiotic resistance. The compounds are a series of substituted 1H and 2H-tetrazol-5-yl phenylsulphonamides.

US2016/0272601 also discloses a series of novel compounds and their use as metallo-β-lactamase inhibitors for use in combination with β-lactam antibiotics. The compounds of this disclosure are thiazole-4-carboxylic acid derivatives.

WO2017/093727 discloses another series of compounds which are inhibitors of metallo-β-lactamases and may be used in the treatment of bacterial infections. The exemplified compounds of this disclosure are a series of substituted 1H-indoles.

It is an aim of certain embodiments of this invention to provide compounds which can prevent or slow unwanted metabolism of β-lactams such as carbapenems, and in particular meropenem. A further aim is to provide formulations of a carbapenem, for example meropenem, with a compound of the invention which is active against Gram-negative bacteria including antibiotic-resistant organisms. It is an aim of certain embodiments of this invention to provide compounds that can be included in the formulations which are active against bacterial strains that are resistant to one or more other antibiotics. In spite of the numerous different antibiotics known in the art for a variety of different infections, there continues to be a need to develop antibiotics that can provide effective treatment in a reliable manner. In addition, there remains a need for drugs which can avoid or reduce the side-effects associated with known antibiotics. A further aim of certain embodiments is to provide treatment which is effective in a selective manner at a chosen site of interest. Another aim of certain embodiments is to develop drugs with a suitable pharmacokinetic profile and duration of action following dosing.

The present invention seeks to overcome the disadvantages of known carbapenems. The present invention also aims to improve the efficacy of existing carbapenems such as meropenem. In certain embodiments, the present invention aims to provide a compound that can restore or prolong the activity of antibiotics (particularly carbapenems) against antibiotic resistant bacterial strains. It is also an aim of certain embodiments of the present invention to increase the antibiotic efficacy of an antibiotic against bacterial strains having a wide spectrum of metallo-β-lactamase enzymes, for example some or all of VIM, NDM, and IMP.

It is an aim of certain embodiments of this invention to provide new antibiotic formulations which are active against resistant strains of Gram-negative bacteria. A further aim of certain embodiments of the present invention is to provide antibiotic formulations in which the metabolised fragment or fragments of the drug after absorption are GRAS (Generally Regarded As Safe). A further aim of the invention is to provide prodrugs which are not species dependent and/or which reduce inter-patient variability due to differences in metabolism. Another aim of the invention is to provide prodrugs which are able to overcome the food effect in the sense that they can be administered to fed or fasted patients without the need to control carefully the dosing schedule relative to meal times.

The novel compounds of the present invention satisfy some or all of the above aims.

DETAILED DESCRIPTION OF THE INVENTION

In one aspect, the invention provides a compound of formula (I), or pharmaceutically acceptable salts thereof:

(I)

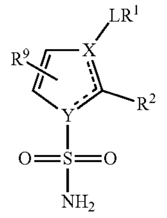

wherein one of X and Y is N and the other is C;

L is a linker group selected from a bond or —$(CH_2)_a$-Q-$(CH_2)_b$— in which, Q is selected from the group comprising: O, NH, $SO_2$, C═C, and C≡C or Q is absent;

$R^1$ is a 6 membered monocyclic aromatic, carbocyclic, heteroaromatic or heterocyclic ring substituted by one $R^3$ group, $R^1$ may be further substituted with 0 or 1 groups selected from halo, $C_{1-6}$ alkyl, or $C_{1-6}$ haloalkyl;

$R^2$ is —C(O)OH or —C(O)OM; wherein M is a group 1 cation;

$R^3$ is selected from: —$CONR^4(CR^aR^b)_nNR^5R^6$, —$CONR^4(CR^aR^b)_nOSO_2OR^5$, —$CONR^4(CR^aR^b)_nCN$, —$CONR^4(CR^aR^b)_nC(═O)OH$, —$CONR^4(CR^aR^b)_nC(═O)NR^7R^8$, —$NR^4CO(CR^aR^b)_nNR^7R^8$, —$NR^4CO(CR^aR^b)_nOSO_2OR^5$, —$NR^4CO(CR^aR^b)_nCN$, —$NR^4CO(CR^aR^b)_nC(═O)OH$, —$NR^4CO(CR^aR^b)_nC(═O)NR^7R^8$, —$SO_2NR^4(CR^aR^b)_nNR^5R^6$, —$SO_2NR^4(CR^aR^b)_nOSO_2OR^5$, —$SO_2NR^4(CR^aR^b)_nCN$, —$SO_2NR^4(CR^aR^b)_nC(═O)OH$, —$SO_2NR^4(CR^aR^b)_nC(═O)NR^7R^8$

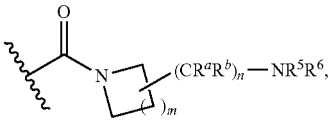

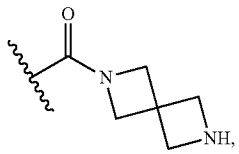

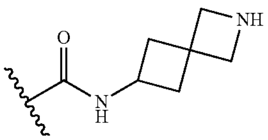

and

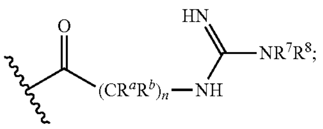

$R^4$ is selected at each occurrence from: H, halo, —OH, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, —$(CH_2)_f$-aryl, —$(CH_2)_d$-heteroaryl, —$(CH_2)_g$-heterocyclyl; wherein $R^4$ may be optionally substituted where chemically possible with one, two or three groups independently selected at each occurrence from the group comprising: halo, —$NH_2$, —$N(C_{1-4}\ alkyl)_2$, —OH, —$SO_2N(C_{1-4}\ alkyl)_2$, —NHC(=O)O$C_{1-6}$ alkyl and —C(=O)O$C_{1-6}$ alkyl;

$R^5$ and $R^6$ are each independently H or $C_{1-6}$ alkyl;

wherein at least one of $R^4$, $R^5$ or $R^6$ is $C_{1-6}$ alkyl when each of $R^4$, $R^5$ and $R^6$ are present;

$R^7$ and $R^8$ are each independently selected at each occurrence from H or $C_{1-4}$ alkyl;

$R^9$ is selected from the group comprising: H, $C_{1-4}$alkyl, and $C_{1-4}$ haloalkyl;

$R^a$ and $R^b$ are each independently selected at each occurrence from: H, halo, —$NH_2$, and $C_{1-4}$ alkyl.

a, b, d, f and g are independently selected as integers from 0 to 3;

m is an integer selected from 1, 2 or 3;

n is an integer selected from 1, 2, 3, 4 or 5; and $\overline{---}$ represents a single or a double bond as required to satisfy valence requirements.

In one aspect, the invention provides a compound of formula (I), or pharmaceutically acceptable salts thereof:

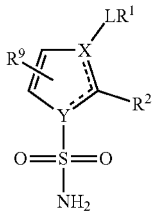

(I)

wherein one of X and Y is N and the other is C;

L is a linker group selected from a bond or —$(CH_2)_a$-Q-$(CH_2)_b$— in which, Q is selected from the group comprising: O, NH, $SO_2$, C=C, and C≡C or Q is absent;

$R^1$ is a 6 membered monocyclic aromatic, heteroaromatic or heterocyclic ring substituted by one $R^3$ group, $R^1$ may be further substituted with 0 or 1 groups selected from halo, $C_{1-6}$ alkyl, or $C_{1-6}$ haloalkyl;

$R^2$ is —C(O)OH or —C(O)OM; wherein M is a group 1 cation;

$R^3$ is selected from the group comprising: —CON$R^4$($CR^aR^b$)$_n$N$R^5R^6$, —CON$R^4$($CR^aR^b$)$_n$OSO$_2$O$R^5$, —CON$R^4$($CR^aR^b$)$_n$CN, —CON$R^4$($CR^aR^b$)$_n$C(=O)OH, —CON$R^4$($CR^aR^b$)$_n$C(=O)N$R^7R^8$, —N$R^4$CO($CR^aR^b$)$_n$N$R^7R^3$, —N$R^4$CO($CR^aR^b$)$_n$OSO$_2$O$R^5$, —N$R^4$CO($CR^aR^b$)$_n$CN, —N$R^4$CO($CR^aR^b$)$_n$C(=O)OH, —N$R^4$CO($CR^aR^b$)$_n$C(=O)N$R^7R^8$, —SO$_2$N$R^4$($CR^aR^b$)$_n$N$R^5R^6$, —SO$_2$N$R^4$($CR^aR^b$)$_n$OSO$_2$O$R^5$, —SO$_2$N$R^4$($CR^aR^b$)$_n$CN, —SO$_2$N$R^4$($CR^aR^b$)$_n$C(=O)OH, —SO$_2$N$R^4$($CR^aR^b$)$_n$C(=O)N$R^7R^8$

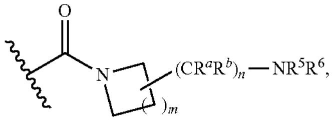

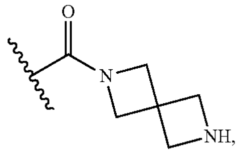

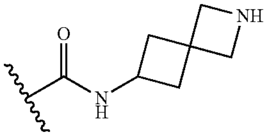

and

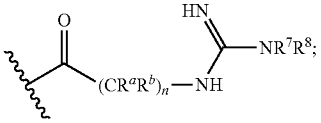

$R^4$ is selected at each occurrence from the group comprising: H, halo, —OH, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, —$(CH_2)_f$-aryl, —$(CH_2)_d$-heteroaryl, —$(CH_2)_g$-heterocyclyl; wherein $R^4$ may be optionally substituted where chemically possible with one, two or three groups independently selected at each occurrence from the group comprising: halo, —$NH_2$, —$N(C_{1-4}\ alkyl)_2$, —OH, —$SO_2N(C_{1-4}\ alkyl)_2$, —NHC(=O)O$C_{1-6}$ alkyl and —C(=O)O$C_{1-6}$ alkyl;

$R^5$ and $R^6$ are each independently H or $C_{1-6}$ alkyl;

wherein at least one of $R^4$, $R^5$ or $R^6$ is $C_{1-6}$ alkyl when each of $R^4$, $R^5$ and $R^6$ are present;

$R^7$ and $R^8$ are each independently selected at each occurrence from H or $C_{1-4}$ alkyl;

$R^9$ is selected from the group comprising: H, $C_{1-4}$alkyl, and $C_{1-4}$ haloalkyl; $R^a$ and $R^b$ are each independently selected at each occurrence from: H, halo, —$NH_2$, and $C_{1-4}$ alkyl.

a, b, d, f and g are independently selected as integers from 0 to 3;

m is an integer selected from 1, 2 or 3;

n is an integer selected from 1, 2, 3, 4 or 5; and $\overline{---}$ represents a single or a double bond as required to satisfy valence requirements.

In another aspect, the invention provides a compound of formula (I), or pharmaceutically acceptable salts thereof:

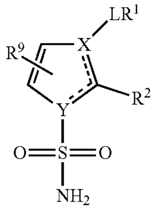

(I)

wherein one of X and Y is N and the other is C;

L is a linker group selected from a bond or —$(CH_2)_a$-Q-$(CH_2)_b$— in which, Q is selected from the group comprising: O, NH, $SO_2$, C=C, and C≡C or Q is absent;

$R^1$ is a 6 membered monocyclic carbocyclic ring substituted by one $R^3$ group, $R^1$ may be further substituted with 0 or 1 groups selected from halo, $C_{1-6}$ alkyl, or $C_{1-6}$ haloalkyl;

$R^2$ is —C(O)OH or —C(O)OM; wherein M is a group 1 cation;

$R^3$ is selected from the group comprising: —$CONR^4(CR^aR^b)_nNR^5R^6$, —$CONR^4(CR^aR^b)_nOSO_2OR^5$, —$CONR^4(CR^aR^b)_nCN$, —$CONR^4(CR^aR^b)_nC$(=O)OH, —$CONR^4(CR^aR^b)_nC$(=O)$NR^7R^8$, —$NR^4CO(CR^aR^b)_nNR^7R^3$, —$NR^4CO(CR^aR^b)_nOSO_2OR^5$, —$NR^4CO(CR^aR^b)_nCN$, —$NR^4CO(CR^aR^b)_nC$(=O)OH, —$NR^4CO(CR^aR^b)_nC$(=O)$NR^7R^8$, —$SO_2NR^4(CR^aR^b)_nNR^5R^6$, —$SO_2NR^4(CR^aR^b)_nOSO_2OR^5$, —$SO_2NR^4(CR^aR^b)_nCN$, —$SO_2NR^4(CR^aR^b)_nC$(=O)OH, —$SO_2NR^4(CR^aR^b)_nC$(=O)$NR^7R^8$

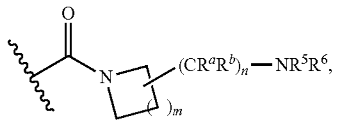

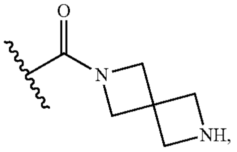

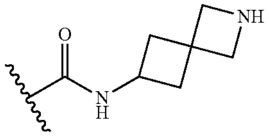

and

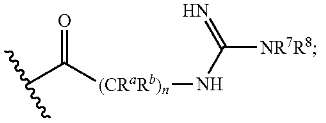

$R^4$ is selected at each occurrence from the group comprising: H, halo, —OH, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, —$(CH_2)_f$-aryl, —$(CH_2)_d$-heteroaryl, —$(CH_2)_g$-heterocyclyl; wherein $R^4$ may be optionally substituted where chemically possible with one, two or three groups independently selected at each occurrence from the group comprising: halo, —$NH_2$, —$N(C_{1-4}$ alkyl$)_2$, —OH, —$SO_2N(C_{1-4}$ alkyl$)_2$, —NHC(=O)$OC_{1-6}$ alkyl and —C(=O)$OC_{1-6}$ alkyl;

$R^5$ and $R^6$ are each independently H or $C_{1-6}$ alkyl;

wherein at least one of $R^4$, $R^5$ or $R^6$ is $C_{1-6}$ alkyl when each of $R^4$, $R^5$ and $R^6$ are present;

$R^7$ and $R^8$ each independently selected at each occurrence from H or $C_{1-4}$ alkyl;

$R^9$ is selected from the group comprising: H, $C_{1-4}$alkyl, and $C_{1-4}$ haloalkyl;

$R^a$ and $R^b$ are each independently selected at each occurrence from: H, halo, —$NH_2$, and $C_{1-4}$ alkyl.

a, b, d, f and g are independently selected as integers from 0 to 3;

m is an integer selected from 1, 2 or 3;

n is an integer selected from 1, 2, 3, 4 or 5; and

- - - represents a single or a double bond as required to satisfy valence requirements.

In an embodiment, the compound of Formula (I) is a compound of Formula (II):

(II)

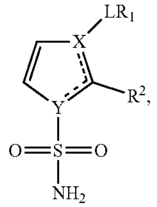

wherein X, Y, L, $R^1$ and $R^2$ are defined according to Formula (I).

In an embodiment, the compound of Formula (I) may be a compound of Formula (III):

(III)

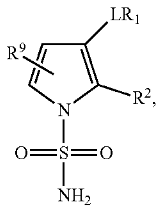

wherein L, $R^1$, $R^2$ and $R^9$ are defined according to Formula (I).

In an embodiment, the compound of Formula (III) may be a compound of Formula (IV):

(IV)

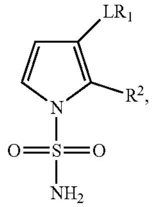

wherein L, $R^1$ and $R^2$ are defined according to Formula (I).

In an embodiment, the compound of Formula (I) may be a compound of Formula (V):

(V)

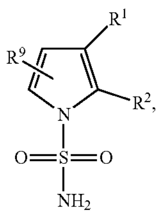

wherein $R^1$, $R^2$ and $R^9$ are defined according to Formula (I).

In an embodiment, the compound of Formula (I) may be a compound of Formula (VI):

(VI)

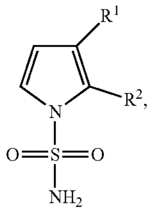

wherein $R^1$ and $R^2$ are defined according to Formula (I).

In embodiments the compound of Formula (I) is a compound of Formula (VII):

(VII)

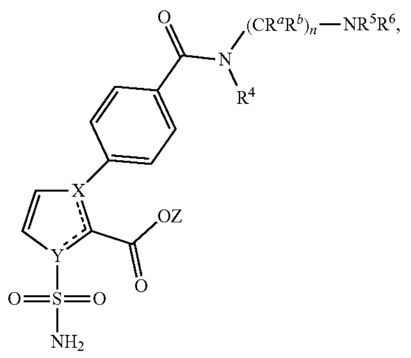

wherein X, Y, $R^4$, $R^5$, $R^6$, $R^a$, $R^b$ and n are defined according to Formula (I) and Z represents H or M.

In embodiments the compound of Formula (I) is a compound of Formula (VIII):

(VIII)

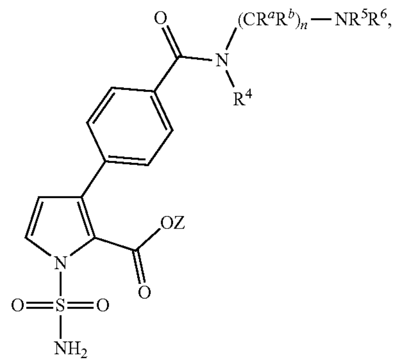

wherein $R^4$, $R^5$, $R^6$, $R^a$, $R^b$ and n are defined according to Formula (I) and Z represents H or M.

Hence, in an embodiment, Y is N and X is C.

In an alternate embodiment, Y is C and X is N.

In embodiments the compound of Formula (I) is a compound of Formula (IX):

(IX)

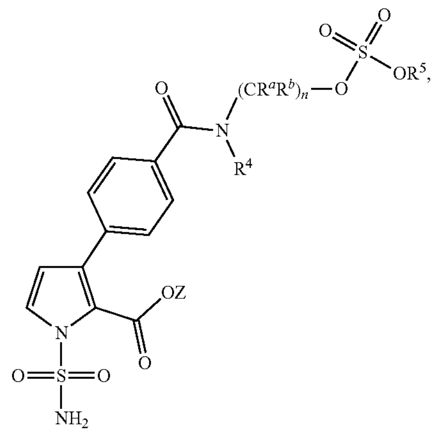

wherein $R^4$, $R^5$, $R^a$, $R^b$ and n are defined according to Formula (I) and Z represents H or M.

Hence, in an embodiment, Y is N and X is C.

In an alternate embodiment, Y is C and X is N.

In embodiments the compound of Formula (I) is a compound of Formula (X):

(X)

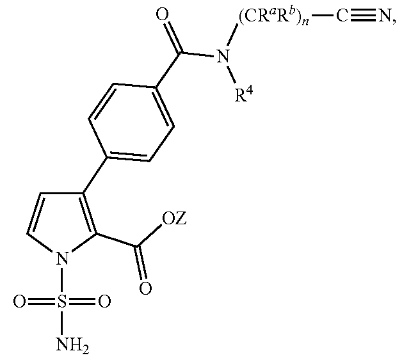

wherein $R^4$, $R^a$, $R^b$ and n are defined according to Formula (I) apply and Z represents H or M.

Hence, in an embodiment, Y is N and X is C.

In an alternate embodiment, Y is C and X is N.

In embodiments the compound of Formula (I) is a compound of Formula (XI):

(XI)

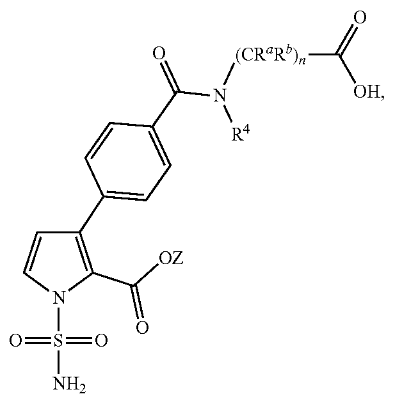

wherein $R^4$, $R^a$, $R^b$ and n are defined according to Formula (I) and Z represents H or M.

Hence, in an embodiment, Y is N and X is C.

In an alternate embodiment, Y is C and X is N.

In embodiments the compound of Formula (I) is a compound of Formula (XII):

(XII)

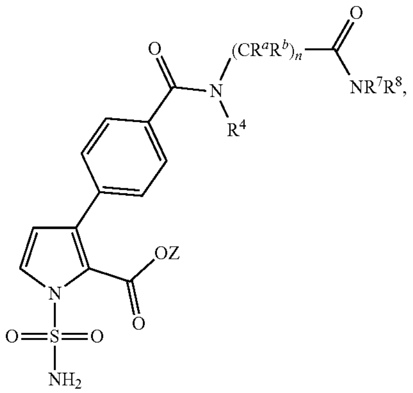

wherein $R^4$, $R^1$, $R^8$, $R^a$, $R^b$ and n are defined according to Formula (I) and Z represents H or M.

Hence, in an embodiment, Y is N and X is C.

In an alternate embodiment, Y is C and X is N.

In embodiments the compound of Formula (I) is a compound of Formula (XIII):

(XIII)

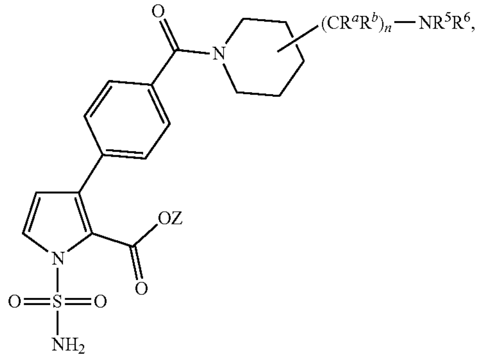

wherein $R^5$, $R^6$, $R^a$, $R^b$ and n are defined according to Formula (I) and Z represents H or M.

Hence, in an embodiment, Y is N and X is C.

In an alternate embodiment, Y is C and X is N.

The following embodiments apply to compounds of any of formulae (I) to (XIII). These embodiments are independent and interchangeable. Any one embodiment may be combined with any other embodiment, where chemically allowed. In other words, any of the features described in the following embodiments may (where chemically allowable) be combined with the features described in one or more other embodiments. In particular, where a compound is exemplified or illustrated in this specification, any two or more of the embodiments listed below, expressed at any level of generality, which encompass that compound may be combined to provide a further embodiment which forms part of the present disclosure.

In an embodiment, $R^1$ is a 6 membered mono-cyclic aromatic, cycloalkyl, heteroaromatic or heterocyclic ring substituted by one $R^3$ group, $R^1$ may be further substituted with 0 or 1 groups selected from halo, $C_{1-6}$ alkyl, or $C_{1-6}$ haloalkyl. The $R^3$ group is substituted on a ring atom in the mono-cyclic ring system where valence considerations allow.

In an embodiment, $R^1$ is a 6 membered mono-cyclic aromatic, heteroaromatic or heterocyclic ring substituted by one $R^3$ group, $R^1$ may be further substituted with 0 or 1 groups selected from halo, $C_{1-6}$ alkyl, or $C_{1-6}$ haloalkyl. The $R^3$ group is substituted on a ring atom in the mono-cyclic ring system where valence considerations allow.

In an embodiment, $R^1$ is a 6 membered mono-cyclic cycloalkyl ring substituted by one $R^3$ group, $R^1$ may be further substituted with 0 or 1 groups selected from halo, $C_{1-6}$ alkyl, or $C_{1-6}$ haloalkyl. The $R^3$ group is substituted on a ring atom in the mono-cyclic ring system where valence considerations allow.

The $R^3$ substituent may be substituted in the meta or para position of the 6 membered ring $R^1$ with respect to the point of attachment of $R^1$ to the remainder of the molecule in the compound of Formula (I). In an embodiment the $R^3$ substituent is preferably substituted in the para position of the 6 membered ring $R^1$ with respect to the point of attachment of $R^1$ to the remainder of the molecule in the compound of Formula (I).

$R^1$ may be a 6-membered heteroaryl, a 6-membered cycloalkyl, a 6-membered aryl, a 6-membered heterocycloalkenyl, or a 6-membered heterocycloalkyl. $R^1$ may be a 6-membered heteroaryl, a 6-membered aryl, a 6-membered heterocycloalkenyl, or a 6-membered heterocycloalkyl. $R^1$ may be a 6-membered cycloalkyl.

In some embodiments, $R^1$ is selected from:

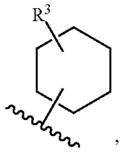,
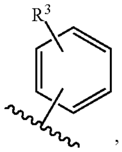,
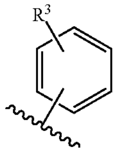and
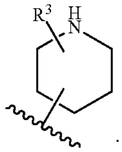.

In some embodiments, $R^1$ is selected from:

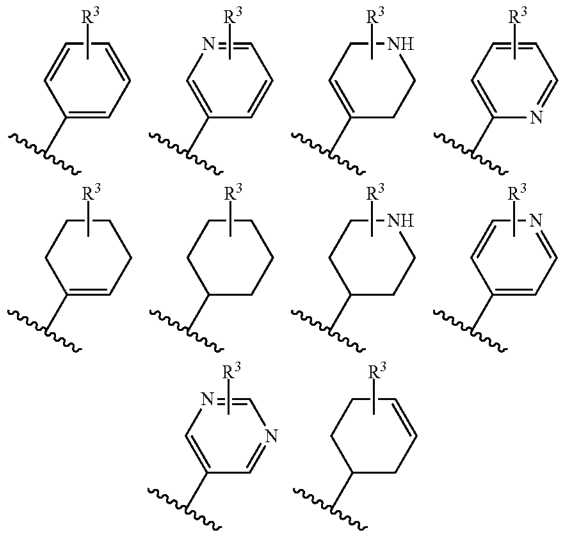

In some embodiments, $R^1$ is selected from:

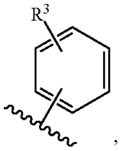, 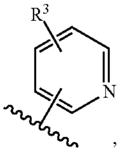, and 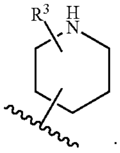.

In some embodiments, $R^1$ is selected from:

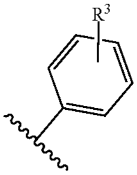
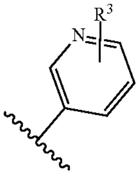
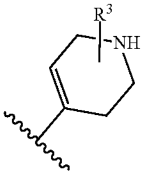
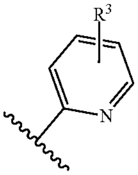
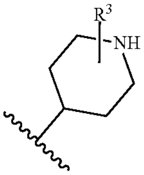
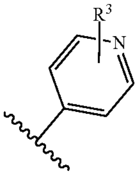
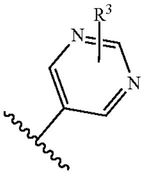

In some embodiments, $R^1$ is aryl, and is preferably phenyl substituted with $R^3$. $R^1$ may be selected from: phenyl, pyridine, tetrahydropyridine, piperidine, and pyrimidine.

In some embodiments, $R^1$ is cycloalkyl, and is preferably cyclohexyl substituted with $R^3$.

In some embodiments, $R^1$ is selected from:

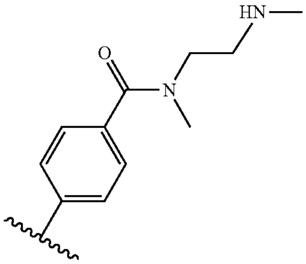
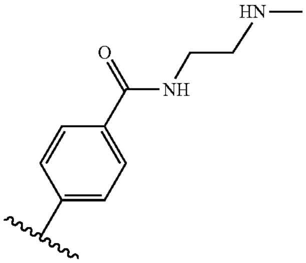

-continued

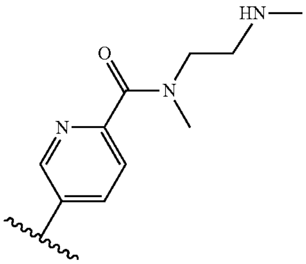
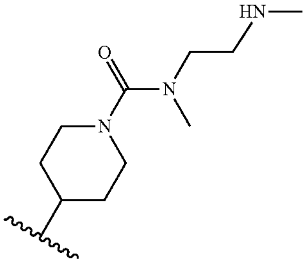
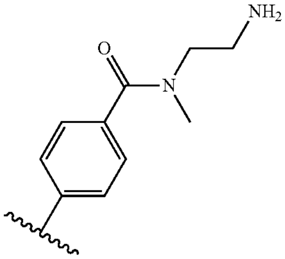
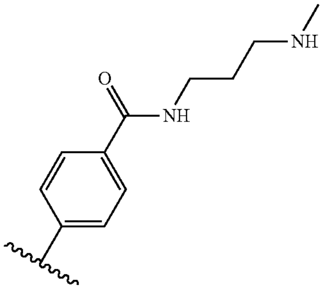
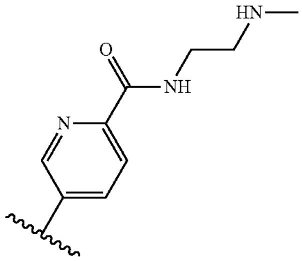
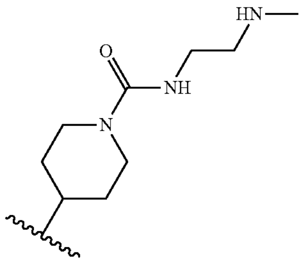

-continued
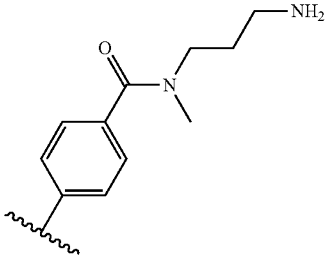
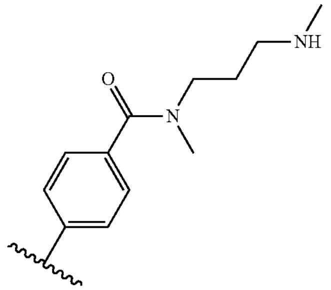
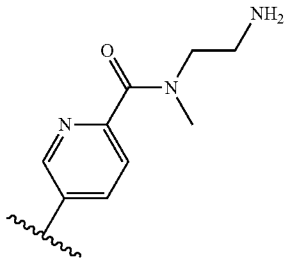
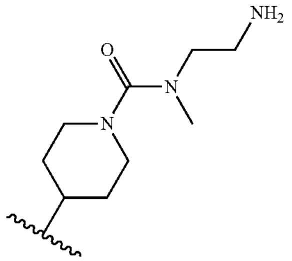
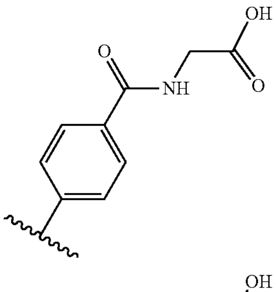
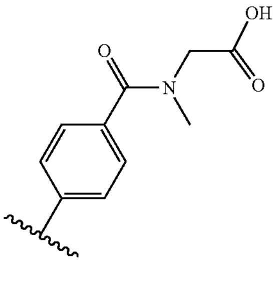
-continued
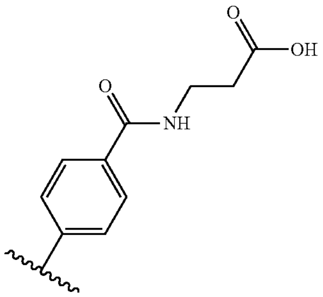
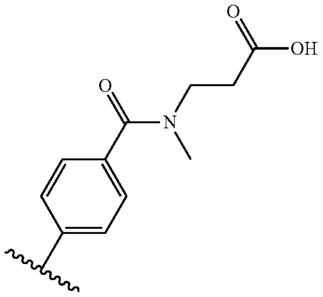
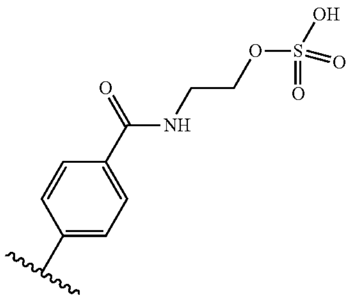
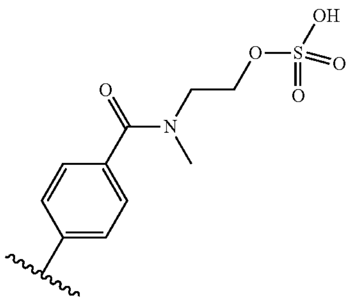
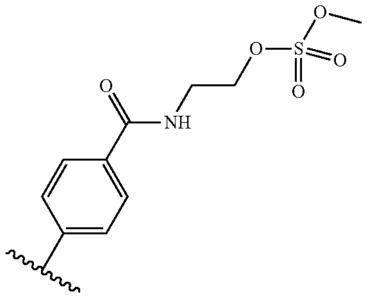

-continued
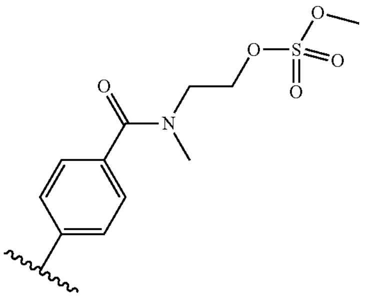
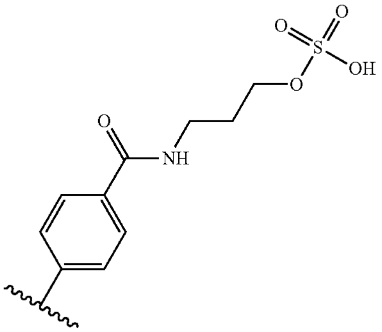
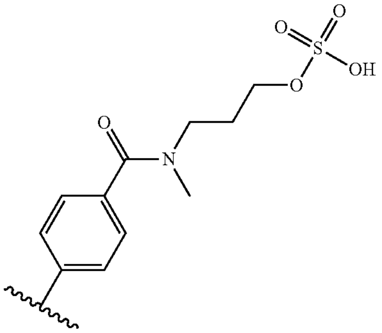
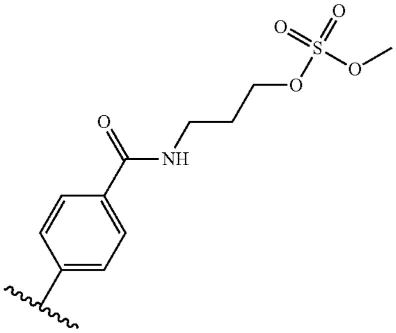
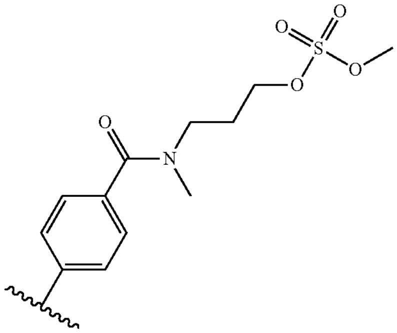
-continued
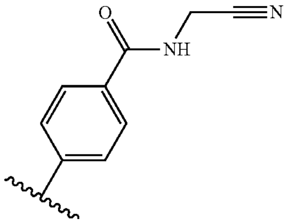
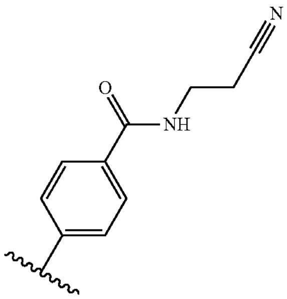
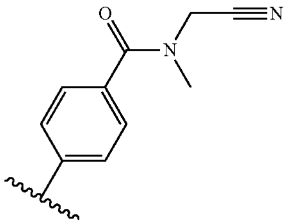
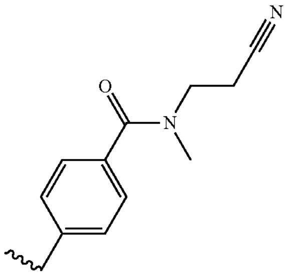
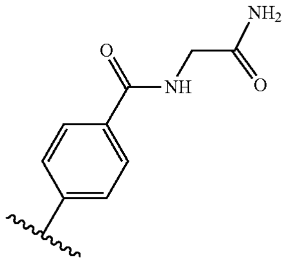
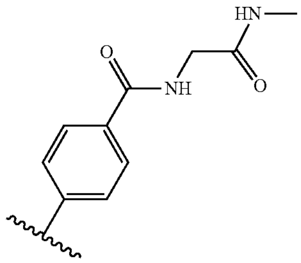

-continued
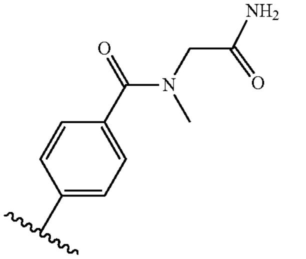
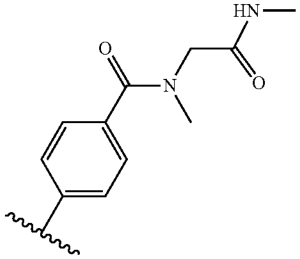
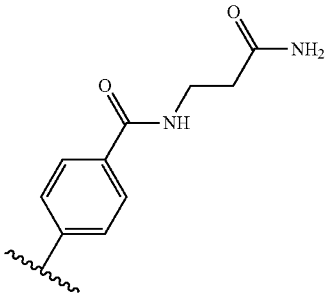
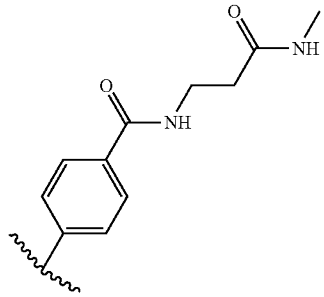
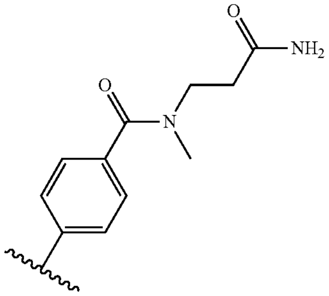
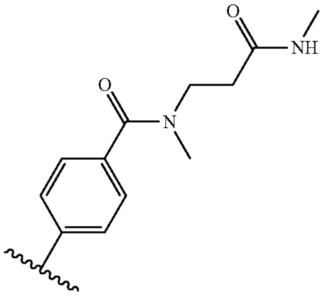
-continued
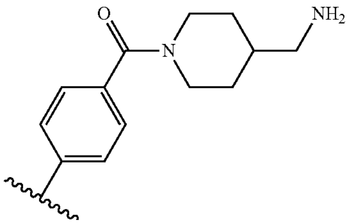
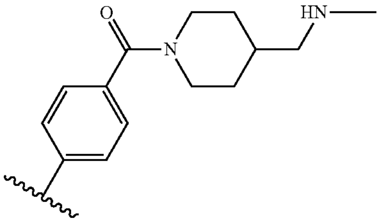
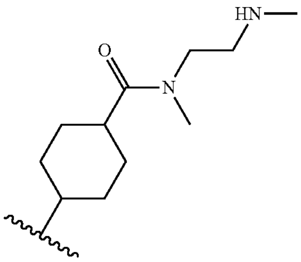
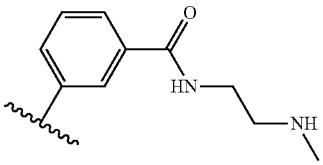
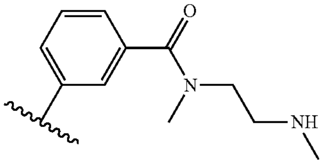
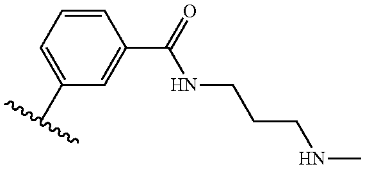
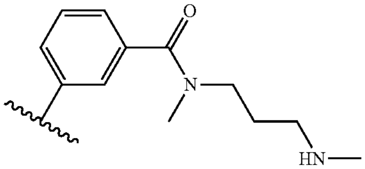
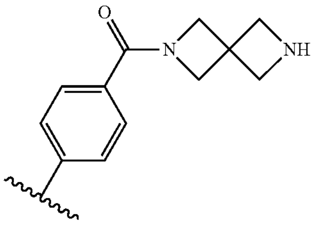

-continued

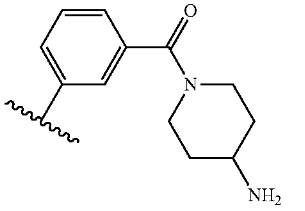

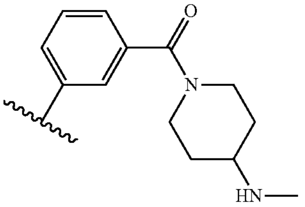

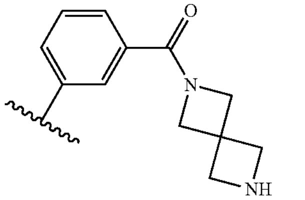

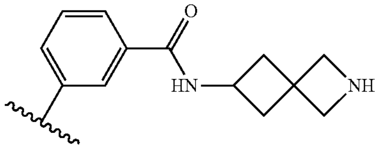

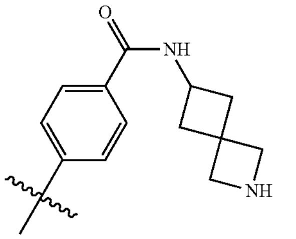

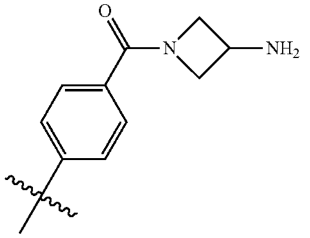

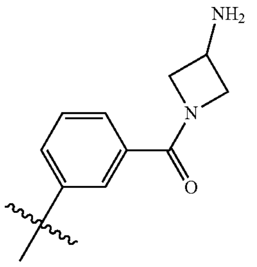

In an alternative embodiment, $R_1$ is a saturated or partially saturated 6 membered carbocylic ring system. Preferred rings include:

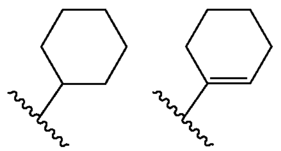

In an alternative embodiment, $R^1$ is a saturated or partially saturated 6 membered heterocyclic ring system. The ring may be carbon-linked or nitrogen linked to the pyrrole core. In the case of carbon-linked rings, preferred rings include:

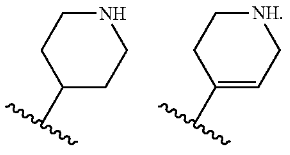 [SMILES: *C1CCNCC1 ; *C1=CCNCC1]

In the case of nitrogen-linked rings, preferred $R^1$ groups include:

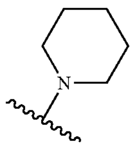 [SMILES: *N1CCCCC1]

In an embodiment, $R^2$ is —C(O)OH or —C(O)OM. In an embodiment, $R^2$ is —C(O)OH. In an embodiment, $R^2$ is —C(O)OM.

In an embodiment, $R^3$ is selected from the group comprising: $—CONR^4(CR^aR^b)_nNR^5R^6$, $—CONR^4(CR^aR^b)_nOSO_2OR^5$, $—CONR^4(CR^aR^b)_nCN$, $—CONR^4(CR^aR^b)_nC(=O)OH$, $—CONR^4(CR^aR^b)_nC(=O)NR^7R^8$,

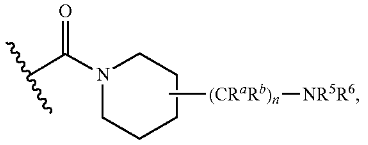

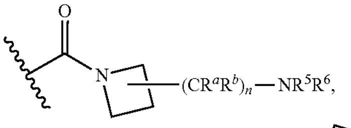

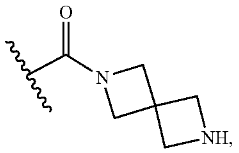

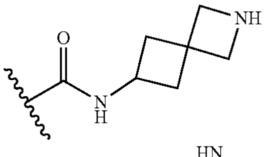

and

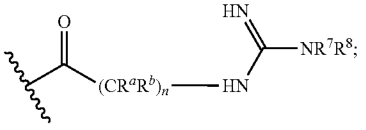

In an embodiment, $R^3$ is selected from the group comprising: $-CONR^4(CR^aR^b)_nNR^5R^6$, $-CONR^4(CR^aR^b)_nOSO_2OR^5$, $-CONR^4(CR^aR^b)_nCN$, $-CONR^4(CR^aR^b)_nC(=O)OH$, $-CONR^4(CR^aR^b)_nC(=O)NR^7R^8$,

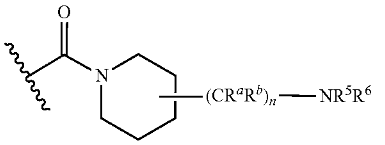

and

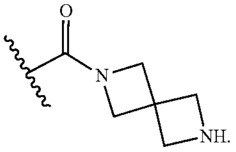

$R^4$ is selected from the group comprising: H, —OH, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, $-(CH_2)_f-C_{6-10}$ aryl, $-(CH_2)_d$-5 to 10 membered heteroaryl, $-(CH_2)_g$-3 to 10 membered heterocyclyl; wherein $R^4$ may be optionally substituted where chemically possible with one, two or three groups independently selected at each occurrence from the group comprising: halo, $-NH_2$, $-N(C_{1-4}\ alkyl)_2$, —OH, $-SO_2N(C_{1-4}\ alkyl)_2$, —NHC(=O)Otert-butyl, and —C(=O)Otert-butyl.

In embodiments, $R^4$ is selected from the group comprising: H, —OH, $C_{1-6}$ alkyl, $C_{1-6}$ haloalkyl, 3 to 10 membered heterocyclyl, $C_{3-8}$ cycloalkyl; wherein each $R^5$ may themselves be optionally substituted where chemically possible with one or two groups independently selected at each occurrence from the group comprising: $-NH_2$, —OH, $-SO_2N(C_{1-4}\ alkyl)_2$, —NHC(=O)Otert-butyl and —C(=O)Otert-butyl.

In embodiments, $R^4$ is selected at each occurrence from the group comprising: H, —OH, methyl, propyl, methylamine, ethylamine, n-propylamine, iso-propylamine, trifluoroethylamine, piperidine, cyclopropyl, cyclopropylamine, $-CH_2OH$, $-(CH_2)_2NHC(=O)$Otert-butyl, methylpyrazole, piperazine, piperazine substituted with —C(=O)Otert-butyl.

In embodiments, $R^4$ is selected from the group comprising: H, substituted or unsubstituted $C_{1-6}$ alkyl, and substituted or unsubstituted $C_{3-8}$ cycloalkyl.

Preferably $R^4$ is H or Me.

$R^5$ and $R^6$ are each independently H or $C_{1-6}$ alkyl. In an embodiment, $R^5$ and $R^6$ are each 10 independently selected from the group comprising: H, Me, Et, $^n$Pr, $^i$Pr and $^n$Bu.

In an embodiment, $R^5$ is H. In an embodiment, $R^5$ is Me or Et.

In an embodiment, $R^6$ is H. In an embodiment, $R^6$ is Me or Et.

In an embodiment, $R^7$ is H. In an embodiment, $R^7$ is Me or Et.

In an embodiment, $R^8$ is H. In an embodiment, $R^8$ is Me or Et. In an embodiment, $R^9$ is H, Me, ethyl or $CF_3$. In an embodiment, $R^9$ is H, Me or $CF_3$. In some embodiments $R^9$ is H.

L may be a bond, $-CH_2-$, $-CH_2NH-$, —O—, or $-OCH_2-$. L may be a bond or $-CH_2-$. L may be a bond. L may be O or NH. L may be $-CH_2-$ or $-CH_2CH_2-$.

In an embodiment, L is a bond or $-CH_2-$, X is C and Y is N. In an embodiment, L is a bond, X is C and Y is N.

In embodiments, a is 0 or 1. In embodiments, a is 0.

In embodiments, b is 0 or 1. In embodiments, b is 0.

In embodiments, d is 0 or 1. In embodiments, d is 0. In embodiments, f is 0 or 1. In embodiments, f is 0.

In embodiments, g is 0 or 1. In embodiments, g is 0. In embodiments M is Na or K, preferably Na.

In an embodiment, Y is N, X is C, $R^9$ is H, L is a bond, and $R^3$ is selected from: $-CONR^4(CR^aR^b)_nNR^5R^6$, $-CONR^4(CR^aR^b)_nOSO_2OR^5$, $-CONR^4(CR^aR^b)_nCN$, $-CONR^4(CR^aR^b)_nC(=O)OH$, $-CONR^4(CR^aR^b)_nC(=O)NR^7R^8$,

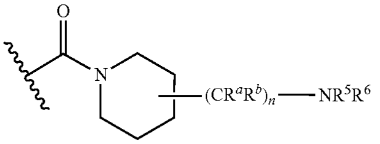

and

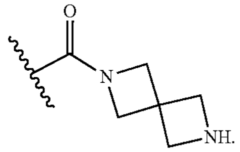

In an embodiment, Y is N, X is C, $R^9$ is H, L is a bond, and $R^3$ is selected from: $-CONR^4(CR^aR^b)_nNR^5R^6$, $-CONR^4(CR^aR^b)_nOSO_2OR^5$, $-CONR^4(CR^aR^b)_nCN$, $-CONR^4(CR^aR^b)_nC(=O)OH$, $-CONR^4(CR^aR^b)_nC(=O)NR^7R^8$,

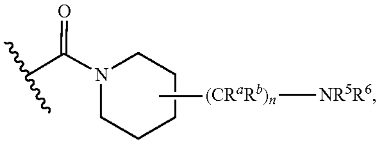

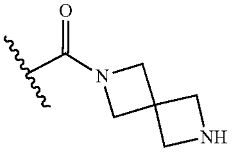

and

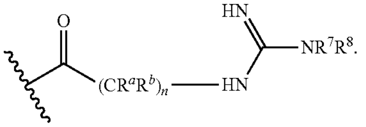

In an embodiment, Y is N, X is C, $R^9$ is H, L is a bond, and $R^3$ is selected from: $-SO_2NR^4(CR^aR^b)_nNR^5R^6$, $-SO_2NR^4(CR^aR^b)_nOSO_2OR^5$, $-SO_2NR^4(CR^aR^b)_nCN$, $-SO_2NR^4(CR^aR^b)_nC(=O)OH$, and $-SO_2NR^4(CR^aR^b)_nC(=O)NR^7R^8$.

In an embodiment, Y is N, X is C, $R^9$ is H, L is a bond, and $R^3$ is selected from: $-NR^4CO(CR^aR^b)_nNR^7R^8$, $-NR^4CO(CR^aR^b)_nOSO_2OR^5$, $-NR^4CO(CR^aR^b)_nCN$, $-NR^4CO(CR^aR^b)_nC(=O)OH$, and $-NR^4CO(CR^aR^b)_nC(=O)NR^7R^8$.

The various embodiments described above for the various substituents may be applied independently of one another. These embodiments apply similarly to all of the other aspects of the invention which are described below.

In an embodiment of the present invention, the compound according to Formula (I) may be a compound selected from:

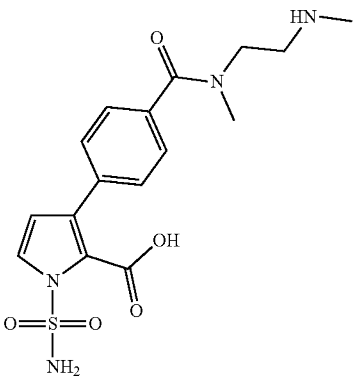
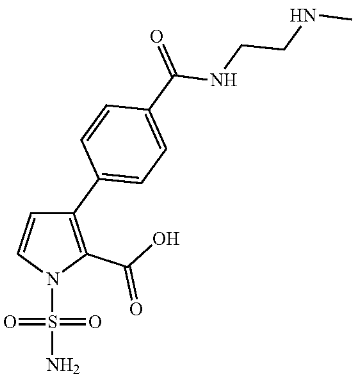
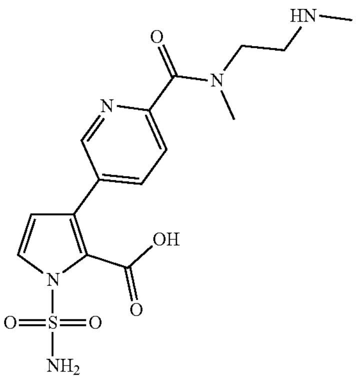
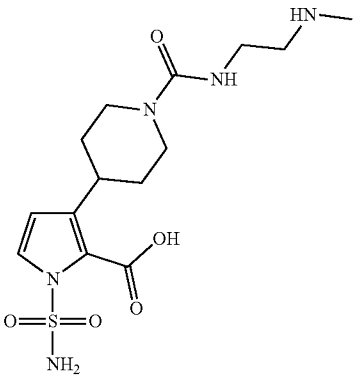
-continued
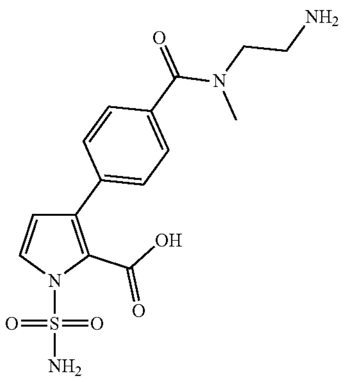
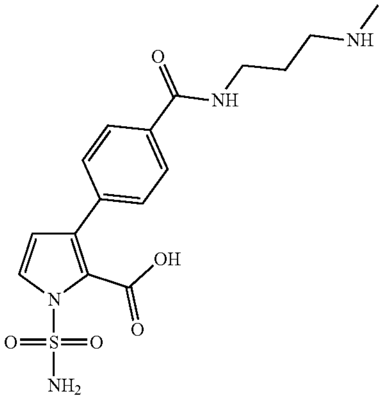
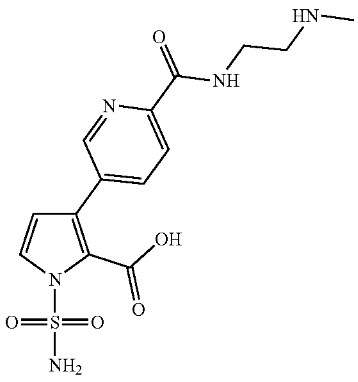
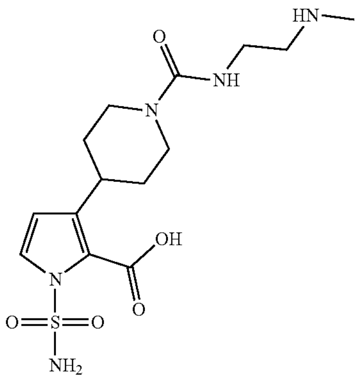

-continued
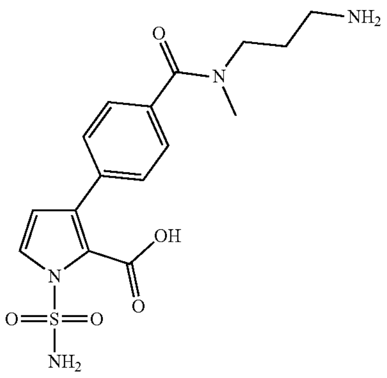
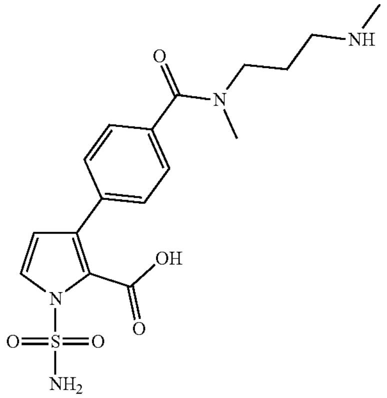
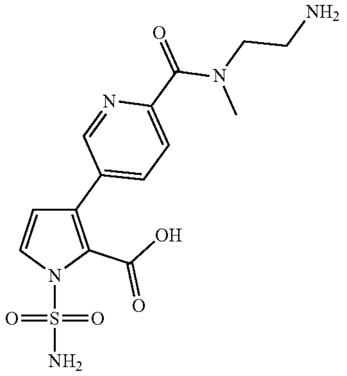
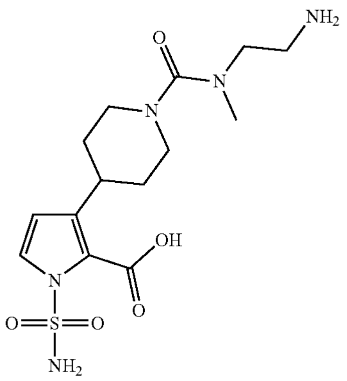
-continued
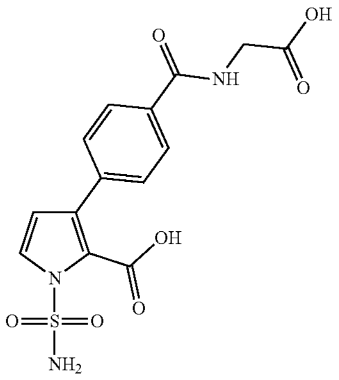
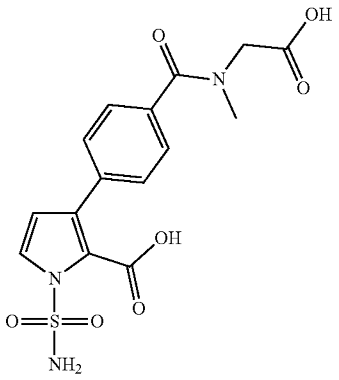
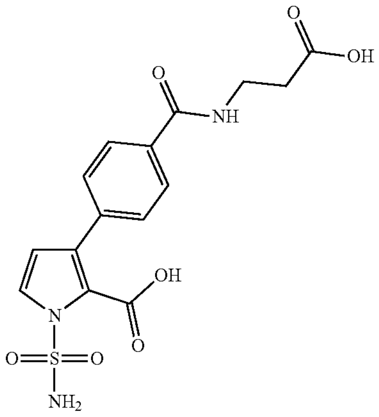
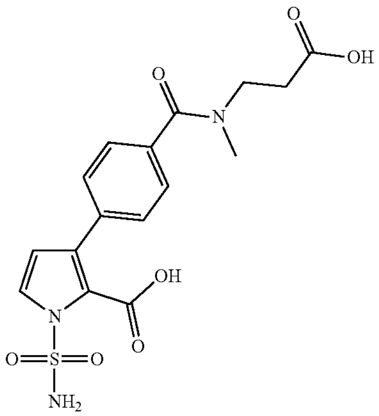

-continued
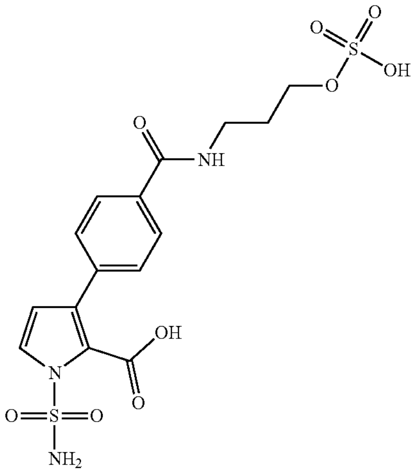
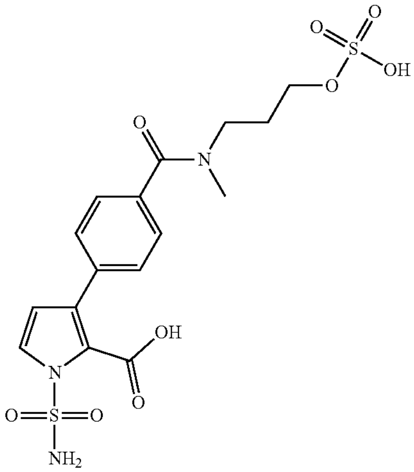
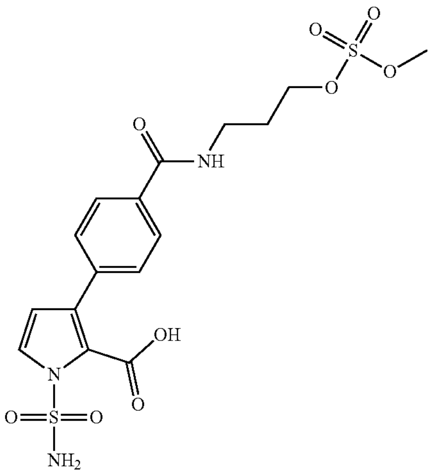
-continued
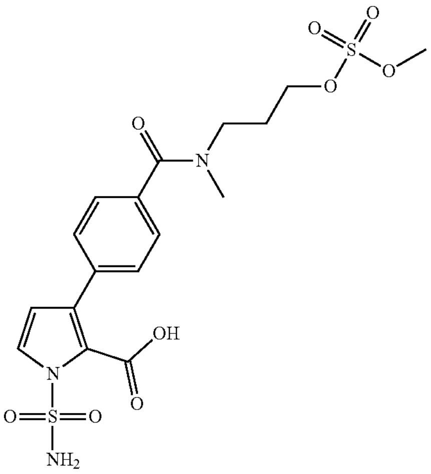
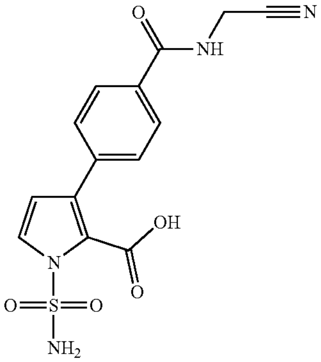
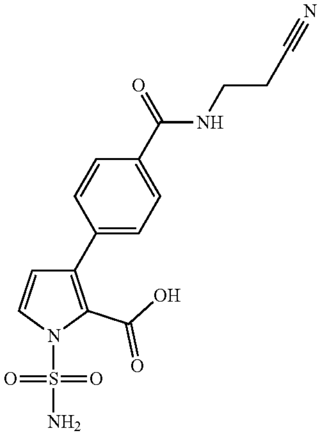
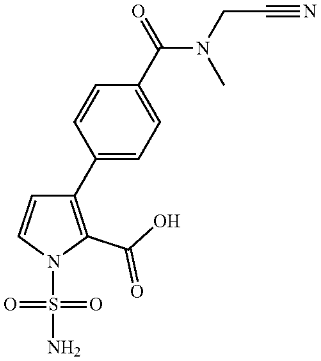

-continued
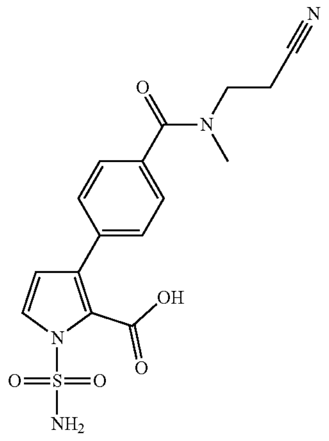
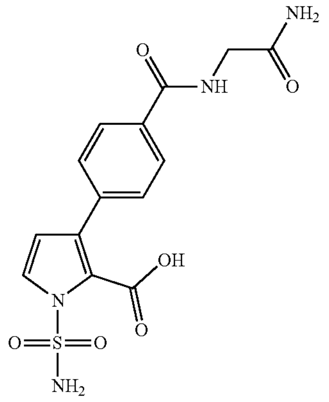
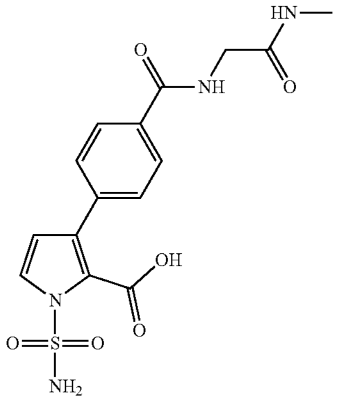
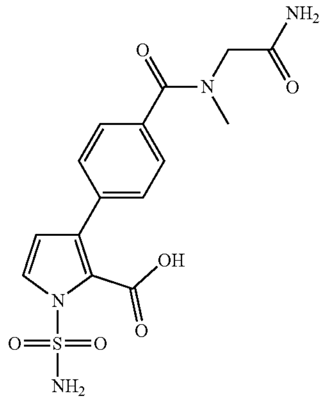
-continued
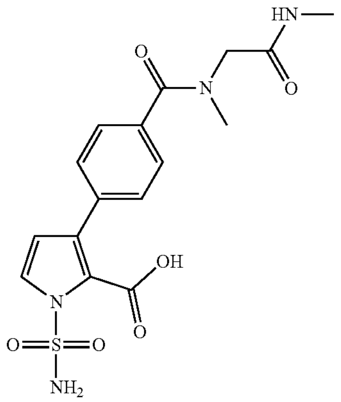
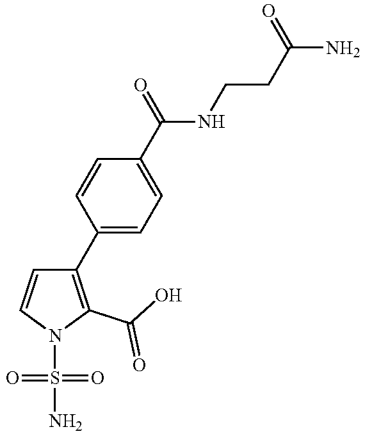
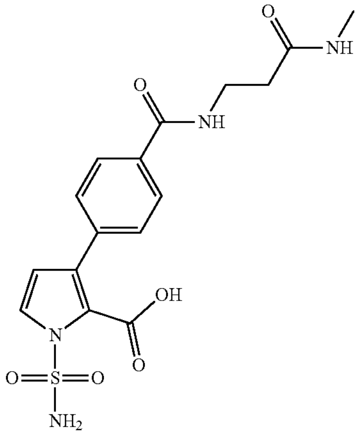
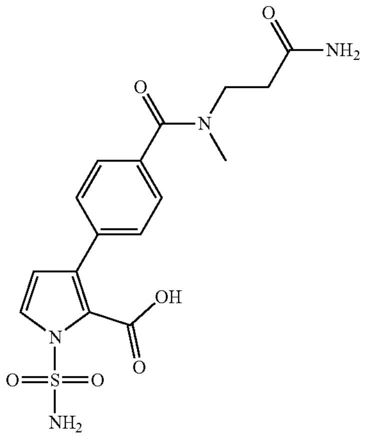

-continued
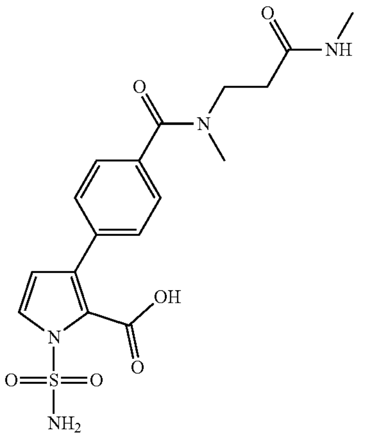
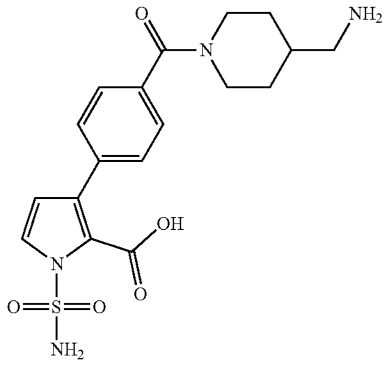
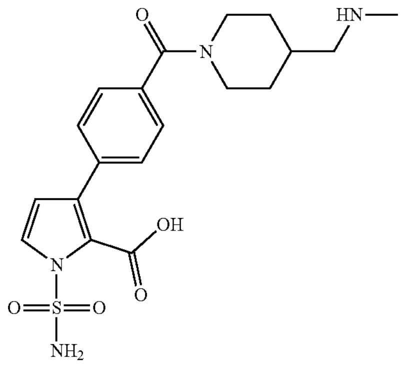
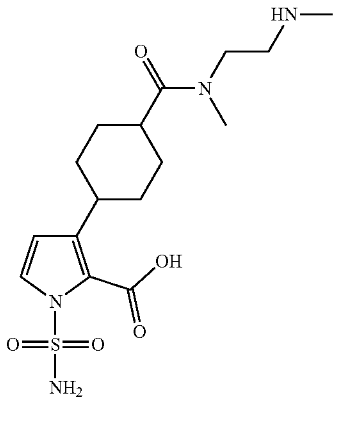
-continued
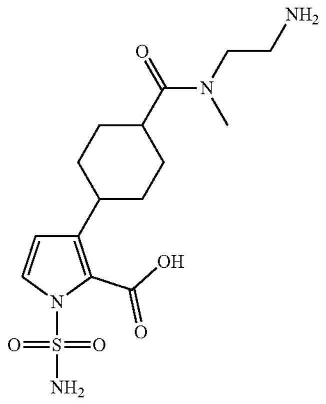
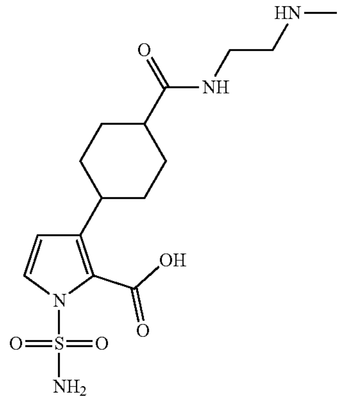
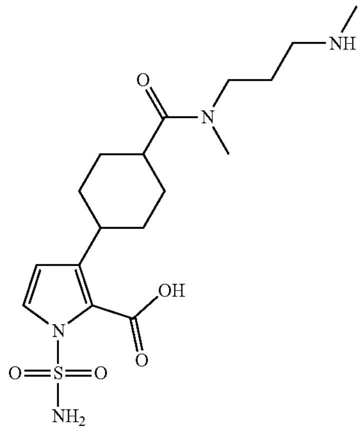
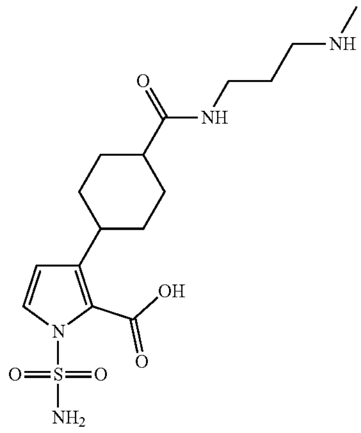

-continued
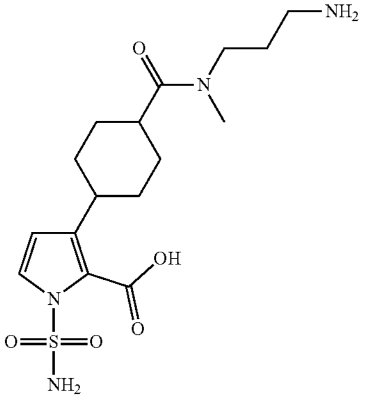
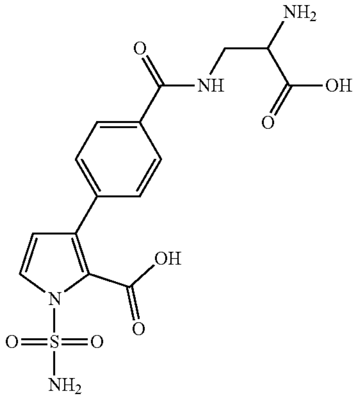
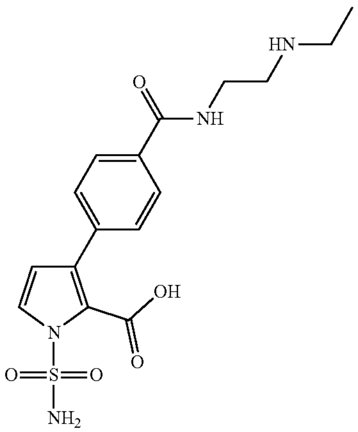
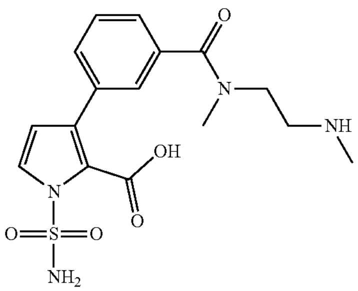
-continued
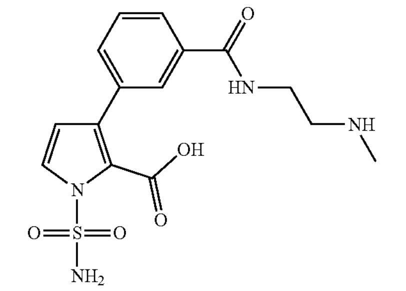
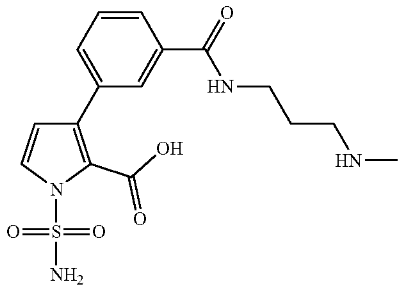
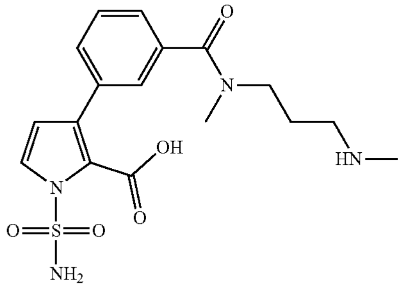
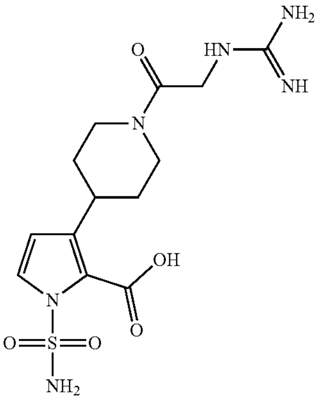
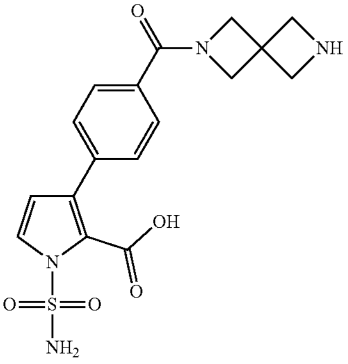

-continued
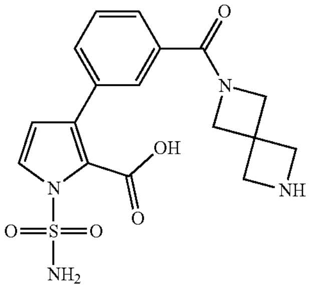
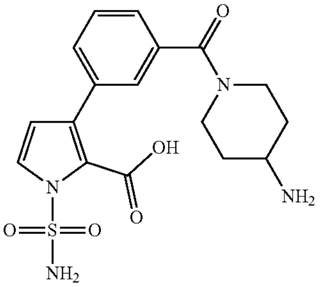
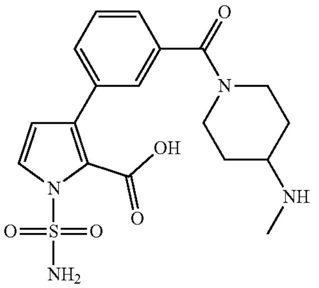
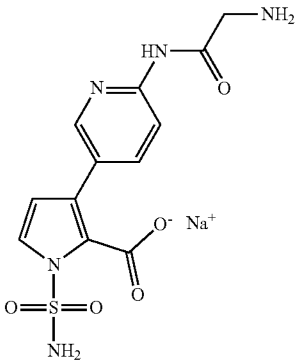
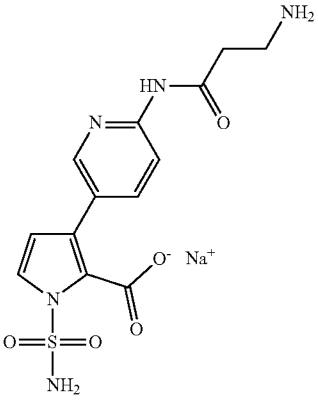
-continued
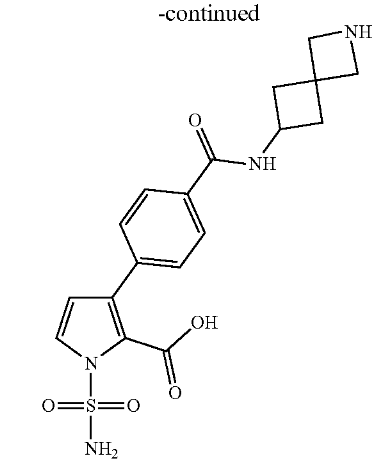
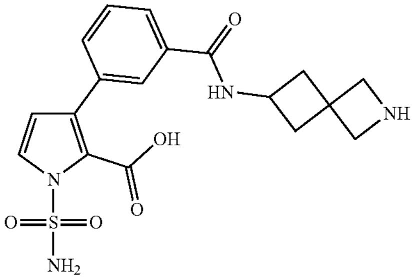
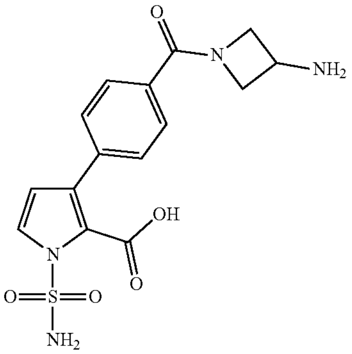
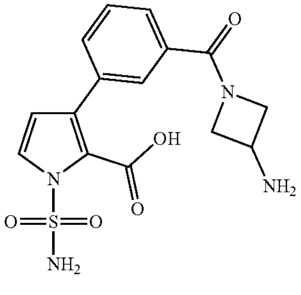
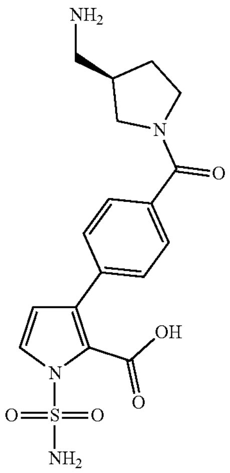
In embodiments, the compound according to Formula (I) may be a compound selected from:

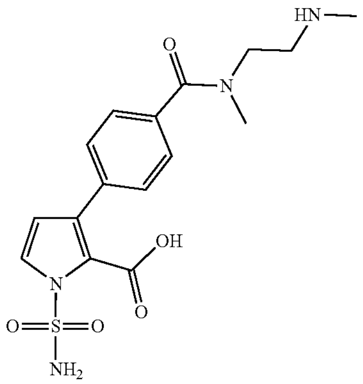
and
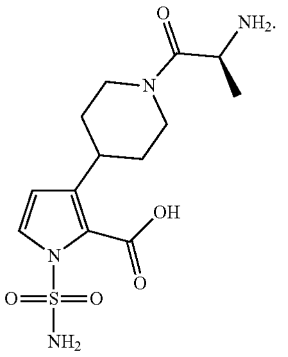
These compounds are particularly soluble compared to certain prior art compounds. They also have fewer off-target interactions than certain prior art compounds.
In embodiments, the compound according to Formula (I) is:
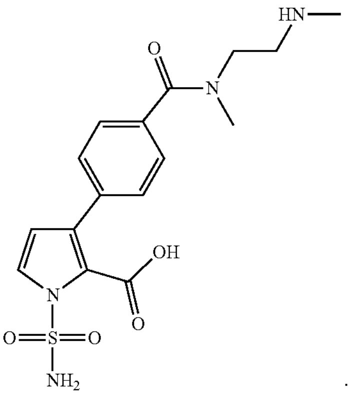 [SMILES: CNCCN(C)C(=O)c1ccc(-c2ccn(S(N)(=O)=O)c2C(=O)O)cc1]
In embodiments, the compound according to Formula (I) is:
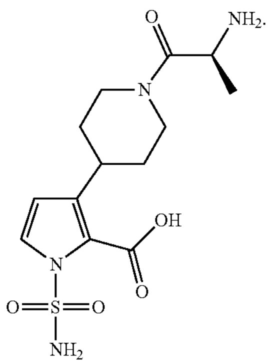 [SMILES: C[C@H](N)C(=O)N1CCC(c2ccn(S(N)(=O)=O)c2C(=O)O)CC1]
In another aspect, the invention provides a compound selected from:
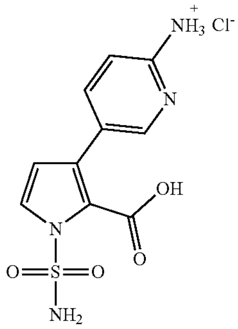
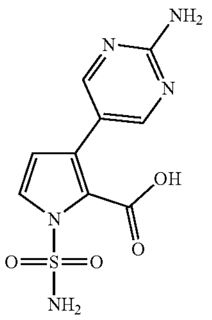
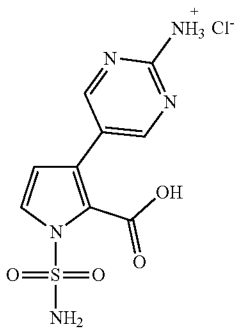
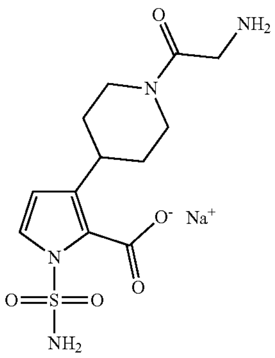
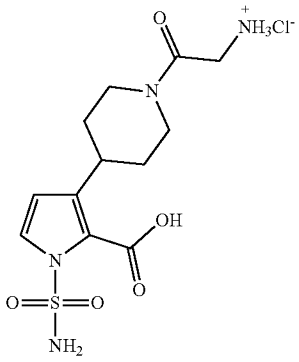
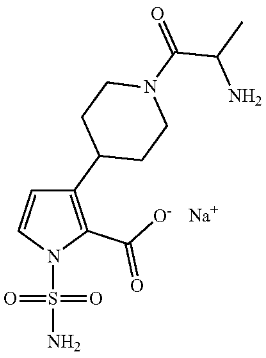

-continued
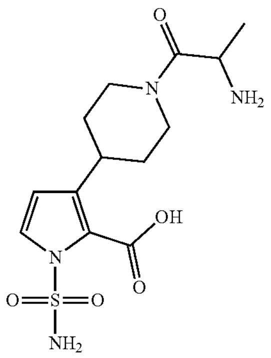
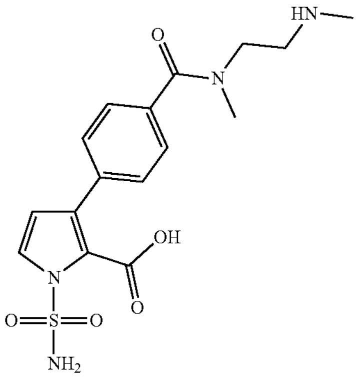
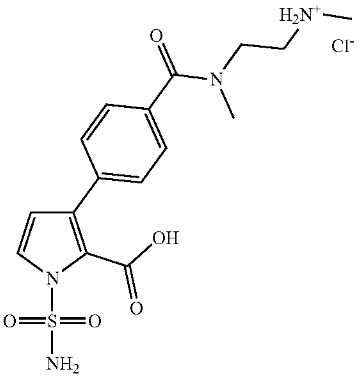
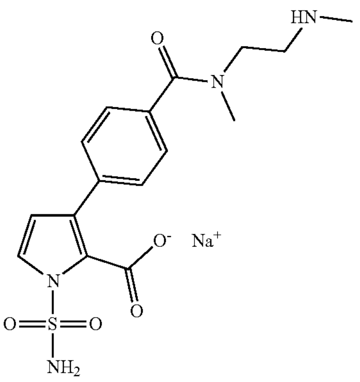
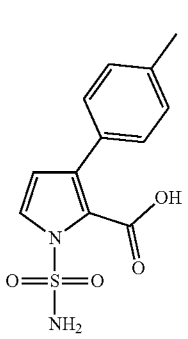
-continued
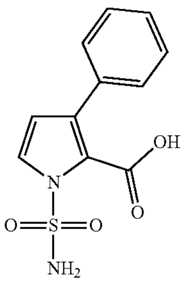
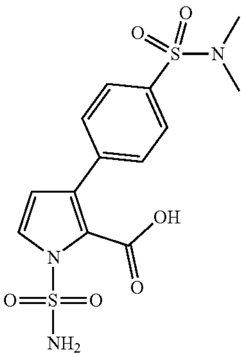
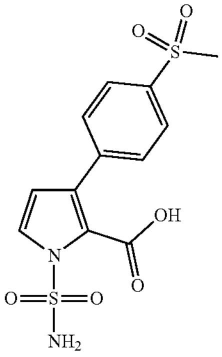
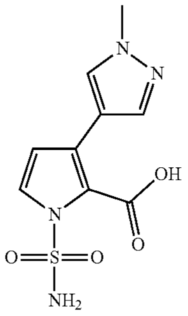
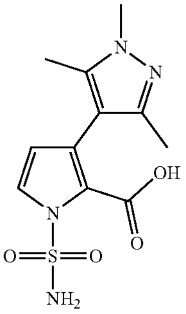
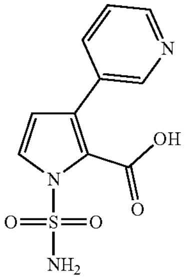
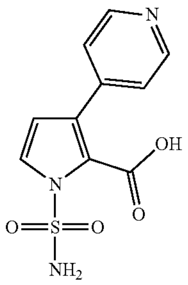
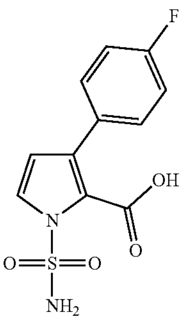
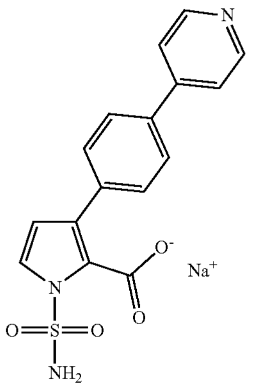

-continued
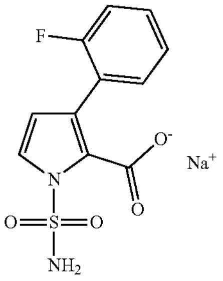
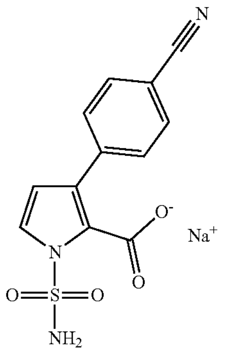
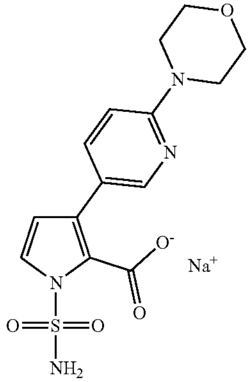
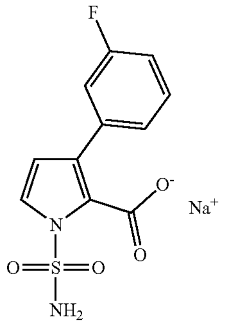
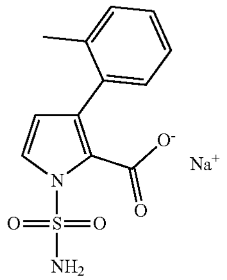
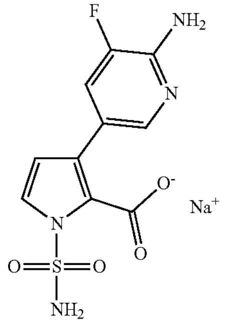
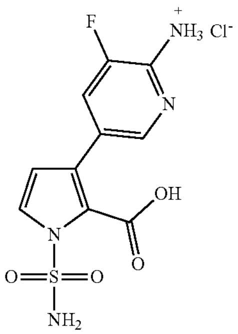
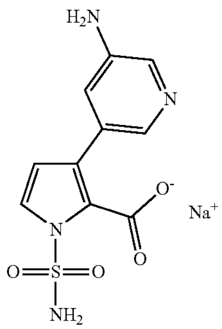
-continued
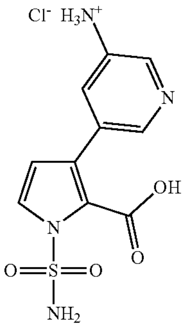
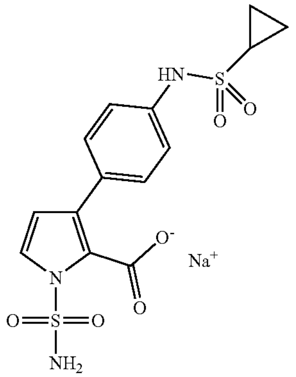
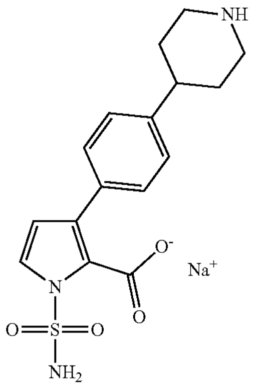
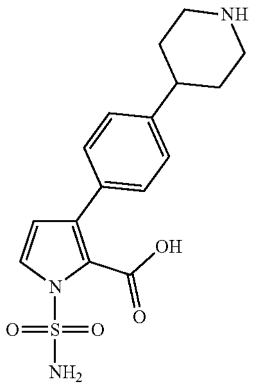
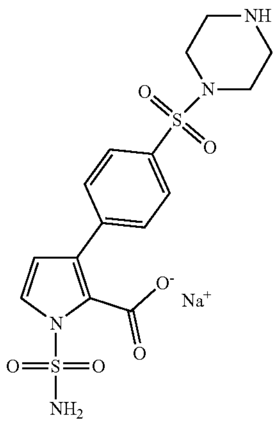
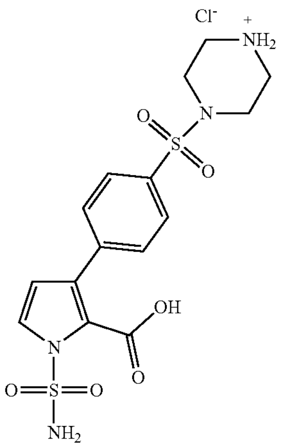
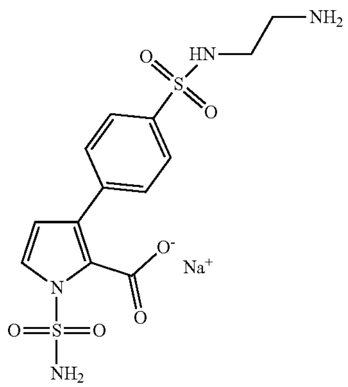

-continued
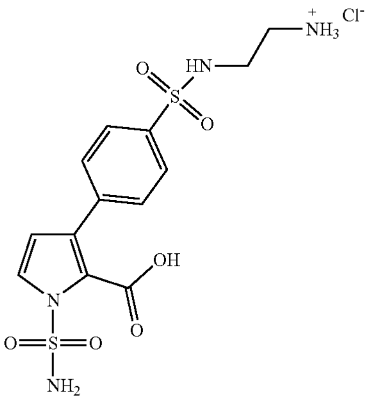
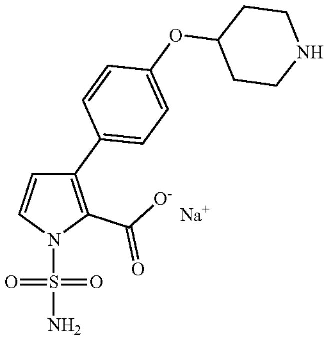
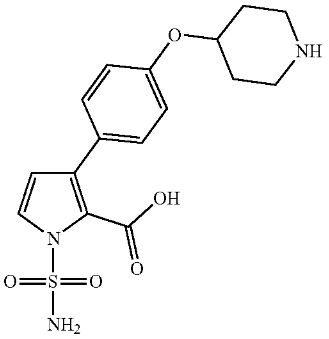
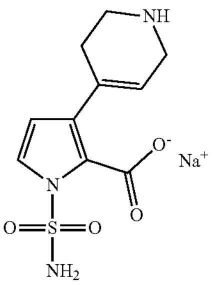
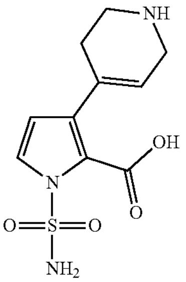
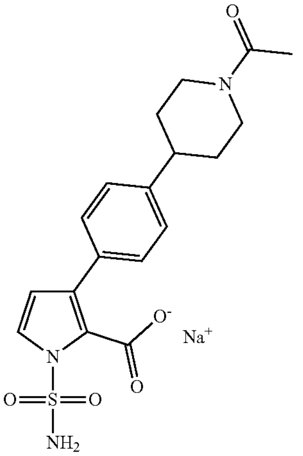
-continued
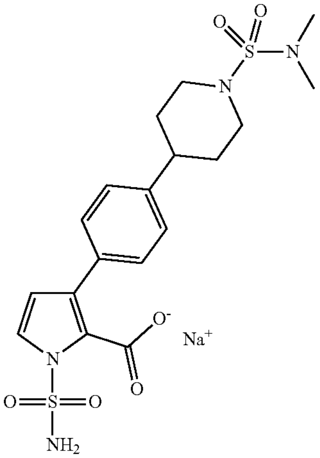
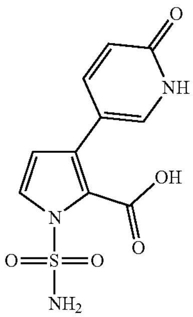
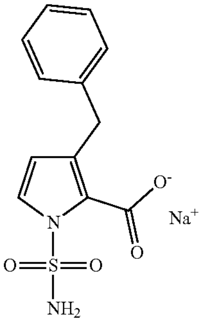
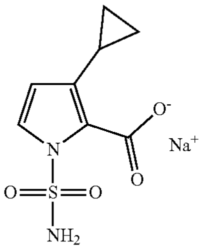
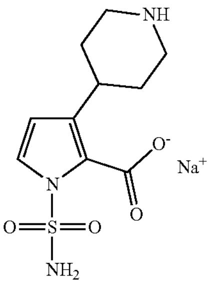
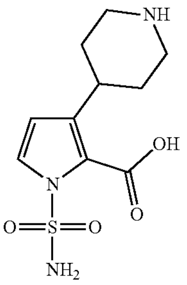
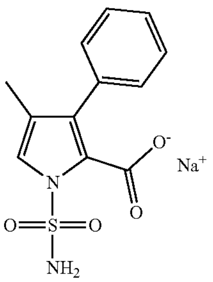
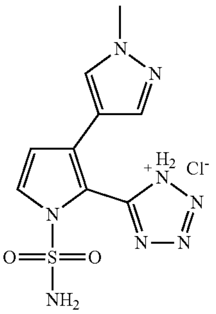
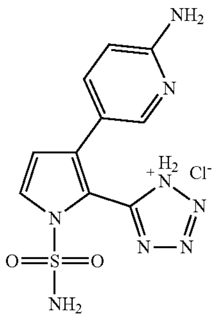
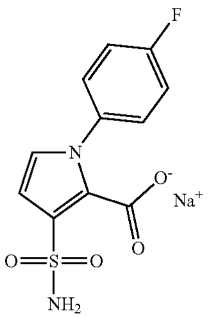

-continued
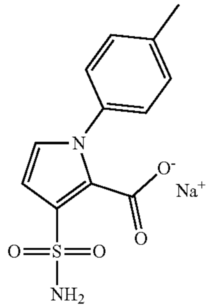
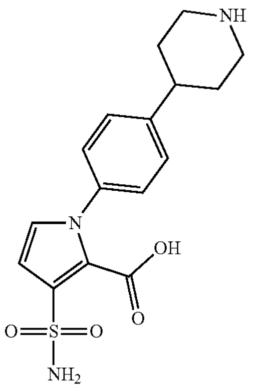
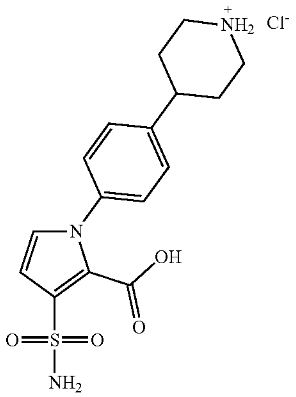
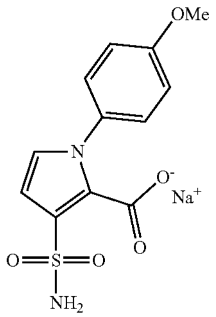
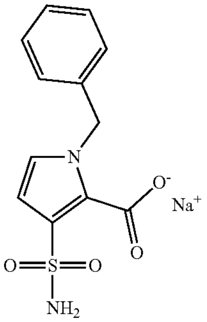
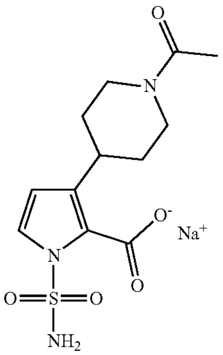
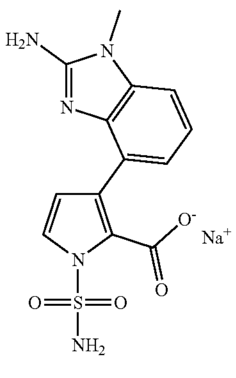
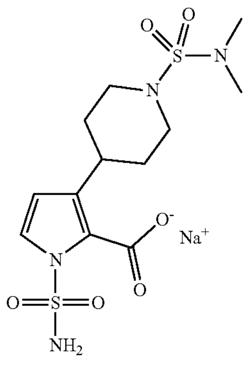
-continued
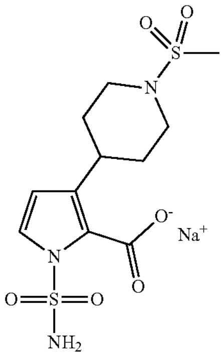
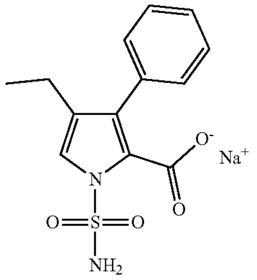
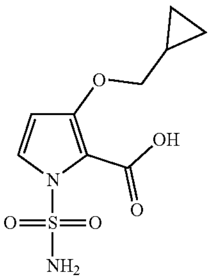
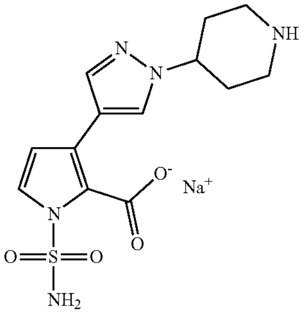
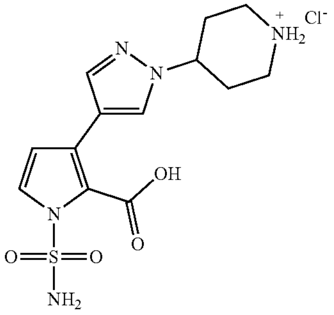
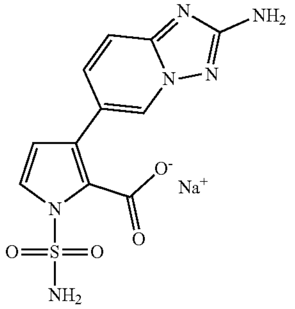
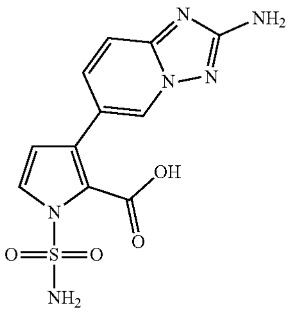
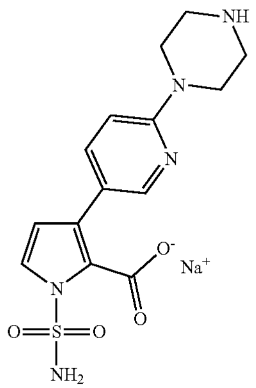

-continued
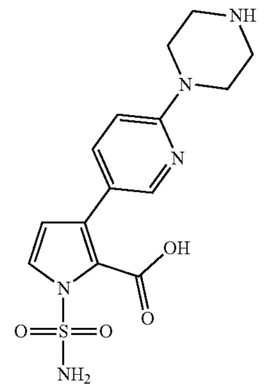
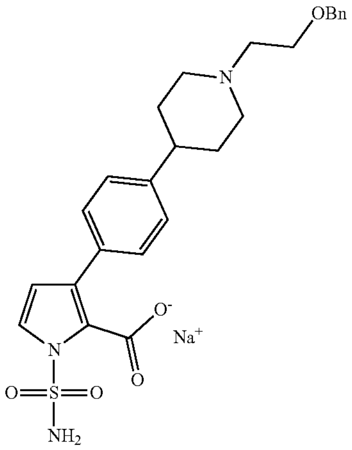
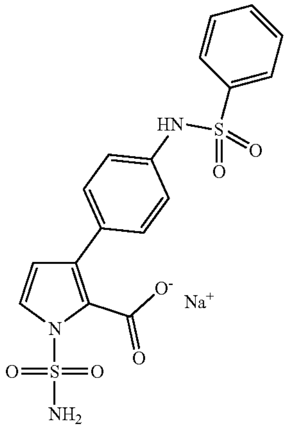
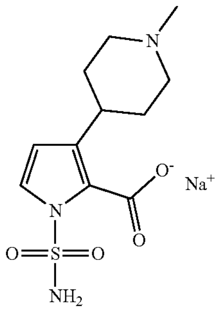
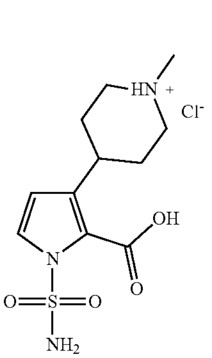
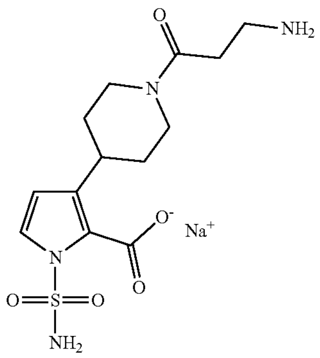
-continued
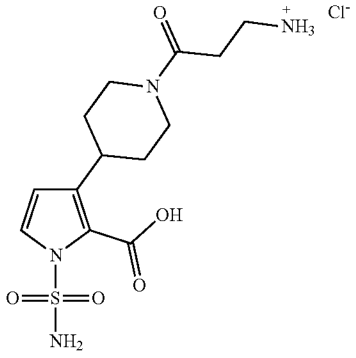
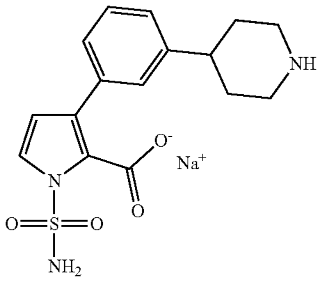
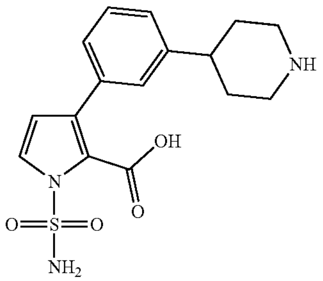
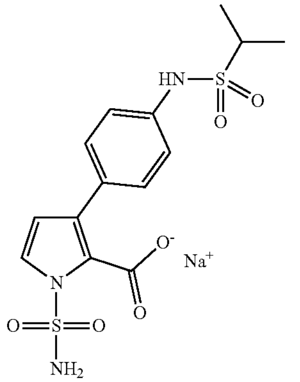
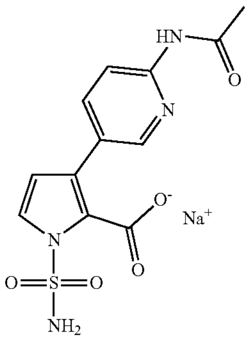
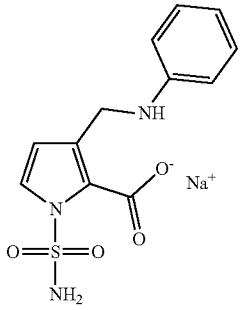
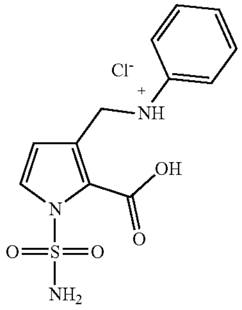

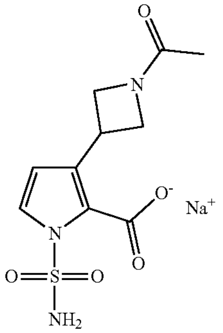
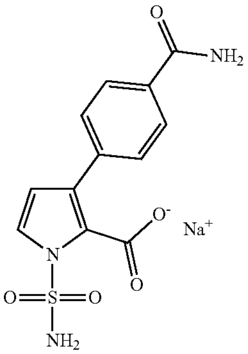
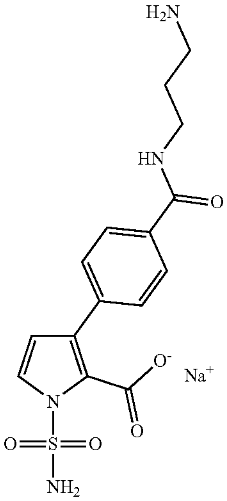
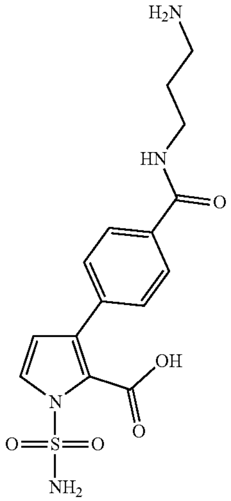
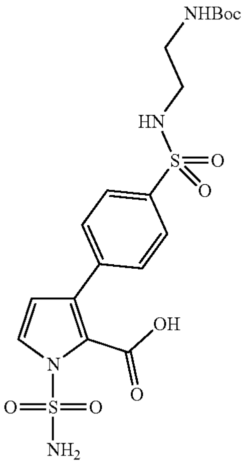
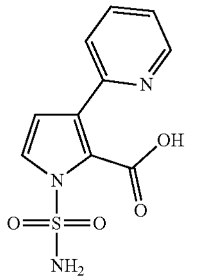
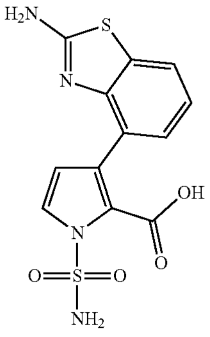
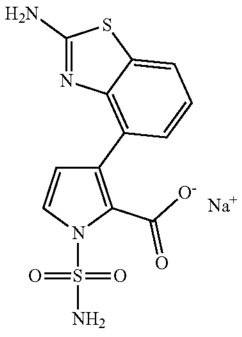
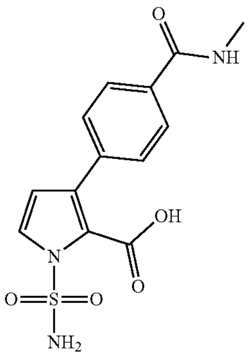
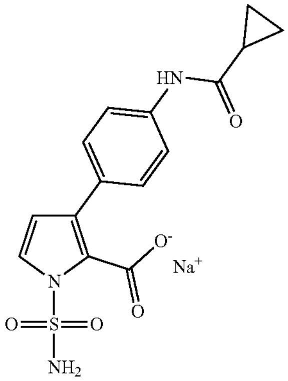
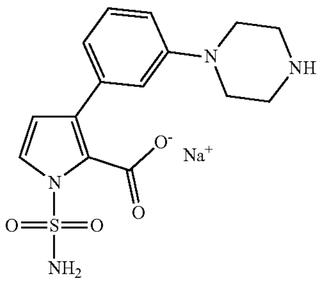
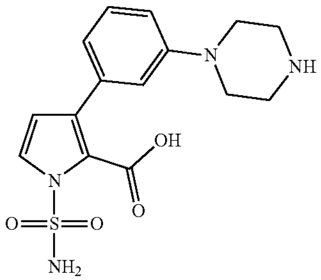
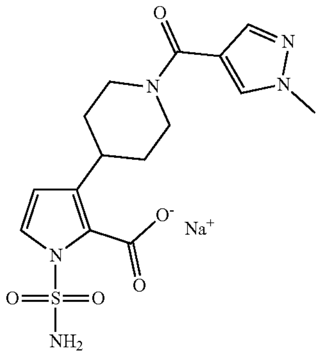
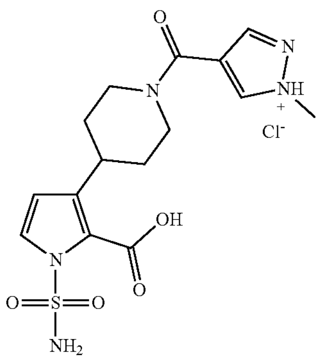

-continued
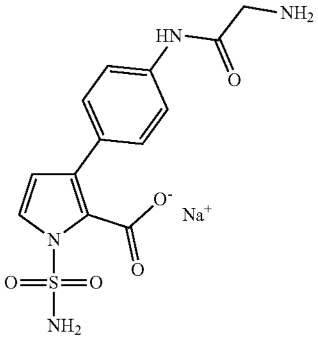
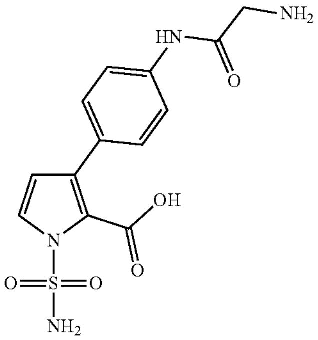
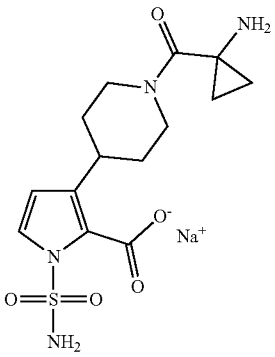
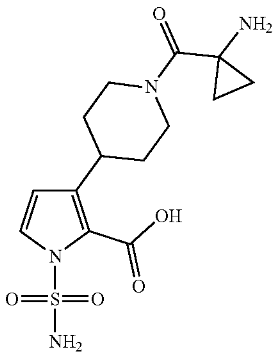
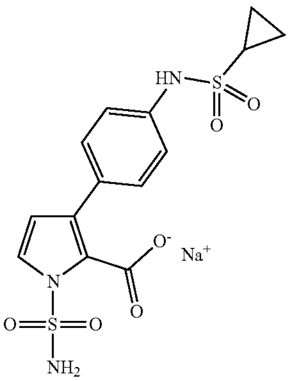
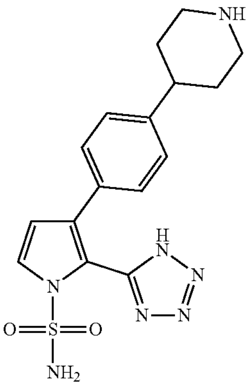
-continued
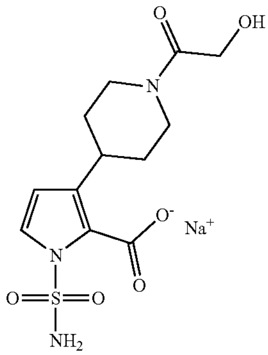
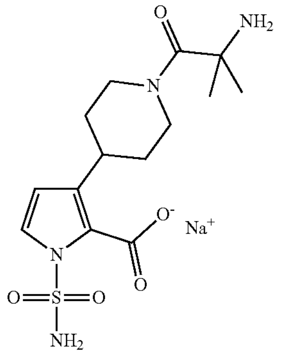
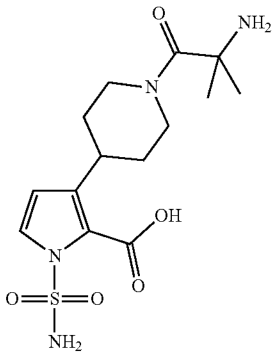
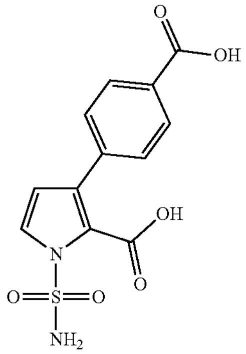
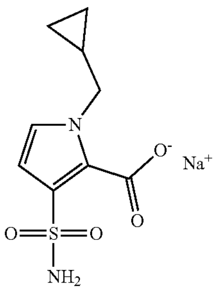
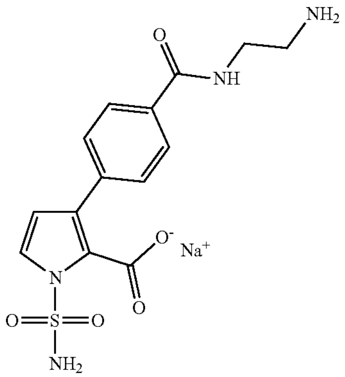
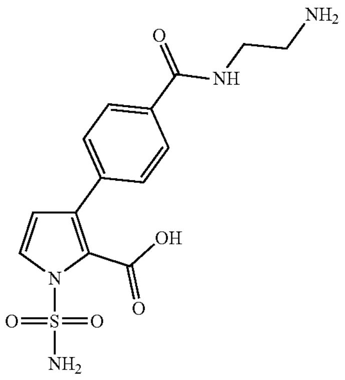

-continued
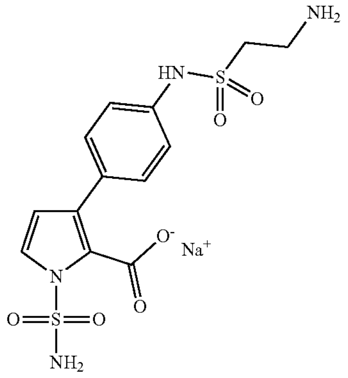
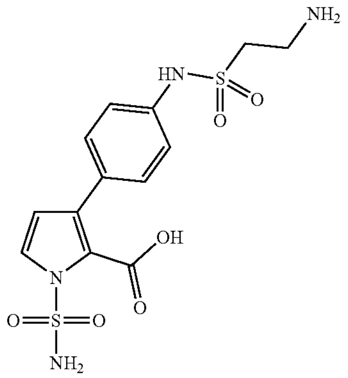
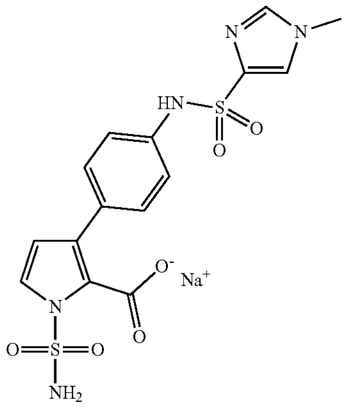
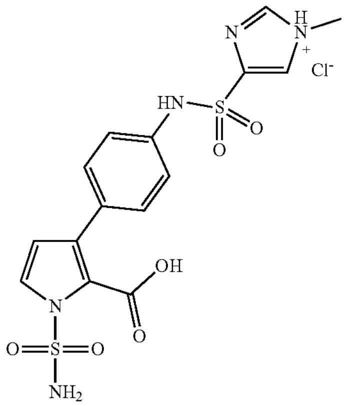
-continued
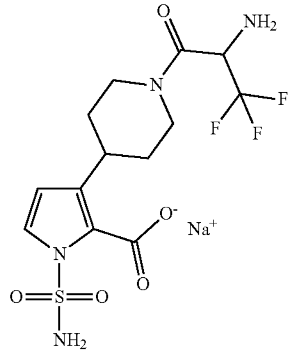
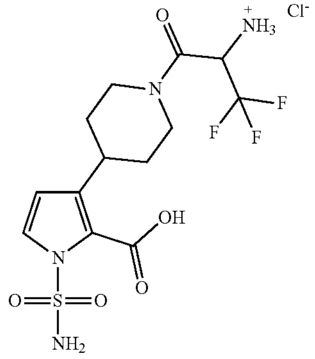
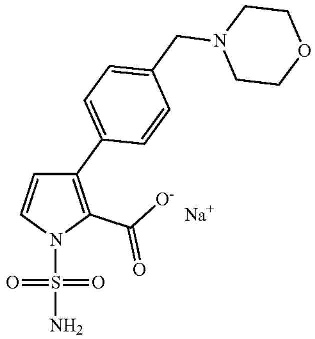
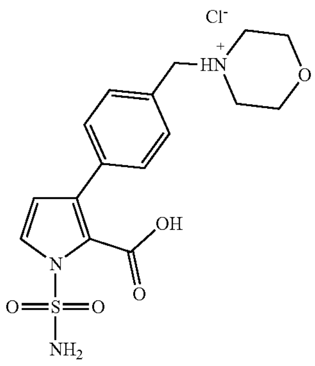 [SMILES: [Cl-] ; NS(=O)(=O)n1ccc(-c2ccc(CN3CCOCC3)cc2)c1C(=O)O]
In another aspect, the invention provides a compound selected from:

-continued
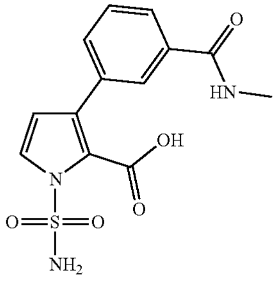
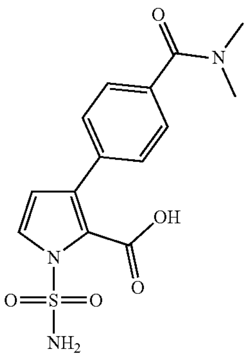
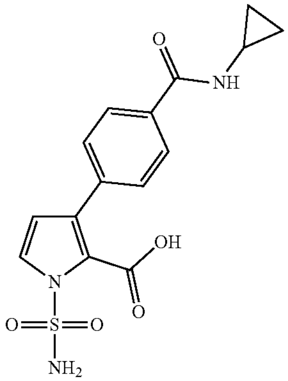
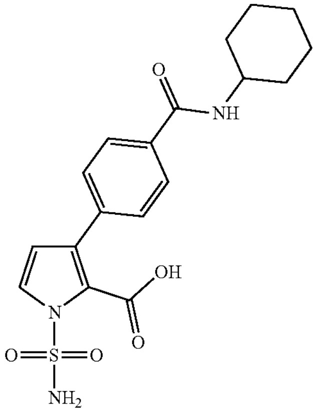
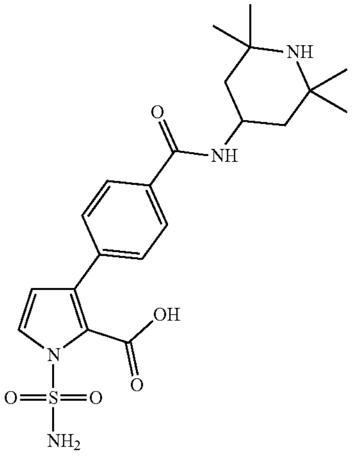
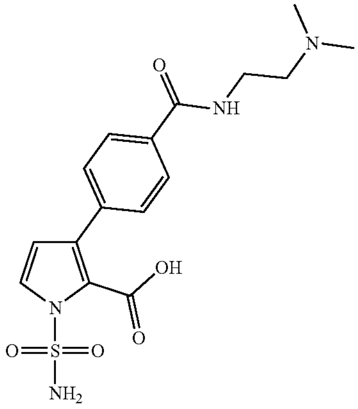
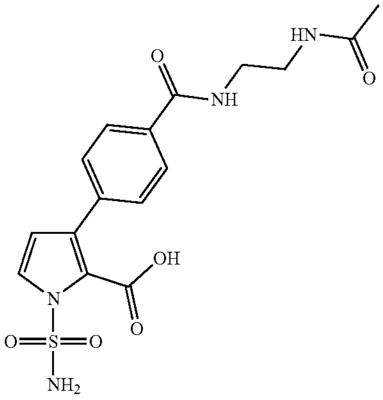
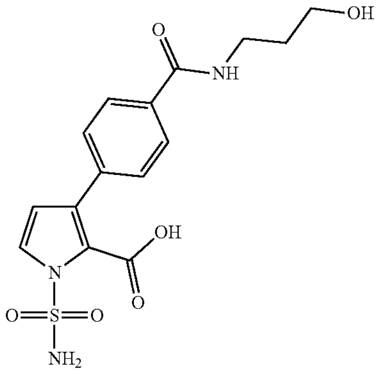
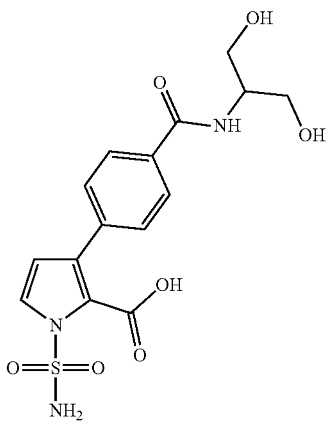

-continued
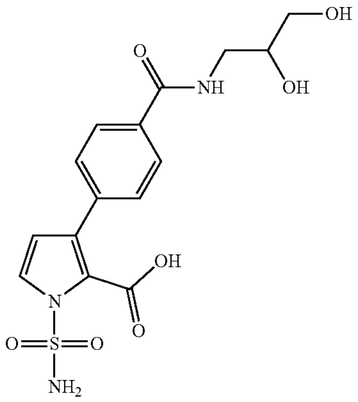
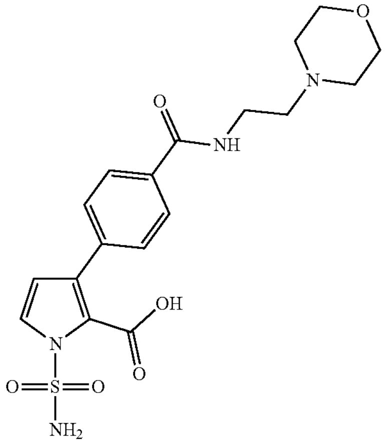
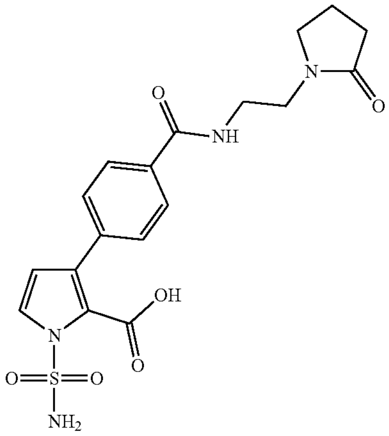
-continued
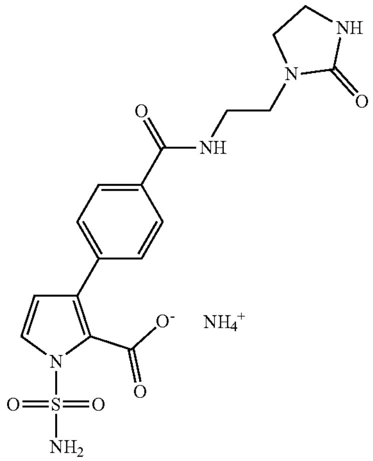
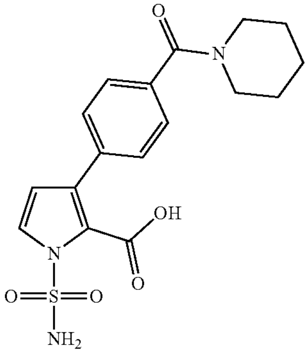
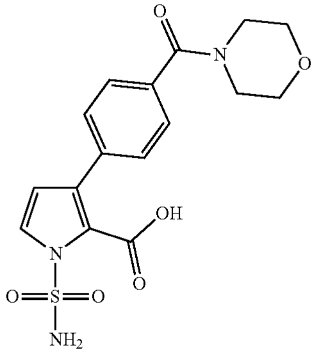
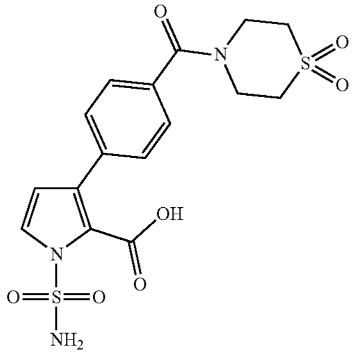

-continued
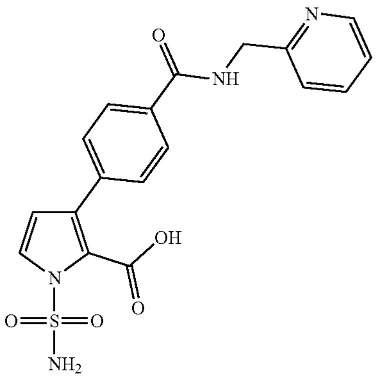
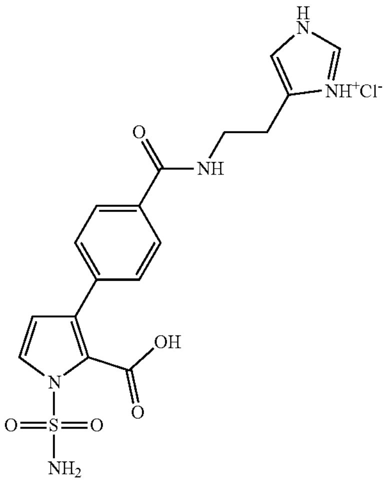
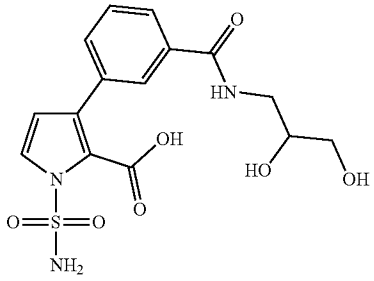
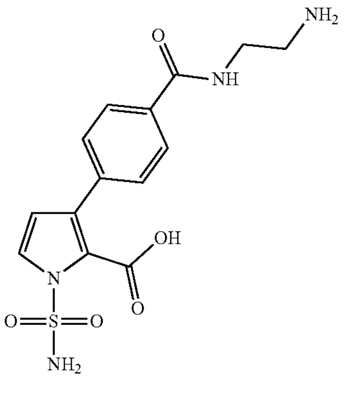
-continued
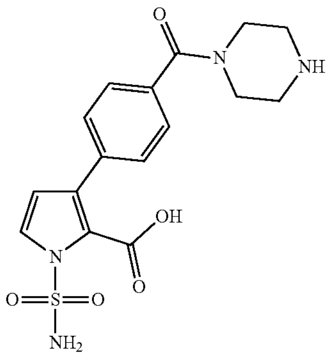
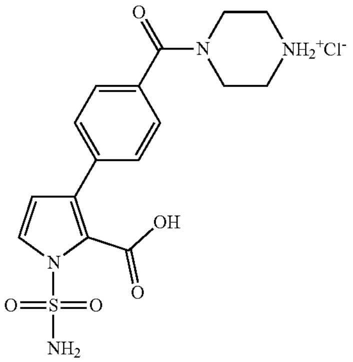
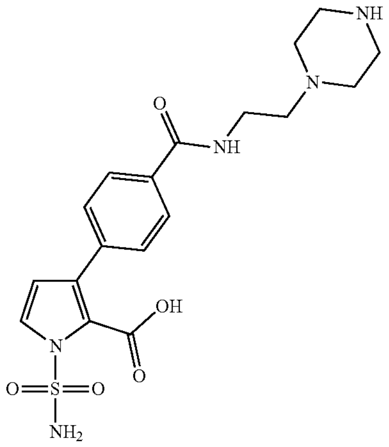
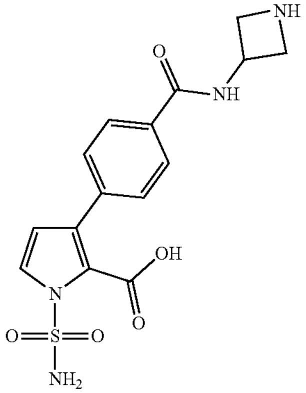

-continued
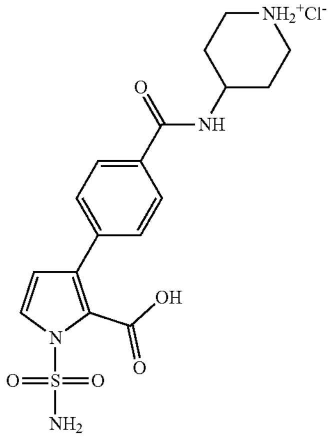
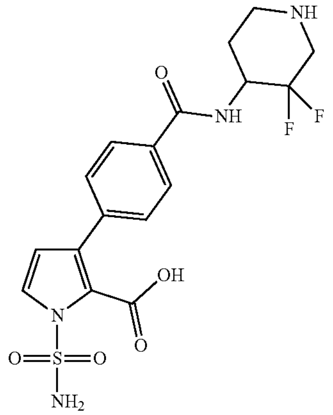
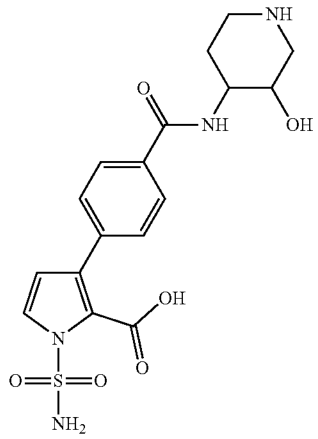
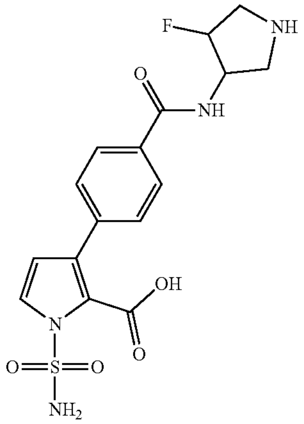
-continued
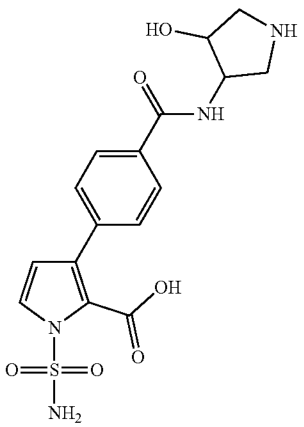
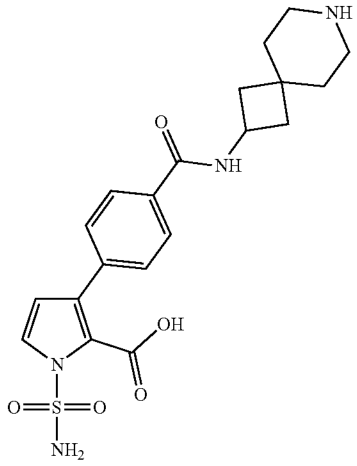
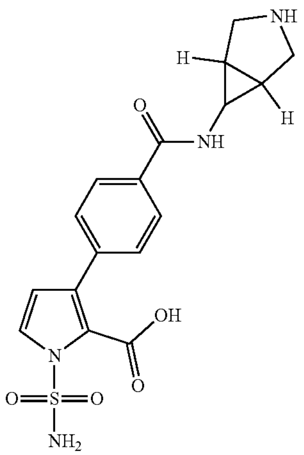
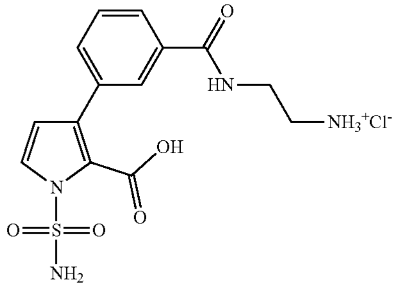

-continued
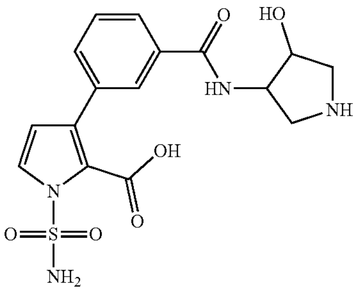
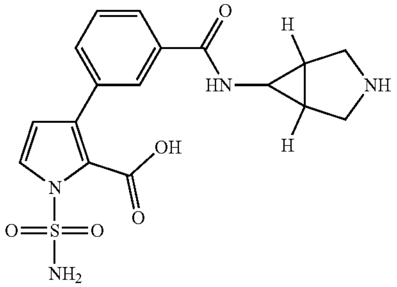
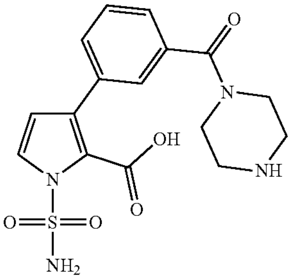
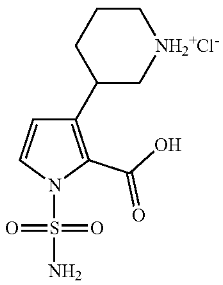
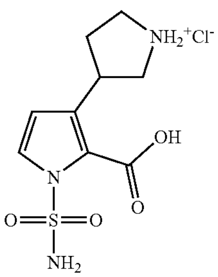
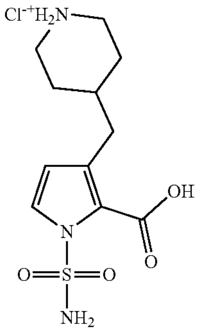
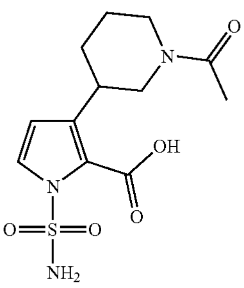
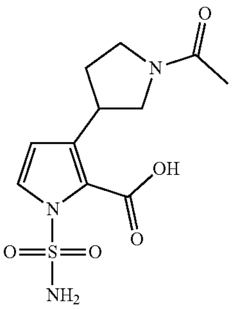
-continued
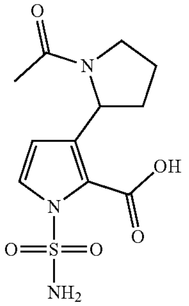
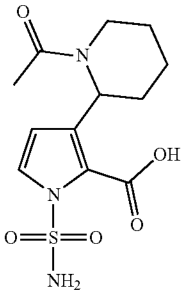
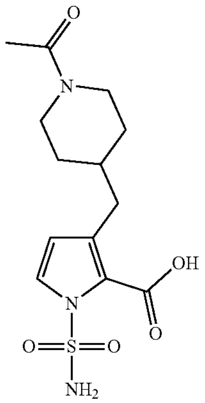
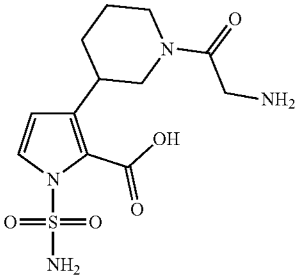
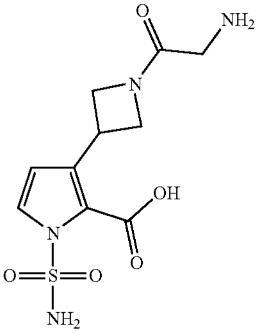
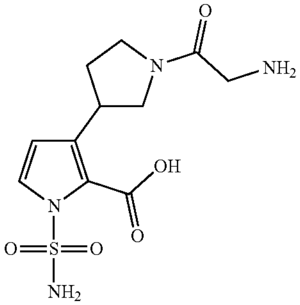
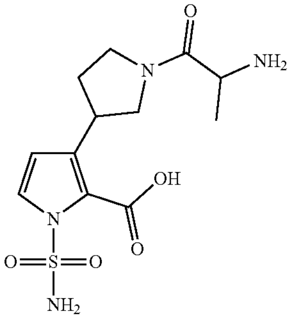
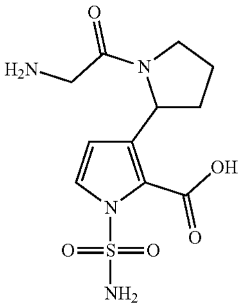
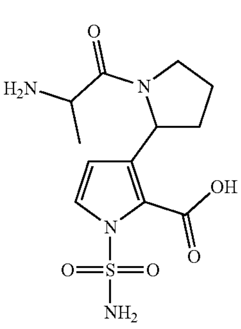
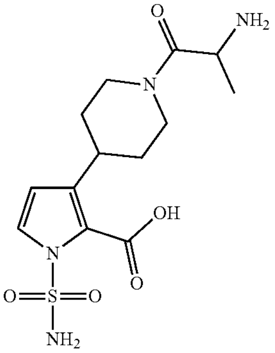

-continued
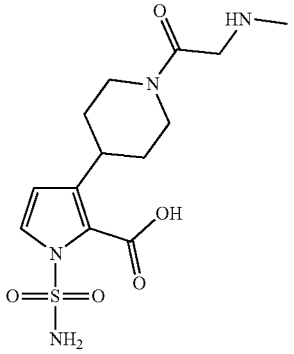
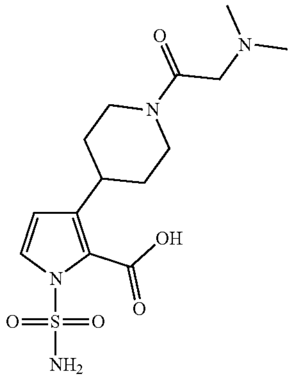
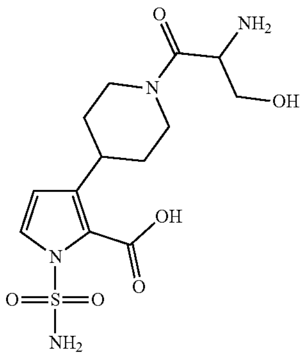
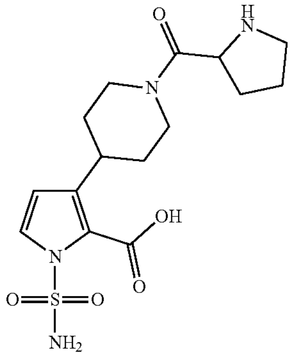
-continued
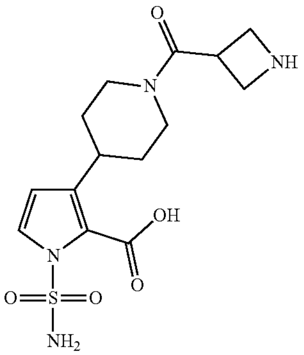
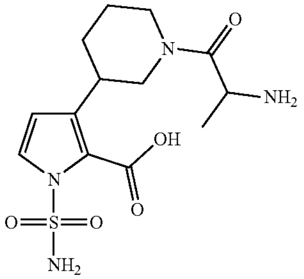
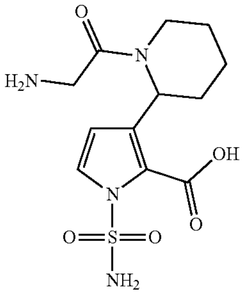
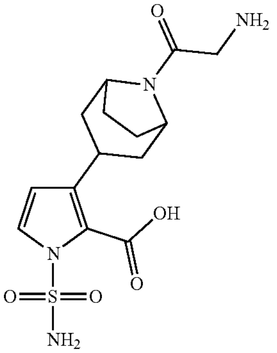
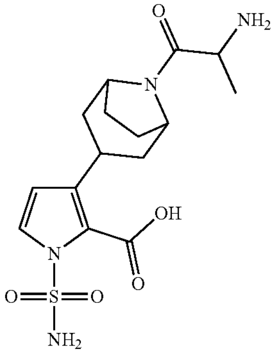
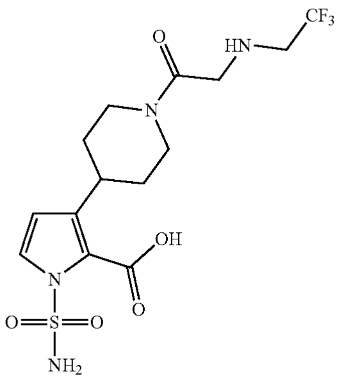

-continued
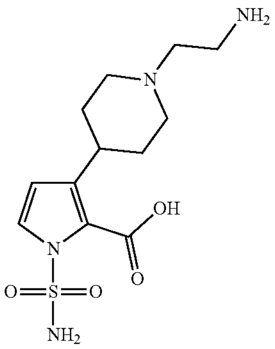
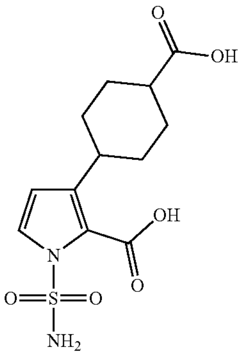
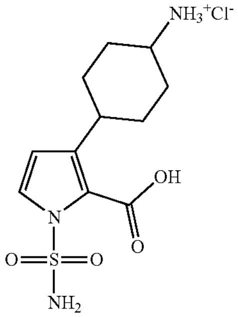
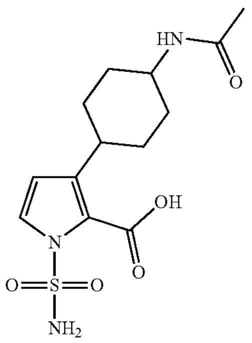
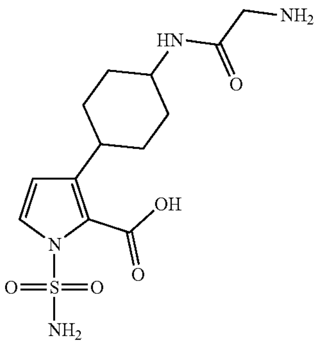
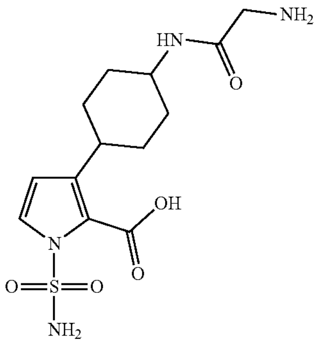
-continued
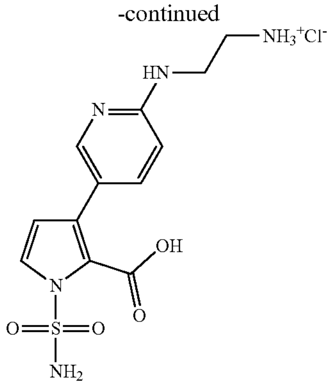
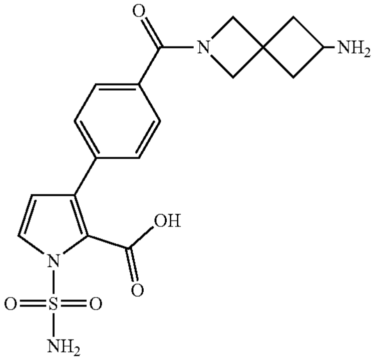
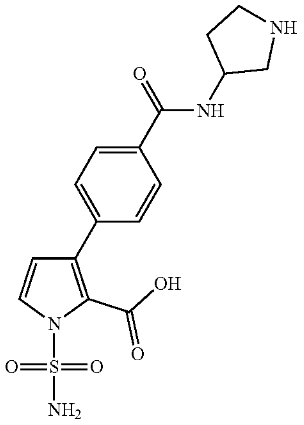
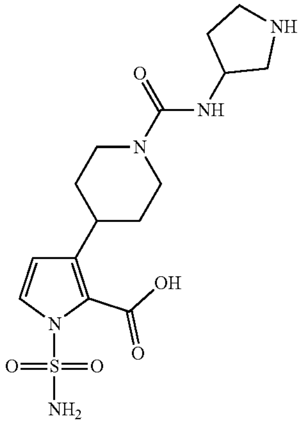
According to a further aspect of the invention there is provided a pharmaceutical composition which comprises a compound of Formula (I), or a pharmaceutically acceptable salt, hydrate or solvate thereof, in association with one or more pharmaceutically acceptable excipients.

Compounds of the invention have been described throughout the present application as a compound or a salt of a compound. It would be understood by the skilled person that a compound can be converted into a salt and a salt can be converted into a compound, in other words the free acid or free base corresponding to the salt. Accordingly, where a compound is disclosed or where a salt is disclosed, the present invention also includes the corresponding salt form, free acid form or free base form, as appropriate. For example, the disclosure of the below salt also covers the disclosure of the corresponding free acid, also shown below. This applies to all compounds or salts disclosed herein.

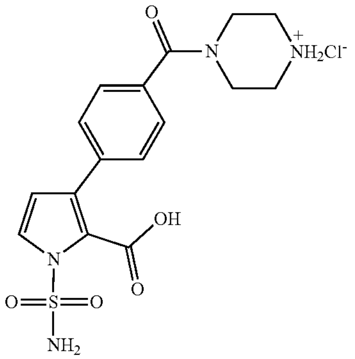

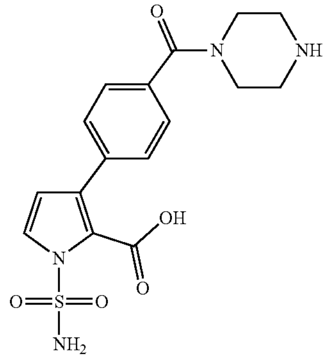

The compounds of the present invention are inhibitors of metallo-β-lactamases (MBLs). As discussed above, many bacteria have developed resistance to β-lactam antibacterials (BLAs) and one of the main resistance mechanisms is the hydrolysis of BLAs by MBLs. The compounds of the invention address this issue. In particular, the inhibition of bacterial MBLs by the compounds of Formula (I) can significantly enhance the activity of BLAs when one or more of these compounds is administered with a compound of the present invention.

Bacterial infections which can be treated using compounds of Formula (I) and compositions containing compounds of Formula (I) include those caused by Gram-negative or Gram-positive bacteria. For example, the bacterial infection may be caused by bacteria from one or more of the following families; *Streptococcus, Acinetobacter, Staphylococcus, Clostridioides, Pseudomonas, Escherichia, Salmonella, Klebsiella, Legionella, Neisseria, Enterococcus, Enterobacter, Serratia, Stenotrophomonas, Aeromonas, Mycobacterium, Morganella, Yersinia, Pasteurella, Haemophilus, Citrobacter, Burkholderia, Brucella*, or *Moraxella.*

Particular examples of bacteria which are targeted by this invention include bacterial strains in the following families of bacteria: *Escherichia, Acinetobacter, Pseudomonas*, and *Klebsiella.*

The bacterial infection may, for example, be caused by one or more bacteria selected from *Escherichia coli, Acinetobacter baumannii, Pseudomonas aeruginosa* or *Klebsiella pneumoniae.*

In one aspect of the present invention, the present invention provides a compound of Formula (I), or a pharmaceutically acceptable salt, hydrate or solvate thereof, for use in the inhibition of metallo-β-lactamase activity.

In another aspect, the present invention provides a compound of Formula (I), or a pharmaceutically acceptable salt, hydrate or solvate thereof, for use in the treatment of a disease or disorder in which metallo-β-lactamase activity is implicated.

In an embodiment, compounds of the present invention may be for use in the treatment of a disease or disorder caused by aerobic or anaerobic Gram-positive or aerobic or anaerobic Gram-negative bacteria. In an embodiment, the disease or disorder is caused by metallo-β-lactamase producing Gram-positive bacteria.

In an embodiment, compounds of the present invention may be for use in the treatment of a disease or disorder selected from: pneumonia, respiratory tract infections, urinary tract infections, intra-abdominal infections, skin and soft tissue infections, bloodstream infections, septicaemia, intra- and post-partum infections, prosthetic joint infections, endocarditis, acute bacterial meningitis and febrile neutropenia.

In an embodiment, compounds of the present invention may be for use in the treatment of a disease or disorder selected from: community acquired pneumonia, nosocomial pneumonia (hospital-acquired/ventilator-acquired), respiratory tract infections associated with cystic fibrosis, non-cystic fibrosis bronchiectasis, COPD, urinary tract infection, intra-abdominal infections, skin and soft tissue infection, bacteraemia, septicaemia, intra- and post-partum infections, prosthetic joint infections, endocarditis, acute bacterial meningitis and febrile neutropenia.

In an embodiment, compounds of the present invention may be for use in the treatment of a disease or disorder selected from: community acquired pneumonia, nosocomial pneumonia (hospital-acquired/ventilator-acquired), respiratory tract infections associated with cystic fibrosis, non-cystic fibrosis bronchiectasis, COPD, urinary tract infection, intra-abdominal infections, skin and soft tissue infection, bacteraemia and septicaemia.

In embodiments, the compounds of the present invention may be for use in a method of treatment, wherein the compound is administered in combination with one or more BLAs.

Administration of the compound or compounds of Formula (I) may be together with one or more BLAs which are all present in the same dosage form or it may be the case that the one or more BLAs are presented in separate dosage forms and the one or more compounds of Formula (I) are presented in separate dosage forms. In a preferred embodiment, an effective antibacterial treatment will consist of a compound of Formula (I) and a BLA. The BLA will preferably be meropenem. In another preferred embodiment, the compound of Formula (I) is co-administered with the BLA, which can preferably be meropenem, in a single formulation i.e. a single dosage form.

The compounds of Formula (I) may be presented in dosage forms which are suitable for oral use (for example as tablets, lozenges, hard or soft capsules, aqueous or oily suspensions, emulsions, dispersible powders or granules, syrups or elixirs), or they may be suitable for topical use (for example as creams, ointments, gels, or aqueous or oily solutions or suspensions). Other suitable dosage forms also include those intended for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing). In a preferred embodiment oral or intravenous administration is preferred, with intravenous administration being most preferred.

Oral dosage formulations may contain, together with the active compound, one or more of the following excipients: diluents, lubricants, binding agents, desiccants, sweeteners, flavourings, colouring agents, wetting agents, and effervescing agents.

If the MBLI and BLA are presented in separate dosage forms, these may be administered simultaneously or sequentially. Usually, it is preferred to administer the MBLI i.e. the compound of Formula (I) of the invention and the BLA i.e. the antibacterial compound in a single dosage form. Preferably this is an intravenous dosage form, and more preferably it is a solid dosage form. Tablets, capsules and caplets are particularly preferred.

The process of contacting a cell, or indeed other biological material or samples, which contain bacteria with compounds of the invention effectively means exposing bacteria to compounds of the invention.

Compounds of Formula (I) are inhibitors of metallo-β-lactamases and the present invention therefore provides a method of inhibiting bacterial metallo-β-lactamase activity in vitro or in vivo. This method comprises contacting a cell with an effective amount of a compound of Formula (I), or a pharmaceutically acceptable salt, hydrate or solvate thereof, or contacting a cell with a pharmaceutical composition containing a compound of Formula (I) or a pharmaceutically acceptable salt, hydrate or solvate thereof.

Accordingly, in one aspect of the invention, there is provided a method of inhibiting bacterial metallo-β-lactamase activity in vitro or in vivo, the method comprising contacting a cell with an effective amount of a compound of Formula (I), or a pharmaceutically acceptable salt, hydrate or solvate thereof; or contacting a cell with a pharmaceutical composition containing a compound of Formula (I) or a pharmaceutically acceptable salt, hydrate or solvate thereof.

The present invention also provides a method for the prevention or treatment of bacterial infection in a patient in need of such treatment, said method comprising administering to said patient a therapeutically effective amount of a combination of an antibacterial agent with a compound of Formula (I) or a pharmaceutically acceptable salt, hydrate or solvate thereof; or administering to said patient a therapeutically effective amount of an antibacterial agent in combination with a pharmaceutical composition containing a compound of Formula (I) or a pharmaceutically acceptable salt, hydrate or solvate thereof.

The present invention also provides a method for the prevention or treatment of a disease or disorder, said method comprising administering to a patient in need of such treatment a therapeutically effective amount of a combination of an antibacterial agent with a compound of Formula (I) or a pharmaceutically acceptable salt, hydrate or solvate thereof; or administering to said patient a therapeutically effective amount of an antibacterial agent in combination with a pharmaceutical composition containing a compound of Formula (I) or a pharmaceutically acceptable salt, hydrate or solvate thereof.

In an embodiment, the present invention provides a method for the prevention or treatment of a disease or disorder caused by aerobic or anaerobic Gram-positive or aerobic or anaerobic Gram-negative bacteria. In an embodiment, the disease or disorder is caused by metallo-β-lactamase producing Gram-positive bacteria.

In an embodiment, the present invention provides a method for the prevention or treatment of a disease or disorder selected from: pneumonia, respiratory tract infections, urinary tract infections, intra-abdominal infections, skin and soft tissue infections, bloodstream infections, septicaemia, intra- and post-partum infections, prosthetic joint infections, endocarditis, acute bacterial meningitis and febrile neutropenia.

In an embodiment, the present invention provides a method for the prevention or treatment of a disease or disorder selected from: community acquired pneumonia, nosocomial pneumonia (hospital-acquired/ventilator-acquired), respiratory tract infections associated with cystic fibrosis, non-cystic fibrosis bronchiectasis, COPD, urinary tract infection, intra-abdominal infections, skin and soft tissue infection, bacteraemia, septicaemia, intra- and post-partum infections, prosthetic joint infections, endocarditis, acute bacterial meningitis and febrile neutropenia.

In an embodiment, the present invention provides a method for the prevention or treatment of a disease or disorder selected from: community acquired pneumonia, nosocomial pneumonia (hospital-acquired/ventilator-acquired), respiratory tract infections associated with cystic fibrosis, non-cystic fibrosis bronchiectasis, COPD, urinary tract infection, intra-abdominal infections, skin and soft tissue infection, bacteraemia and septicaemia.

In an embodiment, the antibacterial agent is a carbapenem. Non limiting examples of carbapenems include: meropenem, faropenem, imipenem, ertapenem, doripenem, panipenem/betamipron and biapenem as well as razupenem, tebipenem, lenapenem and tomopenem.

The present invention also provides a method of inhibiting bacterial infection, said method comprising contacting a cell with an effective amount of a compound of Formula (I), or a pharmaceutically acceptable salt, hydrate or solvate thereof, in combination with a suitable antibacterial agent. The contacting of the cell may occur in vitro or in vivo, with in vivo contact being preferred.

Another aspect of the invention provides a compound of Formula (I), or a pharmaceutically acceptable salt, hydrate or solvate thereof, or a pharmaceutical composition containing a compound of Formula (I) or a pharmaceutically acceptable salt, hydrate or solvate thereof, for use in therapy.

A further aspect of the present invention provides a compound of Formula (I), or a pharmaceutically acceptable salt, hydrate or solvate thereof, or a pharmaceutical containing a compound of Formula (I) or a pharmaceutically acceptable salt, hydrate or solvate thereof, for use in the treatment of a bacterial infection. The treatment may be curative or preventative i.e. prophylactic. In a preferred embodiment, the treatment is curative; this means that the treatment reduces the overall level of bacterial infection.

A further aspect of the invention provides a kit of parts comprising a compound of Formula (I), or a pharmaceutically acceptable salt, hydrate or solvate thereof, or a pharmaceutical composition containing a compound of Formula (I) or a pharmaceutically acceptable salt, hydrate or solvate thereof, and a BLA. The kit may be provided together with instructions for use in treating bacterial infections and/or packaging which provides the combined dose of the compound of Formula (I) and the BLA.

The chemical terms used in the specification have their generally accepted meanings in the art.

The term "halo" refers to fluoro, chloro, bromo and iodo.

The term "alkyl" includes both straight and branched chain alkyl groups and analogues thereof having from 1 to 6 carbon atoms. References to individual alkyl groups such as "propyl" are specific for the straight chain version only and references to individual branched chain alkyl groups such as "isopropyl" are specific for the branched chain version only.

Similarly, a C4 alkyl may be straight chain butyl, secondary butyl (sec-butyl) or tertiary butyl (tert-butyl). At each occurrence the term may have any meaning within the above definition independently of any other usage of the term. The same comment applies to other terms defined in this specification which are used on multiple occasions and which are therefore independently chosen on each occasion from within the overall defined meaning.

For the avoidance of doubt, the term "$C_{3-8}$ cycloalkyl" means a hydrocarbon ring containing from 3 to 8 carbon atoms, for example, cyclopropyl, cyclobutyl, cyclopentyl, cyclohexyl, cycloheptyl or bicyclo[2.2.1]heptyl; and the term "$C_{3-8}$cycloalkenyl" means a hydrocarbon ring containing at least one double bond, for example, cyclobutenyl, cyclopentenyl, cyclohexenyl or cycloheptenyl, such as 3-cyclohexen-1-yl, or cyclooctenyl.

The term "aryl" means a cyclic or polycyclic aromatic ring having from 5 to 12 carbon atoms.

The term aryl includes both monovalent species and divalent species. Examples of aryl groups include, but are not limited to, phenyl, biphenyl, naphthyl and the like. In particular embodiment, an aryl is phenyl.

The heterocyclic ring may be saturated, unsaturated or aromatic. Aromatic heterocyclic species are generally referred to as heteroaryl rings.

The term "heterocyclyl", "heterocyclic" or "heterocycle" means a non-aromatic saturated or partially saturated monocyclic, fused, bridged, or spiro bicyclic heterocyclic ring system(s).

The term heterocyclyl includes both monovalent species and divalent species. Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocycles contain from about 7 to about 17 ring atoms, suitably from 7 to 12 ring atoms. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine.

Other heterocycles include dihydro oxathiolyl, tetrahydro oxazolyl, tetrahydro-oxadiazolyl, tetrahydrodioxazolyl, tetrahydro oxathiazolyl, hexahydrotriazinyl, tetrahydrooxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl.

Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example Advanced Organic Chemistry, by Jerry March, 4th Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

The term "heteroaryl" or "heteroaromatic" means an aromatic mono-, bi-, or polycyclic ring incorporating one or more (for example 1 to 4, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically, the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general, the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3 b]furanyl, 2H-furo[3,2-b]pyranyl, 5H-pyrido[2,3-d]oxazinyl, 1H-pyrazolo[4,3-d]oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydro-pyrido[2,3-b]pyrazinyl and 3,4-dihydro-2H-pyrido[3,2 b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

5- or 6-membered heterocylic rings are preferred.

The various functional groups and substituents making up the compounds of the formula I are typically chosen such that the molecular weight of the compound of the formula I does not exceed 1000. More usually, the molecular weight of the compound will be less than 900, for example less than 800, or less than 700, or less than 650, or less than 600. More preferably, the molecular weight is less than 550 and, for example, is 500 or less.

The invention contemplates pharmaceutically acceptable salts of the compounds of the invention. Suitable pharmaceutically acceptable salts of compounds of the present invention include salts with Group 1 cations (for example $Na^+$), Group II cations (for example $K^+$) or ammonium salts (for example $NH_4^+$). The compounds of the present invention may also form a hydrochloride salt, phosphate salt or salts of other inorganic acid when a basic nitrogen is present in the compound of the invention. The salts may also include the acid addition and base salts of the compounds.

Suitable acid addition salts are formed from acids which form non-toxic salts. Examples include the acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate and hemicalcium salts. For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of the invention may be prepared by for example, one or more of the following methods:

(i) by reacting the compound of the invention with the desired acid or base;

(ii) by removing an acid- or base-labile protecting group from a suitable precursor of the compound of the invention or by ring-opening a suitable cyclic precursor, for example, a lactone or lactam, using the desired acid or base; or (iii) by converting one salt of the compound of the invention to another by reaction with an appropriate acid or base or by means of a suitable ion exchange column.

These methods are typically carried out in solution. The resulting salt may precipitate out and be collected by filtration or may be recovered by evaporation of the solvent. The degree of ionisation in the resulting salt may vary from completely ionised to almost non-ionised Compounds of the invention i.e. compounds of Formula (I) may in some circumstances exist in a number of different tautomeric forms and references to compounds of the formula I include all such forms.

Compounds that have the same molecular formula but differ in the arrangement of their atoms are termed "isomers".

Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric centre, for example, it is bonded to four different groups, it is known as a chiral compound. A chiral compound can exist in the form of either one or both of its pair of enantiomers (in the case of a single chiral center). An enantiomer can be characterized by the absolute configuration of its asymmetric centre and is described by the R- and S-sequencing rules of Cahn-Ingold-Prelog. Where there is more than one chiral centre in a molecule then the number of conceivable stereoisomers is $2^n$ where n is the number of chiral centres; the only exception being the existence of symmetry in the molecule leading to a reduction in the number of isomers from the maximum of $2^n$.

The compounds of this invention may possess one or more asymmetric centres; such compounds can therefore be produced as individual (R)- or (S)-stereoisomers or as mixtures thereof.

Some of the compounds of the invention may have geometric isomeric centres (E- and Z-isomers).

It is to be understood that the present invention encompasses all isomeric forms and mixtures thereof that possess metallo-β-lactamase inhibitory activity.

Methods for the determination of stereochemistry and the separation of stereoisomers are well-known in the art (see discussion in "Advanced Organic Chemistry", 7th edition J. March, John Wiley and Sons, New York, 2013).

Compounds of the Formula I containing an amine function may also form N-oxides. A reference herein to a compound of the Formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid); this is described in general textbooks such as *Advanced Organic Chemistry*, by J. March referred to above. N-oxides can be made in a variety of ways which are known to the skilled person; for example, by reacting the amine compound with m-chloroperoxybenzoic acid (mCPBA) in a solvent such as dichloromethane.

The present invention also encompasses compounds of the invention as defined herein which comprise one or more isotopic substitutions. For example, H may be in any isotopic form, including $^1H$, $^2H(D)$, and $^3H$ (T); C may be in any isotopic form, including $^{12}C$, $^{13}C$, and $^{14}C$; and O may be in any isotopic form, including $^{16}O$ and $^{18}O$; and the like. Similarly, isotopic variants of N, S and P may be utilised.

SYNTHESIS AND EXAMPLES

The following compounds represent examples of compounds which can be synthesised in accordance with the invention. Some of the compounds were also tested in a biological assay and the results are presented below. The compounds show activity as inhibitors of metallo-β-lactamases and thus have utility in the treatment of infections, particularly antibiotic resistant infections.

General Experimental

Microwave assisted reactions were performed using a Biotage Initiator+™ microwave synthesizer in sealed vials.

Throughout this document the following abbreviations have been used:

Bn—benzyl

Boc—tert-butyloxycarbonyl

Cbz—carboxybenzyl

DCM—dichloromethane

DIPEA—N,N-diisopropylethylamine

DME—1,2-dimethoxyethane

DMF—N,N-dimethylformamide

DMSO—dimethyl sulfoxide

HBTU—N,N,N',N'-tetramethyl-O-(1H-benzotriazol-1-yl)uronium hexafluorophosphate Hoveyda-Grubbs Catalyst® 2$^{nd}$ generation—dichloro[1,3-bis(2,4,6-trimethylphenyl)-2-imidazolidinylidene](2-iso-propoxyphenylmethylene)ruthenium(II)

NMP—1-methyl-2-pyrrolidinone

Pd(dppf)$Cl_2$—[1,1'-bis(diphenylphosphino)ferrocene]dichloropalladium(II)

SEM—2-(trimethylsilyl)ethoxymethyl

TFA—trifluoroacetic acid

THF—tetrahydrofuran

XPhos Pd G2—chloro(2-dicyclohexylphosphino-2',4',6'-tri-iso-propyl-1,1'-biphenyl)[2-(2'-amino-1,1'-biphenyl)]palladium(II)

Analytical Methods

All $^{1}H$ and $^{19}F$ NMR spectra were obtained on a Bruker AVI 500 with 5 mm QNP. Chemical shifts are expressed in parts per million (6) and are referenced to the solvent. Coupling constants J are expressed in Hertz (Hz).

LC-MS were obtained on a Waters Alliance ZQ (Methods A, B, C and E) or Waters Acquity H-class UPLC (Method D) using the methods detailed below. Wavelengths were 254 and 210 nm.

Method A

Column: YMC-Triart C18, 2.0×50 mm, 5 μm. Flow rate: 0.8 mL/min. Injection volume: 6 μL Mobile Phase: A=water, B=acetonitrile, C=1:1 water:acetonitrile+1.0% formic acid

| Time | % A | % B | % C |
|---|---|---|---|
| Initial | 90 | 5 | 5 |
| 4.0 | 0 | 95 | 5 |
| 6.0 | 0 | 95 | 5 |

Method B

Column: YMC-Triart C18, 2.0×50 mm, 5 μm. Flow rate: 0.8 mL/min. Injection volume: 6 μL Mobile Phase: A=water, B=acetonitrile, C=1:1 water:acetonitrile+1.0% ammonia (aq.)

| Time | % A | % B | % C |
|---|---|---|---|
| Initial | 90 | 5 | 5 |
| 4.0 | 0 | 95 | 5 |
| 6.0 | 0 | 95 | 5 |

Method C

Column: YMC-Triart C18, 2.0×50 mm, 5 μm. Flow rate: 0.8 mL/min. Injection volume: 6 μL Mobile Phase: A=water, B=acetonitrile, C=1:1 water:acetonitrile+1.0% formic acid

| Time | % A | % B | % C |
|---|---|---|---|
| Initial | 95 | 0 | 5 |
| 2.0 | 95 | 0 | 5 |
| 12.0 | 0 | 95 | 5 |
| 14.0 | 0 | 95 | 5 |

Method D

Column: CSH C18, 2.1×100 mm, 1.7 μm. Flow rate: 0.6 mL/min. Injection volume: 5 μL Mobile Phase: A=water+0.1% formic acid, B=acetonitrile+0.1% formic acid

| Time | % A | % B |
|---|---|---|
| Initial | 98 | 2 |
| 0.5 | 98 | 2 |
| 6.5 | 2 | 98 |
| 7.5 | 2 | 98 |

Method E

Column: YMC-Triart C18, 2.0×50 mm, 5 μm. Flow rate: 0.8 mL/min. Injection volume: 6 μL Mobile Phase: A=water, B=acetonitrile, C=1:1 water:acetonitrile+1.0% ammonia (aq.)

| Time | % A | % B | % C |
|---|---|---|---|
| Initial | 97.5 | 0 | 2.5 |
| 3.0 | 0 | 95 | 5 |
| 5.0 | 0 | 95 | 5 |

Method F

Column: YMC-Triart C18, 2.0×50 mm, 5 μm. Flow rate: 0.8 mL/min. Injection volume: 6 μL Mobile Phase: A=water, B=acetonitrile, C=1:1 water:acetonitrile+1.0% formic acid

| Time | % A | % B | % C |
|---|---|---|---|
| Initial | 97.5 | 0 | 2.5 |
| 3.0 | 0 | 95 | 5 |
| 5.0 | 0 | 95 | 5 |

Preparative HPLC chromatography was carried out using a Waters Auto Lynx Mass Directed Fraction Collector using the methods detailed below.

Method A

Column: CSH C18, 30×100 mm, 5 μm. Flow rate: 80 mL/min. Injection volume: 2500 μL.

Run Time: 6.5 minutes (gradient range below) then 1.25 minutes 95% (% B in A).

Mobile Phase A=water+0.1% formic acid, B=acetonitrile+0.1% formic acid

| Method Name | Gradient Range (% B in A) |
|---|---|
| 0.60-0.80 min. | 2-12% |
| 0.80-1.00 min. | 5-15% |
| 1.00-1.11 min. | 8-18% |
| 1.22-1.33 min. | 15-25% |
| 1.78-1.90 min. | 40-50% |

Intermediate 1: Sodium benzyloxycarbonyl-(2-benzyloxycarbonyl-3-bromo-pyrrol-1-yl)sulfonyl-azanide

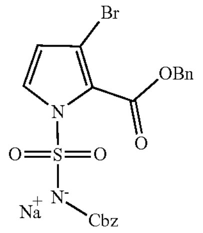

Step A: Benzyl 3-bromo-1H-pyrrole-2-carboxylate

Methyl 3-bromo-1H-pyrrole-2-carboxylate (63 g, 309 mmol) was added to benzyl alcohol (267 g, 2.47 mol) followed by di-n-butyltin oxide (3.84 g, 15.4 mmol) and the mixture stirred at 125° C. for 24 hours. The low boiling materials were removed under reduced pressure. The reaction was heated to 125° C. for a further 4 days. Benzyl alcohol was removed via vacuum distillation and the residue purified through a silica plug eluting with 20-30% diethyl ether in petroleum ether. The residue was dissolved in 20% diethyl ether:petroleum ether and the mixture seeded with product to afford a solid which was stirred for 10 minutes then filtered and dried. The obtained solid was then slurried in petroleum ether for 10 minutes before being filtered to give the desired product as a white solid (72.5 g, 84%).

$^1$H NMR (500 MHz, $CDCl_3$) δ 9.14 (br s, 1H), 7.50-7.30 (m, 5H), 6.82 (d, J=3.2 Hz, 1H), 6.34 (d, J=3.2 Hz, 1H), 5.35 (s, 2H).

Step B: Sodium benzyloxycarbonyl-(2-benzyloxycarbonyl-3-bromo-pyrrol-1-yl)sulfonyl-azanide A suspension of sodium hydride (60% in mineral oil, 23.6 g, 589 mmol) in anhydrous THF (200 mL) was cooled to −10° C. under a nitrogen atmosphere followed by the dropwise addition of a solution of benzyl 3-bromo-1H-pyrrole-2-carboxylate (55 g, 196 mmol) in anhydrous THF (200 mL) over a period of 45 minutes ensuring the temperature was maintained below −5° C. The reaction mixture was allowed to warm to room temperature and stirred for 1 hour before recooling to −10° C. To the reaction mixture was added benzyl N-chlorosulfonylcarbamate (53.9 g, 216 mmol) portionwise over a period of 30 minutes ensuring that the temperature was maintained below −5° C. The reaction mixture was allowed to warm to room temperature and stirred for 2 hours, then recooled to −10° C. and quenched by the dropwise addition of 50:50 water:brine (250 mL). The reaction mixture was extracted into ethyl acetate (3×100 mL) and the combined organic phases washed with brine (200 mL), dried over $MgSO_4$, the solution decanted and concentrated to dryness under reduced pressure. The residue was purified by slurrying in diethyl ether (200 mL), filtered and sucked dry. This solid was reslurried in diethyl ether (250 mL), filtered and sucked dry to give the desired product as a white solid (99.8 g, 99%).

$^1$H NMR (500 MHz, DMSO-$d_6$) δ 7.56-7.52 (m, 2H), 7.36-7.26 (m, 9H), 6.17 (d, J=3.4 Hz, 1H), 5.23 (s, 2H), 4.85 (s, 2H).

LC-MS (Method A): $R_T$=3.38 min, m/z=491.4/493.4 $[M-H]^-$.

Intermediate 2: 4-[2-Benzyloxycarbonyl-1-(benzyloxycarbonylsulfamoyl)pyrrol-3-yl]benzoic acid

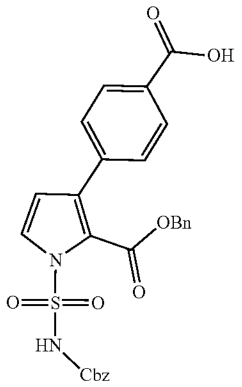 [SMILES: O=C(NS(=O)(=O)n1ccc(-c2ccc(C(=O)O)cc2)c1C(=O)OCc1ccccc1)OCc1ccccc1]

Step A: Benzyl 1-(benzyloxycarbonylsulfamoyl)-3-(4-tert-butoxycarbonylphenyl)pyrrole-2-carboxylate A stirred suspension of sodium benzyloxycarbonyl-(2-benzyloxycarbonyl-3-bromo-pyrrol-1-yl)sulfonyl-azanide (35.0 g, 67.9 mmol), tert-butyl 4-(4,4,5,5-tetramethyl-1,3,2-dioxaborolan-2-yl)benzoate (22.7 g, 74.7 mmol) and XPhos Pd G2 (2.67 g, 3.40 mmol) in 1,4-dioxane (350 mL) was degassed and purged with nitrogen followed by the addition of aqueous potassium phosphate tribasic solution (3 M, 67.92 mL). The mixture was heated at 45° C. for 2 hours. The reaction mixture was allowed to cool, the phases separated and the organic phase concentrated to dryness under reduced pressure. The residue was redissolved in ethyl acetate (300 mL), washed with water (2×300 mL) and saturated sodium bicarbonate solution (2×300 mL), dried over $MgSO_4$, filtered and concentrated to −60 mL under reduced pressure. This was diluted with diethyl ether (150 mL) and the resulting solution added dropwise to petroleum ether with vigorous stirring. The precipitated solid was isolated by filtration and sucked dry to give the desired product as an off-white solid (40.4 g, 100%).

$^1$H NMR (500 MHz, $CDCl_3$) δ 7.61 (br d, J=7.6 Hz, 2H), 7.56 (br s, 1H), 7.11-6.86 (m, 11H), 6.58 (br d, J=6.7 Hz, 2H), 5.87 (br s, 1H), 4.86 (br s, 2H), 4.78 (s, 2H), 1.61 (s, 9H).

LC-MS (Method A): $R_T$=3.93 min, m/z=589.6 $[M-H]^-$.

Step B: 4-[2-Benzyloxycarbonyl-1-(benzyloxycarbonylsulfamoyl)pyrrol-3-yl]benzoic acid To a stirred solution of benzyl 1-(benzyloxycarbonylsulfamoyl)-3-(4-tert-butoxycarbonylphenyl)pyrrole-2-carboxylate (40.5 g, 68.6 mmol) in DCM (300 mL) was added TFA (76 mL, 1.03 mol). The reaction mixture was stirred at room temperature for 1 hour, then concentrated to dryness under reduced pressure. The residue was triturated with isopropanol, filtered and sucked dry to give the desired product as an off-white solid (25.0 g, 68%).

$^1H$ NMR (500 MHz, DMSO-$d_6$) δ 7.85 (br d, J=7.9 Hz, 2H), 7.49 (br s, 1H), 7.44-7.23 (m, 10H), 7.19 (br d, J=6.4 Hz, 2H), 6.51 (br s, 1H), 5.22 (s, 2H), 5.12 (s, 2H).

LC-MS (Method A): $R_T$=3.20 min, m/z=533.5 [M−H]$^-$.

Further Intermediates

The following intermediates were prepared in a similar manner to 4-[2-benzyloxycarbonyl-1-(benzyloxycarbonylsulfamoyl)pyrrol-3-yl]benzoic acid (Intermediate 2).

| Intermediate | Structure | Name | Analytical Data |
|---|---|---|---|
| Intermediate 3 | 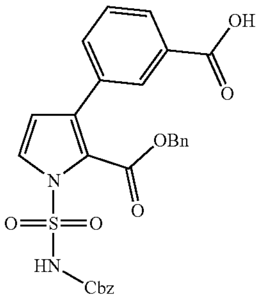 [SMILES: O=C(NS(=O)(=O)n1ccc(-c2cccc(C(=O)O)c2)c1C(=O)OCc1ccccc1)OCc1ccccc1] | 3-[2-Benzyloxy-carbonyl-1-(benzyloxy-carbonylsulfamoyl)pyrrol-3-yl]benzoic acid | $^1H$ NMR (500 MHz, DMSO-$d_6$) δ 7.93 (s, 1H), 7.88 (d, J = 7.5 Hz, 1H), 7.56 (d, J = 7.5 Hz, 1H), 7.49 (br d, J = 2.0 Hz, 1H), 7.45 (br t, J = 7.5 Hz, 1H), 7.34 (m, 5H), 7.26 (m, 3H), 7.16 (br d, J = 6.5 Hz, 2H), 6.50 (br d, J = 2.0 Hz, 1H), 5.18 (s, 2H), 5.11 (s, 2H). LC-MS (Method A): $R_T$ = 3.06 min, m/z = 533.4 [M − H]$^-$ |

Intermediate 4: tert-Butyl (3R)-3-ethynylpyrrolidine-1-carboxylate

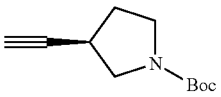

1-Diazo-1-dimethoxyphosphoryl-propan-2-one (85% in acetonitrile, 409 mg, 1.81 mmol) was added to a solution of tert-butyl (3S)-3-formylpyrrolidine-1-carboxylate (524 μL, 1.81 mmol) and potassium carbonate (501 mg, 3.62 mmol) in methanol (10 mL) at ambient temperature and stirred for 1 hour. The reaction mixture was partitioned between DCM (50 mL) and water (20 mL). The organic was separated and the aqueous extracted with DCM (2×20 mL). The combined organics were dried over $Na_2SO_4$, filtered, evaporated under reduced pressure and purified by column chromatography (0-100% ethyl acetate in petroleum ether) to give the desired product as a colourless oil (315 mg, 89%).

$^1H$ NMR (500 MHz, $CDCl_3$) b 3.77-3.41 (m, 2H), 3.39-3.17 (m, 2H), 3.05-2.82 (m, 1H), 2.24-2.08 (m, 2H), 2.02-1.88 (m, 1H), 1.46 (s, 9H).

Further Intermediates

The following intermediates were prepared in a similar manner to tert-butyl (3R)-3-ethynylpyrrolidine-1-carboxylate (Intermediate 4).

| Intermediate | Structure | Name | Analytical Data |
|---|---|---|---|
| Intermediate 5 | 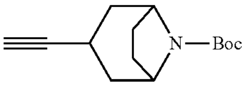 [SMILES: C#CC1CC2CCC(C1)N2C(=O)OC(C)(C)C] | tert-Butyl 3-ethynyl-8-azabicyclo[3.2.1]octane-8-carboxylate | $^1H$ NMR (500 MHz, $CDCl_3$) δ 4.31-4.10 (m, 2H), 2.86-2.76 (br m, 1H), 2.03 (s, 1H), 2.00-1.91 (m, 2H), 1.90-1.71 (m, 4H), 1.70-1.58 (m, 2H), 1.46 (s, 9H). |

Intermediate 6: Benzyl 1-(benzyloxycarbonylsulfamoyl)-3-(4-piperidyl)pyrrole-2-carboxylate hydrochloride

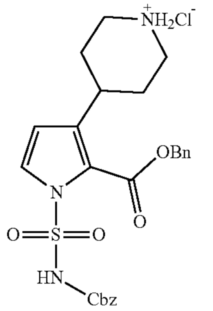

Step A: tert-Butyl 4-(2-benzyloxycarbonyl-1H-pyrrol-3-yl)piperidine-1-carboxylate tert-Butyl 4-ethynylpiperidine-1-carboxylate (29.0 g, 139 mmol) was dissolved in anhydrous 1,4-dioxane (400 mL). To this was added silver carbonate (19.1 g, 69.3 mmol) and the mixture heated to 100° C. Once this temperature was reached the flask was covered with aluminium foil and a solution of benzyl 2-isocyanoacetate (30.3 g, 173 mmol) in anhydrous 1,4-dioxane (150 mL) was added dropwise over 2 hours. Once added, the mixture was maintained at 100° C. for a further 2 hours then evaporated in vacuo, and the resulting black residue was diluted with 60% diethyl ether in petroleum ether. The mixture was flushed through a plug of silica, eluting with 60% diethyl ether in petroleum ether. The obtained fractions were then concentrated in vacuo, triturated with petroleum ether, and any volatiles removed in vacuo to afford the desired product as a pale yellow solid (44 g, 83%).

$^1H$ NMR (500 MHz, DMSO-$d_6$) δ 11.60 (br s, 1H), 7.56-7.28 (m, 5H), 6.90 (s, 1H), 6.12 (s, 1H), 5.27 (s, 2H), 4.11-3.90 (m, 2H), 3.27-3.17 (m, 1H), 2.60-2.50 (m, 2H), 1.75-1.65 (m, 2H), 1.45-1.32 (m, 11H).

LC-MS (Method A): $R_T$=3.95 min, m/z=383.4 $[M-H]^-$.

Step B: tert-Butyl 4-[2-benzyloxycarbonyl-1-(benzyloxycarbonylsulfamoyl)pyrrol-3-yl]piperidine-1-carboxylate, Sodium Salt A suspension of sodium hydride (60% in mineral oil, 5.62 g, 140 mmol) in anhydrous THF (100 mL) was cooled to −10° C. under a nitrogen atmosphere. This was followed by the dropwise addition of a solution of tert-butyl 4-(2-benzyloxycarbonyl-1H-pyrrol-3-yl)piperidine-1-carboxylate (18.0 g, 46.8 mmol) in THF (100 mL) over a period of 30 minutes, ensuring the temperature was maintained below −5° C. The reaction mixture was then allowed to stir for 1 hour at this temperature before re-cooling to −10° C. Benzyl N-chlorosulfonylcarbamate (12.8 g, 51.5 mmol) was added in 2 g batches every 5 minutes, ensuring that the temperature was maintained below −5° C. The reaction mixture was then allowed to warm to room temperature and stirred for 90 minutes before recooling to −10° C. and quenching by the dropwise addition of brine (250 mL). The reaction mixture was extracted into ethyl acetate (3×100 mL) and the combined organic phases washed with brine (200 mL), dried over $MgSO_4$, filtered and concentrated to dryness in vacuo. The residue was dissolved in DCM (30 mL), then diethyl ether was added with stirring, followed by 60% diethyl ether in petroleum ether to afford a cloudy solution. The mixture was stirred for 20 minutes and then filtered under an atmosphere of nitrogen. The obtained solid was re-suspended in diethyl ether, slurried for 30 minutes and filtered to afford the desired product as a colourless solid (23.4 g, 77%).

LC-MS (Method A): $R_T$=2.50 min, m/z=596.5 $[M-H]^-$.

Step C: Benzyl 1-(benzyloxycarbonylsulfamoyl)-3-(4-piperidyl)pyrrole-2-carboxylate hydrochloride tert-Butyl 4-[2-benzyloxycarbonyl-1-(benzyloxycarbonylsulfamoyl)pyrrol-3-yl]piperidine-1-carboxylate, sodium salt (5.60 g, 9.37 mmol) was dissolved in 1,4-dioxane (25 mL), then 4 M HCl in 1,4-dioxane (46.9 mL, 187 mmol) was added. The reaction was then stirred at room temperature for 3 hours before dilution with diethyl ether (100 mL). The product was isolated by trituration, washing with further portions of diethyl ether (2×50 mL) and dried under vacuum to afford the desired product as a colourless solid (4.40 g, 88%).

$^1H$ NMR (500 MHz, DMSO-$d_6$) δ 8.79-8.31 (m, 2H), 7.49-7.28 (m, 11H), 6.17 (br s, 1H), 5.30 (s, 2H), 5.04 (s, 2H), 3.29-3.20 (m, 2H), 3.13-3.02 (m, 1H), 2.76-2.62 (m, 2H), 1.82-1.61 (m, 4H).

LC-MS (Method A): $R_T$=2.71 min, m/z=496.5 $[M-H]^-$.

Further Intermediates

The following intermediates were prepared in a similar manner to benzyl 1-(benzyloxycarbonylsulfamoyl)-3-(4-piperidyl)pyrrole-2-carboxylate hydrochloride (Intermediate 6).

| Intermediate | Structure | Name | Analytical Data |
|---|---|---|---|
| Intermediate 7 | 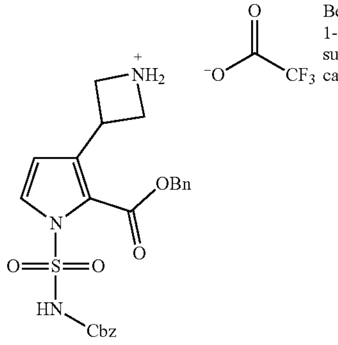 | Benzyl 3-(azetidin-3-yl)-1-(benzyloxycarbonylsulfamoyl)pyrrole-2-carboxylate, TFA salt | $^1H$ NMR (500 MHz, DMSO-$d_6$) δ 8.78 (br s, 1H), 8.52 (br s, 1H), 7.58-7.38 (m, 3H), 7.35-7.24 (m, 8H), 6.31 (d, J = 2.9 Hz, 1H), 5.21 (s, 2H), 4.85 (s, 2H), 4.34-4.14 (m, 1H), 4.10 (br d, J = 8.5 Hz, 2H), 3.99-3.90 (m, 2H). LC-MS (Method A): $R_T$ = 2.70 min, m/z = 470.2 $[M + H]^+$. |

-continued

| Intermediate | Structure | Name | Analytical Data |
|---|---|---|---|
| Intermediate 8* | 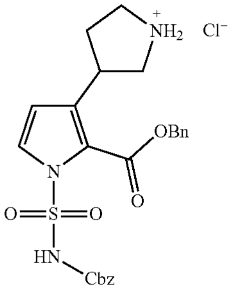 [SMILES: O=C(NS(=O)(=O)n1ccc(C2CCNC2)c1C(=O)OCc1ccccc1)OCc1ccccc1 ; [Cl-]] | Benzyl 1-(benzyloxycarbonyl-sulfamoyl)-3-[pyrrolidin-3-yl]pyrrole-2-carboxylate hydrochloride | LC-MS (Method A): $R_T$ = 2.76 min, m/z = 484.3 $[M + H]^+$. |
| Intermediate 9* | 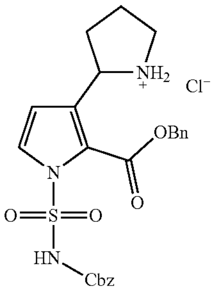 [SMILES: O=C(NS(=O)(=O)n1ccc(C2CCCN2)c1C(=O)OCc1ccccc1)OCc1ccccc1 ; [Cl-]] | Benzyl 1-(benzyloxycarbonyl-sulfamoyl)-3-[pyrrolidin-2-yl]pyrrole-2-carboxylate hydrochloride | $^1$H NMR (500 MHz, DMSO-$d_6$) δ 9.24 (br s, 1H), 8.72 (br s, 1H), 7.56-7.54 (m, 2H), 7.47-7.46 (1H), 7.36-7.29 (m, 8H), 6.44 (br s, 1H), 5.32 (s, 2H), 4.94 (s, 2H), 4.73 (dt, J = 14.6, 7.1 Hz, 2H), 3.29-3.17 (m, 2H), 2.23-2.16 (m, 1H), 2.09-2.02 (m, 1H), 1.98-1.88 (m, 1H). LC-MS (Method A): $R_T$ = 2.86 min, m/z = 482.5 $[M - H]^-$. |
| Intermediate 10* | 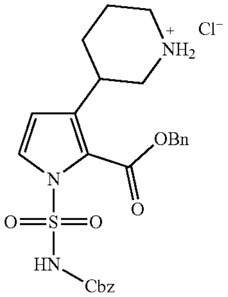 [SMILES: O=C(NS(=O)(=O)n1ccc(C2CCCNC2)c1C(=O)OCc1ccccc1)OCc1ccccc1 ; [Cl-]] | Benzyl 1-(benzyloxycarbonyl-sulfamoyl)-3-[3-piperidyl]pyrrole-2-carboxylate hydrochloride | $^1$H NMR (500 MHz, DMSO-$d_6$) δ 8.99 (br d, J = 9.8 Hz, 1H), 8.81 (br q, J = 10.7 Hz, 1H), 7.50 (d, J = 6.4 Hz, 2H), 7.44 (d, J = 3.4 Hz, 1H), 7.39-7.28 (m, 8H), 6.30 (d, J = 3.4 Hz, 1H), 5.36 (d, J = 12.5 Hz, 1H), 5.31 (d, J = 12.8 Hz, 1H), 5.04 (s, 2H), 3.41-3.33 (m, 1H), 3.22 (br t, J = 12.2 Hz, 2H), 2.97 (q, J = 11.6 Hz, 1H), 2.82 (q, J = 11.6 Hz, 1H), 1.77 (br t, J = 16.3 Hz, 2H), 1.70-1.49 (m, 2H). LC-MS (Method A): $R_T$ = 2.90 min, m/z = 498.3 $[M + H]^+$. |
| Intermediate 11* | 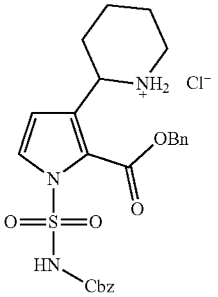 [SMILES: O=C(NS(=O)(=O)n1ccc(C2CCCCN2)c1C(=O)OCc1ccccc1)OCc1ccccc1 ; [Cl-]] | Benzyl 1-(benzyloxycarbonyl-sulfamoyl)-3-[2-piperidyl]pyrrole-2-carboxylate hydrochloride | $^1$H NMR (500 MHz, DMSO-$d_6$) δ 8.68 (br s, 1H), 8.48 (br s, 1H), 7.60-7.58 (m, 2H), 7.42-7.40 (m, 1H), 7.36-7.31 (m, 5H), 7.30-7.28 (m, 3H), 6.30-6.28 (m, 1H), 5.29 (d, J = 12.2 Hz , 1H), 5.24 (d, J = 12.2 Hz, 1H), 4.86 (s, 2H), 4.30-4.24 (m, 1H), 3.27-3.22 (m, 1H), 2.87-2.77 (m, 1H), 1.85-1.57 (m, 6H). LC-MS (Method A): $R_T$ = 2.96 min, m/z = 496.5 $[M - H]^-$. |
| Intermediate 12 | 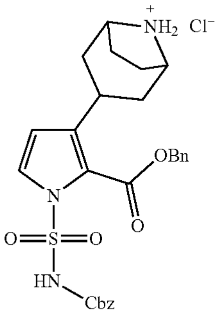 [SMILES: O=C(NS(=O)(=O)n1ccc(C2CC3CCC(C2)N3)c1C(=O)OCc1ccccc1)OCc1ccccc1 ; [Cl-]] | Benzyl 3-(8-azabicyclo[3.2.1]octan-3-yl)-1-(benzyloxycarbonyl-sulfamoyl)pyrrole-2-carboxylate hydrochloride | $^1$H NMR (500 MHz, DMSO-$d_6$) δ 9.20 (br s, 1H), 9.11 (br s, 1H), 7.52-7.29 (m, 11H), 6.30 (d, J = 3.4 Hz, 1H), 5.30 (s, 2H), 5.08 (s, 2H), 3.86 (s, 2H), 3.40-3.32 (m, 1H), 2.04 (t, J = 7.3 Hz, 2H), 1.79 (br s, 2H), 1.61-1.53 (m, 2H), 1.38-1.30 (m, 2H). LC-MS (Method B): $R_T$ = 2.74 min, m/z = 524.4 $[M + H]^+$. |

-continued

| Intermediate | Structure | Name | Analytical Data |
| --- | --- | --- | --- |
| Intermediate 13 | 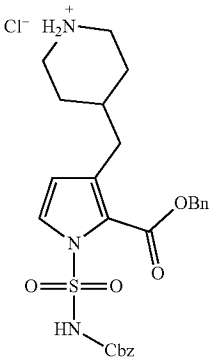 [SMILES: [Cl-] ; O=C(NS(=O)(=O)n1ccc(CC2CCNCC2)c1C(=O)OCc1ccccc1)OCc1ccccc1] | Benzyl 1-(benzyloxycarbonyl-sulfamoyl)-3-(4-piperidylmethyl)pyrrole-2-carboxylate hydrochloride | LC-MS (Method B): $R_T$ = 2.62 min, m/z = 510.4 $[M - H]^-$. |

*Although enantiopure starting materials were used, epimerisation of the chiral centre was observed during synthesis of these intermediates.

Intermediate 14: Benzyl 3-[1-(2-aminoacetyl)-4-piperidyl]-1-(benzyloxycarbonylsulfamoyl)pyrrole-2-carboxylate

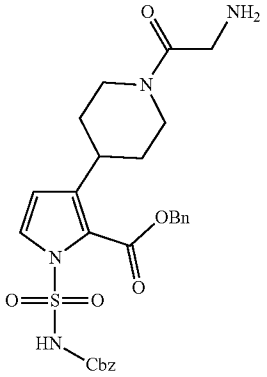 [SMILES: NCC(=O)N1CCC(c2ccn(S(=O)(=O)NC(=O)OCc3ccccc3)c2C(=O)OCc2ccccc2)CC1]

Step A: Benzyl 1-(benzyloxycarbonylsulfamoyl)-3-[1-[2-(tert-butoxycarbonylamino)acetyl]-4-piperidyl]pyrrole-2-carboxylate Benzyl 1-(benzyloxycarbonylsulfamoyl)-3-(4-piperidyl)pyrrole-2-carboxylate hydrochloride (250 mg, 0.47 mmol) was dissolved in DMF (5 mL), then DIPEA (408 µL, 2.34 mmol) was added. The reaction was stirred for 10 minutes, before addition of N-(tert-butoxycarbonyl)glycine (17 µL, 0.47 mmol) and HBTU (213 mg, 0.56 mmol). After stirring at room temperature for 2 hours, the reaction mixture was poured into 1 M aqueous HCl (50 mL), and the resulting solid isolated by filtration and dried under vacuum to afford the desired product as a colourless solid (244 mg, 79%).

$^1$H NMR (500 MHz, DMSO-$d_6$) δ 7.50 (br d, J=7.0 Hz, 2H), 7.44-7.27 (m, 10H), 6.72-6.64 (m, 1H), 6.21 (br d, J=2.7 Hz, 1H), 5.29 (s, 2H), 5.05 (s, 2H), 4.44-4.26 (m, 1H), 3.83-3.70 (m, 4H), 3.10-2.98 (m, 2H), 1.67-1.55 (m, 2H), 1.39 (s, 9H).

LC-MS (Method A): $R_T$=3.74 min, m/z=653.5 $[M-H]^-$.

Step B: Benzyl 3-[1-(2-aminoacetyl)-4-piperidyl]-1-(benzyloxycarbonylsulfamoyl)pyrrole-2-carboxylate Benzyl 1-(benzyloxycarbonylsulfamoyl)-3-[1-[2-(tert-butoxycarbonylamino)acetyl]-4-piperidyl]pyrrole-2-carboxylate (244 mg, 0.37 mmol) was dissolved in 4 M HCl in 1,4-dioxane (1.86 mL), then the reaction stirred at room temperature for 2 hours. Diethyl ether (20 mL) was added, resulting in formation of a colourless solid, which was isolated by filtration and free based on an SCX-2 cartridge eluting with ammonia in methanol to give the desired product as a colourless solid (180 mg, 87%).

$^1$H NMR (500 MHz, DMSO-$d_6$) δ 8.03 (br s, 3H), 7.50 (br d, J=6.9 Hz, 2H), 7.44-7.28 (m, 10H), 6.18 (d, J=3.1 Hz, 1H), 5.30 (s, 2H), 5.06 (s, 2H), 4.38 (br d, J=13.1 Hz, 1H), 3.95-3.76 (m, 2H), 3.69 (br d, J=13.5 Hz, 1H), 3.09 (tt, J=12.0, 3.5 Hz, 1H), 2.83 (br t, J=12.1 Hz, 1H), 2.41-2.39 (m, 1H), 1.66 (br d, J=13.0 Hz, 2H), 1.51 (dq, J=12.6, 3.8 Hz, 1H), 1.35-1.28 (m, 1H). $^1$H NMR is of hydrochloride salt, before passing material through SCX-2 cartridge.

LC-MS (Method A): $R_T$=2.84 min, m/z=553.4 $[M-H]^-$.

Intermediate 15: 4-[2-Benzyloxycarbonyl-1-(benzyloxycarbonylsulfamoyl)pyrrol-3-yl]cyclohex-3-ene-1-carboxylic acid

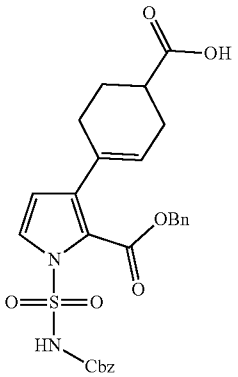 [SMILES: O=C(NS(=O)(=O)n1ccc(C2=CCC(C(=O)O)CC2)c1C(=O)OCc1ccccc1)OCc1ccccc1]

Step A: Benzyl 1-(benzyloxycarbonylsulfamoyl)-3-(4-ethoxycarbonylcyclohexen-1-yl)pyrrole-2-carboxylate A solution of potassium phosphate tribasic (891 mg, 4.20 mmol) in water (2 mL) was added to a solution of XPhos Pd G2 (55.0 mg, 69.9 µmol), sodium benzyloxycarbonyl-(2-benzyloxycarbonyl-3-bromo-pyrrol-1-yl)sulfonyl-azanide (690 mg, 1.40 mmol) and ethyl 4-(4,4,5,5-tetramethyl-1,3,2-dioxaborolan-2-yl)cyclohex-3-ene-1-carboxylate (470 mg, 1.68 mmol) in 1,4-dioxane (10 mL). The reaction mixture was heated to 50° C. under nitrogen and stirred for 6 hours. The mixture was allowed to cool to room temperature, and the resulting layers separated. The organic layer was diluted with brine (30 mL), and the aqueous phase extracted with ethyl acetate (3×20 mL). The combined organic phases were dried over $Na_2SO_4$, filtered and concentrated under reduced pressure. The residue was purified by column chromatography (0-100% ethyl acetate in petroleum ether) to afford the desired product (170 mg, 21%). A second batch of product was obtained from re-purification of mixed fractions (220 mg, 28%).

$^1$H NMR (500 MHz, DMSO-$d_6$) δ 7.49-7.47 (m, 2H), 7.35-7.24 (m, 8H), 7.12 (d, J=3.1 Hz, 1H), 5.99 (d, J=3.1 Hz, 1H), 5.65 (br s, 1H), 5.14 (d, J=3.7 Hz, 2H), 4.84 (s, 2H), 4.07 (q, J=7.0 Hz, 2H), 2.45-2.38 (m, 1H), 2.21-2.13 (m, 4H), 1.93-1.84 (m, 1H), 1.59-1.51 (m, 1H), 1.19 (t, J=7.0 Hz, 3H).

LC-MS (Method A): $R_T$=4.11 min, m/z=565.6 $[M-H]^-$.

Step B: 4-[2-Benzyloxycarbonyl-1-(benzyloxycarbonylsulfamoyl)pyrrol-3-yl]cyclohex-3-ene-1-carboxylic acid Benzyl 1-(benzyloxycarbonylsulfamoyl)-3-(4-ethoxycarbonylcyclohexen-1-yl)pyrrole-2-carboxylate (220 mg, 0.39 mmol) was dissolved in a mixture of ethanol (2 mL) and water (2 mL) followed by the addition of lithium hydroxide monohydrate (41 mg, 0.97 mmol). Stirring was continued at room temperature overnight, followed by the addition of additional lithium hydroxide monohydrate (41 mg, 0.97 mmol). After stirring for a further 24 hours, a third portion of lithium hydroxide monohydrate (41 mg, 0.97 mmol) was added. After a further 6 hours, the reaction was diluted with water and ethyl acetate, then separated. The aqueous layer was acidified with 2 M aqueous HCl (10 mL), then extracted with ethyl acetate (3×10 mL). The organic layer was dried over $Na_2SO_4$, filtered and concentrated in vacuo to afford the desired product as an orange gum (210 mg, 100%).

$^1$H NMR (500 MHz, DMSO-$d_6$) δ 7.47-7.28 (m, 11H), 6.20 (br s, 1H), 5.66 (br d, J=1.7 Hz, 1H), 5.23 (br s, 2H), 5.06 (br s, 2H), 2.34-2.25 (m, 1H), 2.21-2.05 (m, 4H), 1.91-1.81 (m, 1H), 1.53-1.42 (m, 1H).

LC-MS (Method A): $R_T$=3.34 min, m/z=537.5 $[M-H]^-$.

Intermediate 16: Benzyl 3-(4-aminocyclohexen-1-yl)-1-(benzyloxycarbonylsulfamoyl)pyrrole-2-carboxylate hydrochloride

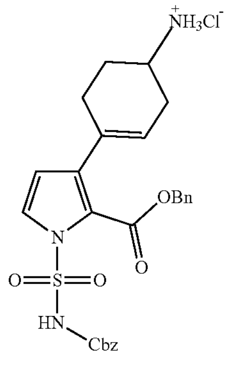

Step A: Benzyl 1-(benzyloxycarbonylsulfamoyl)-3-[4-(tert-butoxycarbonylamino)cyclohexen-1-yl]pyrrole-2-carboxylate To a solution of sodium benzyloxycarbonyl-(2-benzyloxycarbonyl-3-bromo-pyrrol-1-yl)sulfonyl-azanide (2.75 g, 5.57 mmol) and tert-butyl N-[4-(4,4,5,5-tetramethyl-1,3,2-dioxaborolan-2-yl)cyclohex-3-en-1-yl]carbamate (2.16 g, 6.69 mmol) in 1,4-dioxane (30 mL) under argon was added XPhos Pd G2 (219 mg, 279 μmol) followed by potassium phosphate tribasic (3.55 g, 16.7 mmol) and water (6 mL). The reaction mixture was stirred at 50° C. for 90 minutes then diluted with saturated aqueous ammonium chloride (50 mL) and water (50 mL) and extracted with ethyl acetate (2×75 mL). The combined organics were washed with brine (50 mL), dried over $MgSO_4$, filtered and concentrated to dryness. The residue was purified by column chromatography (0-100% ethyl acetate in petroleum ether) to give the desired product as a cream solid (2.49 g, 73%).

$^1$H NMR (500 MHz, $CDCl_3$) δ 7.42 (d, J=3.1 Hz, 1H), 7.21 (br d, J=6.1 Hz, 3H), 7.17-7.05 (m, 8H), 5.76 (br s, 1H), 5.23 (br s, 1H), 5.03-4.90 (m, 2H), 4.87 (s, 2H), 4.41-4.27 (m, 1H), 3.55 (br s, 1H), 2.13-1.86 (m, 4H), 1.77-1.54 (m, 1H), 1.45 (s, 9H), 1.20-1.10 (m, 1H).

LC-MS (Method A): $R_T$=3.96 min, m/z=608.6 $[M-H]^-$.

Step B: Benzyl 3-(4-aminocyclohexen-1-yl)-1-(benzyloxycarbonylsulfamoyl)pyrrole-2-carboxylate hydrochloride A solution of benzyl 1-(benzyloxycarbonylsulfamoyl)-3-[4-(tert-butoxycarbonylamino)cyclohexen-1-yl]pyrrole-2-carboxylate (2.49 g, 4.08 mmol) in 4 M HCl in 1,4-dioxane (30.6 mL) was stirred at 20° C. for 1 hour. The reaction mixture was concentrated to dryness and azeotroped with petroleum ether followed by diethyl ether to give the desired product as a cream solid (2.33 g, quantitative yield).

$^1$H NMR (500 MHz, DMSO-$d_6$) δ 8.20 (br s, 3H), 7.46-7.28 (m, 11H), 6.22 (br d, J=2.7 Hz, 1H), 5.60 (br s, 1H), 5.32-5.18 (m, 2H), 5.05 (s, 2H), 3.07 (br s, 1H), 2.45-2.29 (m, 1H), 2.21 (br s, 2H), 2.18-2.03 (m, 1H), 1.91 (br d, J=10.1 Hz, 1H), 1.65-1.53 (m, 1H).

LC-MS (Method A): $R_T$=2.83 min, m/z=508.5 $[M-H]^-$.

Intermediate 17: Benzyl N-[3-(3a,7a-dihydrobenzotriazol-1-yl)-3-oxo-propyl]carbamate

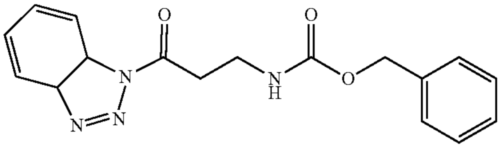 [SMILES: O=C(NCCC(=O)N1N=NC2C=CC=CC21)OCc1ccccc1]

Thionyl chloride (0.98 mL, 13.4 mmol) was added dropwise to a solution of benzotriazole (6.00 g, 50.4 mmol) in anhydrous THF (50 mL) and stirred for 30 minutes at room temperature under nitrogen. 3-(Benzyloxycarbonylamino)propanoic acid (2.5 g, 11.2 mmol) was added portionwise to the reaction mixture and stirred vigorously for 3 hours. The resulting solids were removed by filtration and the filtrates concentrated under reduced pressure. The residue was taken up in ethyl acetate (40 mL) and washed with 2 M aqueous HCl (2×20 mL), saturated aqueous sodium carbonate solution (2×20 mL), brine (10 mL). The remaining organic layer was dried over $MgSO_4$, filtered and concentrated under reduced pressure to afford the desired product as a white solid (3.42 g, 94%). This was used in subsequent steps without further purification.

Intermediate 18: tert-Butyl N-[2-[[5-(4,4,5,5-tetramethyl-1,3,2-dioxaborolan-2-yl)-2-pyridyl]amino]ethyl]carbamate

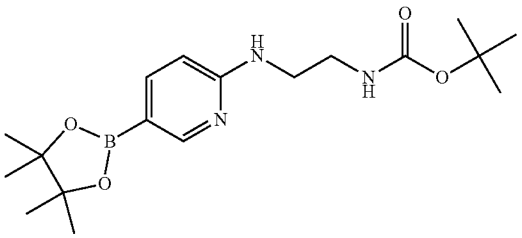 [SMILES: CC(C)(C)OC(=O)NCCNc1ccc(B2OC(C)(C)C(C)(C)O2)cn1]

A stirred solution of tert-butyl N-[2-[(5-bromo-2-pyridyl)amino]ethyl]carbamate (1.50 g, 4.74 mmol), bis(pinacolato)diboron (1.57 g, 6.17 mmol), Pd(dppf)$Cl_2$ (174 mg, 237 μmol) and potassium acetate (931 mg, 9.49 mmol) in 1,4-dioxane (30 mL) was degassed and heated at 90° C. under a nitrogen atmosphere for 3 hours. The reaction mixture was allowed to cool to room temperature, concentrated under reduced pressure, the residue suspended in diethyl ether (40 mL) and the solids removed by filtration. The filtrate was collected, washed with saturated aqueous sodium bicarbonate solution (2×30 mL), dried over $MgSO_4$, filtered and concentrated under reduced pressure. The residue was taken up in a minimum volume of DCM followed by the addition of excess petroleum ether. The resulting saturated solution was filtered and the collected filtrate concentrated under reduced pressure. The residue was purified by column chromatography (50-100% ethyl acetate in petroleum ether) to afford the desired product as a yellow gum (630 mg, 37%).

$^1$H NMR (500 MHz, DMSO-$d_6$) δ 8.21 (d, J=0.9 Hz, 1H), 7.03 (dd, J=8.3, 1.5 Hz, 1H), 6.91 (br t, J=4.8 Hz, 1H), 6.86 (br t, J=5.3 Hz, 1H), 6.41 (d, J=8.3 Hz, 1H), 3.30 (td, J=6.9, 4.8 Hz, 2H), 3.08 (td, J=6.6, 5.3 Hz, 2H), 1.38 (s, 9H), 1.26 (s, 12H).

LC-MS (Method B): $R_T$=3.30 min, m/z=364.3 $[M+H]^+$.

Example 1 (Free Acid): 3-[3-(Methylcarbamoyl)phenyl]-1-sulfamoyl-pyrrole-2-carboxylic

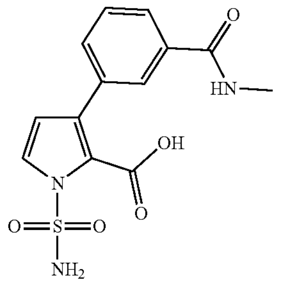 [SMILES: CNC(=O)c1cccc(-c2ccn(S(N)(=O)=O)c2C(=O)O)c1]

Step A: Benzyl 1-(benzyloxycarbonylsulfamoyl)-3-[3-(methylcarbamoyl)phenyl]pyrrole-2-carboxylate To a solution of benzyl 1-(benzyloxycarbonylsulfamoyl)-3-bromo-pyrrole-2-carboxylate (513 mg, 1.04 mmol) and N-methyl-3-(4,4,5,5-tetramethyl-1,3,2-dioxaborolan-2-yl)benzamide (272 mg, 1.04 mmol) in 1,4-dioxane (20 mL) was added XPhos Pd G2 (82 mg, 104 μmol), followed by a solution of potassium phosphate tribasic (662 mg, 3.12 mmol) in water (6 mL) and the reaction mixture heated to 45° C. for 2 hours. The reaction mixture was diluted with water (100 mL), 2 M aqueous HCl (20 mL) and brine (50 mL) and extracted with ethyl acetate (100 mL). The organic phase was dried over $MgSO_4$, filtered and the solvent removed in vacuo. Purification by column chromatography (0-100% ethyl acetate in petroleum ether) gave the desired product as a pale yellow solid (230 mg, 40%).

$^1$H NMR (500 MHz, DMSO-$d_6$) δ 8.46 (m, 1H), 7.85 (s, 1H), 7.74 (d, J=8.0 Hz, 1H), 7.46 (d, J=3.0 Hz, 1H), 7.43 (d, J=8.0 Hz, 1H), 7.37 (d, J=8.0 Hz, 1H), 7.36-7.32 (m, 5H), 7.28-7.23 (m, 3H), 7.20 (m, 2H), 6.45 (d, J=3.0 Hz, 1H), 5.17 (s, 2H), 5.06 (s, 2H), 2.79 (d, J=4.5 Hz, 3H).

LC-MS (Method B): $R_T$=2.29 min, m/z=546.6 $[M-H]^-$.

Step B: 3-[3-(Methylcarbamoyl)phenyl]-1-sulfamoyl-pyrrole-2-carboxylic acid

10% Palladium on carbon (20 mg, 197 μmol) was added to a solution of benzyl 1-(benzyloxycarbonylsulfamoyl)-3-[3-(methylcarbamoyl)phenyl]pyrrole-2-carboxylate (223 mg, 407 μmol) in methanol (20 mL) and stirred under a hydrogen atmosphere for 90 minutes. The reaction mixture was filtered through a pad of Celite® and eluted with methanol (150 mL). The solvent was removed in vacuo, purified by column chromatography (0-100% methanol in ethyl acetate) and triturated with diethyl ether to give the desired product as a white solid (60 mg, 41%).

$^1$H NMR (500 MHz, DMSO-$d_6$) δ 8.62 (br s, 1H), 8.42 (br d, J=4.5 Hz, 1H), 7.89 (s, 1H), 7.69 (d, J=7.5 Hz, 1H), 7.63 (d, J=7.5 Hz, 1H), 7.40 (t, J=7.5 Hz, 1H), 7.27 (m, 1H), 6.33 (d, J=3.0 Hz, 1H), 2.78 (d, J=4.5 Hz, 3H).

LC-MS (Method A): $R_T$=2.24 min, m/z=322.4 $[M-H]^-$

Example 2 (Free Acid): 3-[4-(Dimethylcarbamoyl)phenyl]-1-sulfamoyl-pyrrole-2-carboxylic acid

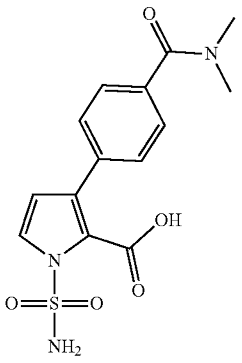 [SMILES: CN(C)C(=O)c1ccc(-c2ccn(S(N)(=O)=O)c2C(=O)O)cc1]

Step A: Benzyl 1-(benzyloxycarbonylsulfamoyl)-3-[4-(dimethylcarbamoyl)phenyl]pyrrole-2-carboxylate HBTU (101 mg, 267 μmol) was added to a solution of 4-[2-benzyloxycarbonyl-1-(benzyloxycarbonylsulfamoyl)pyrrol-3-yl]benzoic acid (119 mg, 223 μmol), 2 M dimethylamine in THF (134 μL) and DIPEA (116 μL, 668 μmol) in dichloromethane (20 mL) and the reaction stirred at room temperature overnight. The reaction was quenched by addition of water (100 mL) and extracted into DCM (2×100 mL). The combined organic phases were dried over $MgSO_4$, filtered and the solvent removed in vacuo. Purification by column chromatography (0-100% ethyl acetate in petroleum ether) followed by 0-40% methanol in ethyl acetate gave the desired product as a white solid (74 mg, 59%).

$^1$H NMR (500 MHz, $CDCl_3$) δ 7.39-7.36 (m, 4H), 7.33-7.27 (m, 11H), 6.28 (d, J=3.0 Hz, 1H), 5.15 (s, 2H), 4.86 (s, 2H), 2.89 (br s, 3H), 2.93 (br s, 3H).

LC-MS (Method B): $R_T$=2.28 min, m/z=560.5 [M−H]$^-$.

Step B: 3-[4-(Dimethylcarbamoyl)phenyl]-1-sulfamoyl-pyrrole-2-carboxylic acid

10% Palladium on carbon (7 mg, 64 μmol) was added to a solution of benzyl 1-(benzyloxycarbonylsulfamoyl)-3-[4-(dimethylcarbamoyl)phenyl]pyrrole-2-carboxylate (74 mg, 132 μmol) in methanol (20 mL) and stirred under 1 atmosphere hydrogen at room temperature for 90 minutes. The reaction mixture was filtered through a pad of Celite® and eluted with methanol (150 mL). The solvent was removed in vacuo and purified by column chromatography (0-100% methanol in ethyl acetate) then trituration with diethyl ether to give the desired product as a white solid (20 mg, 45%).

$^1$H NMR (500 MHz, DMSO-$d_6$) δ 8.33 (br s, 2H), 7.61 (d, J=8.0 Hz, 2H), 7.32 (d, J=8.0 Hz, 2H), 7.10 (d, J=3.0 Hz, 1H), 6.27 (d, J=3.0 Hz, 1H), 2.98 (br s, 6H).

LC-MS (Method A): $R_T$=2.34 min, m/z=336.4 [M−H]$^-$.

Further Examples

The following examples were prepared in a similar manner to 3-[4-(dimethylcarbamoyl)phenyl]-1-sulfamoyl-pyrrole-2-carboxylic acid (Example 2).

| Example | Structure | Name | Analytical Data |
|---|---|---|---|
| Example 3 (free acid)* | 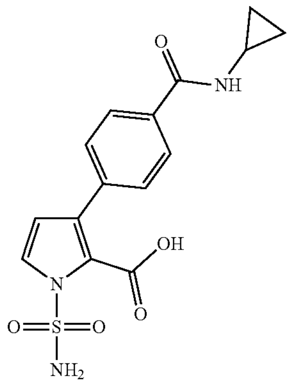 [SMILES: NS(=O)(=O)n1ccc(-c2ccc(C(=O)NC3CC3)cc2)c1C(=O)O] | 3-[4-(Cyclopropylcarbamoyl)phenyl]-1-sulfamoyl-pyrrole-2-carboxylic acid | $^1$H NMR (500 MHz, DMSO-$d_6$) δ 8.83 (br s, 2H), 8.40 (d, J = 4.0 Hz, 1H), 7.74 (d, J = 8.0 Hz, 2H), 7.61 (d, J = 8.0 Hz, 2H), 7.09 (d, J = 3.0 Hz, 1H), 6.28 (d, J = 3.0 Hz, 1H), 2.85 (tq, J = 7.5, 4.0 Hz, 1H), 0.69 (m, 2H), 0.59 (m, 2H). LC-MS (Method A): $R_T$ = 2.42 min, m/z = 348.3 [M − H]$^-$. |
| Example 4 (free acid)†† | 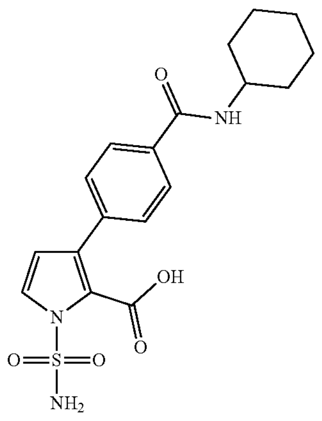 [SMILES: NS(=O)(=O)n1ccc(-c2ccc(C(=O)NC3CCCCC3)cc2)c1C(=O)O] | 3-[4-(Cyclohexylcarbamoyl)phenyl]-1-sulfamoyl-pyrrole-2-carboxylic acid | $^1$H NMR (500 MHz, DMSO-$d_6$) δ 8.72 (br s, 2H), 8.14 (d, J = 8.0 Hz, 1H), 7.77 (d, J = 8.0 Hz, 2H), 7.59 (d, J = 8.0 Hz, 2H), 7.16 (d, J = 3.0 Hz, 1H), 6.30 (d, J = 3.0 Hz, 1H), 3.76 (m, 1H), 1.82 (m, 2H), 1.74 (m, 2H), 1.62 (m, 1H), 1.34-1.29 (m, 4H), 1.12 (m, 1H). LC-MS (Method A): $R_T$ = 3.00 min, m/z = 390.5 [M − H]$^-$. |

-continued

| Example | Structure | Name | Analytical Data |
|---|---|---|---|
| Example 5 (free acid)†† | 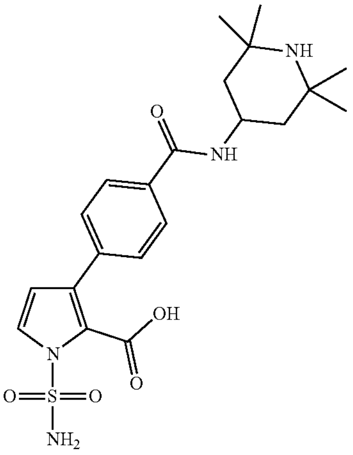 [SMILES: CC1(C)CC(NC(=O)c2ccc(-c3ccn(S(N)(=O)=O)c3C(=O)O)cc2)CC(C)(C)N1] | 1-Sulfamoyl-3-[4-[(2,2,6,6-tetramethyl-4-piperidyl)carbamoyl]phenyl] pyrrole-2-carboxylic acid | $^1$H NMR (500 MHz, DMSO-$d_6$) δ 9.07 (br s, 2H), 8.33 (br s, 1H), 7.74 (d, J = 8.4 Hz, 2H), 7.63 (d, J = 8.4 Hz, 2H), 7.05 (d, J = 3.1 Hz, 1H), 6.26 (d, J = 3.1 Hz, 1H), 4.39-4.30 (m, 1H), 1.99-1.92 (m, 2H), 1.60-1.48 (m, 2H), 1.46-1.31 (m, 12H). LC-MS (Method A): $R_T$ = 2.27 min, m/z = 447.5 [M − H]$^-$. |
| Example 6 (free acid)* | 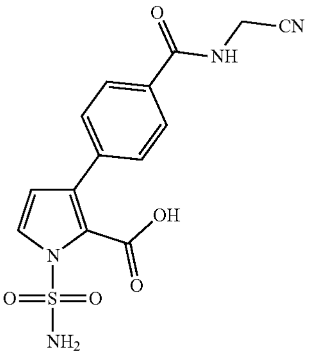 [SMILES: N#CCNC(=O)c1ccc(-c2ccn(S(N)(=O)=O)c2C(=O)O)cc1] | 3-[4-(Cyanomethyl-carbamoyl)phenyl]-1-sulfamoyl-pyrrole-2-carboxylic acid | $^1$H NMR (500 MHz, DMSO-$d_6$) δ 9.25 (br t, J = 5.1 Hz, 1H), 9.00 (br s, 2H), 7.79 (br d, J = 8.2 Hz, 2H), 7.69 (d, J = 8.4 Hz, 2H), 7.06 (br d, J = 2.7 Hz, 1H), 6.29 (br s, 1H), 4.32 (d, J = 5.3 Hz, 2H). LC-MS (method A): $R_T$ = 2.35 min, m/z = 347.3 [M − H]$^-$. |
| Example 7 (free acid)** | 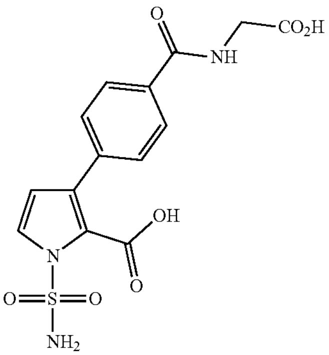 [SMILES: NS(=O)(=O)n1ccc(-c2ccc(C(=O)NCC(=O)O)cc2)c1C(=O)O] | 3-[4-(Carboxymethyl-carbamoyl)phenyl]-1-sulfamoyl-pyrrole-2-carboxylic acid | $^1$H NMR (500 MHz, DMSO-$d_6$) δ 8.94 (br s, 2H), 8.65 (br s, 1H), 7.78 (d, J = 8.0 Hz, 2H), 7.64 (d, J = 8.0 Hz, 2H), 7.07 (d, J = 3.0 Hz, 1H), 6.29 (d, J = 3.0 Hz, 1H), 3.88 (d, J = 5.0 Hz, 2H). LC-MS (Method A): $R_T$ = 2.11 min, m/z = 366.4 [M − H]$^-$. |
| Example 8 (free acid) | 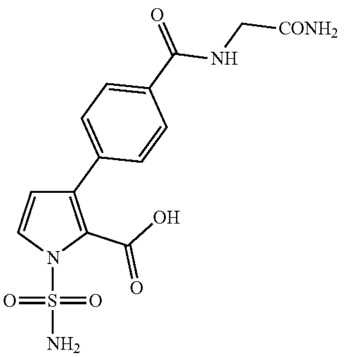 [SMILES: NC(=O)CNC(=O)c1ccc(-c2ccn(S(N)(=O)=O)c2C(=O)O)cc1] | 3-[4-[(2-Amino-2-oxo-ethyl)carbamoyl]phenyl]-1-sulfamoyl-pyrrole-2-carboxylic acid | $^1$H NMR (500 MHz, DMSO-$d_6$) δ 8.93 (br s, 2H), 8.62 (t, J = 6.0 Hz, 1H), 7.80 (d, J = 8.5 Hz, 2H), 7.65 (d, J = 8.5 Hz, 2H), 7.37 (br s, 1H), 7.09 (d, J = 3.0 Hz, 1H), 7.03 (br s, 1H), 6.30 (d, J = 3.0 Hz, 1H), 3.82 (d, J = 6.0 Hz, 2H). LC-MS (Method A): $R_T$ = 2.00 min, m/z = 365.4 [M − H]$^-$. |

-continued

| Example | Structure | Name | Analytical Data |
|---|---|---|---|
| Example 9 (free acid)†† | 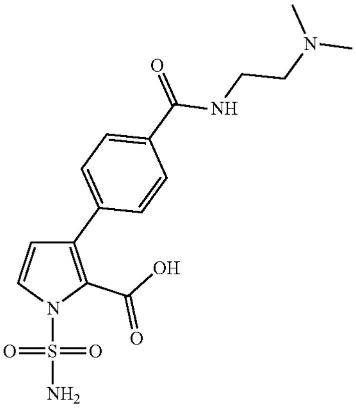 [SMILES: CN(C)CCNC(=O)c1ccc(-c2ccn(S(N)(=O)=O)c2C(=O)O)cc1] | 3-[4-[2-(Dimethylamino) ethylcarbamoyl]phenyl]-1-sulfamoyl-pyrrole-2-carboxylic acid | $^1$H NMR (500 MHz, DMSO-$d_6$) δ 9.02 (br s, 2H), 8.44 (m, 1H), 7.75 (d, J = 8.0 Hz, 2H), 7.61 (d, J = 8.0 Hz, 2H), 7.06 (d, J = 3.0 Hz, 1H), 6.27 (d, J = 3.0 Hz, 1H), 3.41-3.37 (m, 4H), 2.25 (s, 6H). LC-MS (Method A): $R_T$ = 1.92 min, m/z = 379.5 $[M - H]^-$. |
| Example 10 (free acid) | 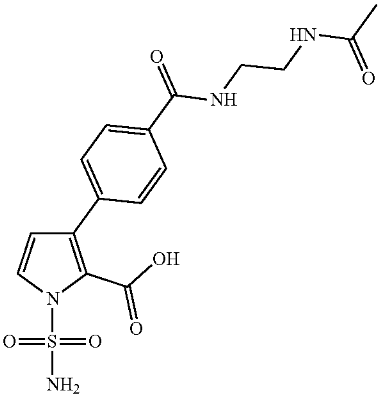 [SMILES: CC(=O)NCCNC(=O)c1ccc(-c2ccn(S(N)(=O)=O)c2C(=O)O)cc1] | 3-[4-(2-Acetamidoethyl-carbamoyl)phenyl]-1-sulfamoyl-pyrrole-2-carboxylic acid | $^1$H NMR (500 MHz, DMSO-$d_6$) δ 8.81 (br s, 2H), 8.50 (t, J = 5.0 Hz, 1H), 8.02 (t, J = 5.5 Hz, 1H), 7.77 (d, J = 8.5 Hz, 2H), 7.61 (d, J = 8.5 Hz, 2H), 7.12 (d, J = 3.0 Hz, 1H), 6.30 (d, J = 3.0 Hz, 1H), 3.31 (m, 2H), 3.22 (m, 2H), 1.82 (s, 3H). LC-MS (Method A): $R_T$ = 2.16 min, m/z = 393.4 $[M - H]^-$. |
| Example 11 (free acid)* | 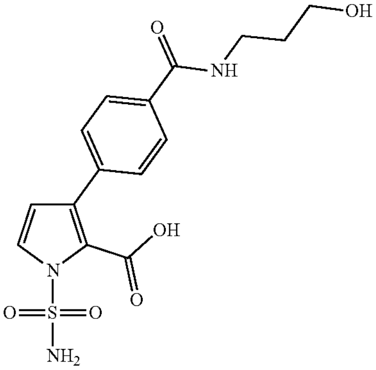 [SMILES: NS(=O)(=O)n1ccc(-c2ccc(C(=O)NCCCO)cc2)c1C(=O)O] | 3-[4-(3-Hydroxypropyl-carbamoyl)phenyl]-1-sulfamoyl-pyrrole-2-carboxylic acid | $^1$H NMR (500 MHz, DMSO-$d_6$) δ 8.96 (br s, 2H), 8.42 (t, J = 5.5 Hz, 1H), 7.75 (d, J = 8.5 Hz, 2H), 7.62 (d, J = 8.5 Hz, 2H), 7.07 (d, J = 3.0 Hz, 1H), 6.27 (d, J = 3.0 Hz, 1H), 4.51 (br s, 1H), 3.47 (m, 2H), 3.32 (m, 2H), 1.68 (quin, J = 6.5 Hz, 2H). LC-MS (Method A): $R_T$ = 2.12 min, m/z = 366.3 $[M - H]^-$. |
| Example 12 (free acid)†† | 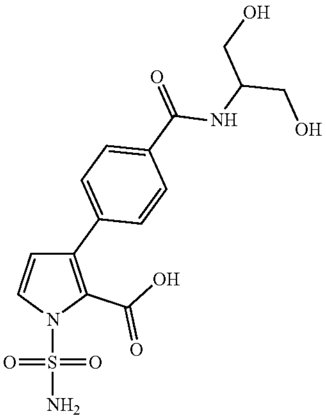 [SMILES: NS(=O)(=O)n1ccc(-c2ccc(C(=O)NC(CO)CO)cc2)c1C(=O)O] | 3-[4-[[2-Hydroxy-1-(hydroxymethyl)ethyl] carbamoyl]phenyl]-1-sulfamoyl-pyrrole-2-carboxylic acid | $^1$H NMR (500 MHz, DMSO-$d_6$) δ 8.94 (br s, 2H), 7.90 (d, J = 8.0 Hz, 1H), 7.78 (d, J = 8.0 Hz, 2H), 7.61 (d, J = 8.0 Hz, 2H), 7.10 (d, J = 3.0 Hz, 1H), 6.29 (d, J = 3.0 Hz, 1H), 4.67 (br s, 2H), 3.96 (m, 1H), 3.53 (m, 4H). LC-MS (Method A): $R_T$ = 1.88 min, m/z = 382.4 $[M - H]^-$. |

-continued

| Example | Structure | Name | Analytical Data |
|---|---|---|---|
| Example 13 (free acid)†† | 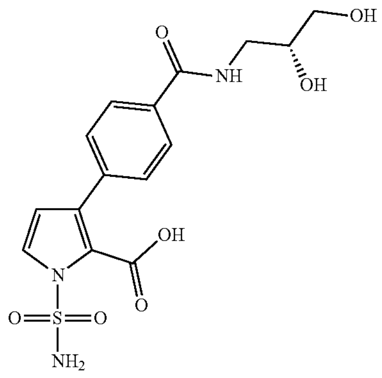 [SMILES: NS(=O)(=O)n1ccc(-c2ccc(C(=O)NC[C@@H](O)CO)cc2)c1C(=O)O] | 3-[4-[[(2R)-2,3-Dihydroxypropyl]carbamoyl]phenyl]-1-sulfamoyl-pyrrole-2-carboxylic acid | $^1$H NMR (500 MHz, DMSO-$d_6$) δ 8.98 (br s, 2H), 8.36 (t, J = 5.5 Hz, 1H), 7.77 (d, J = 8.5 Hz, 2H), 7.61 (d, J = 8.5 Hz, 2H), 7.08 (m, 1H), 6.28 (d, J = 3.0 Hz, 1H), 4.84 (d, J = 4.5 Hz, 1H), 4.58 (m, 1H), 3.64 (m, 1H), 3.43-3.37 (m, 3H), 3.23-3.17 (m, 1H). LC-MS (Method A): $R_T$ = 1.95 min, m/z = 382.4 $[M - H]^-$. |
| Example 14 (free acid) | 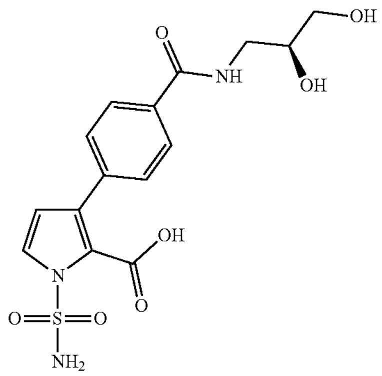 [SMILES: NS(=O)(=O)n1ccc(-c2ccc(C(=O)NC[C@H](O)CO)cc2)c1C(=O)O] | 3-[4-[[(2S)-2,3-Dihydroxypropyl]carbamoyl]phenyl]-1-sulfamoyl-pyrrole-2-carboxylic acid | $^1$H NMR (500 MHz, DMSO-$d_6$) δ 9.06 (br s, 2H), 8.34 (t, J = 5.7 Hz, 1H), 7.77 (d, J = 8.4 Hz, 2H), 7.62 (d, J = 8.4 Hz, 2H), 7.01 (d, J = 3.1 Hz, 1H), 6.27 (d, J = 3.1 Hz, 1H), 4.84 (d, J = 4.9 Hz, 1H), 4.57 (t, J = 5.8 Hz, 1H), 3.67-3.62 (m, 1H), 3.43-3.37 (m, 2H), 3.24-3.17 (m, 2H). The multiplet at 3.43-3.37 ppm is obscured by NMR solvent peak. LC-MS (Method A): $R_T$ = 1.96 min, m/z = 382.4 $[M - H]^-$. |
| Example 15 (free acid) | 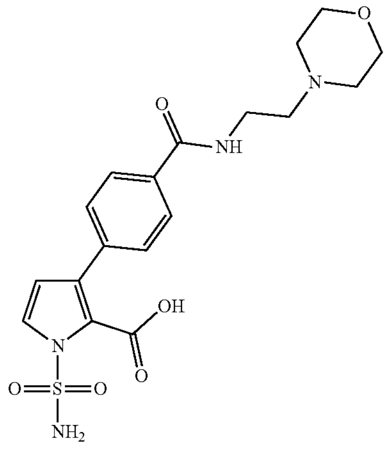 [SMILES: NS(=O)(=O)n1ccc(-c2ccc(C(=O)NCCN3CCOCC3)cc2)c1C(=O)O] | 3-[4-(2-Morpholinoethylcarbamoyl)phenyl]-1-sulfamoyl-pyrrole-2-carboxylic acid | $^1$H NMR (500 MHz, DMSO-$d_6$) δ 9.07 (br s, 2H), 8.34 (br t, J = 5.4 Hz, 1H), 7.74 (d, J = 8.2 Hz, 2H), 7.62 (d, J = 8.2 Hz, 2H), 7.06-7.04 (m, 1H), 6.27 (d, J = 3.1 Hz, 1H), 3.58 (t, J = 4.5 Hz, 4H), 3.42-3.37 (m, 2H), 2.49-2.46 (m, 2H), 2.44-2.41 (m, 4H). The multiplet at 2.49-2.46 ppm is partially obscured by NMR solvent peak. LC-MS (Method A): $R_T$ = 1.84 min, m/z = 421.5 $[M - H]^-$. |

-continued

| Example | Structure | Name | Analytical Data |
|---|---|---|---|
| Example 16 (free acid) | 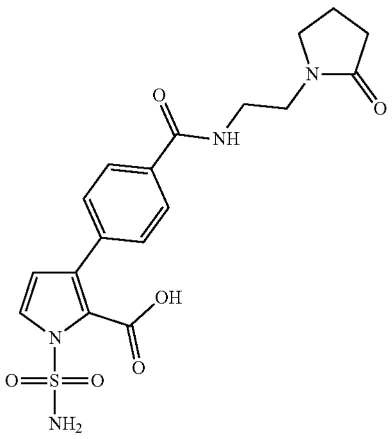 [SMILES: NS(=O)(=O)n1ccc(-c2ccc(C(=O)NCCN3CCCC3=O)cc2)c1C(=O)O] | 3-[4-[2-(2-Oxopyrrolidin-1-yl)ethylcarbamoyl]phenyl]-1-sulfamoyl-pyrrole-2-carboxylic acid | $^{1}$H NMR (500 MHz, DMSO-$d_6$) δ 9.08 (br s, 2H), 8.47 (t, J = 5.5 Hz, 1H), 7.71 (d, J = 8.3 Hz, 2H), 7.62 (d, J = 8.3 Hz, 2H), 7.05 (d, J = 3.0 Hz, 1H), 6.27 (d, J = 3.0 Hz, 1H), 3.44-3.55 (m, 6H), 2.19 (t, J = 8.2 Hz, 2H), 1.91 (quin, J = 7.5 Hz, 2H). The multiplet at 3.44-3.55 ppm is partially obscured by residual water peak. LC-MS (Method A): $R_T$ = 2.28 min, m/z = 419.4 $[M - H]^-$. |
| Example 17 (ammonium salt)†† | 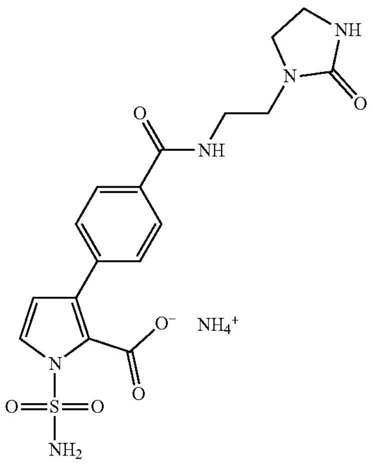 [SMILES: NS(=O)(=O)n1ccc(-c2ccc(C(=O)NCCN3CCNC3=O)cc2)c1C(=O)[O-] ; [NH4+]] | 3-[4-[2-(2-Oxoimidazolidin-1-yl)ethylcarbamoyl]phenyl]-1-sulfamoyl-pyrrole-2-carboxylic acid, ammonium salt | $^{1}$H NMR (500 MHz, DMSO-$d_6$) δ 8.47 (br s, 1H), 7.74 (br d, J = 7.0 Hz, 2H), 7.62 (br d, J = 7.0 Hz, 2H), 8.00-7.40 (br s, 2H), 7.05 (br s, 1H), 6.29 (br d, J = 17.4 Hz, 2H), 3.48-3.16 (m, 8H). LC-MS (Method A): $R_T$ = 2.14 min, m/z = 420.4 $[M - H]^-$. |
| Example 18 (free acid) | 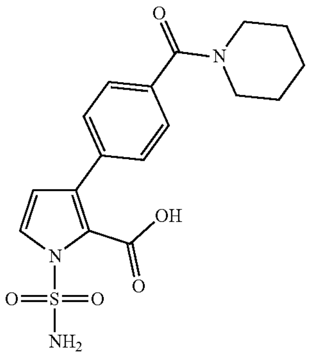 [SMILES: NS(=O)(=O)n1ccc(-c2ccc(C(=O)N3CCCCC3)cc2)c1C(=O)O] | 3-[4-(Piperidine-1-carbonyl)phenyl]-1-sulfamoyl-pyrrole-2-carboxylic acid | $^{1}$H NMR (500 MHz, DMSO-$d_6$) δ 8.87 (br s, 2H), 7.61 (d, J = 8.0 Hz, 2H), 7.27 (d, J = 8.0 Hz, 2H), 7.10 (d, J = 3.0 Hz, 1H), 6.26 (d, J = 3.0 Hz, 1H), 3.57 (br s, 2H), 3.40-3.30 (m, 2H), 1.62 (m, 2H), 1.52 (br s, 4H). Peak at 3.40-3.30 ppm obscured by residual water peak. LC-MS (Method A): $R_T$ = 2.76 min, m/z = 376.4 $[M - H]^-$. |

-continued

| Example | Structure | Name | Analytical Data |
| --- | --- | --- | --- |
| Example 19 (free acid) | 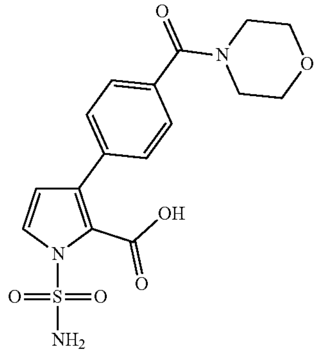 [SMILES: NS(=O)(=O)n1ccc(-c2ccc(C(=O)N3CCOCC3)cc2)c1C(=O)O] | 3-[4-(Morpholine-4-carbonyl)phenyl]-1-sulfamoyl-pyrrole-2-carboxylic acid | $^1$H NMR (500 MHz, DMSO-$d_6$) δ 8.95 (br s, 2H), 7.62 (d, J = 8.0 Hz, 2H), 7.32 (d, J = 8.0 Hz, 2H), 7.08 (d, J = 3.0 Hz, 1H), 6.26 (d, J = 3.0 Hz, 1H), 3.66-3.42 (m, 8H). LC-MS (Method A): $R_T$ = 2.19 min, m/z = 378.4 $[M - H]^-$. |
| Example 20 (free acid) | 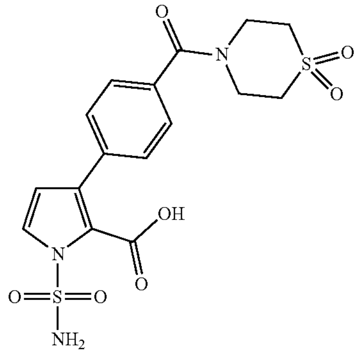 [SMILES: NS(=O)(=O)n1ccc(-c2ccc(C(=O)N3CCS(=O)(=O)CC3)cc2)c1C(=O)O] | 3-[4-(1,1-Dioxo-1,4-thiazinane-4-carbonyl)phenyl]-1-sulfamoyl-pyrrole-2-carboxylic acid | $^1$H NMR (500 MHz, DMSO-$d_6$) δ 9.01 (br s, 2H), 7.64 (d, J = 8.2 Hz, 2H), 7.40 (d, J = 8.2 Hz, 2H), 7.03 (d, J = 3.1 Hz, 1H), 6.25 (d, J = 3.1 Hz, 1H), 3.88 (br s, 4H), 3.26 (br s, 4H). LC-MS (Method A): $R_T$ = 2.31 min, m/z = 426.4 $[M - H]^-$. |
| Example 21 (free acid) | 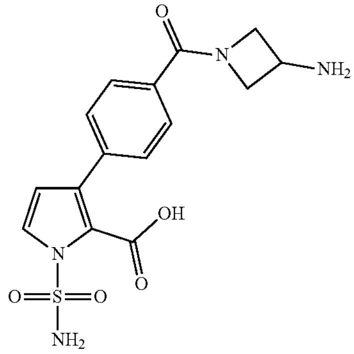 [SMILES: NC1CN(C(=O)c2ccc(-c3ccn(S(N)(=O)=O)c3C(=O)O)cc2)C1] | 3-[4-(3-Aminoazetidine-1-carbonyl)phenyl]-1-sulfamoyl-pyrrole-2-carboxylic acid | $^1$H NMR (500 MHz, DMSO-$d_6$) δ 7.63 (d, J = 8.5 Hz, 2H), 7.52 (d, J = 8.5 Hz, 2H), 7.04 (d, J = 3.0 Hz, 1H), 6.26 (d, J = 3.0 Hz, 1H), 4.45 (m, 1H), 4.19 (m, 1H), 3.93 (m, 1H), 3.73 (m, 1H), 3.66 (m, 1H). LC-MS (Method A): $R_T$ = 1.54 min, m/z = 363.3 $[M - H]^-$. |
| Example 22 (free acid) | 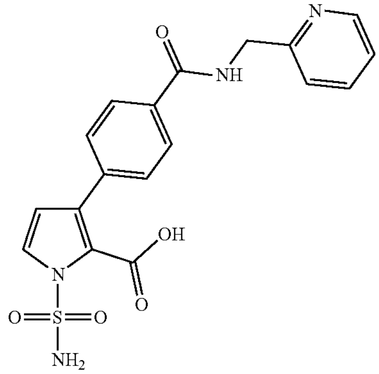 [SMILES: NS(=O)(=O)n1ccc(-c2ccc(C(=O)NCc3ccccn3)cc2)c1C(=O)O] | 3-[4-(2-Pyridylmethylcarbamoyl)phenyl]-1-sulfamoyl-pyrrole-2-carboxylic acid | $^1$H NMR (500 MHz, DMSO-$d_6$) δ 9.08 (t, J = 6.0 Hz, 1H), 8.95 (br s, 2H), 8.52 (d, J = 4.5 Hz, 1H), 7.84 (d, J = 8.5 Hz, 2H), 7.76 (td, J = 8.0, 1.5 Hz, 1H), 7.66 (d, J = 8.5 Hz, 2H), 7.31 (d, J = 8.0 Hz, 1H), 7.27 (dd, J = 7.0, 5.0 Hz, 1H), 7.09 (d, J = 3.0 Hz, 1H), 6.29 (d, J = 3.0 Hz, 1H), 4.58 (d, J = 6.0 Hz, 2H). LC-MS (Method A): $R_T$ = 2.10 min, m/z = 399.4 $[M - H]^-$. |

-continued

| Example | Structure | Name | Analytical Data |
|---|---|---|---|
| Example 23 (hydrochloride salt)*** | 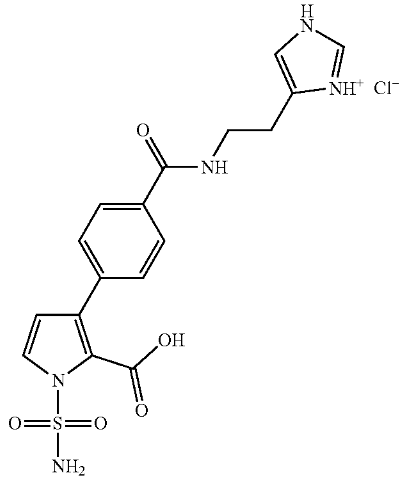 [SMILES: NS(=O)(=O)n1ccc(-c2ccc(C(=O)NCCc3c[nH]c[nH+]3)cc2)c1C(=O)O ; [Cl-]] | 3-[4-[2-(1H-lmidazol-4-yl)ethylcarbamoyl]phenyl]-1-sulfamoyl-pyrrole-2-carboxylic acid hydrochloride | $^1$H NMR (500 MHz, DMSO-$d_6$) δ 14.09 (br s, 2H), 8.96 (s, 1H), 8.70 (t, J = 5.6 Hz, 1H), 8.26 (br s, 2H), 7.83 (d, J = 8.2 Hz, 2H), 7.50-7.42 (m, 4H), 6.42 (d, J = 3.1 Hz, 1H), 3.58 (q, J = 6.6 Hz, 2H), 2.98-2.90 (m, 2H). LC-MS (Method A): $R_T$ = 2.07 min, m/z = 402.3 $[M - H]^-$. |
| Example 24 (free acid)†† | 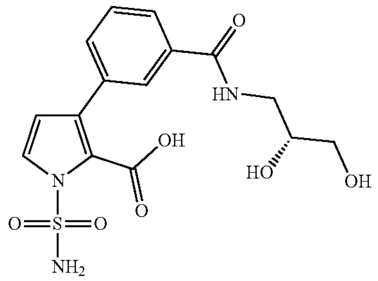 [SMILES: NS(=O)(=O)n1ccc(-c2cccc(C(=O)NC[C@@H](O)CO)c2)c1C(=O)O] | 3-[3-[[(2R)-2,3-Dihydroxy-propyl]carbamoyl]phenyl]-1-sulfamoyl-pyrrole-2-carboxylic acid | $^1$H NMR (500 MHz, DMSO-$d_6$) δ 9.10 (br s, 2H), 8.34 (t, J = 5.5 Hz, 1H), 7.93 (br s, 1H), 7.72 (br d, J = 7.5 Hz, 1H), 7.65 (br d, J = 7.5 Hz, 1H), 7.35 (t, J = 7.5 Hz, 1H), 7.09 (d, J = 3.0 Hz, 1H), 6.26 (d, J = 3.0 Hz, 1H), 4.84 (br d, J = 5.0 Hz, 1H), 4.59 (br t, J = 5.0 Hz, 1H), 3.68-3.62 (m, 1H), 3.42-3.38 (m, 1H), 3.38-3.32 (m, 2H), 3.22 (dd, J = 13.5, 6.5 Hz, 1H). The peak at 3.40-3.32 ppm is partially obscured by residual water peak. LC-MS (Method A): $R_T$ = 0.33 min, m/z = 382.4 $[M - H]^-$. |

*The amide coupling step was performed using DMF as solvent. Amide coupling was performed using the benzyl protected carboxylic acid. *The hydrochloride salt was formed prior to hydrogenation. ††The hydrogenation step was performed with the addition of a solution of ammonia in methanol to ensure solubility.

Example 25 (Free Acid): 3-[4-[Methyl-[2-(methylamino)ethyl]carbamoyl]phenyl]-1-sulfamoyl-pyrrole-2-carboxylic acid

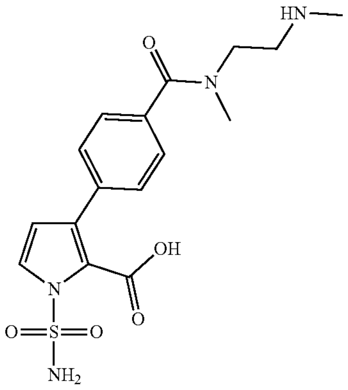 [SMILES: CNCCN(C)C(=O)c1ccc(-c2ccn(S(N)(=O)=O)c2C(=O)O)cc1]

Step A: Benzyl 3-[4-[2-[Benzyloxycarbonyl(methyl)amino]ethyl-methyl-carbamoyl]phenyl]-1-(benzyloxycarbonylsulfamoyl)pyrrole-2-carboxylate To a stirred suspension of 4-[2-benzyloxycarbonyl-1-(benzyloxycarbonylsulfamoyl)pyrrol-3-yl]benzoic acid (19.1 g, 35.7 mmol) in DCM (150 mL) was added DIPEA (31.1 mL, 179 mmol) followed by HBTU (14.9 g, 39.3 mmol) and then benzyl N-methyl-N-[2-(methylamino)ethyl] carbamate hydrochloride (10.2 g, 39.3 mmol). After 1 hour, the reaction mixture was concentrated, re-dissolved in ethyl acetate (200 mL) and washed with saturated aqueous sodium bicarbonate solution (3×200 mL) followed by 2 M aqueous HCl (3×200 mL) and brine (200 mL). The organic phase was dried over $Na_2SO_4$, filtered and concentrated to dryness. The residue was re-concentrated from a mix of DCM/petroleum ether to give the desired product as a creamy foam solid (28.0 g, quantitative yield).

LC-MS (Method A): $R_T$=3.49 min, m/z=737.8 $[M-H]^-$.

Step B: 3-[4-[Methyl-[2-(methylamino)ethyl]carbamoyl]phenyl]-1-sulfamoyl-pyrrole-2-carboxylic acid To a stirred solution of benzyl 3-[4-[2-[benzyloxycarbonyl(methyl)amino]ethyl-methyl-carbamoyl]phenyl]-1-(benzyloxycarbonylsulfamoyl)pyrrole-2-carboxylate (26 g, 35.2 mmol) in methanol (250 mL) was added 7 M ammonia in methanol (10 mL) followed by 10% palladium on carbon (3.75 g, 1.76 mmol). The vessel was purged of air and placed under a hydrogen atmosphere. After 1 hour the reaction mixture was filtered through Celite® and concentrated to a white solid. The crude material from two such experiments was combined and purified in 5 g portions by column chromatography (ethyl acetate:methanol, gradient elution from 50:50 to 0:100 and holding at 0:100 until the product had been eluted), slurried in diethyl ether (100 mL), isolated by filtration and sucked dry under a flow of nitrogen to give the desired product as a white solid (14.0 g, 52% average yield across two reactions).

$^1$H NMR (500 MHz, DMSO-$d_6$) δ 8.82 (br s, 4H), 7.52 (br d, J=5.5 Hz, 2H), 7.33 (br d, J=7.9 Hz, 2H), 7.10 (d, J=3.1 Hz, 1H), 6.26 (d, J=3.4 Hz, 1H), 3.69 (br s, 2H), 3.21-2.54 (m, 8H).

LC-MS (Method C): $R_T$=4.43 min, m/z=379.4 [M−H]$^-$.

Example 25 (Sodium Salt): 3-[4-[Methyl-[2-(methylamino)ethyl]carbamoyl]phenyl]-1-sulfamoyl-pyrrole-2-carboxylic acid, Sodium Salt To a suspension of 3-[4-[methyl-[2-(methylamino)ethyl]carbamoyl]phenyl]-1-sulfamoyl-pyrrole-2-carboxylic acid (200 mg, 0.53 mmol) in a mixture of ethanol (1 mL) and water (0.5 mL) was added 25% w/w aqueous sodium hydroxide solution (84 μL, 0.53 mmol) and the resulting solution stirred at room temperature for 30 minutes. The reaction mixture was concentrated to dryness under reduced pressure and azeotroped with ethanol (2×5 mL).

The residue was slurried in ethanol (2 mL) for 30 minutes, the solid isolated by filtration, washed with diethyl ether (5 mL) and sucked dry to give the desired sodium salt as an off-white solid (132 mg, 56%).

$^1$H NMR (500 MHz, DMSO-$d_6$) δ 7.61 (d, J=7.3 Hz, 2H), 7.29 (d, J=7.6 Hz, 2H), 7.02 (s, 1H), 6.22 (s, 1H), 3.65-3.40 (m, 2H), 2.97 (s, 3H), 2.80-2.58 (m, 2H), 2.24 (br d, J=78.4 Hz, 3H).

LC-MS (Method C): $R_T$=4.64 min, m/z=379.4 [M−H]$^-$.

Further Examples

The following examples were prepared in a similar manner to 3-[4-[methyl-[2-(methylamino)ethyl]carbamoyl]phenyl]-1-sulfamoyl-pyrrole-2-carboxylic acid (Example 25).

| Example | Structure | Name | Analytical Data |
|---|---|---|---|
| Example 26 (free acid) | 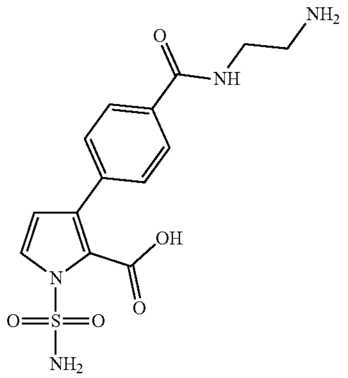 [SMILES: NCCNC(=O)c1ccc(-c2ccn(S(N)(=O)=O)c2C(=O)O)cc1] | 3-[4-(2-Aminoethylcarbamoyl)phenyl]-1-sulfamoyl-pyrrole-2-carboxylic acid | $^1$H NMR (500 MHz, DMSO-$d_6$) δ 8.38 (t, J = 5.7 Hz, 1H), 7.76 (d, J = 8.3 Hz, 2H), 7.62 (d, J = 8.3 Hz, 2H), 7.03 (d, J = 3.1 Hz, 1H), 6.26 (d, J = 3.1 Hz, 1H), 3.31-3.28 (m, 2H), 2.72 (t, J = 6.3 Hz, 2H). Peak at 3.31-3.28 ppm is partially obscured by NMR solvent. LC-MS (Method A): $R_T$ = 1.73 min, m/z = 351.4 [M − H]$^-$. |
| Example 27 (free acid) | 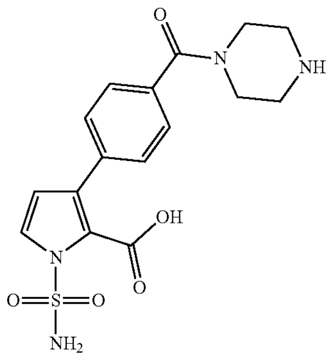 [SMILES: NS(=O)(=O)n1ccc(-c2ccc(C(=O)N3CCNCC3)cc2)c1C(=O)O] | 3-[4-(Piperazine-1-carbonyl)phenyl]-1-sulfamoyl-pyrrole-2-carboxylic acid | $^1$H NMR (500 MHz, DMSO-$d_6$) δ 9.05 (br s, 2H), 7.61 (d, J = 8.1 Hz, 2H), 7.27 (d, J = 8.1 Hz, 2H), 7.03 (d, J = 3.1 Hz, 1H), 6.24 (d, J = 3.1 Hz, 1H), 3.60-3.37 (m, 4H), 2.75-2.65 (m, 4H). Peak at 3.60-3.37 ppm is partially obscured by NMR solvent. LC-MS (Method A): $R_T$ = 1.43 min, m/z = 377.5 [M − H]$^-$. |

-continued

| Example | Structure | Name | Analytical Data |
|---|---|---|---|
| Example 28 (free acid) | 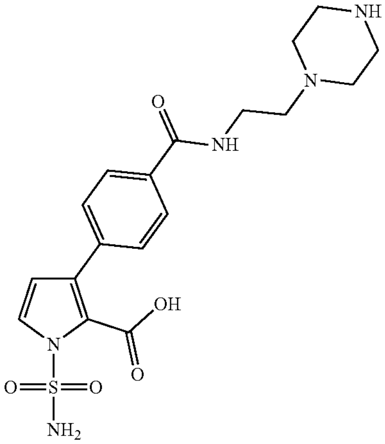 [SMILES: NS(=O)(=O)n1ccc(-c2ccc(C(=O)NCCN3CCNCC3)cc2)c1C(=O)O] | 3-[4-(2-Piperazin-1-ylethylcarbamoyl)phenyl]-1-sulfamoyl-pyrrole-2-carboxylic acid | $^1$H NMR (500 MHz, DMSO-$d_6$) δ 8.98-8.54 (br s, 3H), 8.39 (br s, 1H), 7.77 (d, J = 8.2 Hz, 2H), 7.62 (d, J = 8.2 Hz, 2H), 7.08 (br d, J = 2.7 Hz, 1H), 6.28 (d, J = 3.1 Hz, 1H), 3.43-3.37 (m, 4H), 3.04 (br s, 4H), 2.60 (br s, 4H). LC-MS (Method B): $R_T$ = 0.43 min, m/z = 420.4 $[M - H]^-$. |
| Example 29 (free acid)*, † | 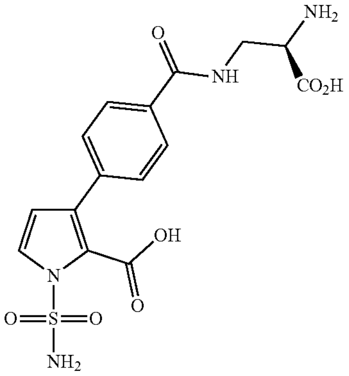 [SMILES: N[C@H](CNC(=O)c1ccc(-c2ccn(S(N)(=O)=O)c2C(=O)O)cc1)C(=O)O] | 3-[4-[[(2R)-2-Amino-2-carboxy-ethyl]carbamoyl]phenyl]-1-sulfamoyl-pyrrole-2-carboxylic acid | $^1$H NMR (500 MHz, DMSO-$d_6$) δ 8.85 (br s, 1H), 7.84 (br d, J = 8.2 Hz, 2H), 7.57 (br d, J = 8.2 Hz, 2H), 7.29 (d, J = 3.1 Hz, 1H), 6.37 (d, J = 3.1 Hz, 1H), 3.81-3.52 (m, 3H). LC-MS (Method A): $R_T$ = 1.76 min, m/z = 395.4 $[M - H]^-$. |
| Example 30 (free acid) | 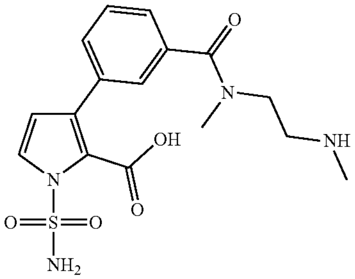 [SMILES: CNCCN(C)C(=O)c1cccc(-c2ccn(S(N)(=O)=O)c2C(=O)O)c1] | 3-[3-[Methyl-[2-(methylamino)ethyl]carbamoyl]phenyl]-1-sulfamoyl-pyrrole-2-carboxylic acid | $^1$H NMR (500 MHz, DMSO-$d_6$) δ 9.33-8.60 (br m, 3H),7.45 (br d, J = 4.5 Hz, 2H), 7.31 (br s, 1H), 7.28-7.23 (m, 1H), 7.16 (d, J = 3.0 Hz, 1H), 6.30 (d, J = 3.0 Hz, 1H), 3.52-3.44 (m, 2H), 3.21-3.15 (m, 2H), 2.95 (s, 3H), 2.70 (s, 3H). LC-MS (Method A): $R_T$ = 0.47 min, m/z = 379.4 $[M - H]^-$. |
| Example 31 (free acid)† | 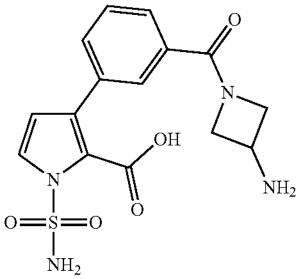 [SMILES: NC1CN(C(=O)c2cccc(-c3ccn(S(N)(=O)=O)c3C(=O)O)c2)C1] | 3-[3-(3-Aminoazetidine-1-carbonyl)phenyl]-1-sulfamoyl-pyrrole-2-carboxylic acid | $^1$H NMR (500 MHz, DMSO-$d_6$) δ 7.81 (br s, 1H), 7.63 (br d, J = 7.5 Hz, 1H), 7.43 (br d, J = 8.0 Hz, 1H), 7.39-7.34 (m, 1H), 7.05 (d, J = 3.0 Hz, 1H), 6.23 (d, J = 3.0 Hz, 1H), 4.50 (br t, J = 8.0 Hz, 1H), 4.20 (br t, J = 8.5 Hz, 1H), 4.0 (br dd, J = 8.5, 5.5 Hz, 1H), 3.84-3.78 (m, 1H), 3.78-3.72 (m, 1H). LC-MS (Method A): $R_T$ = 1.74 min, m/z = 363.3 $[M - H]^-$. |

*The free carboxylic acid was introduced with benzyl protection. †The hydrogenation step was performed in the absence of ammonia due to sufficient methanol solubility of the starting material.

Example 32 (Free Acid): 3-[4-[2-(Ethylamino)ethylcarbamoyl]phenyl]-1-sulfamoyl-pyrrole-2-carboxylic acid

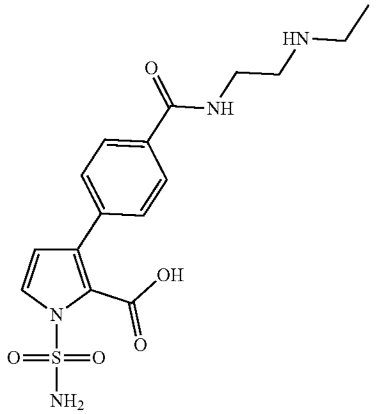 [SMILES: CCNCCNC(=O)c1ccc(-c2ccn(S(N)(=O)=O)c2C(=O)O)cc1]

Step A: Benzyl 1-(benzyloxycarbonylsulfamoyl)-3-[4-[2-[tert-butoxycarbonyl(ethyl)amino]ethylcarbamoyl]phenyl]pyrrole-2-carboxylate HBTU (228 mg, 0.60 mmol) was added to a solution of 4-[2-benzyloxycarbonyl-1-(benzyloxycarbonylsulfamoyl) pyrrol-3-yl]benzoic acid (268 mg, 0.50 mmol), tert-butyl N-(2-aminoethyl)-N-ethyl-carbamate (104 mg, 0.55 mmol) and DIPEA (262 μL, 1.50 mmol) in DCM (20 mL) and the reaction allowed to stir at room temperature overnight. The reaction was quenched by the addition of water (100 mL) and extracted into DCM (2×100 mL). The combined organic phases were dried over $MgSO_4$, filtered and the solvent removed in vacuo. Purification by column chromatography (0-100% ethyl acetate in petroleum ether then 0-100% methanol in ethyl acetate) followed by trituration in diethyl ether gave the desired product as a white solid (200 mg, 57%).

$^1$H NMR (500 MHz, DMSO-$d_6$) δ 8.50 (br d, J=21.4 Hz, 1H), 7.76 (br s, 2H), 7.41-7.37 (m, 4H), 7.34-7.26 (m, 9H), 6.31 (d, J=3.0 Hz, 1H), 5.16 (s, 2H), 4.88 (s, 2H), 3.43-3.26 (m, 4H), 3.26-3.17 (m, 2H), 1.42-1.32 (m, 9H), 1.08-1.01 (m, 3H). Peak corresponding to 2H obscured by water peak.

LC-MS (Method B): $R_T$=2.64 min, m/z=703.8 [M−H]$^-$.

Step B: Benzyl 1-(benzyloxycarbonylsulfamoyl)-3-[4-[2-(ethylamino)ethylcarbamoyl]phenyl]pyrrole-2-carboxylate 4 M HCl in 1,4-dioxane (10 mL) was added to a suspension of benzyl 1-(benzyloxycarbonylsulfamoyl)-3-[4-[2-[tert-butoxycarbonyl(ethyl)amino]ethylcarbamoyl]phenyl] pyrrole-2-carboxylate (200 mg, 0.28 mmol) in DCM (10 mL) and the reaction mixture allowed to stir at room temperature for 2 hours. The solvent was removed in vacuo and free based on an SCX-2 cartridge eluting with ammonia in methanol to give the desired product as a white solid (60 mg, 35%).

LC-MS (Method A): $R_T$=2.96 min, m/z=603.6 [M−H]$^-$.

Step C: 3-[4-[2-(Ethylamino)ethylcarbamoyl]phenyl]-1-sulfamoyl-pyrrole-2-carboxylic acid 10% Palladium on carbon (5 mg) was added to a solution of benzyl 1-(benzyloxycarbonylsulfamoyl)-3-[4-[2-(ethylamino)ethylcarbamoyl]phenyl]pyrrole-2-carboxylate (60 mg, 99 μmol) in a mixture of methanol (20 mL) and 1 M ammonia in methanol (20 mL) and the reaction mixture stirred under a hydrogen atmosphere for 90 minutes. The reaction mixture was filtered through a pad of Celite® and eluted with methanol (150 mL). The solvent was removed in vacuo and the residue purified by column chromatography (30-100% methanol in ethyl acetate) followed by trituration with diethyl ether to give the desired product as a white solid (23 mg, 58%).

$^1$H NMR (500 MHz, DMSO-$d_6$) δ 9.17 (br s, 1H), 8.38 (br s, 2H), 7.84 (d, J=8.5 Hz, 2H), 7.63 (d, J=8.5 Hz, 2H), 7.11 (d, J=3.0 Hz, 1H), 6.29 (d, J=3.0 Hz, 1H), 3.57-3.48 (m, 2H), 3.00 (t, J=6.0 Hz, 2H), 2.87 (q, J=7.0 Hz, 2H), 1.12 (t, J=7.0 Hz, 3H).

LC-MS (Method A): $R_T$=1.99 mL, m/z=379.4 [M−H]$^-$.

Further Examples

The following examples were prepared in a similar manner to 3-[4-[2-(ethylamino)ethylcarbamoyl]phenyl]-1-sulfamoyl-pyrrole-2-carboxylic acid (Example 32).

| Example | Structure | Name | Analytical Data |
|---|---|---|---|
| Example 33 (HCl salt) †, ‡‡ | 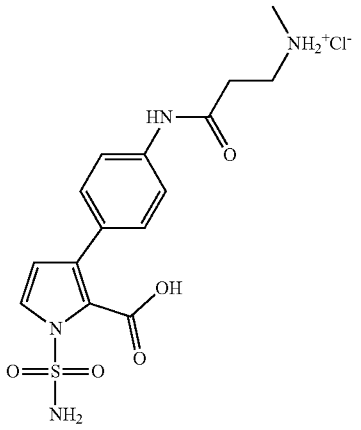 | 3-[4-[2-(Methylamino) ethylcarbamoyl] phenyl]-1-sulfamoyl-pyrrole-2-carboxylic acid hydrochloride | $^1$H NMR (500 MHz, DMSO-$d_6$) δ 9.57 (br s, 1H), 8.76 (br s, 3H), 7.90 (d, J = 8.0 Hz, 2H), 7.62 (d, J = 8.0 Hz, 2H), 7.14 (d, J = 3.0 Hz, 1H), 6.30 (d, J = 3.0 Hz, 1H), 3.68-3.52 (m, 2H), 3.15-3.08 (m, 2H), 2.58 (s, 3H). LC-MS (Method A): $R_T$ = 1.74 min, m/z = 365.3 [M − H]$^-$. |

-continued

| Example | Structure | Name | Analytical Data |
| --- | --- | --- | --- |
| Example 34 (HCl salt) *, †, ‡‡ | 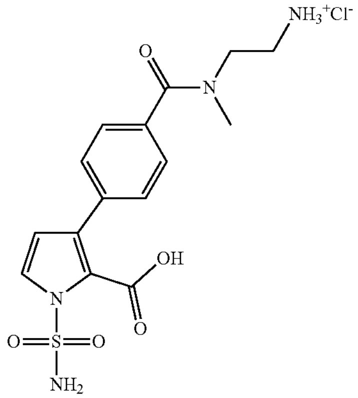 | 3-[4-[2-Aminoethyl(methyl) carbamoyl]phenyl]-1-sulfamoyl-pyrrole-2-carboxylic acid hydrochloride | $^1$H NMR (500 MHz, DMSO-$d_6$) δ 8.60-8.19 (br s, 5H), 7.54-7.22 (br m, 5H), 6.37 (br s, 1H), 3.70 (br s, 2H), 3.06 (br s, 2H), 2.99 (s, 3H). LC-MS (method A): $R_T$ = 1.68 min, m/z = 365.3 $[M - H]^-$. |
| Example 35 (free acid) ‡ | 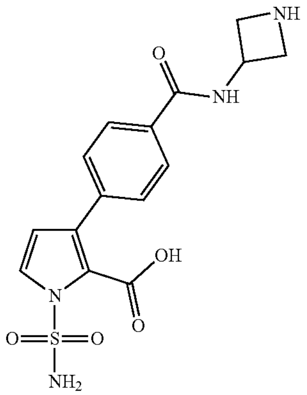 [SMILES: NS(=O)(=O)n1ccc(-c2ccc(C(=O)NC3CNC3)cc2)c1C(=O)O] | 3-[4-(Azetidin-3-ylcarbamoyl)phenyl]-1-sulfamoyl-pyrrole-2-carboxylic acid | $^1$H NMR (500 MHz, DMSO-$d_6$) δ 9.67 (d, J = 7.5 Hz, 1H), 8.88 (br s, 3H), 7.84 (d, J = 8.5 Hz, 2H), 7.66 (d, J = 8.5 Hz, 2H), 7.12 (d, J = 3.0 Hz, 1H), 6.30 (d, J = 3.0 Hz, 1H), 4.84 (sxt, J = 7.5 Hz, 1H), 4.27-4.20 (m, 2H), 4.08-4.02 (m, 2H). LC-MS (Method A): $R_T$ = 1.78 min, m/z = 363.3 $[M - H]^-$. |
| Example 36 (HCl salt) †, ‡‡ | 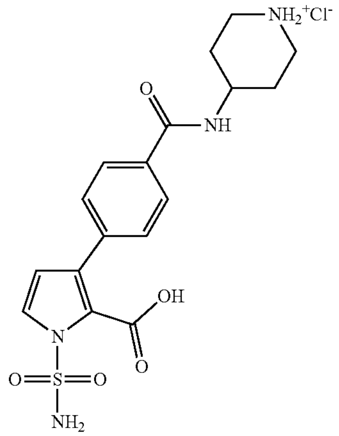 | 3-[4-(4-Piperidylcarbamoyl) phenyl]-1-sulfamoyl-pyrrole-2-carboxylic acid hydrochloride | $^1$H NMR (500 MHz, DMSO-$d_6$) δ 8.48 (d, J = 7.5 Hz, 1H), 7.80 (d, J = 8.5 Hz, 2H), 7.60 (d, J = 8.5 Hz, 2H), 7.12 (d, J = 3.0 Hz, 1H), 6.29 (d, J = 3.0 Hz, 1H), 4.10-4.02 (m, 1H), 3.42-3.35 (m, 2H), 3.00-2.92 (m, 2H), 1.98-1.93 (m, 2H), 1.85-1.77 (m, 2H). LC-MS (Method A): $R_T$ = 1.91 min, m/z = 391.4 $[M - H]^-$. |

-continued

| Example | Structure | Name | Analytical Data |
| --- | --- | --- | --- |
| Example 37 (free acid) ‡‡ | 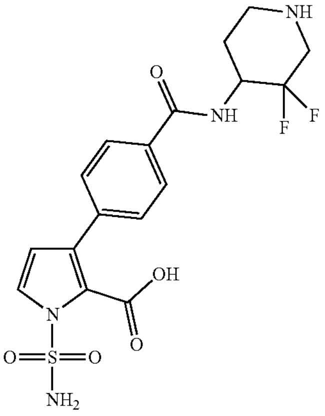 [SMILES: NS(=O)(=O)n1ccc(-c2ccc(C(=O)NC3CCNCC3(F)F)cc2)c1C(=O)O] | 3-[4-[(3,3-Difluoro-4-piperidyl)carbamoyl]phenyl]-1-sulfamoyl-pyrrole-2-carboxylic acid | $^1$H NMR (500 MHz, DMSO-$d_6$) δ 8.91 (br s, 8.43 (d, J = 9.0 Hz, 7.82 (d, J = 8.5 Hz, 7.62 (d, J = 8.5 Hz, 7.12 (d, J = 3.0 Hz, 6.30 (d, J = 3.0 Hz, 1H), 4.58-4.45 (m, 1H), 3.45-3.35 (m, 1H), 2.97 (br d, J = 12.5 Hz, 1H), 2.92-2.83 (m, 1H), 2.67-2.60 (m, 1H), 1.85-1.75 (m, 2H). Peak at 3.45-3.35 ppm partially obscured by water peak. LC-MS (Method A): $R_T$ = 2.02 min, m/z = 427.4 $[M - H]^-$. |
| Example 38 (free acid) | 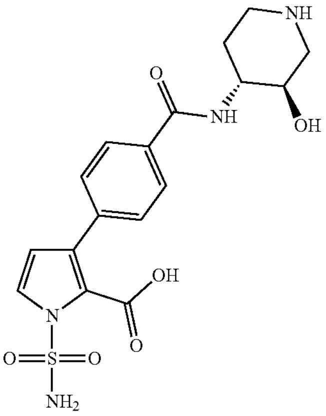 [SMILES: NS(=O)(=O)n1ccc(-c2ccc(C(=O)N[C@@H]3CCNC[C@H]3O)cc2)c1C(=O)O] | 3-[4-[[(3R,4R)-3-Hydroxy-4-piperidyl]carbamoyl]phenyl]-1-sulfamoyl-pyrrole-2-carboxylic acid | $^1$H NMR (500 MHz, DMSO-$d_6$) δ 8.25 (d, J = 7.5 Hz, 1H), 7.79 (d, J = 8.0 Hz, 2H), 7.62 (d, J = 8.0 Hz, 2H), 7.06 (d, J = 3.0 Hz, 1H), 6.27 (d, J = 3.0 Hz, 1H), 5.16 (br s, 1H), 3.84-3.75 (m, 1H), 3.64-3.57 (m, 1H), 3.15 (br dd, J = 12.0, 4.5 Hz, 1H), 3.06-2.99 (m, 1H), 2.70-2.62 (m, 1H), 1.95-1.88 (m, 1H), 1.56-1.45 (m, 1H). LC-MS (Method A): $R_T$ = 1.90 min, m/z = 407.4 $[M - H]^-$. |
| Example 39 (free acid) | 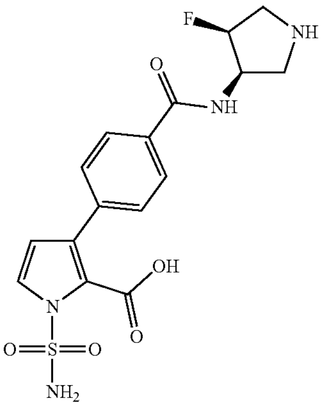 [SMILES: NS(=O)(=O)n1ccc(-c2ccc(C(=O)N[C@@H]3CNC[C@@H]3F)cc2)c1C(=O)O] (racemic mixture) | 3-[4-[[cis-4-Fluoropyrrolidin-3-yl]carbamoyl]phenyl]-1-sulfamoyl-pyrrole-2-carboxylic acid | $^1$H NMR (500 MHz, DMSO-$d_6$) δ 8.51 (br, d J = 6.7 Hz, 1H), 7.81 (d, J = 8.2 Hz, 2H), 7.63 (d, J = 8.2 Hz, 2H), 7.10 (d, J = 3.0 Hz, 1H), 6.31 (d, J = 3.0 Hz, 1H), 5.25 (br dt, J = 54, 3 Hz, 1H), 4.61-4.49 (m, 1H), 3.62-3.46 (m, 2H), 3.17 (br t, J = 11.0 Hz, 2H). LC-MS (Method A): $R_T$ = 2.00 min, m/z = 395.4 $[M - H]^-$. |

-continued

| Example | Structure | Name | Analytical Data |
|---|---|---|---|
| Example 40 (free acid) | 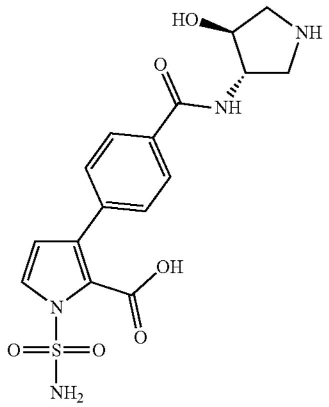 [SMILES: NS(=O)(=O)n1ccc(-c2ccc(C(=O)N[C@H]3CNC[C@@H]3O)cc2)c1C(=O)O] | 3-[4-[[(3S,4S)-4-Hydroxypyrrolidin-3-yl]carbamoyl]phenyl]-1-sulfamoyl-pyrrole-2-carboxylic acid | $^1$H NMR (500 MHz, DMSO-$d_6$) δ 9.03 (s, 1H), 8.43 (br s, 2H), 7.73 (d, J = 8.1 Hz, 2H), 7.52 (d, J = 8.1 Hz, 2H), 7.12 (d, J = 3.1 Hz, 1H), 6.25 (d, J = 3.1 Hz, 1H), 5.85 (s, 1H), 4.41 (br t, J = 6.0 Hz, 1H), 4.23 (br s, 1H), 3.54 (dd, J = 12.3, 6.0 Hz, 1H), 3.46-3.42 (m, 2H), 3.09 (d, J = 12.3 Hz, 1H). LC-MS (Method A): $R_T$ = 1.57 min, m/z = 393.4 $[M - H]^-$. |
| Example 41 (free acid) ‡ | 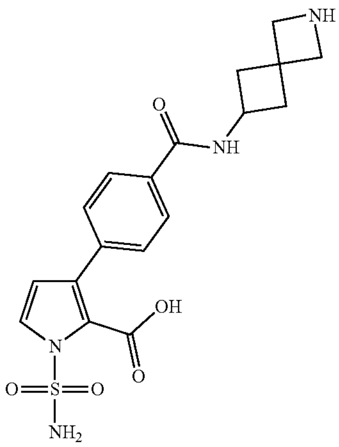 [SMILES: NS(=O)(=O)n1ccc(-c2ccc(C(=O)NC3CC4(CNC4)C3)cc2)c1C(=O)O] | 3-[4-(2-Azaspiro[3.3]heptan-6-ylcarbamoyl)phenyl]-1-sulfamoyl-pyrrole-2-carboxylic acid | $^1$H NMR (500 MHz, DMSO-$d_6$) δ 9.03-8.33 (m, 5H), 7.76 (d, J = 8.0 Hz, 2H), 7.61 (d, J = 8.0 Hz, 2H), 7.09 (d, J = 3.1 Hz, 1H), 6.30 (d, J = 3.1 Hz, 1H), 4.27 (sextet, J = 7.9 Hz, 1H), 4.03 (s, 2H), 3.87 (s, 2H), 2.59-2.54 (m, 2H), 2.30-2.24 (m, 2H). The multiplet at 2.59-2.54 is obscured by NMR solvent. LC-MS (Method A): $R_T$ = 1.99 min, m/z = 403.4 $[M - H]^-$. |
| Example 42 (free acid) ‡ | 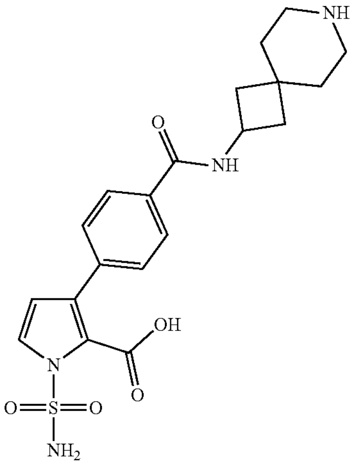 [SMILES: NS(=O)(=O)n1ccc(-c2ccc(C(=O)NC3CC4(CCNCC4)C3)cc2)c1C(=O)O] | 3-[4-(7-Azaspiro[3.5]nonan-2-ylcarbamoyl)phenyl]-1-sulfamoyl-pyrrole-2-carboxylic acid | $^1$H NMR (500 MHz, DMSO-$d_6$) δ 8.88 (br s, 4H), 8.54 (d, J = 7.8 Hz, 1H), 7.77 (d, J = 8.2 Hz, 2H), 7.60 (d, J = 8.2 Hz, 2H), 7.10 (d, J = 3.2 Hz, 1H), 6.27 (d, J = 3.2 Hz, 1H), 4.42 (sextet, J = 8.2 Hz, 1H), 2.97-2.92 (m, 2H), 2.87-2.83 (m, 2H), 2.19-2.14 (m, 2H), 1.88-1.83 (m, 2H), 1.68-1.63 (m, 2H), 1.61-1.56 (m, 2H). LC-MS (Method A): $R_T$ = 2.03 min, m/z = 431.4 $[M - H]^-$. |

-continued

| Example | Structure | Name | Analytical Data |
|---|---|---|---|
| Example 43 (free acid) †, ‡‡ | 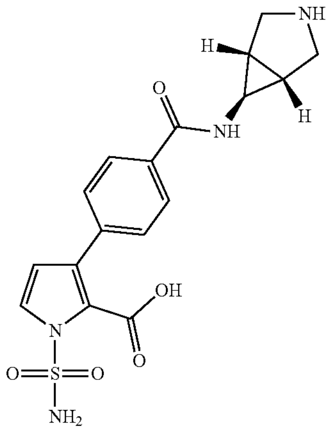 [SMILES: NS(=O)(=O)n1ccc(-c2ccc(C(=O)N[C@H]3[C@@H]4CNC[C@@H]43)cc2)c1C(=O)O] | 3-[4-[[(1S,5R)-3-Azabicyclo[3.1.0]hexan-6-yl]carbamoyl]phenyl]-1-sulfamoyl-pyrrole-2-carboxylic acid | $^1$H NMR (500 MHz, DMSO-d$_6$) δ 8.56 (br s, 2H), 8.48 (d, J = 3.2 Hz, 1H), 7.72 (d, J = 8.4 Hz, 2H), 7.61 (d, J = 8.4 Hz, 2H), 7.57 (d, J = 3.2 Hz, 1H), 6.28 (d, J = 3.2 Hz, 1H), 3.41-3.21 (m, 4H), 2.86 (br s, 1H), 2.16 (br s, 2H). Multiplet at 3.41-3.21 is obscured by residual water peak. LC-MS (Method A): R$_T$ = 1.93 min, m/z = 389.4 [M − H]$^-$. |
| Example 27 (HCl salt) *, †, ‡‡ | 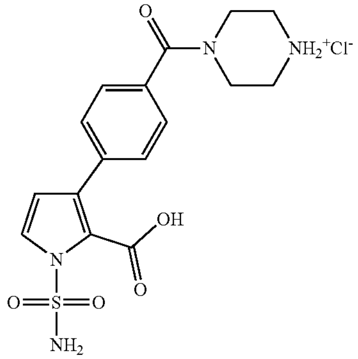 | 3-[4-(Piperazine-1-carbonyl)phenyl]-1-sulfamoyl-pyrrole-2-carboxylic acid hydrochloride | $^1$H NMR (500 MHz, DMSO-d$_6$) δ 7.60 (d, J = 8.0 Hz, 2H), 7.27 (d, J = 8.0 Hz, 2H), 7.03 (d, J = 3.0 Hz, 1H), 6.23 (d, J = 3.0 Hz, 1H), 3.49 (br s, 2H), 2.68 (br s, 4H), 2.54-2.48 (m, 2H). Signal at 2.54-2.48 ppm obscured by residual solvent peak. LC-MS (Method A): R$_T$ = 1.48 min, m/z = 377.3 [M − H]$^-$. |
| Example 44 (free acid) | 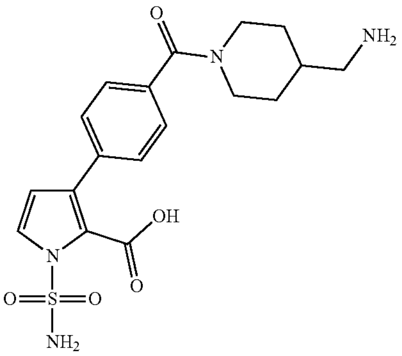 [SMILES: NCC1CCN(C(=O)c2ccc(-c3ccn(S(N)(=O)=O)c3C(=O)O)cc2)CC1] | 3-[4-[4-(Aminomethyl)piperidine-1-carbonyl]phenyl]-1-sulfamoyl-pyrrole-2-carboxylic acid | $^1$H NMR (500 MHz, DMSO-d$_6$) δ 8.06 (br s, 4H), 7.60 (d, J = 8.0 Hz, 2H), 7.29 (d, J = 8.0 Hz, 2H), 7.07 (d, J = 3.0 Hz, 1H), 6.27 (d, J = 3.0 Hz, 1H), 4.45 (br s, 1H), 4.10 (br s, 1H), 3.80-3.60 (m, 1H), 3.00 (br s, 1H), 2.74 (br s, 1H), 1.89-1.72 (m, 2H), 1.72-1.57 (m, 1H), 1.18-1.11 (m, 2H). A further 1H not observed due to obscuring by water/solvent peak. LC-MS (Method F): R$_T$ = 4.34 min, m/z = 405.4 [M − H]$^-$. |
| Example 45 (free acid) | 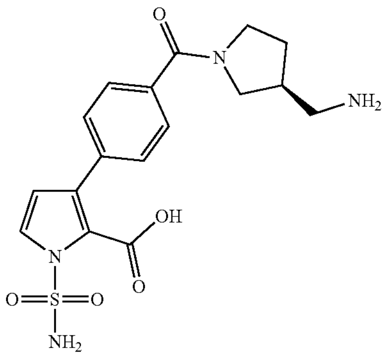 [SMILES: NC[C@@H]1CCN(C(=O)c2ccc(-c3ccn(S(N)(=O)=O)c3C(=O)O)cc2)C1] | 3-[4-[(3S)-3-(Aminomethyl)pyrrolidine-1-carbonyl]phenyl]-1-sulfamoyl-pyrrole-2-carboxylic acid | $^1$H NMR (500 MHz, DMSO-d$_6$) δ 8.15 (br s, 4H), 7.62-7.58 (m, 2H), 7.45 (br d, J = 8.0 Hz, 1H), 7.42 (br d, J = 8.0 Hz, 1H), 7.07 (d, J = 3.2 Hz, 1H), 6.27-6.25 (m, 1H), 3.71-3.64 (m, 1H), 3.60-3.48 (m, 2H), 3.30-3.23 (m, 2H), 3.30-3.23 (m 2H), 2.90-2.77 (m, 2H), 2.07-1.96 (m, 1H), 1.70-1.60 (m, 1H). The multiplet at 3.30-3.23 is obscured due to water/solvent peak. LC-MS (Method A): R$_T$ = 1.77 min, m/z = 391.3 [M − H]$^-$. |

-continued

| Example | Structure | Name | Analytical Data |
|---|---|---|---|
| Example 46 (free acid) | 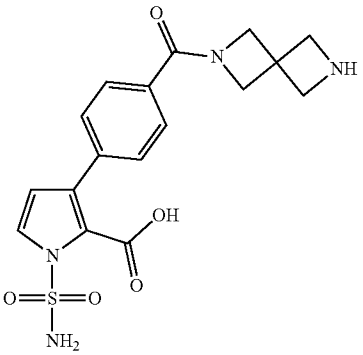 [SMILES: NS(=O)(=O)n1ccc(-c2ccc(C(=O)N3CC4(CNC4)C3)cc2)c1C(=O)O] | 3-[4-(2,6-Diazaspiro[3.3]heptane-2-carbonyl)phenyl]-1-sulfamoyl-pyrrole-2-carboxylic acid | $^1$H NMR (500 MHz, DMSO-d$_6$) δ 8.89 (br s, 2H), 7.62 (d, J = 8.2 Hz, 2H), 7.53 (d, J = 8.2 Hz, 2H), 7.08 (d, J = 3.1 Hz, 1H), 6.27 (d, J = 3.1 Hz, 1H), 4.50 (s, 2H), 4.21 (s, 2H), 4.14 (d, J = 10.0 Hz, 2H), 4.10 (d, J = 10.0 Hz, 2H). LC-MS (Method A): $R_T$ = 1.68 min, m/z = 389.4 $[M - H]^-$. |
| Example 47 (HCl salt) †, ‡‡ | 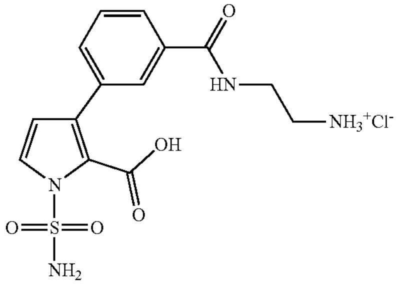 | 3-[3-(2-Aminoethylcarbamoyl) phenyl]-1-sulfamoyl-pyrrole-2-carboxylic acid hydrochloride | $^1$H NMR (500 MHz, DMSO-d$_6$) δ 8.55 (t, J = 5.0 Hz, 1H), 8.19 (br s, 4H), 7.94 (s, 1H), 7.67-7.57 (m, 2H), 7.32 (t, J = 7.5Hz, 1H), 7.09 (d, J = 3.0 Hz, 1H), 6.20 (d, J = 3.0 Hz, 1H), 3.48-3.42 (m, 2H), 2.92 (t, J = 6.0 Hz, 2H). LC-MS (Method A): $R_T$ = 1.82 min, m/z= 351.3 $[M - H]^-$. |
| Example 48 (free acid) | 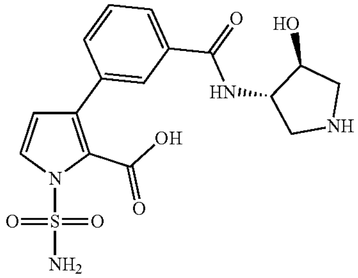 [SMILES: NS(=O)(=O)n1ccc(-c2cccc(C(=O)N[C@H]3CNC[C@@H]3O)c2)c1C(=O)O] | 3-[3-[[(3S,4S)-4-Hydroxypyrrolidin-3-yl]carbamoyl]phenyl]-1-sulfamoyl-pyrrole-2-carboxylic acid | $^1$H NMR (500 MHz, DMSO-d$_6$) δ 8.87 (br s, 2H), 8.39 (d, J = 7.0 Hz, 1H), 7.77 (br s, 1H), 7.36 (d, J = 7.0 Hz, 1H), 7.18 (d, J = 8.0 Hz, 1H), 7.16 (d, J = 3.0 Hz, 1H), 6.83 (t, J = 8.0 Hz, 1H), 6.27 (d, J = 3.0 Hz, 1H), 5.82 (br s, 1H), 4.38 (t, J = 6.5 Hz, 1H), 3.56 (br dd, J = 12.5, 6.5 Hz, 1H), 3.43 (br d, J = 12.5 Hz, 1H), 3.38 (br d, J = 12.5 Hz, 1H), 3.18-3.14 (m, 1H). LC-MS (Method A): $R_T$ = 1.80 min, m/z = 393.3 $[M - H]^-$. |
| Example 49 (free acid) ‡ | 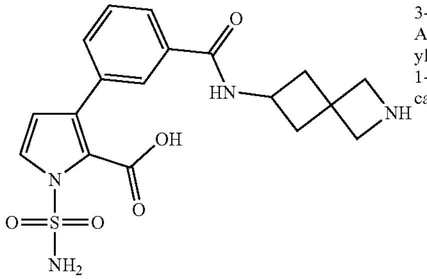 | 3-[3-(2-Azaspiro[3.3]heptan-6-ylcarbamoyl)phenyl]-1-sulfamoyl-pyrrole-2-carboxylic acid | $^1$H NMR (500 MHz, DMSO-d$_6$) δ 8.52 (d, J = 7.5 Hz, 1H), 8.23 (br s, 2H), 7.92 (s, 1H), 7.66 (d, J = 7.5 Hz, 1H), 7.62 (d, J = 7.5 Hz, 1H), 7.34 (t, J = 7.5 Hz, 1H), 7.07 (d, J = 3.0 Hz, 1H), 6.24 (d, J = 3.0 Hz, 1H), 4.32-4.24 (m, 1H), 3.77 (s, 2H), 3.65 (s, 2H), 2.22-2.14 (m, 2H). A further 1H not observed due to obscuring by water/solvent peak. LC-MS (Method A): RT = 2.08 min, m/z = 403.4 $[M - H]^-$. |

-continued

| Example | Structure | Name | Analytical Data |
|---|---|---|---|
| Example 50 (free acid) | 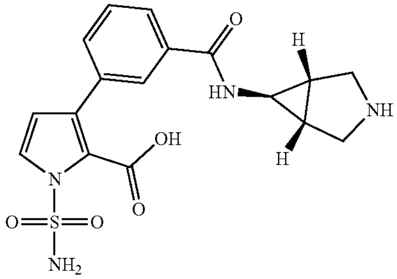 [SMILES: NS(=O)(=O)n1ccc(-c2cccc(C(=O)N[C@H]3[C@@H]4CNC[C@@H]43)c2)c1C(=O)O] | 3-[3-[[(1S,5R)-3-Azabicyclo[3.1.0]hexan-6-yl]carbamoyl]phenyl]-1-sulfamoyl-pyrrole-2-carboxylic acid | $^1$H NMR (500 MHz, DMSO-$d_6$) δ 8.66 (br s, 2H), 8.48 (br d, J = 4.0 Hz, 1H), 7.89 (s, 1H), 7.67-7.62 (m, 2H), 7.37 (t, J = 7.5 Hz, 1H), 7.10 (d, J = 3.0 Hz, 1H), 6.25 (d, J = 3.0 Hz, 1H), 3.21 (d, J = 11.0 Hz, 2H), 3.13 (d, J = 11.0 Hz, 2H), 2.88-2.83 (m, 1H), 1.84 (br s, 2H). LC-MS (Method A): $R_T$ = 2.12 min, m/z = 389.4 $[M - H]^-$. |
| Example 51 (free acid) | 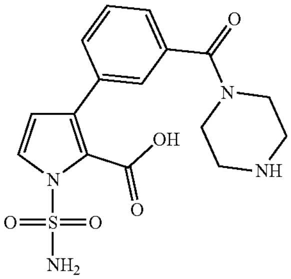 [SMILES: NS(=O)(=O)n1ccc(-c2cccc(C(=O)N3CCNCC3)c2)c1C(=O)O] | 3-[3-(Piperazine-1-carbonyl)phenyl]-1-sulfamoyl-pyrrole-2-carboxylic acid | $^1$H NMR (500 MHz, DMSO-$d_6$) δ 8.64 (br s, 4H), 7.64 (s, 1H), 7.52 (d, J = 7.5 Hz, 1H), 7.41 (t, J = 7.5 Hz, 1H), 7.29 (d, J = 7.5 Hz, 1H), 7.12 (d, J = 3.0 Hz, 1H), 6.27 (d, J = 3.0 Hz, 1H), 3.80-3.55 (br m, 4H), 3.07 (br s, 4H). LC-MS (Method A): $R_T$ = 1.78 min, m/z = 377.4 $[M - H]^-$. |
| Example 52 (free acid) | 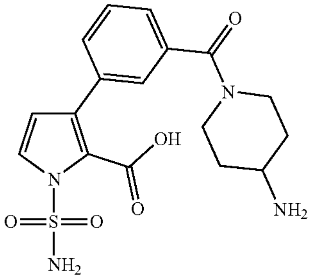 [SMILES: NC1CCN(C(=O)c2cccc(-c3ccn(S(N)(=O)=O)c3C(=O)O)c2)CC1] | 3-[3-(4-Aminopiperidine-1-carbonyl)phenyl]-1-sulfamoyl-pyrrole-2-carboxylic acid | $^1$H NMR (500 MHz, DMSO-$d_6$) δ 8.16 (br s, 4H), 7.57-7.53 (m, 2H), 7.39-7.33 (m, 1H), 7.18 (d, J = 7.5 Hz, 1H), 7.08 (d, J = 3.0 Hz, 1H), 6.23 (d, J = 3.0 Hz, 1H), 4.40 (br s, 1H), 3.76 (br s, 1H), 3.23-3.14 (m, 1H), 3.06 (br s, 1H), 2.83 (br s, 1H), 1.91 (br s, 1H), 1.84 (br s, 1H), 1.45-1.37 (m, 2H). LC-MS (Method A): $R_T$ = 0.35 min, m/z = 391.4 $[M - H]^-$. |
| Example 53 (free acid) ‡ | 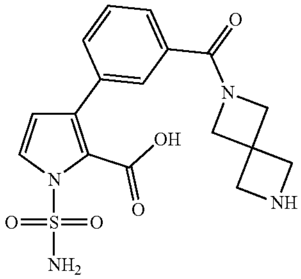 [SMILES: NS(=O)(=O)n1ccc(-c2cccc(C(=O)N3CC4(CNC4)C3)c2)c1C(=O)O] | 3-[3-(2,6-Diazaspiro[3.3]heptane-2-carbonyl)phenyl]-1-sulfamoyl-pyrrole-2-carboxylic acid | $^1$H NMR (500 MHz, DMSO-$d_6$) δ 8.64 (br s, 2H), 7.86 (s, 1H), 7.63 (d, J = 7.5 Hz, 1H), 7.43-7.37 (m, 2H), 7.08 (d, J = 3.0 Hz, 1H), 6.27 (d, J = 3.0 Hz, 1H), 4.46 (br s, 2H), 4.17 (br s, 2H), 3.99 (br s, 4H). LC-MS (Method A): $R_T$ = 1.96 min, m/z = 389.4 $[M - H]^-$. |

*The amide coupling step was performed using DMF as solvent.

†The hydrogenation step was performed in the absence of ammonia.

‡TFA was used in place of HCl for the Boc deprotection step.

‡‡Conversion to the free base by passing down an SCX-2 cartridge was not performed.

Example 54 (Free Acid): 1-Sulfamoyl-3-[4-(3-sulfooxypropylcarbamoyl)phenyl]pyrrole-2-carboxylic acid

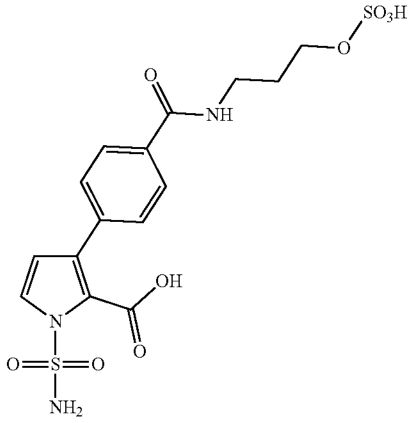 [SMILES: NS(=O)(=O)n1ccc(-c2ccc(C(=O)NCCCOS(=O)(=O)O)cc2)c1C(=O)O]

Sulfur trioxide pyridine complex (48 mg, 299 μmol) was added to a solution of benzyl 1-(benzyloxycarbonylsulfamoyl)-3-[4-(3-hydroxypropylcarbamoyl)phenyl]pyrrole-2-carboxylate (57 mg, 97 μmol) in pyridine (5 mL) and the reaction mixture heated to 60° C. for 3 hours. The solvent was concentrated in vacuo, DCM (50 mL) and water (50 mL) was added and the phases separated. The organic phase was washed with water (50 mL) and tetrabutylammonium hydrogensulfate (36 mg, 107 μmol) was added to the combined aqueous phases. The aqueous phase was extracted with DCM (2×75 mL) and the organic phase washed with brine (75 mL), dried over $MgSO_4$, filtered and the solvent removed in vacuo. The resulting residue was dissolved in methanol (25 mL) and 10% palladium on carbon (6 mg, 56 μmol) was added before hydrogenation under a hydrogen atmosphere for 3 hours. The reaction mixture was filtered through a pad of Celite® and eluted with methanol (150 mL). The solvent was removed in vacuo and purification by column chromatography (0-100% methanol in ethyl acetate) gave the desired product as a white solid (18 mg, 41%).

$^1$H NMR (500 MHz, DMSO-$d_6$) δ 8.79 (brs, 2H), 8.40 (t, J=6.0 Hz, 1H), 7.77 (d, J=8.5 Hz, 2H), 7.63 (d, J=8.5 Hz, 2H), 7.12-7.07 (m, 1H), 6.30 (d, J=3.0 Hz, 1H), 3.80 (t, J=6.5 Hz, 2H), 3.44-3.23 (m, 2H), 1.77 (quin, J=6.5 Hz, 2H). The peak at 3.44-3.23 ppm is obscured by residual water peak.

LC-MS (Method A): $R_T$=2.28 min, m/z=446.3 [M−H]$^-$.

Example 55 (HCl salt): 3-[3-Piperidyl]-1-sulfamoyl-pyrrole-2-carboxylic acid hydrochloride

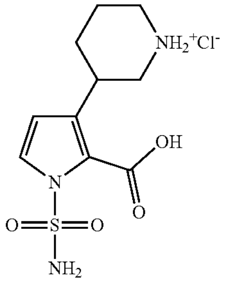

To a solution of benzyl 1-(benzyloxycarbonylsulfamoyl)-3-[3-piperidyl]pyrrole-2-carboxylate hydrochloride (186 mg, 375 μmol) in methanol (10 mL) was added 10% palladium on carbon (40 mg, 18.7 μmol) and the resulting suspension stirred under 1 atmosphere hydrogen at room temperature for 5 hours. The reaction mixture was filtered through Celite®, concentrated to dryness under reduced pressure, slurried in diethyl ether and dried under reduced pressure to give the desired product as a white solid (87 mg, 85%).

$^1$H NMR (500 MHz, DMSO-$d_6$) δ 13.41 (brs, 1H), 9.09 (brs, 1H), 8.99 (brs, 1H), 8.19 (br s, 2H), 7.40 (d, J=3.1 Hz, 1H), 6.31 (d, J=3.4 Hz, 1H), 3.60 (tt, J=12.2, 3.4 Hz, 1H), 3.28-3.21 (m, 2H), 2.95 (br t, J=10.2 Hz, 1H), 2.85 (br t, J=12.1 Hz, 1H), 1.89-1.81 (m, 2H), 1.79-1.68 (m, 1H), 1.66-1.56 (m, 1H).

LC-MS (Method C): $R_T$=0.97 min, m/z=272.3 [M−H]$^-$.

Further Examples

The following examples were prepared in a similar manner to 3-[3-piperidyl]-1-sulfamoyl-pyrrole-2-carboxylic acid hydrochloride (Example 55).

| Example | Structure | Name | Analytical Data |
| --- | --- | --- | --- |
| Example 56 (HCl salt) | 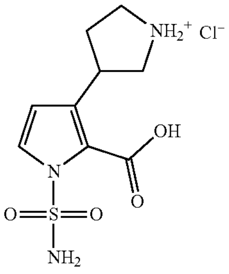 [SMILES: NS(=O)(=O)n1ccc(C2CC[NH2+]C2)c1C(=O)O ; [Cl-]] | 3-(Pyrrolidin-3-yl)-1-sulfamoyl-pyrrole-2-carboxylic acid hydrochloride | $^1$H NMR (500 MHz, DMSO-$d_6$) δ 13.41 (br s, 1H), 9.37 (br s, 1H), 9.21 (br s, 1H), 8.09 (br s, 2H), 7.45 (d, J = 3.0 Hz, 1H), 6.42 (d, J = 3.0 Hz, 1H), 4.00-3.80 (m, 1H), 3.58-3.45 (m, 1H), 3.26-3.09 (m, 2H), 3.07-2.90 (m, 1H), 2.31-2.15 (m, 1H), 2.00-1.83 (m, 1H). LC-MS (Method A): $R_T$ = 0.58 min, m/z = 260.1 [M + H]$^+$. |

-continued

| Example | Structure | Name | Analytical Data |
|---|---|---|---|
| Example 57 (HCl salt) | 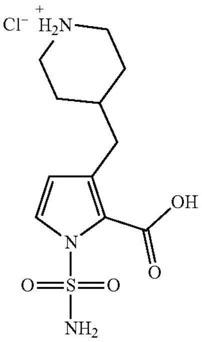 [SMILES: [Cl-] ; NS(=O)(=O)n1ccc(CC2CCNCC2)c1C(=O)O] | 3-(4-Piperidylmethyl)-1-sulfamoyl-pyrrole-2-carboxylic acid hydrochloride | $^1$H NMR (500 MHz, DMSO-$d_6$) δ 9.13 (br s, 2H), 7.06 (d, J = 3.0 Hz, 1H), 5.97 (d, J = 3.0 Hz, 1H), 3.26-3.18 (m, 2H), 2.76 (d, J = 7.5 Hz, 2H), 2.75-2.65 (m, 2H), 1.78-1.68 (m, 1H), 1.68-1.61 (m, 2H), 1.42-1.31 (m, 2H). LC-MS (Method A): $R_T$ = 1.36 min, m/z = 286.3 $[M-H]^-$. |

Example 58 (Free Acid): 3-[1-Acetyl-3-piperidyl]-1-sulfamoyl-pyrrole-2-carboxylic acid

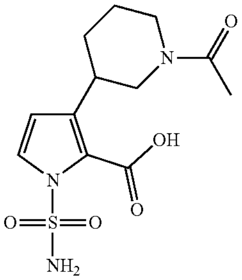 [SMILES: CC(=O)N1CCCC(c2ccn(S(N)(=O)=O)c2C(=O)O)C1]

Step A: Benzyl 3-(1-acetyl-3-piperidyl)-1-(benzyloxycarbonylsulfamoyl)pyrrole-2-carboxylate A mixture of benzyl 1-(benzyloxycarbonylsulfamoyl)-3-[3-piperidyl]pyrrole-2-carboxylate hydrochloride (466 mg, 0.94 mmol) and triethylamine (300 µL, 2.15 mmol) in DCM (5 mL) was cooled to 0° C. followed by the dropwise addition of acetyl chloride (68 µL, 1.12 mmol).

The reaction mixture was allowed to warm to room temperature and stirred for 1 hour. The residue was washed with water (2×5 mL), brine (5 mL), dried over $MgSO_4$, filtered and concentrated to dryness under reduced pressure. The residue was purified by column chromatography (DCM:methanol, gradient elution from 100:0 to 90:10), redissolved in ethyl acetate (10 mL) and washed with water (2×10 mL) then brine (10 mL). The organic phase was dried over $MgSO_4$, filtered and concentrated to dryness under reduced pressure to give the desired product as an off-white solid (262 mg, 52%).

$^1$H NMR (500 MHz, DMSO-$d_6$) δ 7.53-7.45 (m, 3H), 7.44-7.34 (m, 8H), 6.34 (brs, 1H), 5.41-5.29 (m, 2H), 5.11 (d, J=7.9 Hz, 2H), 4.40 (br d, J=12.5 Hz, 1H), 3.86-3.68 (m, 1H), 3.09-2.89 (m, 2H), 2.65-2.45 (m, 1H), 2.06 (s, 1.4H), 1.89 (s, 1.6H), 1.86-1.75 (m, 1H), 1.72-1.51 (m, 2H), 1.35-1.17 (m, 2H). A complex spectrum is observed due constrained rotation.

LC-MS (Method A): $R_T$=3.37 min, m/z=540.3 $[M+H]^+$.

Step B: 3-[1-Acetyl-3-piperidyl]-1-sulfamoyl-pyrrole-2-carboxylic acid

To a solution of benzyl 3-(1-acetyl-3-piperidyl)-1-(benzyloxycarbonylsulfamoyl)pyrrole-2-carboxylate (262 mg, 0.49 mmol) in methanol (10 mL) was added 10% palladium on carbon (52 mg, 24 µmol) and the resulting suspension stirred under 1 atmosphere hydrogen at room temperature for 6 hours. The reaction mixture was filtered through Celite®, concentrated to dryness under reduced pressure, slurried in diethyl ether and dried under reduced pressure to give the desired product as a white solid (125 mg, 82%).

$^1$H NMR (500 MHz, DMSO-$d_6$) δ 8.34 (br s, 2H), 7.37-7.29 (m, 1H), 6.29-6.21 (m, 1H), 4.48-4.31 (m, 1H), 3.92-3.77 (m, 1H), 3.29-3.19 (m, 1H), 3.06-2.83 (m, 1H), 2.60-2.44 (m, 1H), 2.02 (s, 3H), 1.91-1.82 (m, 1H), 1.77-1.28 (m, 3H).

LC-MS (Method C): $R_T$=5.78 min, m/z=314.4 $[M-H]^-$.

Further Examples

The following examples were prepared in a similar manner to 3-[1-acetyl-3-piperidyl]-1-sulfamoyl-pyrrole-2-carboxylic acid (Example 58).

| Example | Structure | Name | Analytical Data |
|---|---|---|---|
| Example 59 (free acid) | 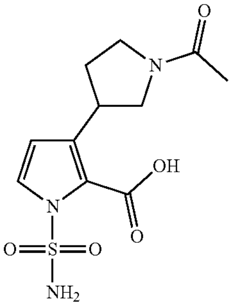 [SMILES: CC(=O)N1CCC(c2ccn(S(N)(=O)=O)c2C(=O)O)C1] | 3-[1-Acetylpyrrolidin-3-yl]-1-sulfamoyl-pyrrole-2-carboxylic acid | $^1$H NMR (500 MHz, DMSO-$d_6$) δ 8.81-7.80 (m, 2H), 7.36-7.29 (m, 1H), 6.32-6.20 (m, 1H), 4.25-3.05 (m, 5H), 2.25-1.80 (m, 5H). LC-MS (Method A): $R_T$ = 1.99 min, m/z = 302.2 $[M + H]^+$. |
| Example 60 (free acid) | 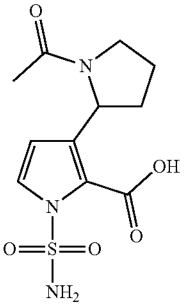 [SMILES: CC(=O)N1CCCC1c1ccn(S(N)(=O)=O)c1C(=O)O] | 3-[1-Acetylpyrrolidin-2-yl]-1-sulfamoyl-pyrrole-2-carboxylic acid | $^1$H NMR (500 MHz, DMSO-$d_6$) δ 9.56 (br s, 2H), 7.04 (d J = 3.1 Hz, 0.8H), 6.95 (d, J = 3.1 Hz, 0.2H), 5.80 (d, J = 3.1 Hz, 0.8H), 5.77 (d, J = 3.1 Hz, 0.2H), 5.68-5.66 (m, 0.8H), 5.52 (br d, J = 7.8 Hz, 0.2H), 3.52-3.28 (m, 2H), 2.25-2.21 (m, 0.8H), 2.06-2.02 (m, 0.2H), 1.97 (s, 0.6H), 1.84-1.73 (m, 3H), 1.71 (s, 2.4H). Peaks show complex splitting due to observing multiple rotamers. LC-MS (Method A): $R_T$ = 5.13 min, m/z = 300.3 $[M - H]^-$. |
| Example 61 (free acid) | 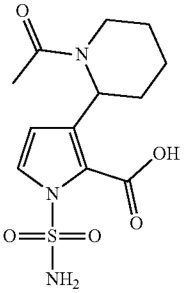 [SMILES: CC(=O)N1CCCCC1c1ccn(S(N)(=O)=O)c1C(=O)O] | 3-[1-Acetyl-2-piperidyl]-1-sulfamoyl-pyrrole-2-carboxylic acid | $^1$H NMR (500 MHz, DMSO-$d_6$) δ 9.44 (br s, 2H), 7.01 (br s, 1H), 6.09 (br s, 0.8 H), 5.98 (br s, 0.2H), 5.92 (s, 0.2H), 5.85 (s, 0.8H), 4.38-4.32 (m, 1H), 2.92 (br t, J = 11.9 Hz, 1H), 1.88 (s, 3H), 1.80-1.68 (m, 2H), 1.50-1.26 (m, 4H). Peaks show complex splitting due to observing multiple rotamers. LC-MS (Method A): $R_T$ = 2.44 min, m/z = 314.4 $[M - H]^-$. |
| Example 62 (free acid) | 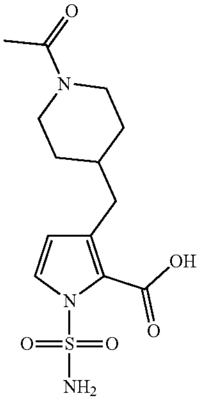 [SMILES: CC(=O)N1CCC(Cc2ccn(S(N)(=O)=O)c2C(=O)O)CC1] | 3-[(1-Acetyl-4-piperidyl)methyl]-1-sulfamoyl-pyrrole-2-carboxylic acid | $^1$H NMR (500 MHz, DMSO-$d_6$) δ 9.14 (br s, 2H), 7.06 (br d, J = 2.5 Hz, 1H), 5.94 (d, J = 2.5 Hz, 1H), 4.29 (d, J = 13.0 Hz, 1H), 3.75 (d, J = 13.0 Hz, 1H), 2.97-2.87 (m, 1H), 2.68 (d, J = 7.0 Hz, 2H), 2.50-2.40 (m, 1H), 1.96 (s, 3H), 1.77-1.65 (m, 1H), 1.62-1.55 (m, 2H), 1.13-1.02 (m, 1H), 1.02-0.88 (m, 1H). LC-MS (Method A): $R_T$ = 2.32 min, m/z = 328.3 $[M - H]^-$. |

Example 63 (Free Acid): 3-[1-(2-Aminoacetyl)-3-piperidyl]-1-sulfamoyl-pyrrole-2-carboxylic acid

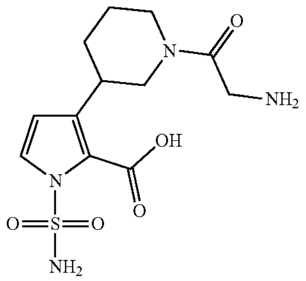 [SMILES: NCC(=O)N1CCCC(c2ccn(S(N)(=O)=O)c2C(=O)O)C1]

Step A: Benzyl 1-(benzyloxycarbonylsulfamoyl)-3-[1-[2-(tert-butoxycarbonylamino)acetyl]-3-piperidyl]pyrrole-2-carboxylate To a solution of N-(tert-butoxycarbonyl)glycine (194 mg, 1.11 mmol) in DCM (5 mL) was added DIPEA (875 μL, 5.02 mmol) followed by HBTU (419 mg, 1.11 mmol). After stirring at room temperature for 5 minutes, benzyl 1-(benzyloxycarbonylsulfamoyl)-3-[3-piperidyl]pyrrole-2-carboxylate hydrochloride (500 mg, 1.00 mmol) was added before stirring at room temperature for 1 hour. The reaction mixture was concentrated to dryness under reduced pressure, redissolved in ethyl acetate (10 mL), washed with saturated sodium bicarbonate solution (2×10 mL), 2 M aqueous HCl (2×10 mL) and brine (10 mL), dried over $MgSO_4$, filtered and concentrated to dryness under reduced pressure. The residue was purified by column chromatography (petroleum ether:ethyl acetate, gradient elution from 90:10 to 0:100) to give the desired product as an off-white solid (427 mg, 65%).

$^1H$ NMR (500 MHz, $CDCl_3$) δ 7.50 (t, J=3.6 Hz, 1H), 7.42-7.27 (m, 10H), 6.13 (br s, 1H), 5.65-5.41 (m, 1H), 5.40-5.21 (m, 2H), 5.20-5.07 (m, 2H), 4.65-4.51 (m, 1H), 3.92 (br d, J=3.7 Hz, 1H), 3.84-3.56 (m, 2H), 3.20-3.04 (m, 1H), 2.98-2.82 (m, 1H), 2.54 (br t, J=12.4 Hz, 1H), 1.98-1.85 (m, 1H), 1.75-1.64 (m, 1H), 1.48 (s, 4.5H), 1.45 (s, 4.5H), 1.37-1.05 (m, 2H). Complex splitting observed due to constrained rotation.

LC-MS (Method A): $R_T$=3.80 min, m/z=653.7 $[M-H]^-$.

Step B: Benzyl 3-[1-(2-aminoacetyl)-3-piperidyl]-1-(benzyloxycarbonylsulfamoyl)pyrrole-2-carboxylate A solution of benzyl 1-(benzyloxycarbonylsulfamoyl)-3-[1-[2-(tert-butoxycarbonylamino)acetyl]-3-piperidyl]pyrrole-2-carboxylate (504 mg, 770 μmol) in 4 M HCl in 1,4-dioxane (2 mL) was stirred at room temperature for 2 hours. The reaction mixture was concentrated to dryness under reduced and free based on an SCX-2 cartridge eluting with ammonia in methanol to give the desired product as an off-white solid (320 mg, 75%).

$^1H$ NMR (500 MHz, DMSO-$d_6$) δ 7.73 (br s, 3H), 7.61-7.50 (m, 2H), 7.36-7.23 (m, 9H), 6.05 (dd, J=8.9, 3.1 Hz, 1H), 5.29-5.14 (m, 2H), 4.84 (s, 2H), 4.38 (br d, J=12.2 Hz, 1H), 3.95-3.74 (m, 2H), 3.67 (br t, J=11.7 Hz, 1H), 3.07-2.91 (m, 1H), 2.89-2.79 (m, 1H), 2.71-2.61 (m, 1H), 1.90-1.77 (m, 1H), 1.76-1.51 (m, 2H), 1.48-1.21 (m, 1H). Complex splitting observed due to constrained rotation.

LC-MS (Method A): $R_T$=2.85 min, m/z=555.4 $[M+H]^+$.

Step C: 3-[1-(2-Aminoacetyl)-3-piperidyl]-1-sulfamoyl-pyrrole-2-carboxylic acid

To a solution of benzyl 3-[1-(2-aminoacetyl)-3-piperidyl]-1-(benzyloxycarbonylsulfamoyl)pyrrole-2-carboxylate (320 mg, 577 μmol) in a mixture of methanol (9 mL) and 7 M ammonia in methanol (1 mL) was added 10% palladium on carbon (61 mg, 29 μmol) and the resulting suspension stirred under 1 atmosphere hydrogen at room temperature for 6 hours. The reaction mixture was filtered through Celite®, concentrated to dryness under reduced pressure, slurried in diethyl ether and dried under reduced pressure to give the desired product as a white solid (125 mg, 66%).

$^1H$ NMR (500 MHz, DMSO-$d_6$) δ 9.06 (br s, 2H), 8.29 (br s, 3H), 7.09-6.99 (m, 1H), 6.10-6.03 (m, 1H), 4.46-4.29 (m, 2H), 4.00-3.89 (m, 1H), 3.86-3.77 (m, 1H), 3.35-3.27 (m, 1H), 2.70 (dd, J=12.7, 11.4 Hz, 1H), 2.66-2.58 (m, 1H), 1.89-1.69 (m, 3H), 1.45-1.33 (m, 1H). Complex splitting observed due to constrained rotation. Peaks are resolved at 80° C.

LC-MS (Method C): $R_T$=4.52 min, m/z=329.4 $[M-H]^-$.

Further Examples

The following examples were prepared in a similar manner to 3-[1-(2-aminoacetyl)-3-piperidyl]-1-sulfamoyl-pyrrole-2-carboxylic acid (Example 63).

| Example | Structure | Name | Analytical Data |
| --- | --- | --- | --- |
| Example 64 (free acid) | 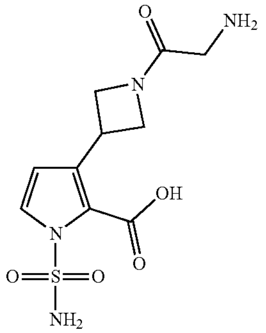 [SMILES: NCC(=O)N1CC(c2ccn(S(N)(=O)=O)c2C(=O)O)C1] | 3-[1-(2-Aminoacetyl)azetidin-3-yl]-1-sulfamoyl-pyrrole-2-carboxylic acid | $^1H$ NMR (500 MHz, DMSO-$d_6$) δ 8.53 (br s, 5H), 7.11 (d, J = 3.2 Hz, 1H), 6.24 (d, J = 3.1 Hz, 1H), 4.55-4.45 (m, 1H), 4.43-4.29 (m, 1H), 4.22 (t, J = 9.2 Hz, 1H), 4.03 (br t, J = 7.5 Hz, 1H), 3.88 (br dd, J = 9.2, 7.0 Hz, 1H), 3.72-3.57 (m, 1H), 3.53-3.50 (m, 1H). LC-MS (Method F): $R_T$ = 0.92 min, m/z = 301.4 $[M-H]^-$. |

-continued

| Example | Structure | Name | Analytical Data |
|---|---|---|---|
| Example 65 (free acid) | 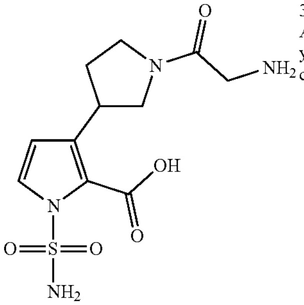 | 3-[1-(2-Aminoacetyl)pyrrolidin-3-yl]-1-sulfamoyl-pyrrole-2-carboxylic acid | $^1$H NMR (500 MHz, DMSO-$d_6$) δ 9.23-7.48 (m, 4H), 7.09-7.01 (m, 1H), 6.11-6.00 (m, 1H), 4.23-3.98 (m, 1H), 3.82-3.04 (m, 6H), 2.20-1.79 (m, 2H). Complex splitting observed due ot constrained rotation. LC-MS (Method A): $R_T$ = 0.94 min, m/z = 317.2 $[M + H]^+$. |
| Example 66 (free acid) | 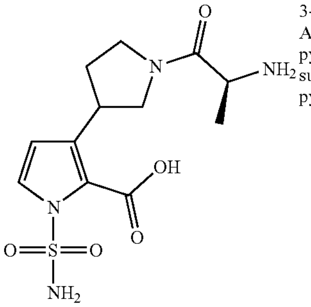 (mixture of diastereomers) | 3-[1-[(2S)-2-Aminopropanoyl] pyrrolidin-3-yl]-1-sulfamoyl-pyrrole-2-carboxylic acid | $^1$H NMR (500 MHz, DMSO-$d_6$) δ 7.09-7.01 (m, 1H), 6.13-6.02 (m, 1H), 4.30-2.99 (m, 6H), 2.23-1.79 (m, 2H), 1.35-1.30 (m, 3H). Complex splitting observed due to mixture of diastereomers and constrained rotation. LC-MS (Method A): $R_T$ = 0.87 min, m/z = 331.2 $[M + H]^+$. |
| Example 67 (free acid) | 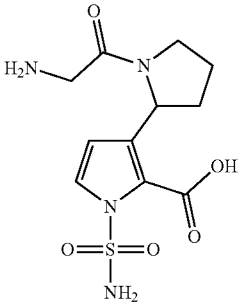 [SMILES: NCC(=O)N1CCCC1c1ccn(S(N)(=O)=O)c1C(=O)O] | 3-[(2S)-1-(2-Aminoacetyl)pyrrolidin-2-yl]-1-sulfamoyl-pyrrole-2-carboxylic acid | $^1$H NMR (500 MHz, DMSO-$d_6$) δ 7.07 (d, J = 3.2 Hz, 0.8H), 6.94 (d, J = 3.1 Hz, 0.2H), 5.86 (d, J = 3.2 Hz, 0.8H), 5.81 (d, J = 3.1 Hz, 0.2H), 5.77 (dd, J = 7.7, 2.8 Hz, 0.8H), 5.63 (br d, J = 7.7 Hz, 0.2H), 3.75-3.65 (m, 1H), 3.61-3.51 (m, 2H), 2.94-2.91 (m, 1H), 2.27-2.19 (m, 1H), 1.91-1.72 (m, 3H). Complex splitting observed due to constrained rotation. LC-MS (Method A): $R_T$ = 1.01 min, m/z = 315.3 $[M - H]^-$. |
| Example 68 (free acid) | 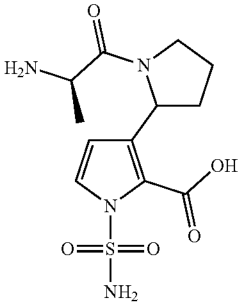 [SMILES: C[C@@H](N)C(=O)N1CCCC1c1ccn(S(N)(=O)=O)c1C(=O)O] (mixture of diastereomers) | 3-[1-[(2S)-2-Aminopropanoyl]pyrrolidin-2-yl]-1-sulfamoyl-pyrrole-2-carboxylic acid | $^1$H NMR (500 MHz, DMSO-$d_6$) δ 7.37 (br s, 2H), 7.08-6.94 (m, 1H), 6.09-5.58 (m, 2H), 4.12-4.02 (m, 1H), 3.79-3.47 (m, 3H), 2.28-2.07 (m, 1H), 2.01-1.71 (m, 4H), 1.34-1.23 (m, 3H). Complex splitting observed due to mixture of diastereomers and constrained rotation. LC-MS (Method A): $R_T$ = 0.42 min, m/z = 329.4 $[M - H]^-$. |

-continued

| Example | Structure | Name | Analytical Data |
|---|---|---|---|
| Example 69 (free acid) * | 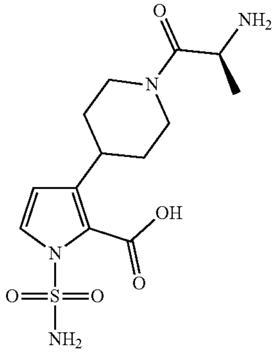 [SMILES: C[C@H](N)C(=O)N1CCC(c2ccn(S(N)(=O)=O)c2C(=O)O)CC1] | 3-[1-[(2S)-2-Aminopropanoyl]-4-piperidyl]-1-sulfamoyl-pyrrole-2-carboxylic acid | $^1$H NMR (500 MHz, $D_2O$) δ 7.11 (t, J = 3.8 Hz, 1H), 6.13 (dd, J = 9.2, 3.4 Hz, 1H), 4.50-4.42 (m, 1H), 4.42-4.32 (m, 1H), 3.82 (br d, J = 13.1 Hz, 1H), 3.26-3.15 (m, 2H), 2.84-2.72 (m, 1H), 1.89-1.73 (m, 2H), 1.60-1.46 (m, 2H), 1.42 (dd, J = 22.0, 6.7 Hz, 3H). LC-MS (Method C): $R_T$ = 2.94 min, m/z = 343.5 $[M-H]^-$. |
| Example 70 (free acid) | 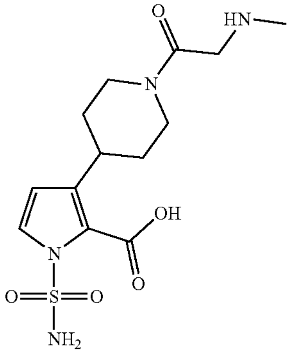 [SMILES: CNCC(=O)N1CCC(c2ccn(S(N)(=O)=O)c2C(=O)O)CC1] | 3-[1-[2-(Methylamino)acetyl]-4-piperidyl]-1-sulfamoyl-pyrrole-2-carboxylic acid | $^1$H NMR (500 MHz, $D_2O$) δ 7.10 (d, J = 3.2 Hz, 1H), 6.12 (d, J = 3.2 Hz, 1H), 4.39-4.35 (m, 1H), 4.04 (d, J = 16.3 Hz, 1H), 3.98 (d, J = 16.3 Hz, 1H), 3.69-3.64 (m, 1H), 3.22-3.12 (m, 2H), 2.81-2.74 (m, 1H), 2.67 (s, 3H), 1.81-1.75 (m, 2H), 1.57-1.47 (m, 2H). LC-MS (Method A): $R_T$ = 0.94 min, m/z = 343.4 $[M-H]^-$. |
| Example 71 (free acid) | 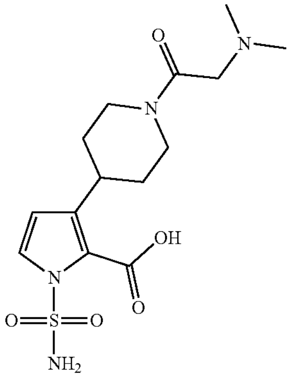 [SMILES: CN(C)CC(=O)N1CCC(c2ccn(S(N)(=O)=O)c2C(=O)O)CC1] | 3-[1-[2-(Dimethylamino)acetyl]-4-piperidyl]-1-sulfamoyl-pyrrole-2-carboxylic acid | $^1$H NMR (500 MHz, $D_2O$) δ 7.09 (d, J = 3.2 Hz, 1H), 6.10 (d, J = 3.2 Hz, 1H), 4.41-4.36 (m, 1H), 3.83-3.74 (m, 2H), 3.21-3.11 (m, 2H), 2.78-2.71 (m, 2H), 2.61 (s, 6H), 1.82-1.76 (m, 2H), 1.55-1.44 (m, 2H). LC-MS (Method A): $R_T$ = 1.52 min, m/z = 357.2 $[M-H]^-$. |
| Example 72 (free acid) | 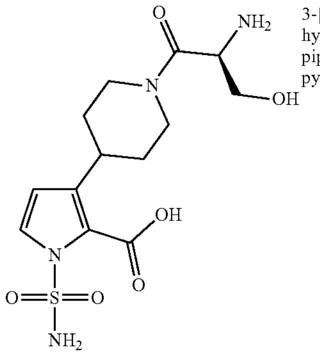 | 3-[1-[(2S)-2-Amino-3-hydroxy-propanoyl]-4-piperidyl]-1-sulfamoyl-pyrrole-2-carboxylic acid | $^1$H NMR (500 MHz, DMSO-$d_6$) δ 9.72-9.14 (m, 2H), 6.96 (d, J = 3.2 Hz, 1H), 5.98-5.92 (m, 1H), 5.05-4.86 (m, 1H), 4.56-4.44 (m, 1H), 4.16-3.91 (m, 2H), 3.71-3.49 (m, 2H), 3.12-2.97 (m, 2H), 1.85-1.65 (m, 2H), 1.51-1.23 (m, 2H). LC-MS (Method A): $R_T$ = 1.01 min, m/z = 359.3 $[M-H]^-$. |

-continued

| Example | Structure | Name | Analytical Data |
|---|---|---|---|
| Example 73 (free acid) | 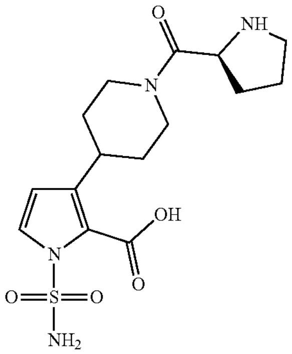 [SMILES: NS(=O)(=O)n1ccc(C2CCN(C(=O)[C@@H]3CCCN3)CC2)c1C(=O)O] | 3-[1-[(2S)-Pyrrolidine-2 carbonyl]-4-piperidyl]-1-sulfamoyl-pyirole-2-carboxylic acid | $^1H$ NMR (500 MHz, Methanol-$d_4$) δ 7.07-6.99 (m, 1H), 5.94 (dd, J = 3.3, 5.4 Hz, 1H), 4.52-4.45 (m, 1H), 4.08-3.97 (m, 1H), 3.94-3.86 (m, 1H), 3.57-3.45 (m, 1H), 3.16-3.03 (m, 2H), 2.87-2.66 (m, 2H), 2.24-2.12 (m, 1H), 1.89-1.55 (m, 5H), 1.40 (m, 2H). LC-MS (Method A): $R_T$ = 1.63 min, m/z = 369.4 $[M - H]^-$. |
| Example 74 (free acid) | 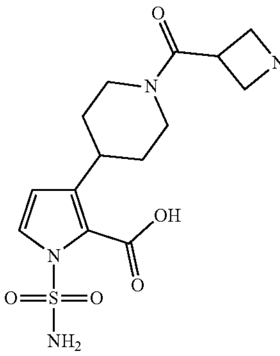 | 3-[1-(Azetidine-3-carbonyl)-4-piperidyl]-1-sulfamoyl-pyrrole-2-carboxylic acid | $^1H$ NMR (500 MHz, DMSO-$d_6$) δ 6.96 (d, J = 3.1 Hz, 1H), 5.95 (d, J = 3.1 Hz, 1H), 4.49-4.44 (m, 1H), 4.05-4.01 (m, 1H), 3.98-3.94 (m, 3H), 3.89-3.82 (m, 1H), 3.63-3.50 (m, 2H), 3.02-2.96 (m, 1H), 2.65-2.48 (m, 1H), 1.77-1.70 (br m, 2H), 1.40-1.29 (m, 2H). Peak at 2.65-2.48 ppm partially obscured by residual solvent peak.d LC-MS (Method A): $R_T$ = 1.38 min, m/z = 355.4 $[M - H]^-$. |
| Example 75 (free acid) | 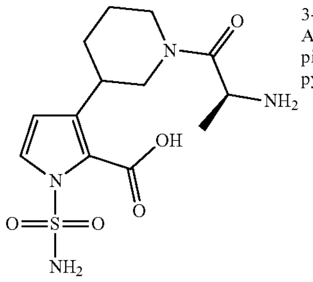 (mixture of diastereomers) | 3-[1-[(2S)-2-Aminopropanoyl]-3-piperidyl]-1-sulfamoyl-pyrrole-2-carboxylic acid | $^1H$ NMR (500 MHz, DMSO-$d_6$) δ 9.11 (br s, 2H), 8.03 (br s, 3H), 7.08-6.98 (m, 1H), 6.11-6.01 (m, 1H), 4.84 (q, J = 7.0 Hz, 0.4H), 4.51-4.22 (m, 1.6H), 4.13 (br d, J = 12.5 Hz, 0.4H), 3.95-3.78 (m, 0.6H), 3.62-3.24 (m, 1H), 3.08-2.72 (m, 1H), 2.67-2.54 (m, 1H), 1.89-1.62 (m, 3H), 1.55-1.20 (m, 4H). Complex splitting observed due to mixture of diastereomers and constrained rotation. Peaks are resolved at 80° C. LC-MS (Method C): $R_T$ = 4.80 min, m/z = 343.4 $[M - H]^-$ & $R_T$ = 4.89 min, m/z = 343.4 $[M - H]^-$. |
| Example 76 (free acid) | 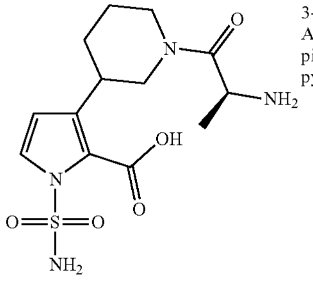 (diastereomer 1) | 3-[1-[(2S)-2-Aminopropanoyl]-3-piperidyl]-1-sulfamoyl-pyrrole-2-carboxylic acid | $^1H$ NMR (500 MHz, DMSO-$d_6$) δ 7.03 (d, J = 3.2 Hz, 0.75H), 7.00 (d, J = 3.1 Hz, 0.25H), 6.09 (d, J = 3.2 Hz, 0.75H), 6.03 (d, J = 3.1 Hz, 0.25H), 4.48-4.30 (m, 2H), 3.93 (br d, J = 13.0 Hz, 0.75H), 3.84 (br d, J = 12.4 Hz, 0.25H), 3.61-3.50 (m, 1H), 3.09-3.03 (m, 0.25H), 2.85 (t, J = 12.4 Hz, 0.75H), 2.67-2.54 (m, 2H), 1.87-1.67 (m, 3H), 1.50-1.25 (m, 5H). Complex splitting observed due to constrained rotation. LC-MS (Method D): $R_T$ = 2.14 min, m/z = |

-continued

| Example | Structure | Name | Analytical Data |
|---|---|---|---|
| | | | 343.2 [M − H]$^-$. Preparative HPLC (Method A): 0.80-1.00 minutes. |
| Example 77 (free acid) | 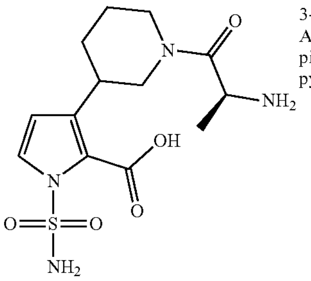 (diastereomer 2) | 3-[1-[(2S)-2-Aminopropanoyl]-3-piperidyl]-1-sulfamoyl-pyrrole-2-carboxylic acid | $^1$H NMR (500 MHz, DMSO-$d_6$) δ 7.05 (d, J = 3.2 Hz, 1H), 6.06 (d, J = 3.2 Hz, 1H), 4.91 (q, J = 7.0 Hz, 1H), 4.41 (br d, J = 12.2 Hz, 1H), 4.17 (br d, J = 12.7 Hz, 1H), 3.29-3.23 (m, 2H), 2.63-2.57 (m, 1H), 1.87-1.75 (m, 3H), 1.47-1.36 (m, 1H), 1.28 (d, J = 6.7 Hz, 3H). Peak at 3.29-3.23 ppm is obscured by NMR solvent. Complex splitting observed due to constrained rotation. LC-MS (Method D): $R_T$ = 2.19 min, m/z = 343.2 [M − H]$^-$. Preparative HPLC (Method A): 0.80-1.00 minutes. |
| Example 78 (free acid) | 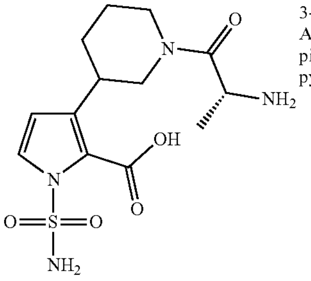 (diastereomer 1) | 3-[1-[(2R)-2-Aminopropanoyl]-3-piperidyl]-1-sulfamoyl-pyrrole-2-carboxylic acid | $^1$H NMR (500 MHz, DMSO-$d_6$) δ 7.03 (d, J = 3.2 Hz, 0.75H), 7.00 (d, J = 3.1 Hz, 0.25H), 6.09 (d, J = 3.2 Hz, 0.75H), 6.03 (d, J = 3.1 Hz, 0.25H), 4.48-4.30 (m, 2H), 3.93 (br d, J = 13.0 Hz, 0.75H), 3.84 (br d, J = 12.4 Hz, 0.25H), 3.61-3.50 (m, 1H), 3.09-3.03 (m, 0.25H), 2.85 (t, J = 12.4 Hz, 0.75H), 2.67-2.54 (m, 2H), 1.87-1.67 (m, 3H), 1.50-1.25 (m, 5H). Complex splitting observed due to constrained rotation. LCMS (Method D): $R_T$: 2.16 min, m/z = 343.2 [M − H]$^-$. |
| Example 79 (free acid) | 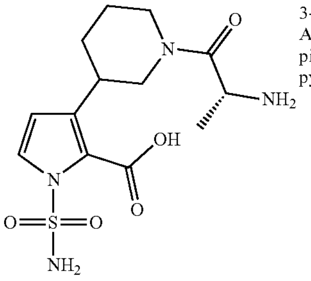 (diastereomer 2) | 3-[1-[(2R)-2-Aminopropanoyl]-3-piperidyl]-1-sulfamoyl-pyrrole-2-carboxylic acid | $^1$H NMR (500 MHz, DMSO-$d_6$) δ 7.05 (d, J = 3.2 Hz, 1H), 6.06 (d, J = 3.2 Hz, 1H), 4.91 (q, J = 7.0 Hz, 1H), 4.41 (br d, J = 12.2 Hz, 1H), 4.17 (br d, J = 12.7 Hz, 1H), 3.29-3.23 (m, 2H), 2.63-2.57 (m, 1H), 1.87-1.75 (m, 3H), 1.47-1.36 (m, 1H), 1.28 (d, J = 6.7 Hz, 3H). Peak at 3.29-3.23 ppm is obscured by NMR solvent. Complex splitting observed due to constrained rotation. LCMS (Method D): $R_T$: 2.26 min, m/z = 343.2 [M − H]$^-$. |

-continued

| Example | Structure | Name | Analytical Data |
|---|---|---|---|
| Example 80 (free acid) | 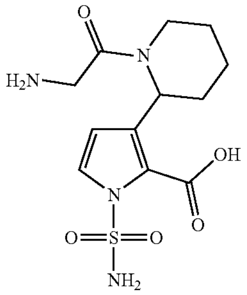 [SMILES: NCC(=O)N1CCCCC1c1ccn(S(N)(=O)=O)c1C(=O)O] | 3-[1-(2-Aminoacetyl)-2-piperidyl]-1-sulfamoyl-pyrrole-2-carboxylic acid | $^1$H NMR (500 MHz, DMSO-$d_6$) δ 7.66-7.13 (br m, 2H) 7.05 (br d, J = 2.6 Hz, 1H), 6.21 (br s, 1H), 5.91-5.89 (m, 1H), 4.36-4.30 (m, 1H), 3.96-3.92 (m, 1H), 3.71-3.61 (m, 1H), 3.08-3.02 (m, 1H) 1.87-1.71 (m, 2H), 1.65-1.53 (m, 2H), 1.45-1.21 (m, 2H). Complex splitting observed due to constrained rotation. LC-MS (Method A): $R_T$ = 0.50 min, m/z = 329.4 $[M - H]^-$. |
| Example 81 (free acid) | 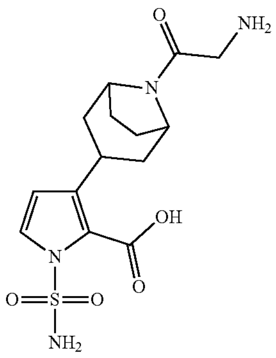 [SMILES: NCC(=O)N1C2CCC1CC(c1ccn(S(N)(=O)=O)c1C(=O)O)C2] | 3-[8-(2-Aminoacetyl)-8-azabicyclo[3.2.1]octan-3-yl]-1-sulfamoyl-pyrrole-2-carboxylic acid | $^1$H NMR (500 MHz, DMSO-$d_6$) δ 6.97 (s, 1H), 5.92 (s, 1H), 5.78 (s, 1H), 4.55-4.49 (m, 2H), 4.24-4.16 (m, 1H), 4.12-4.05 (m, 1H), 3.72 (d, J = 11.2 Hz, 1H), 3.63 (d, J = 11.2 Hz, 1H), 2.02-1.91 (m, 1H), 1.89-1.74 (m, 3H), 1.71-1.61 (m, 3H), 1.59-1.50 (m, 1H). Peaks show complex splitting from a mixture of endo and exo compounds. LC-MS (Method E): $R_T$ = 0.41 min, m/z = 355.4 $[M - H]^-$. |
| Example 82 (free acid) | 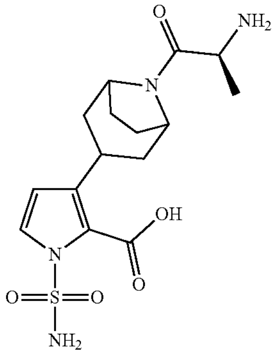 [SMILES: C[C@H](N)C(=O)N1C2CCC1CC(c1ccn(S(N)(=O)=O)c1C(=O)O)C2] | 3-[8-[(2S)-2-Aminopropanoyl]-8-azabicyclo[3.2.1]octan-3-yl]-1-sulfamoyl-pyrrole-2-carboxylic acid | $^1$H NMR (500 MHz, DMSO-$d_6$) δ 6.98 (s, 1H), 5.93 (s, 1H), 4.61 (s, 1H), 4.49-4.38 (m, 1H), 4.38-4.04 (m, 2H), 4.91-4.80 (m, 1H), 2.10-1.46 (m, 9H), 1.41-1.25 (m, 3H). Peaks show complex splitting from a mixture of endo and exo compounds. LC-MS (Method E): $R_T$ = 0.39 min, m/z = 371.2 $[M + H]^+$. |

*The amide coupling was performed with the Cbz-protected amino acid, followed by hydrogenation with $Pd(OH)_2/C$ catalyst.

Example 83 (Free Acid): 3-[1-(2-Guanidinoacetyl)-4-piperidyl]-1-sulfamoyl-pyrrole-2-carboxylic acid

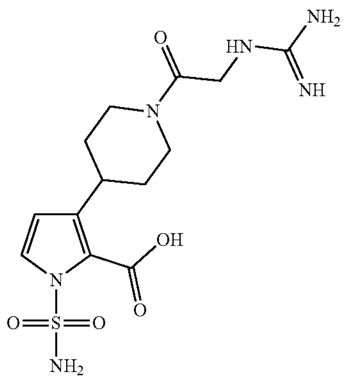 [SMILES: N=C(N)NCC(=O)N1CCC(c2ccn(S(N)(=O)=O)c2C(=O)O)CC1]

Step A: Benzyl 1-(benzyloxycarbonylsulfamoyl)-3-[1-(2-guanidinoacetyl)-4-piperidyl]pyrrole-2-carboxylate Benzyl 3-[1-(2-aminoacetyl)-4-piperidyl]-1-(benzyloxycarbonylsulfamoyl)pyrrole-2-carboxylate (180 mg, 0.32 mmol) was suspended in acetonitrile (5 mL), then DIPEA (282 μL, 1.62 mmol) was added. After stirring for 10 minutes, N,N'-di-Boc-1H-pyrazole-1-carboxamidine (101 mg, 0.32 mmol) was added, and the mixture was allowed to stir at room temperature for 18 hours. The reaction mixture was diluted with 1 M aqueous HCl (20 mL), and the precipitated solid isolated by filtration. This was dissolved into 4 M HCl in 1,4-dioxane (972 μL), and stirred at room temperature for 2 hours. Diethyl ether (20 mL) was added, resulting in formation of a colourless solid, which was isolated by filtration. This was free based on an SCX-2 cartridge eluting with ammonia in methanol and concentrated in vacuo to afford the desired product as a colourless solid (60 mg, 31%).

$^1$H NMR (500 MHz, DMSO-$d_6$) δ 7.60 (d, J=3 Hz, 1H), 7.30-7.20 (m, 10H), 7.17-6.99 (m, 2H), 5.95 (d, J=3.1 Hz, 1H), 5.20 (s, 2H), 4.84 (s, 2H), 4.45-4.37 (m, 1H), 4.16-3.98 (m, 3H), 3.71-3.64 (m, 1H), 3.05-2.85 (m, 2H), 1.72-1.31 (m, 4H).

LC-MS (Method A): $R_T$=3.05 min, m/z=595.4 $[M-H]^-$.

Step B: 3-[1-(2-Guanidinoacetyl)-4-piperidyl]-1-sulfamoyl-pyrrole-2-carboxylic acid 10% Palladium on carbon (11 mg, 5.0 μmol) was added to a solution of benzyl 1-(benzyloxycarbonylsulfamoyl)-3-[1-(2-guanidinoacetyl)-4-piperidyl]pyrrole-2-carboxylate (60 mg, 0.10 mmol) in 1,4-dioxane (5 mL) and stirred under 1 atmosphere of hydrogen for 5 hours. The reaction mixture was filtered through a Celite® pad and washed with methanol (20 mL). The combined filtrates were concentrated under reduced pressure and azeotroped with diethyl ether (2×5 mL) to afford the desired product as a colourless solid (38 mg, 87%).

$^1$H NMR (500 MHz, DMSO-$d_6$) δ 9.64-9.01 (br, 1H), 7.61-7.06 (br, 6H), 6.99 (d, J=3.1 Hz, 1H), 5.97 (d, J=3.1 Hz, 1H), 4.47 (br d, J=11.1 Hz, 1H), 4.17-4.02 (m, 2H), 3.78-3.61 (m, 2H), 3.58-3.46 (m, 1H), 3.10-3.00 (m, 1H), 1.82-1.70 (m, 2H), 1.59-1.45 (m, 1H), 1.42-1.30 (m, 1H).

LC-MS (Method A): $R_T$=1.66 min, m/z=371.3 $[M-H]^-$.

Example 84 (Free Acid): 1-Sulfamoyl-3-[1-[2-(2,2,2-trifluoroethylamino)acetyl]-4-piperidyl]pyrrole-2-carboxylic acid

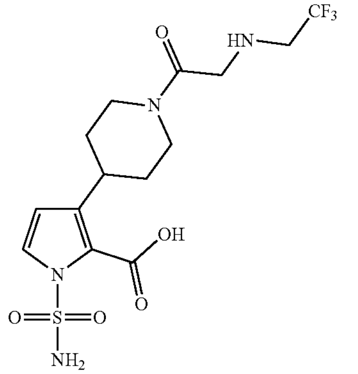 [SMILES: NS(=O)(=O)n1ccc(C2CCN(C(=O)CNCC(F)(F)F)CC2)c1C(=O)O]

Step A: Benzyl 1-(benzyloxycarbonylsulfamoyl)-3-[1-[2-(2,2,2-trifluoroethylamino)acetyl]-4-piperidyl]pyrrole-2-carboxylate 2,2,2-Trifluoroethyl trifluoromethanesulfonate (20 μL, 0.14 mmol) was added to a solution of benzyl 3-[1-(2-aminoacetyl)-4-piperidyl]-1-(benzyloxycarbonylsulfamoyl)pyrrole-2-carboxylate (85 mg, 144 μmol) in a mixture of THF (0.5 mL) and DMF (0.5 mL) and stirred at room temperature for 2 hours. The reaction mixture was charged with triethylamine (60 uL, 0.43 mmol) and stirred at room temperature for 48 hours. The reaction mixture was recharged with 2,2,2-trifluoroethyl trifluoromethanesulfonate (20 μL, 0.14 mmol) and stirred for a further 90 minutes. The reaction mixture was quenched with water (10 mL) and extracted into ethyl acetate (3×10 mL). The combined extracts were washed with 50:50 water:brine (2×10 mL), dried over $MgSO_4$, filtered, concentrated under reduced pressure and purified by column chromatography (40-100% ethyl acetate in petroleum ether) to afford the desired product as a white solid (22 mg, 24%).

LC-MS (Method A): RT=3.50 min, m/z=635.7 $[M-H]^-$.

Step B: 1-Sulfamoyl-3-[1-[2-(2,2,2-trifluoroethylamino)acetyl]-4-piperidyl]pyrrole-2-carboxylic acid 10% Palladium on carbon (7.4 mg, 3.5 μmol) was added to a solution of benzyl 1-(benzyloxycarbonylsulfamoyl)-3-[1-[2-(2,2,2-trifluoroethylamino)acetyl]-4-piperidyl]pyrrole-2-carboxylate (22 mg, 0.35 mmol) in methanol (1 mL) and stirred under 1 atmosphere of hydrogen for 3 hours. The reaction mixture was filtered through a Celite® pad, washed with methanol (20 mL) and the filtrate collected, concentrated under reduced pressure and azeotroped with diethyl ether (2×5 mL) to afford the desired product as a white solid (11 mg, 69%).

$^1$H NMR (500 MHz, DMSO-$d_6$) δ 9.48 (br s, 2H), 6.96 (br s, 1H), 5.96 (br s, 1H), 4.49-4.44 (m, 1H), 3.78-3.73 (m, 1H), 3.65-3.58 (m, 1H), 3.54-3.44 (m, 3H), 3.00-2.93 (m, 1H), 1.75-1.69 (2H), 1.47-1.24 (m, 5H).

$^{19}$F NMR (470 MHz, DMSO-$d_6$) 5-70.77 (s, 3F).

LC-MS (Method A): $R_T$=2.16 min, m/z=411.4 $[M-H]^-$.

Example 85 (Free Acid): 3-[1-(2-Aminoethyl)-4-piperidyl]-1-sulfamoyl-pyrrole-2-carboxylic acid

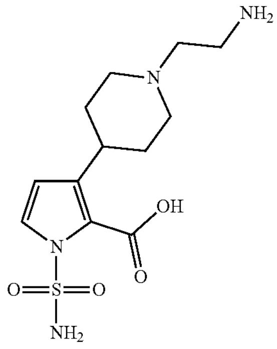 [SMILES: NCCN1CCC(c2ccn(S(N)(=O)=O)c2C(=O)O)CC1]

Step A: Benzyl 3-[1-[2-(benzyloxycarbonylamino)ethyl]-4-piperidyl]-1-(benzyloxycarbonylsulfamoyl)pyrrole-2-carboxylate Triethylamine (78 μL, 562 μmol) was added to a solution of benzyl 1-(benzyloxycarbonylsulfamoyl)-3-(4-piperidyl)pyrrole-2-carboxylate hydrochloride (100 mg, 187 μmol) and benzyl (2-bromoethyl)carbamate (48 mg, 187 μmol) in DMF (2 mL). The reaction was stirred at 50° C. overnight, then quenched with saturated aqueous sodium bicarbonate solution (10 mL) and extracted into ethyl acetate (3×5 mL). The combined organic layers were dried over $Na_2SO_4$, filtered, concentrated in vacuo and purified by column chromatography (0-100% ethyl acetate in petroleum ether) to afford the desired product (30 mg, 24%).

$^1$H NMR (500 MHz, DMSO-$d_6$) δ 7.96 (s, 1H), 7.59-7.51 (m, 2H), 7.42-7.24 (m, 13H), 5.76 (s, 1H), 5.20 (s, 2H), 5.06 (s, 2H), 4.84 (s, 2H), 3.61 (br t, J=6.2 Hz, 1H), 1.89-1.65 (m, 4H), 1.24 (s, 8H).

LC-MS (Method A): $R_T$=3.42 min, m/z=673.8 $[M-H]^-$.

Step B: 3-[1-(2-Aminoethyl)-4-piperidyl]-1-sulfamoyl-pyrrole-2-carboxylic acid

10% Palladium on carbon (2.2 mg, 2.1 μmol) was added to a solution of benzyl 3-[1-[2-(benzyloxycarbonylamino)ethyl]-4-piperidyl]-1-(benzyloxycarbonylsulfamoyl)pyrrole-2-carboxylate (30 mg, 42 μmol) in methanol (2 mL) and stirred under 1 atmosphere of hydrogen for 5 hours. The reaction mixture was filtered through a Celite® pad, washed with 1 M ammonia in methanol (20 mL) and the filtrate collected and concentrated under reduced pressure. The residue was purified by column chromatography (0-100% 1 M $NH_3$/methanol in ethyl acetate) to give the desired product as an off-white solid (4 mg, 24%).

$^1$H NMR (500 MHz, Methanol-$d_4$) δ 7.02 (d, J=3.4 Hz, 1H), 5.97 (d, J=3.2 Hz, 1H), 2.89-2.81 (m, 4H), 2.49-2.43 (m, 1H), 2.13-2.05 (m, 2H), 1.86-1.77 (m, 2H), 1.66-1.53 (m, 2H), 0.84-0.73 (m, 2H).

LC-MS (Method A): $R_T$=0.41 min, m/z=315.4 $[M-H]^-$.

Example 86 (Free Acid): 3-(4-Carboxycyclohexyl)-1-sulfamoyl-pyrrole-2-carboxylic acid

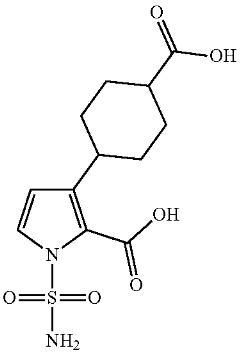

10% Palladium on carbon (24 mg, 11 μmol) was added to a solution of 4-[2-benzyloxycarbonyl-1-(benzyloxycarbonylsulfamoyl)pyrrol-3-yl]cyclohex-3-ene-1-carboxylic acid (30 mg, 56 μmol) in methanol (5 mL) and the mixture stirred under 1 atmosphere of hydrogen at room temperature overnight. The mixture was diluted with methanol, then filtered through a pad of Celite®. Volatiles were removed in vacuo and the residue triturated with diethyl ether and dried under vacuum to give the desired product as an off-white solid (17 mg, 82%).

$^1$H NMR (500 MHz, DMSO-$d_6$) δ 13.66-12.76 (br, 1H), 12.72-11.84 (br, 1H), 8.25-7.90 (m, 2H), 7.32 (br s, 1H), 6.11 (d, J=2.9 Hz, 1H), 3.20-3.04 (m, 1H), 2.17-2.04 (m, 2H), 2.03-1.91 (m, 1H), 1.69-1.60 (m, 2H), 1.58-1.34 (m, 4H).

LC-MS (Method A): $R_T$=2.39 min, m/z=315.3 $[M-H]^-$.

Example 87 (Free Acid): 3-[4-[Methyl-[2-(methylamino)ethyl]carbamoyl]cyclohexyl]-1-sulfamoyl-pyrrole-2-carboxylic acid

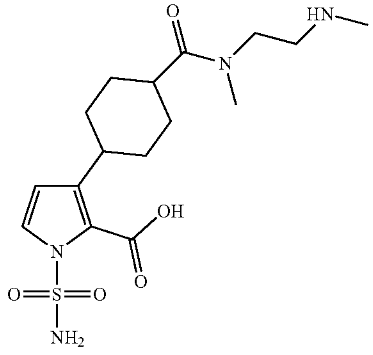 [SMILES: CNCCN(C)C(=O)C1CCC(c2ccn(S(N)(=O)=O)c2C(=O)O)CC1]

Step A: Benzyl 3-[4-[2-[benzyloxycarbonyl(methyl)amino]ethyl-methyl-carbamoyl]cyclohexen-1-yl]-1-(benzyloxycarbonylsulfamoyl)pyrrole-2-carboxylate To a stirred suspension of 4-[2-benzyloxycarbonyl-1-(benzyloxycarbonylsulfamoyl)pyrrol-3-yl]cyclohex-3-ene-1-carboxylic acid (90 mg, 167 μmol) in DCM (5 mL) was added DIPEA (146 μL, 0.84 mmol). HBTU (70 mg, 184 μmol) was added, then after several minutes benzyl N-methyl-N-[2-(methylamino)ethyl]carbamate hydrochloride (48 mg, 184 μmol). The reaction was stirred at room temperature for 2 hours, then concentrated, diluted with ethyl acetate (20 mL) and washed with saturated aqueous sodium bicarbonate solution (3×10 mL), followed by 2 M aqueous HCl (10 mL). The organic phase was then dried over $Na_2SO_4$, filtered and concentrated in vacuo to give the desired product as an off-white solid (121 mg, 97%).

$^1H$ NMR (500 MHz, DMSO-$d_6$) δ 7.45-7.21 (m, 16H), 6.23 (br s, 1H), 5.70 (br s, 1H), 5.24 (s, 2H), 5.10-4.98 (m, 4H), 3.70-3.30 (m, 6H), 3.00-2.74 (m, 6H), 2.25-2.04 (m, 3H), 2.03-1.89 (m, 1H), 1.69-1.55 (m, 1H), 1.54-1.32 (m, 1H). Peaks at 3.70-3.30 ppm are obscured by residual water.

LC-MS (Method A): $R_T$=3.72 min, m/z=743.6 $[M+H]^+$.

Step B: 3-[4-[Methyl-[2-(methylamino)ethyl]carbamoyl]cyclohexyl]-1-sulfamoyl-pyrrole-2-carboxylic acid 10% palladium on carbon (69 mg, 33 μmol) was added to a solution of benzyl 3-[4-[2-[benzyloxycarbonyl(methyl)amino]ethyl-methyl-carbamoyl]cyclohexen-1-yl]-1-(benzyloxycarbonylsulfamoyl)pyrrole-2-carboxylate (121 mg, 163 μmol) in methanol (5 mL). The mixture was stirred under 1 atmosphere of hydrogen at room temperature for 3 hours. The reaction mixture was then diluted with methanol and filtered through Celite®, washing with 1 M ammonia in methanol. The combined filtrates were concentrated in vacuo, re-dissolved in 0.2 M ammonia in methanol and a further portion of 10% palladium on carbon (35 mg, 16 μmol) added. The reaction was stirred under 1 atmosphere of hydrogen at room temperature overnight, then diluted with methanol and filtered through Celite® washing with 1 M ammonia in methanol. Volatiles were removed in vacuo to give the desired product as a colourless solid (45 mg, 68%).

$^1H$ NMR (500 MHz, DMSO-$d_6$) δ 6.94 (t, J=3.0 Hz, 1H), 5.98 (d, J=3.1 Hz, 0.8H), 5.95 (s, 0.2H), 3.01 (br d, J=13.1 Hz, 3H), 2.80 (br d, J=6.0 Hz, 3H), 2.33-2.25 (m, 4H), 2.22-2.11 (m, 2H), 1.82-1.63 (m, 6H), 1.57-1.48 (m, 2H). Mixture of cis and trans isomers observed.

LC-MS (Method A): $R_T$=2.15 min, m/z=385.5 $[M-H]^-$ & $R_T$=2.03 min, m/z=385.5 $[M-H]^-$.

Example 88 (HCl salt): 3-(4-Aminocyclohexyl)-1-sulfamoyl-pyrrole-2-carboxylic acid

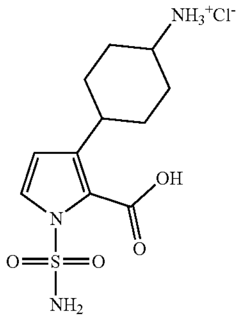

To a solution of benzyl 3-(4-aminocyclohexen-1-yl)-1-(benzyloxycarbonylsulfamoyl)pyrrole-2-carboxylate hydrochloride (150 mg, 275 μmol) in methanol (15 mL) was added 10% palladium on carbon (17 mg, 162 μmol) and stirred under 1 atmosphere hydrogen at room temperature for 24 hours. The reaction mixture was filtered through Celite®, washed with methanol and the filtrates concentrated to dryness. The solid was triturated with diethyl ether and the solvent decanted off twice to give the desired product as a light tan solid (82 mg, 87%).

$^1H$ NMR (500 MHz, DMSO-$d_6$) δ 13.20 (br s, 1H), 8.32-8.05 (br m, 5H), 7.36 (m, 1H), 6.50 (d, J=3.1 Hz, 0.5H), 6.23 (d, J=3.1 Hz, 0.5H), 3.75-3.43 (m, 1H), 3.17-3.06 (br m, 1H), 2.04-1.40 (m, 8H). Mixture of cis and trans isomers observed.

LC-MS (Method A): $R_T$=0.42 min, m/z=286.4 $[M-H]^-$.

Example 89 (Free Acid): 3-(4-Acetamidocyclohexyl)-1-sulfamoyl-pyrrole-2-carboxylic acid

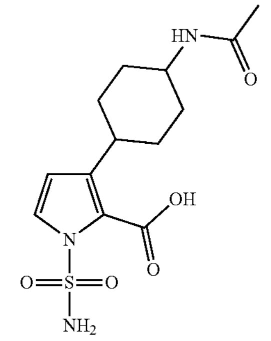 [SMILES: CC(=O)NC1CCC(c2ccn(S(N)(=O)=O)c2C(=O)O)CC1]

Step A: Benzyl 3-(4-acetamidocyclohexen-1-yl)-1-(benzyloxycarbonylsulfamoyl)pyrrole-2-carboxylate A mixture of HBTU (153 mg, 403 μmol), DIPEA (320 μL, 1.83 mmol) and acetic acid (23 μL, 403 μmol) in DCM (10 mL) was stirred for 5 minutes at 20° C., then benzyl 3-(4-aminocyclohexen-1-yl)-1-(benzyloxycarbonylsulfamoyl)pyrrole-2-carboxylate hydrochloride (200 mg, 366 μmol) was added and stirred for a further 3 hours. The reaction 15 mixture was concentrated to dryness, redissolved in ethyl acetate (50 mL), washed with saturated sodium bicarbonate solution (50 mL), 1 M aqueous HCl (50 mL) and brine (50 mL). The organic phase was dried over $MgSO_4$, filtered, concentrated to dryness and purified by column chromatography (0-100% ethyl acetate in petroleum ether) to give the desired product as a white solid (132 mg, 65%).

$^1H$ NMR (500 MHz, $CDCl_3$) δ 7.49-7.36 (m, 1H), 7.30 (m, 8H), 7.28-7.22 (m, 3H), 6.05-5.97 (m, 1H), 5.55-5.47 (m, 2H), 5.29-5.13 (m, 2H), 5.08 (s, 2H), 4.02 (br s, 1H), 2.32-2.09 (m, 3H), 2.00-1.93 (m, 3H), 1.85-1.75 (m, 1H), 1.71-1.55 (m, 1H), 1.52-1.35 (m, 1H).

LC-MS (Method A): $R_T$=3.24 min, m/z=552.3 $[M+H]^+$.

Step B: 3-(4-Acetamidocyclohexyl)-1-sulfamoyl-pyrrole-2-carboxylic acid

To a solution of benzyl 3-(4-acetamidocyclohexen-1-yl)-1-(benzyloxycarbonylsulfamoyl)pyrrole-2-carboxylate (132 mg, 239 μmol) in methanol (15 mL) was added 10% palladium on carbon (15 mg, 141 μmol) and stirred under a hydrogen atmosphere at room temperature for 24 hours. The reaction mixture was filtered through Celite®, washed with methanol and concentrated to dryness. The residue was triturated with diethyl ether and the solvent decanted off twice to give the desired product as a tan solid (43 mg, 52%).

$^{1}$H NMR (500 MHz, DMSO-$d_6$) δ 8.47 (br s, 2H), 7.85-7.73 (m, 1H), 7.30-7.19 (m, 1H), 6.25-6.10 (m, 1H), 3.61-3.30 (m, 2H), 1.92-1.17 (m, 11H). Mixture of cis- and trans isomers observed.

LC-MS (Method A): $R_T$=2.23 min, m/z=328.4 $[M-H]^-$.

Example 90 (Free Acid): 3-[4-[(2-Aminoacetyl)amino]cyclohexyl]-1-sulfamoyl-pyrrole-2-carboxylic acid (Mixture of Stereoisomers)

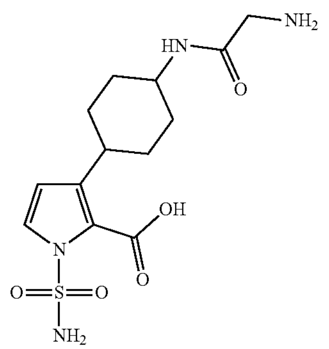 [SMILES: NCC(=O)NC1CCC(c2ccn(S(N)(=O)=O)c2C(=O)O)CC1]

Step A: Benzyl 1-(benzyloxycarbonylsulfamoyl)-3-[4-[[2-(tert-butoxycarbonylamino)acetyl]amino]cyclohexen-1-yl]pyrrole-2-carboxylate A mixture of N-(tert-butoxycarbonyl)glycine (71 mg, 403 μmol), HBTU (153 mg, 403 μmol) and DIPEA (320 μL, 1.83 mmol) in DCM (10 mL) was stirred for 5 minutes at room temperature, then benzyl 3-(4-aminocyclohexen-1-yl)-1-(benzyloxycarbonylsulfamoyl)pyrrole-2-carboxylate hydrochloride (200 mg, 366 μmol) was added and stirred for a further 20 hours. The reaction mixture was concentrated to dryness, redissolved in ethyl acetate (50 mL), washed with saturated sodium bicarbonate solution (50 mL), 1 M aqueous HCl (50 mL) and brine (50 mL). The organic phase was dried over $MgSO_4$ and purified by column chromatography (0-100% ethyl acetate in petroleum ether) to give the desired product as a white solid (196 mg, 80%).

$^{1}$H NMR (500 MHz, DMSO-$d_6$) δ 7.64 (br d, J=7.5 Hz, 1H), 7.46-7.29 (m, 11H), 7.25 (d, J=3.1 Hz, 1H), 6.87 (br t, J=5.3 Hz, 1H), 6.18 (d, J=3.1 Hz, 1H), 5.61 (br s, 1H), 5.25-5.19 (m, 2H), 5.01 (s, 2H), 3.75 (br s, 1H), 3.52 (br d, J=5.0 Hz, 2H), 2.25-2.14 (m, 3H), 1.96-1.85 (m, 1H), 1.70 (br d, J=9.3 Hz, 1H), 1.45 (m, 1H), 1.35 (s, 9H).

LC-MS (Method A): $R_T$=3.52 min, m/z=667.5 $[M+H]^+$.

Step B: Benzyl 3-[4-[(2-aminoacetyl)amino]cyclohexen-1-yl]-1-(benzyloxycarbonylsulfamoyl)pyrrole-2-carboxylate A solution of benzyl 1-(benzyloxycarbonylsulfamoyl)-3-[4-[[2-(tert-butoxycarbonylamino)acetyl]amino]cyclohexen-1-yl]pyrrole-2-carboxylate (196 mg, 294 μmol) in 4 M HCl in dioxane (10 mL) was stirred at room temperature for 90 minutes.

The reaction mixture was concentrated to dryness and free based on an SCX-2 column eluting with ammonia in methanol to give the desired product as a cream solid (127 mg, 76%).

$^{1}$H NMR (500 MHz, DMSO-$d_6$) δ 8.21 (d, J=7.5 Hz, 1H), 7.50 (br d, J=6.9 Hz, 4H), 7.46-7.26 (m, 9H), 7.13 (d, J=3.1 Hz, 1H), 6.02 (d, J=3.1 Hz, 1H), 5.63 (br s, 1H), 5.15 (d, J=1.8 Hz, 2H), 4.84 (s, 2H), 3.87-3.77 (m, 1H), 3.48 (s, 2H), 2.33-2.17 (m, 3H), 2.03-1.86 (m, 1H), 1.85-1.67 (m, 1H), 1.56-1.38 (m, 1H).

LC-MS (Method A): $R_T$=2.85 min, m/z=567.4 $[M+H]^+$.

Step C: 3-[4-[(2-Aminoacetyl)amino]cyclohexyl]-1-sulfamoyl-pyrrole-2-carboxylic acid To a solution of benzyl 3-[4-[(2-aminoacetyl)amino]cyclohexen-1-yl]-1-(benzyloxycarbonylsulfamoyl)pyrrole-2-carboxylate (127 mg, 224 μmol) in methanol (15 mL) with a few drops of 7 M ammonia in methanol was added 10% palladium on carbon (14 mg, 132 μmol) and stirred under a hydrogen atmosphere at room temperature for 3 days. The reaction mixture was filtered through Celite®, washed with methanol and concentrated to dryness. The residue was triturated with diethyl ether and the solvent decanted off twice to give the desired product as a tan solid (1.42 mg, 2%).

$^{1}$H NMR (500 MHz, DMSO-$d_6$) δ 8.81-8.02 (br m, 5H), 7.08-6.95 (m, 1H), 6.08-6.02 (m, 1H), 4.02-3.52 (m, 4H), 1.98-1.19 (m, 8H). Mixture of cis and trans isomers observed.

LC-MS (Method A): $R_T$=1.60 min, m/z=343.4 $[M-H]^-$ & $R_T$=1.77 min, m/z=343.4 $[M-H]^-$.

Example 91 (Free Acid) & Example 92 (Free Acid): 3-[4-[(2-Aminoacetyl)amino]cyclohexyl]-1-sulfamoyl-pyrrole-2-carboxylic acid (Separated Stereoisomers)

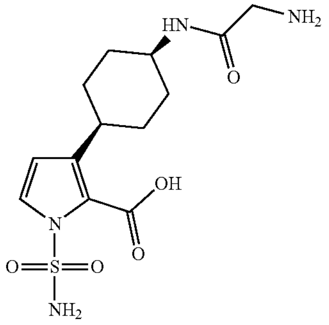

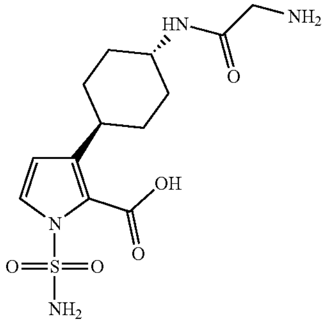

3-[4-[(2-Aminoacetyl)amino]cyclohexyl]-1-sulfamoyl-pyrrole-2-carboxylic acid (60 mg, 174 μmol) was separated using preparative HPLC (Method A, 0.60-0.80 minutes). The individual product fractions were passed through an SCX-2 column eluting with ammonia in methanol to give isomer 1 as a white solid (6.4 mg, 9%) and isomer 2 as a white solid (8.9 mg, 14%).

Isomer 1: $^1$H NMR (500 MHz, DMSO-$d_6$) δ 8.37-7.83 (br m, 5H), 6.93-6.88 (m, 1H), 6.05 (d, J=3.4 Hz, 1H), 4.07-3.99 (m, 1H), 3.56 (s, 2H), 3.49-3.40 (m, 1H), 1.75-1.50 (m, 8H).

LC-MS (Method A): $R_T$=1.68 min, m/z=343.4 $[M-H]^-$.

Isomer 2: $^1$H NMR (500 MHz, DMSO-$d_6$) δ 8.91-8.00 (br m, 5H), 7.05-7.00 (m, 1H), 6.05 (d, J=3.1 Hz, 1H), 3.65-3.58 (m, 3H), 3.42-3.37 (m, 1H), 1.92-1.81 (m, 2H), 1.77 (br d, J=11.6 Hz, 2H), 1.44-1.27 (m, 4H).

LC-MS (Method A): $R_T$=1.73 min, m/z=343.4 $[M-H]^-$.

Example 93 (sodium salt): 3-[6-[(2-Aminoacetyl)amino]-3-pyridyl]-1-sulfamoyl-pyrrole-2-carboxylic acid, sodium salt

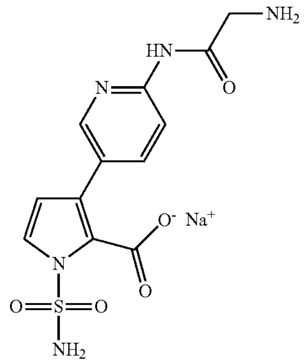 [SMILES: NCC(=O)Nc1ccc(-c2ccn(S(N)(=O)=O)c2C(=O)[O-])cn1 ; [Na+]]

Step A: Benzyl 3-(6-Amino-3-pyridyl)-1-(benzyloxycarbonylsulfamoyl)pyrrole-2-carboxylate, sodium salt A mixture of sodium benzyloxycarbonyl-(2-benzyloxycarbonyl-3-bromo-pyrrol-1-yl)sulfonyl-azanide (2.00 g, 4.05 mmol), 6-aminopyridine-3-boronic acid (726 mg, 5.26 mmol) and sodium carbonate (1.29 g, 12.2 mmol) in a mixture of 1,4-dioxane (20 mL) and water (10 mL) was degassed by bubbling nitrogen for 15 minutes followed by the addition of Pd(dppf)$Cl_2$ (296 mg, 0.40 mmol). The resulting mixture was heated to reflux under a nitrogen atmosphere for 1 hour, then allowed to cool to room temperature, diluted with water (30 mL) and extracted into ethyl acetate (3×30 mL). The combined organic phases were washed with brine (30 mL), dried over $MgSO_4$, filtered and concentrated to dryness under reduced pressure. The residue was purified by column chromatography (dichloromethane: methanol, gradient elution from 100:0 to 80:20) followed by column chromatography (ethyl acetate:methanol:1M ammonia in methanol, gradient elution from 100:0:0 to 80:20:0 to 80:0:30) then slurried in diethyl ether to give the desired product as a tan solid (685 mg, 33%).

$^1$H NMR (500 MHz, DMSO-$d_6$) δ 7.95 (dd, J=2.7, 0.6 Hz, 1H), 7.40-7.45 (m, 3H), 7.25-7.35 (m, 9H), 6.44-6.48 (m, 1H), 6.19 (br d, J=2.7 Hz, 2H), 6.15 (d, J=3.2 Hz, 1H), 5.13 (s, 2H), 4.86 (s, 2H).

LC-MS (Method A): RT=2.71 min, m/z=506.9 $[M+H]^+$.

Step B: Benzyl 3-[6-[[2-(benzyloxycarbonylamino)acetyl]amino]-3-pyridyl]-1-(benzyloxycarbonylsulfamoyl)pyrrole-2-carboxylate, sodium salt A solution of benzyl 3-(6-amino-3-pyridyl)-1-(benzyloxycarbonylsulfamoyl)pyrrole-2-carboxylate, sodium salt (200 mg, 378 μmol) and benzyl N-[2-(benzotriazol-1-yl)-2-oxo-ethyl]carbamate (176 mg, 567 μmol) in THF (3 mL) was heated to 70° C. under microwave irradiation for 2 hours. The reaction mixture was charged with additional benzyl N-[2-(benzotriazol-1-yl)-2-oxo-ethyl]carbamate (176 mg, 567 μmol) and irradiated for a further 1 hour at 70° C. The reaction mixture was quenched with water (10 mL) and extracted into ethyl acetate (3×20 mL). The combined organic phases were washed with brine (20 mL), dried over $MgSO_4$, filtered and concentrated under reduced pressure. The residue was purified by column chromatography (ethyl acetate:petroleum ether, gradient elution from 10:90 to 100:0) to afford the desired product as a white solid (112 mg, 43%).

$^1$H NMR (500 MHz, DMSO-$d_6$) δ 10.49 (s, 1H), 8.31 (d, J=1.8 Hz, 1H), 7.97 (brd, J=8.3 Hz, 1H), 7.70 (dd, J=8.3, 2.1 Hz, 1H), 7.56 (br t, J=6.1 Hz, 1H), 7.40-7.37 (m, 5H), 7.35-7.25 (m, 11H), 6.28 (d, J=3.1 Hz, 1H), 5.15 (s, 2H), 5.07 (s, 2H), 4.87 (s, 2H), 3.89 (br d, J=6.1 Hz, 2H).

LC-MS (Method B): $R_T$=2.45 min, m/z=698.4 $[M+H]^+$.

Step C: 3-[6-[(2-Aminoacetyl)amino]-3-pyridyl]-1-sulfamoyl-pyrrole-2-carboxylic acid, sodium salt 10% Palladium on carbon (24 mg, 11 μmol) was added to a solution of benzyl 3-[6-[[2-(benzyloxycarbonylamino)acetyl]amino]-3-pyridyl]-1-(benzyloxycarbonylsulfamoyl)pyrrole-2-carboxylate, sodium salt (77 mg, 110 μmol) in a mixture of 7 M ammonia methanol (0.3 mL) and methanol (2 mL) and stirred under an atmosphere of hydrogen at room temperature for 3 hours. The reaction mixture was filtered through a pad of Celite®, washed with methanol (2×10 mL) then 7 M ammonia in methanol (10 mL). The combined filtrates were concentrated under reduced pressure, slurried with diethyl ether (3×5 mL) and dried under reduced pressure to afford the desired product as a white solid (20 mg, 45%).

$^1$H NMR (500 MHz, Methanol-$d_4$) δ 8.34 (d, J=2.1 Hz, 1H), 8.00 (brs, 1H), 7.84 (dd, J=8.5, 2.4 Hz, 1H), 7.11 (d, J=3.2 Hz, 1H), 6.18 (d, J=3.2 Hz, 1H), 3.41-3.38 (m, 2H).

LC-MS (Method A): $R_T$=1.01 min, m/z=338.3 $[M-H]^-$.

Further Examples

The following examples were prepared in a similar manner to 3-[6-[(2-aminoacetyl)amino]-3-pyridyl]-1-sulfamoyl-pyrrole-2-carboxylic acid, sodium salt (Example 93).

| Example | Structure | Name | Analytical Data |
|---|---|---|---|
| Example 94 (sodium salt) | 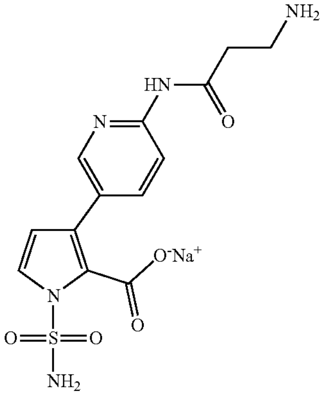 | 3-[6-(3-Aminopropanoylamino)-3-pyridyl]-1-sulfamoyl-pyrrole-2-carboxylic acid, sodium salt | $^1$H NMR (500 MHz, Methanol-$d_4$) δ 8.34 (d, J = 2.0 Hz, 1H), 7.93 (br d, J = 8.5 Hz, 1H), 7.82 (dd, J = 8.5, 2.0 Hz, 1H), 7.10 (d, J = 3.1 Hz, 1H), 6.12 (d, J = 3.1 Hz, 1H), 2.88 (t, J = 6.5 Hz, 2H), 2.48 (t, J = 6.5 Hz, 2H). LC-MS (Method A): $R_T$ = 1.18 min, m/z = 352.3 $[M - H]^-$. |

Example 95 (HCl salt): 3-[6-(2-Aminoethylamino)-3-pyridyl]-1-sulfamoyl-pyrrole-2-carboxylic acid hydrochloride

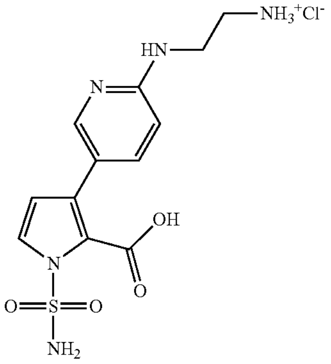

Step A: Benzyl 1-(benzyloxycarbonylsulfamoyl)-3-[6-[2-(tert-butoxycarbonylamino)ethylamino]-3-pyridyl]pyrrole-2-carboxylate To a solution of sodium benzyloxycarbonyl-(2-benzyloxycarbonyl-3-bromo-pyrrol-1-yl)sulfonyl-azanide (200 mg, 387 μmol) and tert-butyl N-[2-[[5-(4,4,5,5-tetramethyl-1,3,2-dioxaborolan-2-yl)-2-pyridyl]amino]ethyl]carbamate (211 mg, 465 μmol) in 1,4-dioxane (3.2 mL) was added XPhos Pd G2 (31 mg, 39 μmol) followed by a solution of potassium phosphate tribasic (329 mg, 1.6 mmol) in water (1.0 mL). The vial was degassed then heated to 45° C. under microwave irradiation for 2 hours. The reaction mixture was diluted with water (10 mL) and extracted into ethyl acetate (3×10 mL). The organic extracts were washed with 2 M aqueous HCl (2×20 mL), brine (20 mL), dried over $MgSO_4$, filtered and concentrated under reduced pressure. The residue was purified by column chromatography (ethyl acetate: petroleum ether:methanol, gradient elution from 30:70:0 to 100:0:0 then 80:0:20) to afford the desired product as a white solid (146 mg, 58%).

$^1$H NMR (500 MHz, DMSO-$d_6$) δ 7.99 (s, 1H), 7.44-7.42 (m, 3H), 7.34-7.26 (m, 10H), 6.88 (br t, J=4.7 Hz, 1H), 6.47 (br s, 1H), 6.15 (d, J=1.7 Hz, 1H), 5.13 (s, 2H), 4.85 (s, 2H), 3.31-3.27 (m, 2H), 3.13-3.08 (m, 2H), 1.38 (s, 9H).

LC-MS (Method B): $R_T$=2.41 min, m/z=648.5 $[M-H]^-$.

Step B: Benzyl 3-[6-(2-aminoethylamino)-3-pyridyl]-1-(benzyloxycarbonylsulfamoyl)pyrrole-2-carboxylate hydrochloride 4 M HCl in 1,4-dioxane (0.5 mL) was added to a solution of benzyl 1-(benzyloxycarbonylsulfamoyl)-3-[6-[2-(tert-butoxycarbonylamino)ethylamino]-3-pyridyl]pyrrole-2-carboxylate (146 mg, 225 μmol) in dichloromethane (0.5 mL) and stirred for 1 hour at room temperature. The reaction mixture was diluted with dichloromethane (5 mL), concentrated under reduced pressure and azetroped with dichloromethane (3×5 mL) to afford the desired product as an off white solid (141 mg, quantitative yield).

$^1$H NMR (500 MHz, DMSO-$d_6$) δ 8.07-8.03 (m, 4H), 7.83 (brs, 1H), 7.44-7.40 (m, 3H), 7.35-7.28 (m, 9H), 6.94 (br s, 1H), 6.33 (d, J=3.1 Hz, 1H), 5.19 (s, 2H), 4.93 (s, 2H), 3.64-3.60 (m, 2H), 3.09-3.04 (m, 2H).

LC-MS (Method A): $R_T$=2.50 min, m/z=548.4 $[M-H]^-$.

Step C: 3-[6-(2-Aminoethylamino)-3-pyridyl]-1-sulfamoyl-pyrrole-2-carboxylic acid hydrochloride 10% Palladium on carbon (18 mg, 8.5 μmol) was added to a solution of benzyl 3-[6-(2-aminoethylamino)-3-pyridyl]-1-(benzyloxycarbonylsulfamoyl)pyrrole-2-carboxylate hydrochloride (50 mg, 85 μmol) in methanol (2 mL) and the reaction mixture stirred under 1 atmosphere of hydrogen at room temperature for 1 hour. The reaction mixture was filtered through a pad of Celite® and washed with methanol (2×10 mL) then 7 M ammonia in methanol (10 mL). The combined washings were concentrated under reduced pressure, slurried with diethyl ether (3×5 mL) and dried under reduced pressure to afford the desired product as a yellow solid (13 mg, 34%).

$^1$H NMR (500 MHz, DMSO-$d_6$) δ 13.24 (br s, 1H), 8.18 (br s, 2H), 8.06 (s, 1H), 7.98 (br s, 2H), 7.47 (br d, J=2.1 Hz, 1H), 6.37 (br s, 1H), 3.60-3.56 (m, 2H), 3.06-3.01 (m, 2H).

LC-MS (Method A): $R_T$=0.53 min, m/z=324.3 $[M-H]^-$.

Biological Example 1

Compounds of the invention were tested in a metallo-β-lactamase inhibition assay to investigate mechanism of action of the compounds. Results are reported as the concentration of test article required to inhibit enzyme activity by 50% ($IC_{50}$). Compounds exhibited $IC_{50}$ values consistent with potent, specific inhibition of the tested metallo-β-lactamase.

Inhibition of metallo-β-lactamase enzyme function was performed at 37° C. in buffer at pH 7.5 (50 mM HEPES, 150 mM NaCl, 0.1 mM ZnSO4, 20 μg/mL PEG4000), containing 1.5 nM NDM-1, 100 μM nitrocefin, and a range of concentrations of compound. Absorbance at 490 nm was measured using a BMG LABTECH FLUOstar Omega microplate reader every minute for 30 minutes. $IC_{50s}$ were determined from the average increase in OD per minute versus the Log 10 concentration of compound using GraphPad Prism. The data is provided in Table 1 below.

TABLE 1

| Example No | NDM-1 $IC_{50}$ (nM) |
|---|---|
| 1 | 223.45 |
| 2 | 110.95 |
| 6 | 843.0 |
| 7 | 650.5 |
| 8 | 404.85 |
| 9 | 373.1 |
| 10 | 373.8 |
| 11 | 527.1 |
| 12 | 1057.5 |
| 13 | 565.6 |
| 15 | 1791.8 |
| 16 | 622.75 |
| 17 | 393.7 |
| 21 | 78.0 |
| 25 | 318.8 |
| 26 | 420.15 |
| 27 | 130.7 |
| 31 | 3330.0 |
| 32 | 1060.9 |
| 35 | 200.4 |
| 36 | 409.55 |
| 38 | 652.3 |
| 43 | 272.6 |
| 44 | 186.95 |
| 47 | 163.3 |
| 58 | 433.2 |
| 59 | 1609.0 |
| 63 | 1761.5 |
| 69 | 1483 |
| 72 | 1567 |
| 73 | 567.55 |
| 74 | 1553.9 |
| 85 | 399.15 |
| 87 | 248.15 |
| 93 | 161.64 |
| 94 | 2489 |
| 95 | 377 |

MICs were determined by exposing bacteria to serial dilutions of antibacterial agents in MHB-II (cation-adjusted Mueller-Hinton Broth pH 7.4) according to Clinical and Laboratory Standards Institute (CLSI) broth microdilution guidelines (Cockerill et al., 2012).

Combination MIC were performed as described for MIC determinations with the addition of 4 mg/L test article to MHB-II.

Cytotoxicity was evaluated in human Hep G2 cells (ATCC HB-8065) seeded at a density of $2\times10^5$ cells per well and incubated for 24 h at 37° C., 5% $CO_2$. Cells were exposed to a doubling dilution series of test article. After 24 h exposure, the viability of the cells was determined using CellTiter-Glo® (Promega, WI, USA) according to the manufacturer's instructions. Results are reported as the concentration of test article required to reduce cell viability by 50% ($CC_{50}$).

The following literature references provide additional information on the assay methods used in the assessment of compounds of the invention and the disclosures of these documents in relation to such methods is specifically incorporated herein. For the avoidance of doubt, it is intended that the disclosures of the methods in each of those documents specifically forms part of the teaching and disclosure of this invention. The last two references below provide methodology to establish and demonstrate the existence of synergy and thus the procedures described therein can be used to demonstrate synergistic activity between the compounds of the invention and carbapenems such as meropenem.

COCKERILL, F. R., WICKLER, M. A., ALDER, J., DUDLAY, M. N., ELIOPOULOS, G. M., FERRARO, M. J., HARDY, D. J. ANDHECHT, D. W., HINDLER, J. A., PATEL, J. B., POWEL, M., SWENSON, J. M., THOMPRON, J. B., TRACZEWSKI, M. M., TURNIDGE, J. A., WEINSTEIN, M. P., & ZIMMER, B. L. 2012. Methods for Dilution Antimicrobial Susceptibility Tests for Bacteria that Grow Aerobically (M07-A9). Wayne: Clinical and Laboratory Standards Institute.

PILLAI, S. K., MOELLERING, R. C., & ELIOPOULOS, G. M. 2005. Antimicrobial combinations. In: Antibiotics in Laboratory Medicine. Philadelphia: Lippincott Williams and Wilkins, pp. 365-440.

BURKHART, C. G., BURKHART, C. N., & ISHAM, N. 2006. Synergistic Antimicrobial Activity by Combining an Allylamine with Benzoyl Peroxide with Expanded Coverage against Yeast and Bacterial Species. British Journal of Dermatology 154(2): 341-344.

Biological Example 2

Compounds of the invention were tested and shown to result in a significant improvement in meropenem activity as presented in the tables below. All of the compounds tested resulted in significant improvement in meropenem activity against a variety of different bacterial strains relative to the baseline study using meropenem only. Some of the compounds tested improved meropenem MICs by more than 10 or 20 times in comparison with meropenem alone. Even the least active compounds of those tested showed activities that improved meropenem MICs by at least 4 times in comparison with meropenem alone.

The compounds are effective against a wide range of different bacteria when used in conjunction with meropenem.

The compounds of the invention were tested against a primary panel of bacterial strains, columns I-V of Table 2. As appropriate, compounds considered suitable for further investigation were tested against a secondary panel of bacterial strains, columns VI and VII of Table 2.

TABLE 2

| Meropenem combination MICs (μg/mL) | | | | | | | |
|---|---|---|---|---|---|---|---|
| Ex No | I *E. coli* ATCCBAA-2452 NDM-1 | II *E. coli* NCTC13476 IMP | III *K. pneumoniae* ATCC BAA2146 NDM-1 | IV *A. baumannii* SG698 NDM-1 | V *K. pneumoniae* NCTC13440 VIM-1 | VI *K. pneumoniae* NCTC13443 NDM-1 | VII *K. pneumoniae* NCTC13439 VIM-1 |
| Meropenem | 1 | 4 | 16 | 8 | 1 | 128 | 0.5 |
| 1 | A | A | B | Not tested | B | Not tested | Not tested |
| 2 | A | A | B | Not tested | B | Not tested | Not tested |
| 3 | A | A | C | D | B | Not tested | Not tested |
| 4 | B | Not tested | Not tested | Not tested | Not tested | Not tested | Not tested |
| 5 | B | Not tested | Not tested | Not tested | Not tested | Not tested | Not tested |
| 6 | A | A | B | C | A | Not tested | Not tested |
| 7 | A | A | B | C | A | D | A |
| 8 | A | A | B | Not tested | A | Not tested | Not tested |
| 9 | A | A | B | C | A | Not tested | Not tested |
| 10 | A | A | C | Not tested | B | Not tested | Not tested |
| 11 | A | A | B | C | A | Not tested | Not tested |
| 12 | A | A | B | C | A | Not tested | Not tested |
| 13 | A | A | B | C | A | E | A |
| 14 | A | Not tested | Not tested | Not tested | Not tested | Not tested | Not tested |
| 15 | A | A | C | Not tested | B | Not tested | Not tested |
| 16 | A | A | D | Not tested | B | Not tested | Not tested |
| 17 | A | A | c | Not tested | A | Not tested | Not tested |
| 18 | B | B | c | Not tested | Not tested | Not tested | Not tested |
| 19 | B | A | c | Not tested | B | Not tested | Not tested |
| 20 | B | A | c | Not tested | Not tested | Not tested | Not tested |
| 21 | A | A | B | B | A | D | B |
| 22 | B | A | D | Not tested | B | Not tested | Not tested |
| 23 | A | Not tested | Not tested | Not tested | Not tested | Not tested | Not tested |
| 24 | A | Not tested | Not tested | Not tested | Not tested | Not tested | Not tested |
| 25 | A | A | B | C | B | D | B |
| 26 | A | A | B | C | A | c | A |
| 27 | A | A | B | B | A | Not tested | Not tested |
| 28 | A | Not tested | Not tested | Not tested | Not tested | Not tested | Not tested |
| 29 | A | A | Not tested | Not tested | Not tested | Not tested | Not tested |
| 30 | A | Not tested | Not tested | Not tested | Not tested | Not tested | Not tested |
| 31 | A | A | B | Not tested | A | Not tested | Not tested |
| 32 | A | A | B | Not tested | B | Not tested | Not tested |
| 33 | A | A | B | C | A | D | A |
| 34 | A | A | B | C | B | Not tested | Not tested |
| 35 | A | A | B | C | A | Not tested | Not tested |
| 36 | A | A | B | C | B | Not tested | Not tested |
| 37 | B | A | D | Not tested | B | Not tested | Not tested |
| 38 | A | A | B | C | A | E | A |
| 39 | A | A | C | Not tested | A | Not tested | Not tested |
| 40 | A | Not tested | Not tested | Not tested | Not tested | Not tested | Not tested |
| 41 | A | Not tested | Not tested | Not tested | Not tested | Not tested | Not tested |
| 42 | A | Not tested | Not tested | Not tested | Not tested | Not tested | Not tested |
| 43 | A | A | C | C | A | Not tested | Not tested |
| 44 | A | A | B | C | A | D | B |
| 45 | A | Not tested | Not tested | Not tested | Not tested | Not tested | Not tested |
| 46 | A | Not tested | Not tested | Not tested | Not tested | Not tested | Not tested |
| 47 | A | A | B | C | A | E | A |
| 48 | A | Not tested | Not tested | Not tested | Not tested | Not tested | Not tested |
| 49 | A | Not tested | Not tested | Not tested | Not tested | Not tested | Not tested |
| 50 | A | Not tested | Not tested | Not tested | Not tested | Not tested | Not tested |
| 51 | A | Not tested | Not tested | Not tested | Not tested | Not tested | Not tested |
| 52 | A | Not tested | Not tested | Not tested | Not tested | Not tested | Not tested |
| 53 | A | Not tested | Not tested | Not tested | Not tested | Not tested | Not tested |
| 54 | A | A | B | D | B | Not tested | Not tested |
| 55 | B | Not tested | Not tested | Not tested | Not tested | Not tested | Not tested |
| 56 | B | Not tested | Not tested | Not tested | Not tested | Not tested | Not tested |
| 57 | B | A | C | C | B | Not tested | Not tested |
| 58 | A | A | B | C | A | Not tested | Not tested |
| 59 | A | A | C | Not tested | A | Not tested | Not tested |
| 60 | A | Not tested | Not tested | Not tested | Not tested | Not tested | Not tested |
| 61 | A | Not tested | Not tested | Not tested | Not tested | Not tested | Not tested |
| 62 | A | A | C | D | B | Not tested | Not tested |
| 63 | A | A | B | Not tested | A | Not tested | Not tested |
| 64 | A | Not tested | Not tested | Not tested | Not tested | Not tested | Not tested |
| 65 | A | Not tested | Not tested | Not tested | Not tested | Not tested | Not tested |
| 66 | A | Not tested | Not tested | Not tested | Not tested | Not tested | Not tested |
| 67 | B | Not tested | Not tested | Not tested | Not tested | Not tested | Not tested |
| 68 | B | Not tested | Not tested | Not tested | Not tested | Not tested | Not tested |
| 69 | A | A | B | C | B | E | B |

TABLE 2-continued

| Meropenem combination MICs (μg/mL) | | | | | | | |
|---|---|---|---|---|---|---|---|
| Ex No | I *E. coli* ATCCBAA-2452 NDM-1 | II *E. coli* NCTC13476 IMP | III *K. pneumoniae* ATCC BAA2146 NDM-1 | IV *A. baumannii* SG698 NDM-1 | V *K. pneumoniae* NCTC13440 VIM-1 | VI *K. pneumoniae* NCTC13443 NDM-1 | VII *K. pneumoniae* NCTC13439 VIM-1 |
| 70 | A | Not tested | Not tested | Not tested | Not tested | Not tested | Not tested |
| 71 | B | Not tested | Not tested | Not tested | Not tested | Not tested | Not tested |
| 72 | A | A | B | C | B | Not tested | Not tested |
| 73 | A | A | B | Not tested | B | Not tested | Not tested |
| 74 | A | A | B | Not tested | B | Not tested | Not tested |
| 75 | A | Not tested | Not tested | Not tested | Not tested | Not tested | Not tested |
| 76 | A | Not tested | Not tested | Not tested | Not tested | Not tested | Not tested |
| 77 | A | Not tested | Not tested | Not tested | Not tested | Not tested | Not tested |
| 78 | B | Not tested | Not tested | Not tested | Not tested | Not tested | Not tested |
| 79 | A | Not tested | Not tested | Not tested | Not tested | Not tested | Not tested |
| 80 | A | Not tested | Not tested | Not tested | Not tested | Not tested | Not tested |
| 81 | B | Not tested | Not tested | Not tested | Not tested | Not tested | Not tested |
| 82 | B | Not tested | Not tested | Not tested | Not tested | Not tested | Not tested |
| 83 | A | A | C | C | B | Not tested | Not tested |
| 84 | B | Not tested | Not tested | Not tested | Not tested | Not tested | Not tested |
| 85 | A | A | B | Not tested | B | Not tested | Not tested |
| 86 | A | A | c | Not tested | B | Not tested | Not tested |
| 87 | A | A | B | C | B | Not tested | Not tested |
| 88 | A | Not tested | Not tested | Not tested | Not tested | Not tested | Not tested |
| 89 | A | A | C | Not tested | B | Not tested | Not tested |
| 90 | A | A | Not tested | Not tested | Not tested | Not tested | Not tested |
| 91 | A | Not tested | Not tested | Not tested | Not tested | Not tested | Not tested |
| 92 | A | Not tested | Not tested | Not tested | Not tested | Not tested | Not tested |
| 93 | A | A | B | C | A | D | A |
| 94 | A | A | B | C | B | Not tested | Not tested |
| 95 | A | A | B | C | B | D | A |

Key to Table.
The following letters in Table 2 above represent the MIC (minimum inhibitory concentration) values in μg/ml: A ≤ 0.1, B ≤ 1, C ≤ 5, D ≤ 10, E ≤ 40 and F ≤ 80.

Biological Example 3

Compounds were also tested for cytotoxicity. The data below in Table 3 shows that the tested compounds did not exhibit any significant cytotoxic activity.

TABLE 3

| Cytotoxicity Assay | |
|---|---|
| Example No | HepG2 $CC_{50}$ (μg/mL) |
| 1 | >256 |
| 2 | >256 |
| 3 | >256 |
| 6 | >256 |
| 7 | >256 |
| 8 | >128 |
| 9 | >256 |
| 10 | >256 |
| 11 | >256 |
| 12 | >128 |
| 13 | >256 |
| 15 | >256 |
| 16 | >256 |
| 17 | >256 |
| 21 | >256 |
| 25 | >256 |
| 26 | >256 |
| 27 | >256 |
| 31 | >256 |
| 32 | >256 |
| 33 | >256 |
| 35 | >256 |
| 36 | >256 |
| 38 | >256 |
| 43 | >256 |

TABLE 3-continued

| Cytotoxicity Assay | |
|---|---|
| Example No | HepG2 $CC_{50}$ (μg/mL) |
| 44 | >256 |
| 47 | >256 |
| 54 | >256 |
| 57 | >256 |
| 59 | >256 |
| 62 | >256 |
| 63 | >256 |
| 69 | >256 |
| 72 | >256 |
| 73 | >256 |
| 74 | >256 |
| 83 | >256 |
| 85 | >128 |
| 87 | >256 |
| 93 | >256 |
| 94 | >256 |
| 95 | >256 |

Biological Example 4

Compounds were also tested in a solubility study. Each sample (2 mg) was weighed into a clear 1.75 mL vial followed by the addition of saline (40 μL, to make up to 50 mg/mL). Unless indicated otherwise, the compounds were tested as the free base. Each resulting mixture was vortexed (if required) and the solubility of each was identified visually.

| Example No | Solubility |
|---|---|
| 25 | Soluble |
| 69 | Soluble |
| WO2019/220125-Example 45 | Insoluble |
| WO2019/220125-Example 51 (HCl salt) | Borderline solubility |
| WO2019/220125-Example 62 | Soluble |
| WO2019/220125-Example 63 | Insoluble |

Biological Example 5

Compounds were also tested for off-target inhibition in a Cerep SafetyScreen44 Panel. The data below in Table 4 shows that, of the four compounds tested, two compounds did not inhibit any of the 44 targets in ≥50% inhibition while the other two compounds resulted in ≥50% inhibition of 2 of the 44 targets.

TABLE 5

| Off-Target Inhibition | |
|---|---|
| Example No | Number of targets ≥50% inhibition at 100 μM |
| WO2019/220125-Example 1 | 2 |
| WO2019/220125-Example 25 | 2 |
| 25 | 0 |
| 69 | 0 |

The invention claimed is:

1. A compound of formula (I) or a pharmaceutically acceptable salt, hydrate, or stereoisomer thereof:

(I)

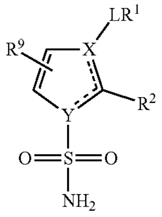

wherein one of X and Y is N and the other is C;

L is a linker group selected from the group consisting of a bond and —$(CH_2)_a$-Q-$(CH_2)_b$— in which, Q is selected from the group consisting of: O, NH, $SO_2$, C═C, and C≡C, or Q is absent;

$R^1$ is a 6 membered monocyclic aromatic, carbocyclic, heteroaromatic, or heterocyclic ring substituted by one $R^3$ group, $R^1$ may be further substituted with 0 or 1 group selected from the group consisting of halo, $C_{1-6}$ alkyl, and $C_{1-6}$ haloalkyl;

$R^2$ is —C(O)OH or —C(O)OM; wherein M is a group 1 cation;

$R^3$ is selected from the group consisting of: —$CONR^4(CR^aR^b)_nNR^5R^6$, —$CONR^4(CR^aR^b)_nOSO_2OR^5$, —$CONR^4(CR^aR^b)_nCN$, —$CONR^4(CR^aR^b)_nC$(═O)OH, —$CONR^4(CR^aR^b)_nC$(═O)$NR^7R^8$, —$NR^4CO(CR^aR^b)_nNR^7R^8$, —$NR^4CO(CR^aR^b)_nOSO_2OR^5$, —$NR^4CO(CR^aR^b)_nCN$, —$NR^4CO(CR^aR^b)_nC$(═O)OH, —$NR^4CO(CR^aR^b)_nC$(═O)$NR^7R^8$, —$SO_2NR^4(CR^aR^b)_nNR^5R^6$, —$SO_2NR^4(CR^aR^b)_nOSO_2OR^5$, —$SO_2NR^4(CR^aR^b)_nCN$, —$SO_2NR^4(CR^aR^b)_nC$(═O)OH, —$SO_2NR^4(CR^aR^b)_nC$(═O)$NR^7R^8$,

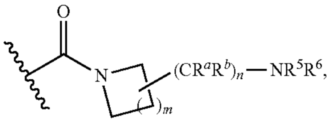

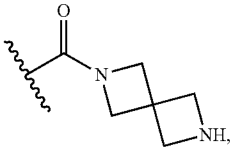

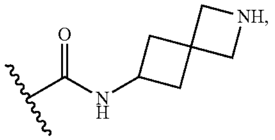

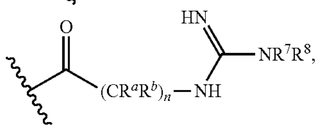

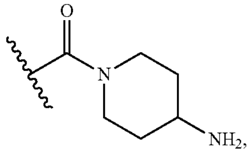

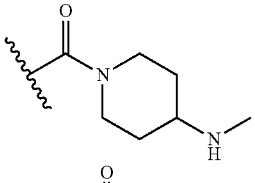

, and

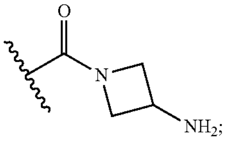

$R^4$ is independently selected at each occurrence from the group consisting of: H, halo, —OH, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, —$(CH_2)_f$-aryl, —$(CH_2)_d$-heteroaryl, and —$(CH_2)_g$-heterocyclyl; wherein $R^4$ may be optionally substituted where chemically possible with one, two, or three groups independently selected at each occurrence from the group consisting of: halo, —$NH_2$, —$N(C_{1-4}$ alkyl$)_2$, —OH, —$SO_2N(C_{1-4}$ alkyl$)_2$, —NHC(═O)O$C_{1-6}$ alkyl, and —C(═O)O$C_{1-6}$ alkyl;

$R^5$ and $R^6$ are each independently H or $C_{1-6}$ alkyl;

wherein at least one of $R^4$, $R^5$, or $R^6$ is $C_{1-6}$ alkyl when each of $R^4$, $R^5$, and $R^6$ are present;

$R^7$ is selected from the group consisting of H and $C_{1-4}$ alkyl;

$R^8$ is selected from methyl and ethyl;

$R^9$ is selected from the group consisting of: H, $C_{1-4}$ alkyl, and $C_{1-4}$ haloalkyl;

$R^a$ and $R^b$ are each, at each occurrence, independently selected from the group consisting of: H, halo, —$NH_2$, and $C_{1-4}$ alkyl;

a, b, d, f, and g are each independently integers selected from the group consisting of 0 to 3;

m is an integer selected from the group consisting of 1, 2, and 3;

n is an integer selected from the group consisting of 1, 2, 3, 4, and 5; and

- - - represents a single or a double bond as required to satisfy valence requirements.

2. A compound according to claim 1, wherein Y is N and X is C.

3. A compound according to claim 1, wherein $R^3$ is selected from the group consisting of: —$CONR^4(CR^aR^b)_nNR^5R^6$, —$CONR^4(CR^aR^b)_nOSO_2OR^5$, —$CONR^4(CR^aR^b)_nCN$, —$CONR^4(CR^aR^b)_nC(=O)OH$, —$CONR^4(CR^aR^b)_nC(=O)NR^7R^8$,

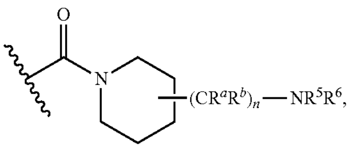

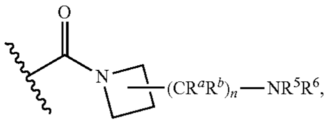

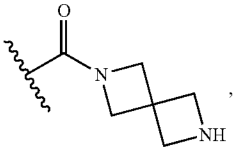

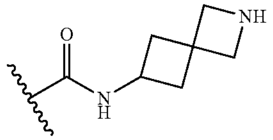

and

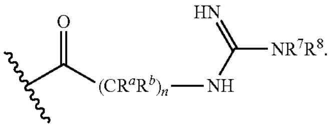

4. A compound as claimed in claim 1, wherein $R^3$ is selected from the group consisting of: —$CONH(CH_2)_2NHMe$, —$CON(Me)(CH_2)_2NHMe$, —$CONH(CH_2)_3NHMe$, —$CONH(CH_2)_3OSO_2OH$, —$CON(Me)(CH_2)_3OSO_2OH$, —$CONH(CH_2)_3OSO_2OMe$, —$CON(Me)(CH_2)_3OSO_2OMe$, —$CONHCH_2CN$, —$CONH(CH_2)_2CN$, —$CON(Me)CH_2CN$, —$CON(Me)(CH_2)_2CN$, —$CONH(CH_2)_2C(=O)OH$, —$CON(Me)(CH_2)_2C(=O)OH$, —$CONHCH_2C(=O)OH$, —$CON(Me)CH_2C(=O)OH$, —$CONHCH_2C(=O)NHMe$, —$CONMeCH_2C(=O)NHMe$, —$CONH(CH_2)_2C(=O)NHMe$, and —$CONMe(CH_2)_2C(=O)NHMe$.

5. A compound as claimed in claim 1, wherein $R^4$ is selected at each occurrence from the group consisting of: H, halo, substituted or unsubstituted $C_{1-6}$ alkyl, and substituted or unsubstituted $C_{3-8}$ cycloalkyl.

6. A compound as claimed in claim 5, wherein $R^4$ is independently, at each occurrence, selected from the group consisting of H and Me.

7. A compound as claimed in claim 6, wherein $R^5$ and $R^6$ are each independently selected from the group consisting of: H, Me, Et, $^n$Pr, $^i$Pr, and $^n$Bu.

8. A compound as claimed in claim 1, wherein $R^5$ and $R^6$ are each independently H or Me.

9. A compound as claimed in claim 1, wherein the compound is selected from the group consisting of:

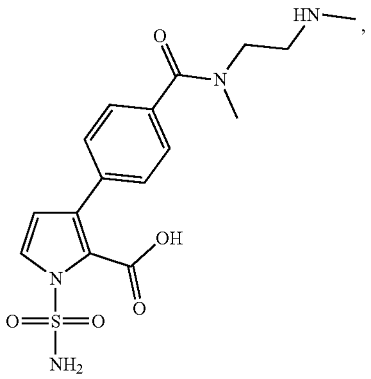

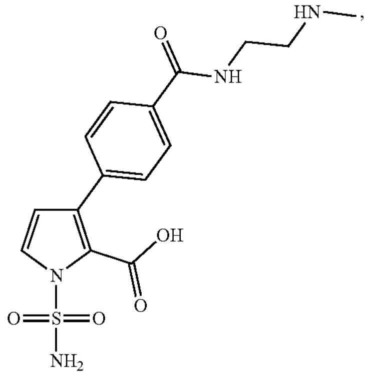

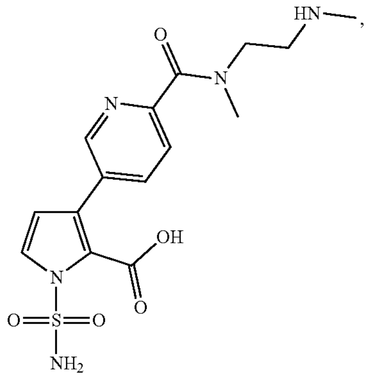

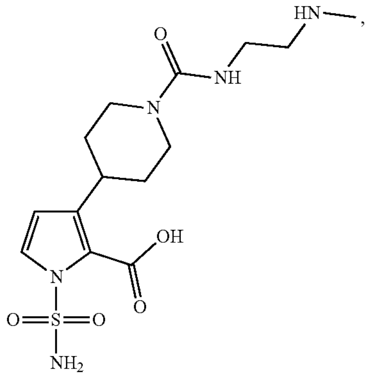

-continued
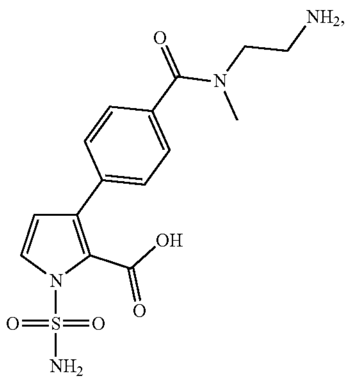
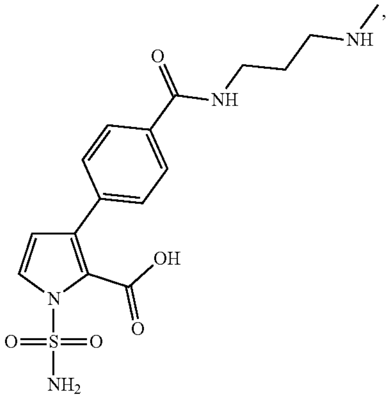
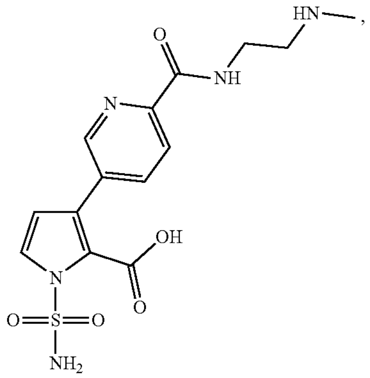
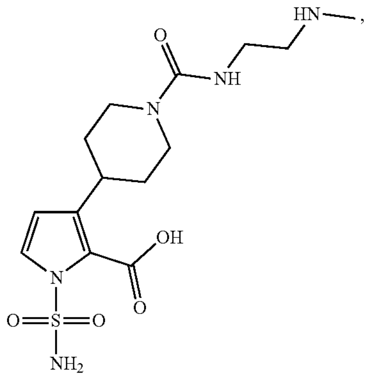
-continued
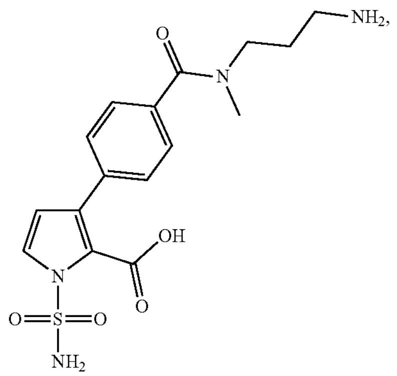
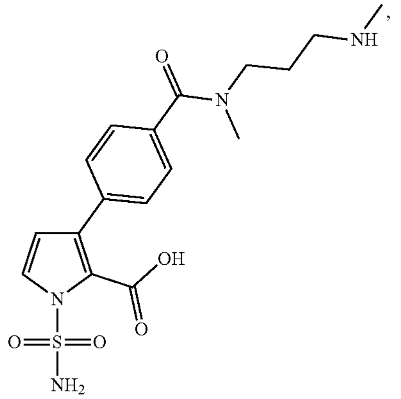
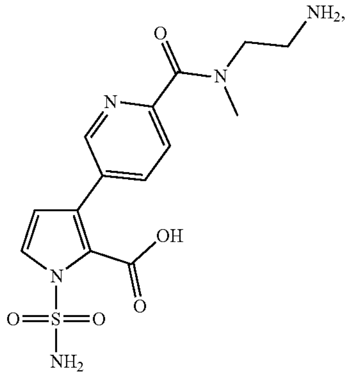
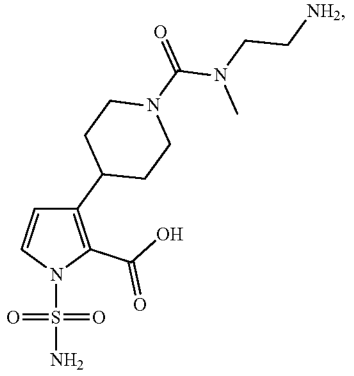

-continued
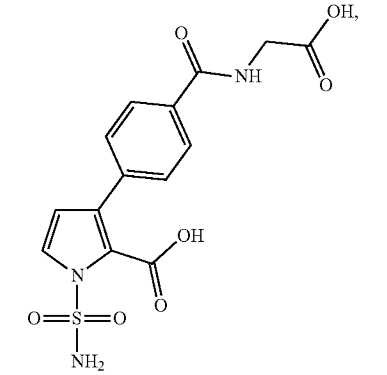
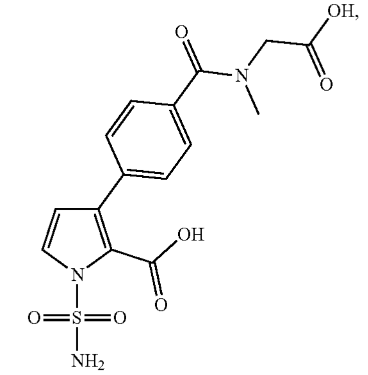
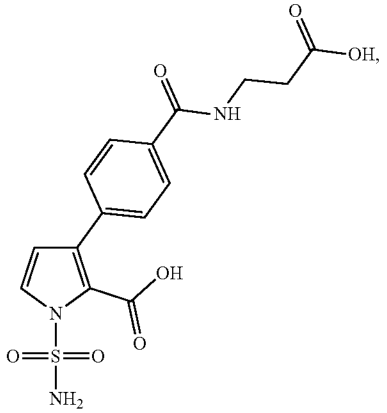
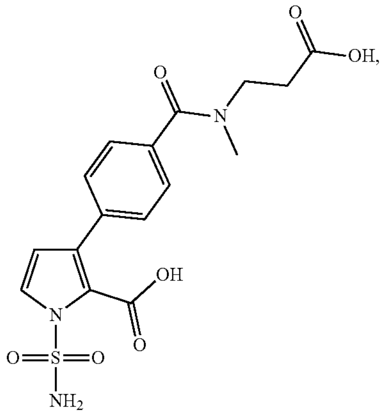
-continued
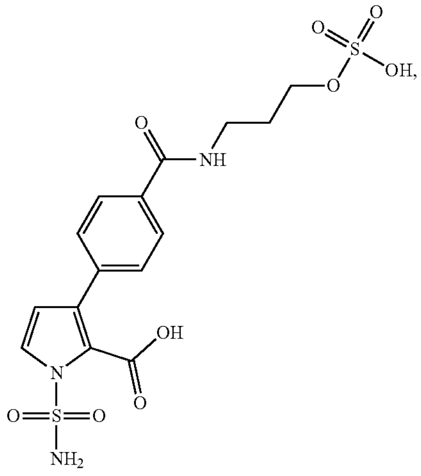
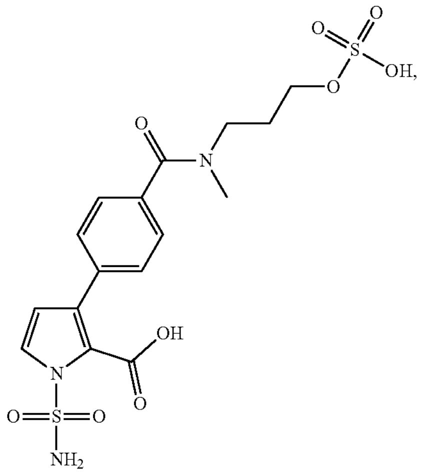
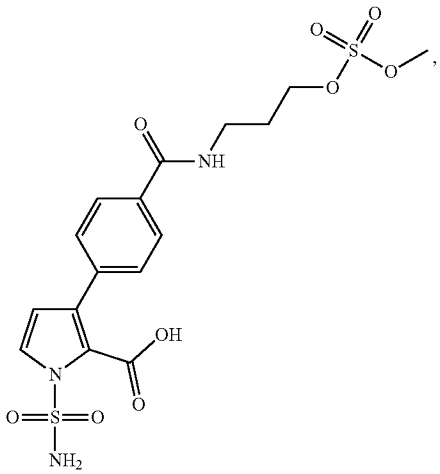

-continued
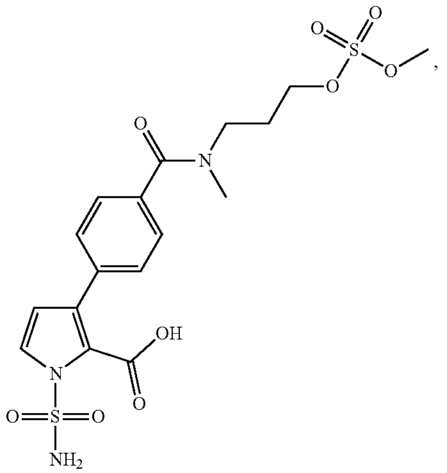
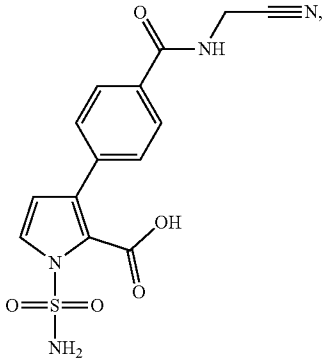
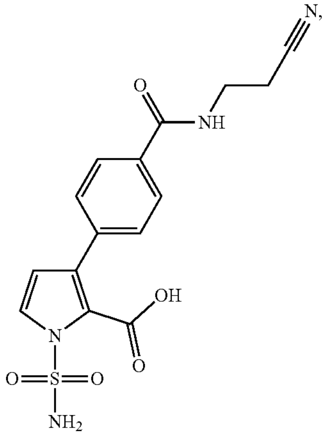
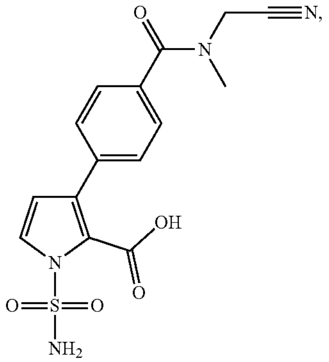
-continued
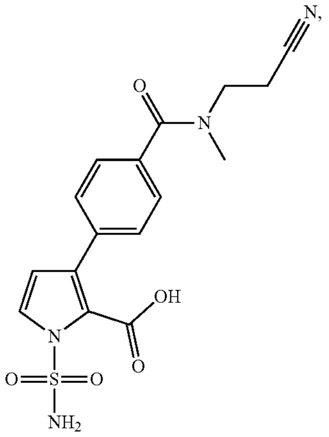
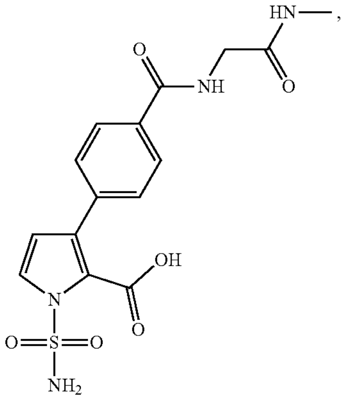
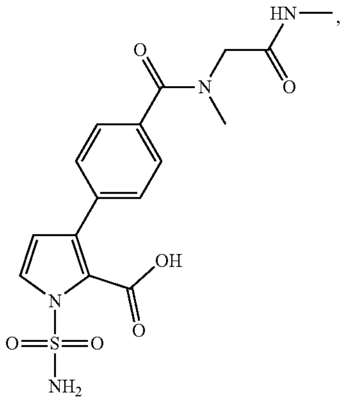
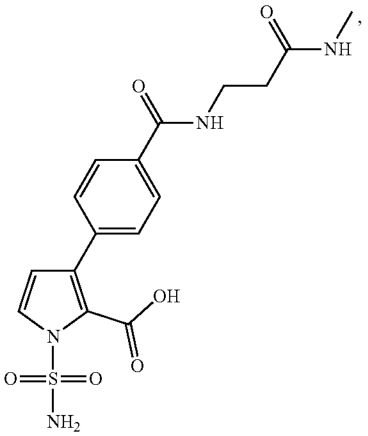

-continued
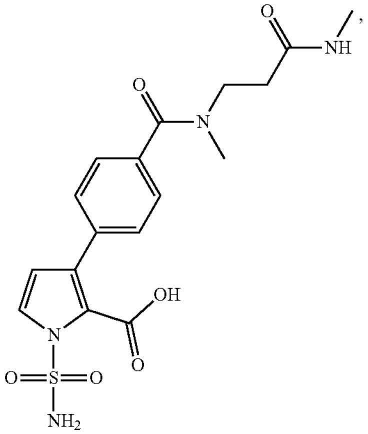
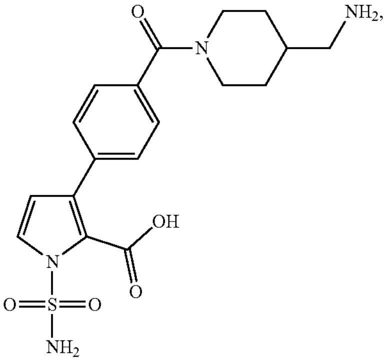
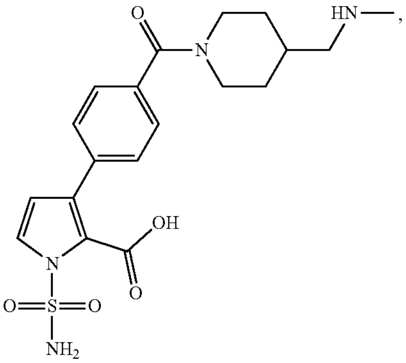
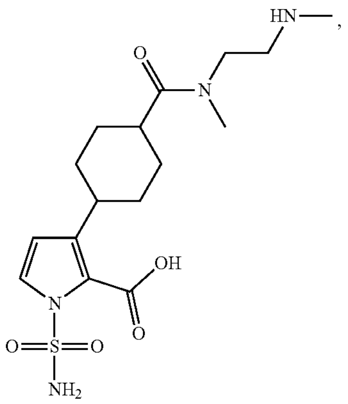
-continued
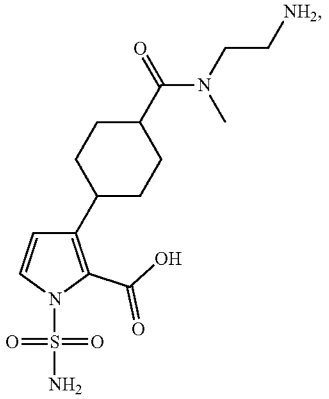
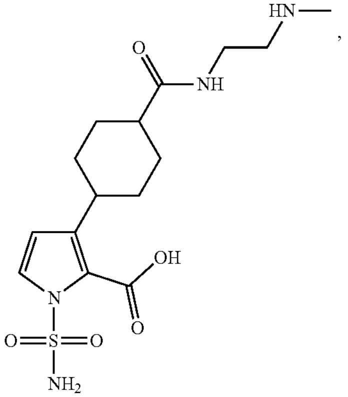
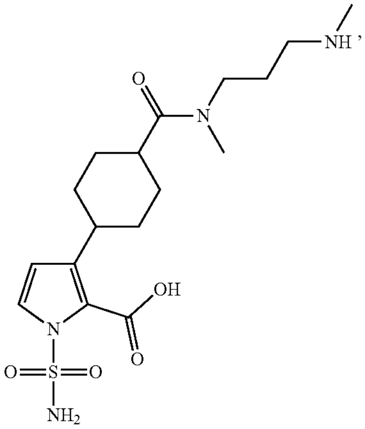
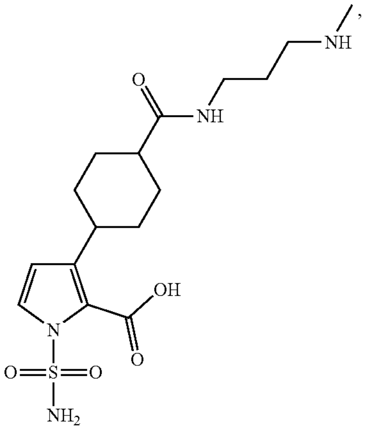

-continued
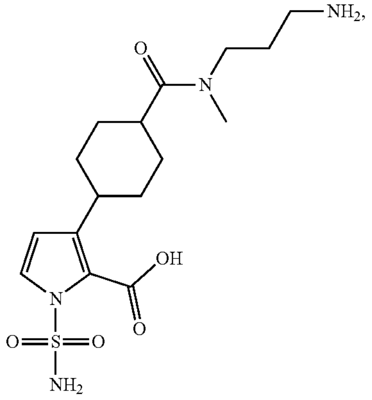
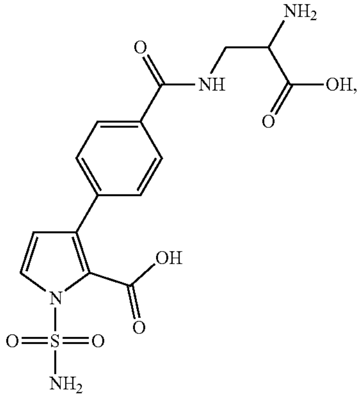
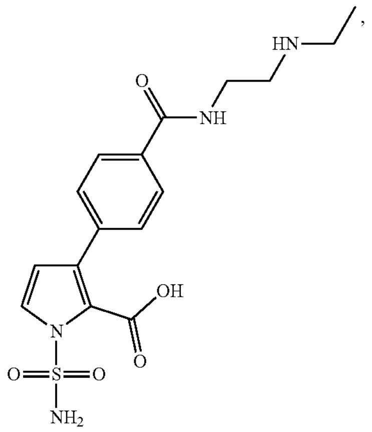
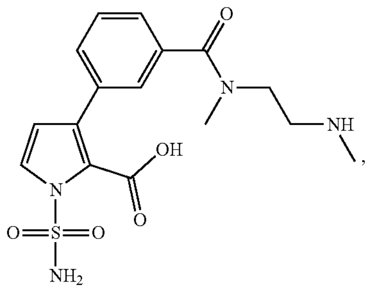
-continued
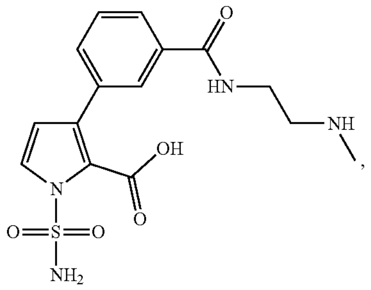
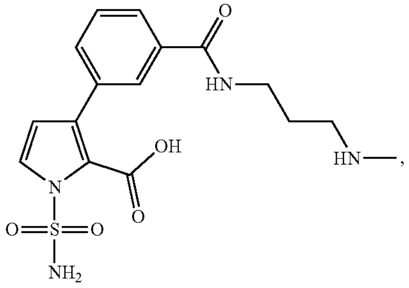
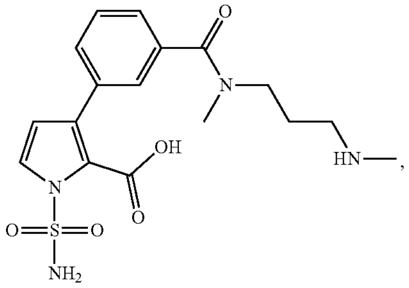
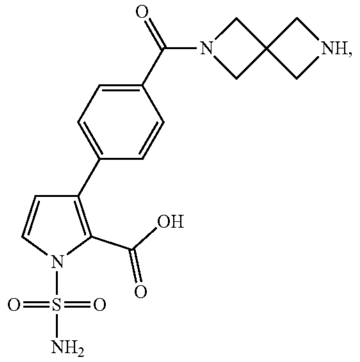
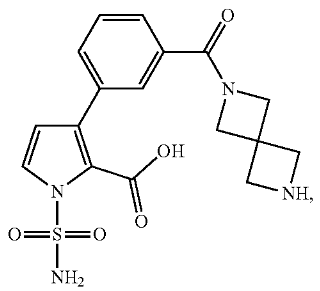

-continued

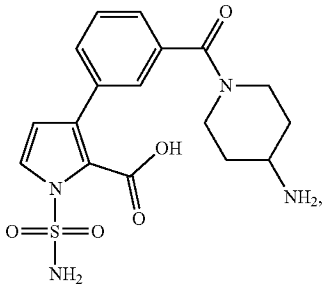

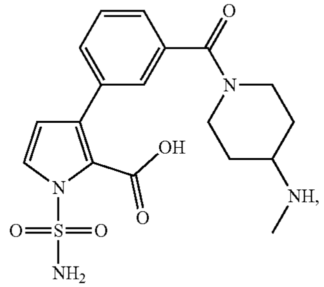

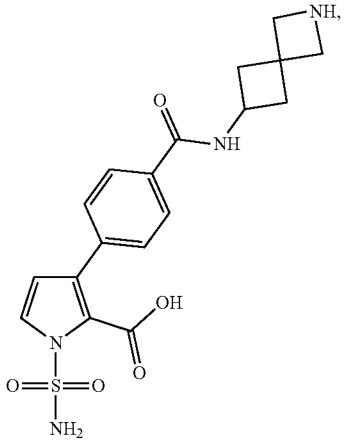

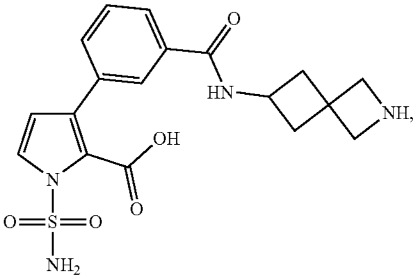

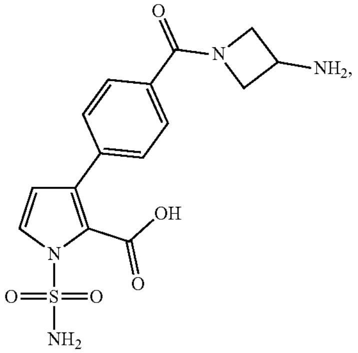

-continued

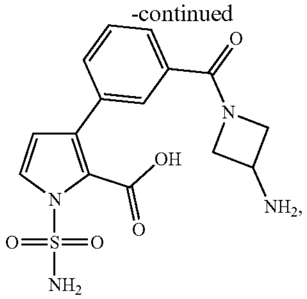

and

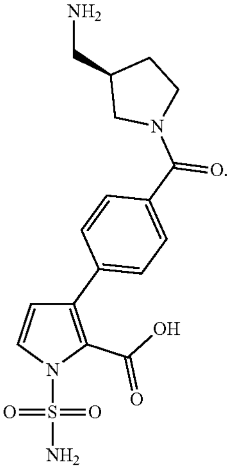

10. A pharmaceutical composition comprising a compound of claim 1, or a pharmaceutically acceptable salt, hydrate or stereoisomer thereof, and one or more pharmaceutically acceptable excipients.

11. The pharmaceutical composition of claim 10, wherein the composition further comprises an antibacterial agent.

12. The pharmaceutical composition of claim 11, wherein the antibacterial agent is a carbapenem.

13. The pharmaceutical composition of claim 12, wherein the carbapenem is selected from the group consisting of: meropenem, faropenem, imipenem, ertapenem, doripenem, panipenem/betamipron and biapenem, razupenem, tebipenem, lenapenem, and tomopenem.

14. The pharmaceutical composition of claim 12, wherein the antibacterial agent is meropenem.

15. A method for the prevention or treatment of bacterial infection in a patient in need of such treatment, said method comprising administering to said patient a therapeutically effective amount of a combination of an antibacterial agent and a compound of claim 1.

16. The method of claim 15, wherein the bacterial infection is caused by aerobic or anaerobic Gram-positive, or aerobic or anaerobic Gram-negative bacteria.

17. The method of claim 16, wherein the bacterial infection is caused by metallo-β-lactamase producing Gram-positive bacteria.

18. The method of claim 16, wherein the bacterial infection is selected from the group consisting of: pneumonia, respiratory tract infections, urinary tract infections, intra-abdominal infections, skin and soft tissue infections, bloodstream infections, septicaemia, intra- and post-partum infections, prosthetic joint infections, endocarditis, acute bacterial meningitis, and febrile neutropenia.

* * * * *